US009371549B2

(12) United States Patent
Silverman et al.

(10) Patent No.: US 9,371,549 B2
(45) Date of Patent: Jun. 21, 2016

(54) BIOREFINERY SYSTEM, METHODS AND COMPOSITIONS THEREOF

(71) Applicant: Calysta Energy, Inc., Menlo Park, CA (US)

(72) Inventors: Joshua Silverman, Sunnyvale, CA (US); Sol M. Resnick, Encinitas, CA (US); Michael Mendez, San Diego, CA (US); Renee Saville, Mountain View, CA (US); Sungwon Lee, Fremont, CA (US); Luan Nguyen, San Ramon, CA (US)

(73) Assignee: Calysta, Inc., Menlo Park, CA (US)

( * ) Notice: Subject to any disclaimer, the term of this patent is extended or adjusted under 35 U.S.C. 154(b) by 8 days.

(21) Appl. No.: 13/941,027

(22) Filed: Jul. 12, 2013

(65) Prior Publication Data

US 2014/0013658 A1 Jan. 16, 2014

Related U.S. Application Data

(60) Provisional application No. 61/671,542, filed on Jul. 13, 2012.

(51) Int. Cl.

| | |
|---|---|
| ***C12P 7/64*** | (2006.01) |
| ***C12N 15/74*** | (2006.01) |
| ***C12P 5/00*** | (2006.01) |
| ***C10G 3/00*** | (2006.01) |
| ***C10L 1/02*** | (2006.01) |
| ***C10L 1/04*** | (2006.01) |
| ***C12N 9/16*** | (2006.01) |
| ***C12N 9/00*** | (2006.01) |
| ***C12N 1/16*** | (2006.01) |
| ***C12N 1/20*** | (2006.01) |
| ***C12N 9/10*** | (2006.01) |
| ***C10G 47/00*** | (2006.01) |

(52) U.S. Cl.

CPC . *C12P 7/649* (2013.01); *C10G 3/00* (2013.01); *C10G 3/50* (2013.01); *C10G 47/00* (2013.01); *C10L 1/02* (2013.01); *C10L 1/04* (2013.01); *C12N 1/16* (2013.01); *C12N 1/20* (2013.01); *C12N 9/1029* (2013.01); *C12N 9/16* (2013.01); *C12N 9/93* (2013.01); *C12N 15/74* (2013.01); *C12P 5/00* (2013.01); *C12P 7/6409* (2013.01); *C12P 7/6463* (2013.01); *C12Y 301/02* (2013.01); *C12Y 602/01003* (2013.01); *C10G 2300/1014* (2013.01); *C10L 2200/0469* (2013.01); *C10L 2270/02* (2013.01); *C10L 2270/04* (2013.01); *C10L 2290/26* (2013.01); *C12Y 203/01039* (2013.01); *C12Y 604/01002* (2013.01); *Y02E 50/13* (2013.01); *Y02P 20/52* (2015.11); *Y02P 30/20* (2015.11)

(58) Field of Classification Search

None

See application file for complete search history.

(56) References Cited

U.S. PATENT DOCUMENTS

| | | | |
|---|---|---|---|
| 4,269,940 | A | 5/1981 | Patel et al. |
| 6,492,135 | B1 | 12/2002 | Larsen |
| 6,689,601 | B2 | 2/2004 | Koffas et al. |
| 6,818,424 | B2 | 11/2004 | DiCosimo et al. |
| 7,026,464 | B2 | 4/2006 | Dicosimo et al. |
| 7,098,005 | B2 | 8/2006 | Dicosimo et al. |
| 7,579,163 | B2 | 8/2009 | Eriksen et al. |
| 7,799,550 | B2 | 9/2010 | Moen et al. |
| 8,062,392 | B2 | 11/2011 | Bryan et al. |
| 8,093,306 | B2 | 1/2012 | Blevins et al. |
| 8,129,154 | B2 | 3/2012 | Burk et al. |
| 8,129,155 | B2 | 3/2012 | Trawick et al. |
| 8,153,850 | B2 | 4/2012 | Hall et al. |
| 8,168,686 | B2 | 5/2012 | Blevins et al. |
| 8,173,044 | B1 | 5/2012 | Cheiky et al. |
| 8,177,870 | B2 | 5/2012 | Herrema et al. |
| 8,592,198 | B2 | 11/2013 | Moen et al. |
| 2003/0003528 | A1 | 1/2003 | Brzostowicz et al. |
| 2005/0054030 | A1 | 3/2005 | Schnoor et al. |
| 2005/0163802 | A1 | 7/2005 | Jorgensen et al. |
| 2006/0057726 | A1 | 3/2006 | Sharpe |
| 2008/0026005 | A1 | 1/2008 | Miguez et al. |
| 2008/0057554 | A1 | 3/2008 | Huhnke et al. |
| 2009/0263877 | A1 | 10/2009 | Eriksen et al. |
| 2010/0068772 | A1 | 3/2010 | Downey |
| 2010/0221813 | A1 | 9/2010 | Miguez et al. |
| 2010/0248344 | A1 | 9/2010 | Schroder et al. |
| 2010/0297749 | A1 | 11/2010 | Aravanis et al. |
| 2011/0165639 | A1 | 7/2011 | Ascon et al. |
| 2011/0236919 | A1 | 9/2011 | Zahn et al. |
| 2012/0003705 | A1 | 1/2012 | Jin et al. |

(Continued)

FOREIGN PATENT DOCUMENTS

| | | |
|---|---|---|
| EP | 0 296 484 A2 | 12/1988 |
| EP | 1 265 982 B1 | 9/2004 |

(Continued)

OTHER PUBLICATIONS

Chen, "A microbial polyhydroxyalkanoates (PHA) based bio- and materials industry," *Chem. Soc. Rev.* 38:2434-2446, 2009.

Fang et al., "Characterization of methanotrophic bacteria on the basis of intact phospholipid profiles," *FEMS Microbiology Letters* 189:67-72, 2000.

Folch et al., "A Simple Method for the Isolation and Purification of Total Lipides From Animal Tissues," *J. Biol. Chem.* 226(1):497-509, May 1957.

Hanson et al., "Methanotrophic Bacteria," *Microbiological Reviews* 60(2):439-471, Jun. 1996.

Helm et al., "Characterizing a stable methane-utilizing mixed culture used in the synthesis of a high-quality biopolymer in an open system," *Journal of Applied Microbiology* 101:387-395, 2006.

Höfer et al., "Production of functionalized polyhydroxyalkanoates by genetically modified *Methylobacterium extorquens* strains," *Microbial Cell Factories* 9:70, 2010, 13 pages.

Kim et al., "Creating auxotrophic mutants in *Methylophilus methylotrophus* AS1 by combining electroporation and chemical mutagenesis," *Appl. Microbiol Biotechnol.* 48:105-108, 1997.

(Continued)

*Primary Examiner* — Paul Holland

(74) *Attorney, Agent, or Firm* — Seed IP Law Group PLLC

(57) ABSTRACT

The present disclosure relates to bioengineering approaches for producing biofuel and, in particular, to the use of a $C_1$ metabolizing microorganism reactor system for converting $C_1$ substrates, such as methane or methanol, into biomass and subsequently into biofuels, bioplastics, or the like.

30 Claims, 6 Drawing Sheets

(56) References Cited

U.S. PATENT DOCUMENTS

| | | | |
|---|---|---|---|
| 2012/0116138 | A1 | 5/2012 | Goodall et al. |
| 2012/0142983 | A1 | 6/2012 | Vermeiren et al. |
| 2013/0189763 | A1 | 7/2013 | Dalla-Betta et al. |
| 2014/0024872 | A1 | 1/2014 | Silverman et al. |

FOREIGN PATENT DOCUMENTS

| | | | | |
|---|---|---|---|---|
| EP | 1 497 409 | B1 | | 5/2006 |
| EP | 1 183 326 | B1 | | 3/2007 |
| EP | 1 478 376 | B1 | | 9/2010 |
| EP | 1 419 234 | B1 | | 3/2011 |
| EP | 2 427 200 | B1 | | 4/2014 |
| WO | 01/60974 | A2 | | 8/2001 |
| WO | 02/18617 | A2 | | 3/2002 |
| WO | 03/016460 | A1 | | 2/2003 |
| WO | 03/068003 | A1 | | 8/2003 |
| WO | 03/072133 | A2 | | 9/2003 |
| WO | 03/089625 | A2 | | 10/2003 |
| WO | WO 2007136762 | A2 | * | 11/2007 |
| WO | WO 2009009391 | A2 | * | 1/2009 |
| WO | WO 2009140695 | A1 | * | 11/2009 |
| WO | WO 2009151342 | A1 | * | 12/2009 |
| WO | 2010/128312 | A2 | | 10/2010 |
| WO | 2011/038132 | A1 | | 3/2011 |
| WO | 2012/045022 | A2 | | 4/2012 |
| WO | 2012/088071 | A2 | | 6/2012 |
| WO | 2014/012055 | A1 | | 1/2014 |

OTHER PUBLICATIONS

Madison et al., "Metabolic Engineering of Poly(3-Hydroxyalkanoates): From DNA to Plastic," *Microbiology and Molecular Biology Reviews* 63(1):21-53, Mar. 1999.

Marx et al., "Development of improved versatile broad-host-range vectors for use in methylotrophs and other Gram-negative bacteria," *Microbiology* 147:2065-2075, 2001.

McDonald et al., "Molecular Ecology Techniques for the Study of Aerobic Methanotrophs," *Applied and Environmental Microbiology* 74(5): 1305- 1315, Mar. 2008.

Ramsay et al., "Production of Poly-(β-Hydroxybutyric-Co-β-Hydroxyvaleric) Acids," Applied and Environmental Microbiology 56(7):2093-2098, Jul. 1990.

Stolyar et al., "Role of multiple gene copies in particulate methane monooxygenase activity in the methane-oxidizing bacterium *Methylococcus capsulatus* Bath," *Microbiology* 145:1235-1244, 1999.

Templeton et al., "Variable carbon isotope fractionation expressed by aerobic $CH_4$-oxidizing bacteria," *Geochimica et Cosmochimica Acta* 70:1739-1752, 2006.

Toyama et al., "Construction of insertion and deletion *mxa* mutants of *Methylobacterium extorquens* AM1 by electroporation," *FEMS Microbiology Letters* 166:1-7, 1998.

Vuilleumier et al., "Genome Sequence of the Haloalkaliphilic Methanotrophic Bacterium *Methylomicrobium alcaliphilum* 20Z," *Journal of Bacteriology* 194(2):551-552, Jan. 2012.

Zellner et al., "A study of three anaerobic methanogenic bioreactors reveals that syntrophs are diverse and different from reference organisms," *FEMS Microbiology Ecology* 22:295-301, 1997.

Henstra et al., "Microbiology of synthesis gas fermentation for biofuel production," *Current Opinion in Biotechnology* 18:200-206 (2007).

Jahnke, "The effects of growth temperature on the methyl sterol and phospholipid fatty acid composition of *Methylococcus capsulatus* (Bath)," *FEMS Microbiology Letters* 93:209-212 (1992).

Kaluzhnaya et al., "Taxonomic Characterization of New Alkaliphilic and Alkalitolerant Methanotrophs from Soda Lakes of the Southeastern Transbaikal Region and description of *Methylomicrobium buryatense* sp.nov.," *System. Appl. Microbiol.* 24:166-176 (2001).

Kosa et al., "Lipids from heterotrophic microbes: advances in metabolism research," *Trends in Biotechnology* 29(2):53-61 (Feb. 2011).

Lee et al., "Heterologous Co-expression of *accA, fabD*, and Thioesterase Genes for Improving Long-Chain Fatty Acid Production in *Pseudomonas aeruginosa* and *Escherichia coli," Appl Biochem Biotechnol* 167:24-38 (2012).

Schrader et al., "Methanol-based industrial biotechnology: current status and future perspectives of methylotrophic bacteria," *Trends in Biotechnology* 27(2):107-115 (Feb. 1, 2009).

Summons et al., "Carbon isotopic fractionation in lipids from methanotrophic bacteria: Relevance for interpretation of the geochemical record of biomarkers," *Geochimica et Cosmochimica Acta*. 58(13):2853-2863 (1994).

Keeling et al., "Monthly Atmospheric 13C/12C Isotopic Ratios for 11 SIO Stations," Trends: A Compendium of Data on Global Change Carbon Dioxide Information Analysis Center, Oak Ridge National Laboratory, U.S. Department of Energy, Oak Ridge, Tenn., U.S.A. (3 pages) (Feb. 16, 2010).

Kendall et al., "Resources on Isotopes—Periodic Table—Carbon," Isotope Tracers Project, Menlo Park, Calif (4 pages) http://wwwrcamnl.wr.usgs.gov/isoig/period/c_iig (1995).

Park et al., "Metabolic Fractionation of C13 & C12 in Plants," Plant Physiology 36(2):133-138 (Mar. 1961).

Stein et al., "Genome Sequence of the Obligate Methanotroph *Methylosinus trichosporium* Strain OB3b," *Journal of Bacteriology* 192(24):6497-6498 (Dec. 2010).

* cited by examiner

SEQUENCE LISTING

<160> NUMBER OF SEQ ID NOS: 104

<210> SEQ ID NO 1
<211> LENGTH: 1731
<212> TYPE: DNA
<213> ORGANISM: Artificial Sequence
<220> FEATURE:
<223> OTHER INFORMATION: Mutated M. trichosporium fadD sequence

<400> SEQUENCE: 1
acccatgaca gacgcatgac tcgcgctcga cccttacgcc gcgcgtccct gactcgcctc 60
ttaaaccgcc gagcgtcgcg ccggacatcg atcccgccga gccgcgcact ctggtcgagg 120
tgtttcgtcg cagcgtcgcc gcgcattccg acaaaatcgc gctcgagagc ttcggcgcga 180
cgctgacctt cgcgcaattc gacggcgccg cgcgcgccat cgccgccttt ctgcaatcgc 240
agggcctgaa gaagggcgat cgcgtcgcga tcatgtcgcc caatgtgatg gcctatccgc 300
cgatcatctt cggcgtgctg ctcgccggcg gcgcggtggt caacgtcaat ccgctctaca 360
cgccgagcga gctctccttt cagatcaatg attccggcgc gcgcatcgtc ttcgtgctgg 420
agaatttcgc ccatacggtc gaagccgcat ggcccgacat gtcgatcgat ctcgcggtcg 480
tcgtcacgcc aggcgatctg ctcgggctca aaggcaagct cgtcgatttc gtctcgcgct 540
atgtgaaatg cgccgtgcgg ccctatcagc tgccgacgag catgcgcttt cgcgatatca 600
tgaagcaagg ctcggcgcgc tcgggcgcgc gacgtctaga tcgcaccgga cgatctcgct 660
tttctgcaat atacgggcgg cacgaccggc gtcgccaagg gagcgatgct gctccaccgc 720
aatgtcgcgg ccaatgtggc gcaagcgacc gcctggctgc atccgtttct gctggaggcg 780
tccgggcgcg agcggccgca gaagatggtg gcggcgctgc cgctctagca cattttcggc 840
ctcaccgcct gtctgctggt gctggtgcgc atcggcggct cctgcctgct catcgccaat 900
ccgcgcgaca tcgccggctt cgtgaagacg ctgcgcaagt cgcgcttctc gatgatctcc 960
ggcgtcaaca cgctctatgc ggcgctcgcc gatcatccgt aattcgcgca ggtcgacttc 1020
tctcgcctcg tcttctgcat cgccggcggc atggcgacgc aggacgtcgt cgcgcgcaaa 1080
tggagagcga tcaccggccg cccgatcatc gaaggctatg ggctctccga gacctcgccg 1140
gtcgtcgcct gcaacaggcc cgatctcgag taattctccg gctcgatcgg ctatccgcat 1200
ccctcgaccg ccgtgtcgat ccgcgcgccc tcgggcgagc cggttccgat cggcgagcgc 1260
ggggagctgt gcgtgaaggg tccgcaggtg atgccgggat attggaatcg ccccgcctag 1320
accgaggcgg cgttcacgcc ggacgggttt tttcgcaccg gcgatgtggc gatcatgctg 1380
ccggacggac aggtgaagct cgtcgatcgt ttgaagtaga tgattctcgt ctccggcttc 1440
aacgtctatc cgaacgaggt cgagaatgtg ctggtgcagc atcccaaggt gaaggaggcg 1500
gcggtgatcg gcgttcccga tccgcattcg ggctaggcgc cgctcgcctt catcgtgccg 1560
cgcgacgcca gcgtcaccgg ccaggagctg catgatttct gccgcaagac gctgacgcac 1620
tataaggcgc cgaagcattt ctaattccgc gacagcctgc cgaagagcaa tgtcggcaag 1680
gtgctgcggc gcgtgctgcg cgacgaggtg caagcgcgag ccgaatgagg a 1731

<210> SEQ ID NO 2
<211> LENGTH: 927
<212> TYPE: DNA
<213> ORGANISM: Artificial Sequence
<220> FEATURE:
<223> OTHER INFORMATION: Codon optimized E. Coli FabD sequence

<400> SEQUENCE: 2

```
atgacgcaat tcgctttcgt tttcccggga caaggttcgc aaactgttgg aatgctcgct     60

gatatggccg cctcgtaccc gatcgtcgag gaaacgttcg ccgaggccag cgcggcgctg    120

gggtacgacc tgtgggccct cacccagcag ggcccggccg aggaactcaa caagacctgg    180

cagacgcagc ctgccctcct gaccgcctcg gtcgcgctct atcgtgtgtg gcagcagcag    240

ggcggcaagg cgcccgccat gatggccggc cacagcctgg gcgagtactc cgccctcgtg    300

tgcgcgggcg tgatcgactt cgcggacgcc gtccgcctgg tcgagatgcg cggcaagttc    360

atgcaggaag ccgtccccga gggcacgggc gctatggcgg cgatcatcgg cctcgacgat    420

gcctccatcg ccaaggcgtg cgaggaagcg gccgagggcc aggtcgtcag cccggtgaat    480

ttcaactcgc ccggtcaggt cgtcattgcc ggccataaag aggccgtcga gcgcgcgggc    540

gccgcgtgca aggccgccgg cgcgaagcgc gcgttgcccc tcccggtcag cgtcccgtcc    600

cattgcgcgc tgatgaagcc ggcggccgac aagctggccg tggagctcgc gaagatcacc    660

ttcaatgcgc cgaccgtccc ggtggtcaat aacgtcgacg tcaagtgcga aacgaacggc    720

gatgccatcc gcgacgcgct cgtccggcag ctgtataacc cggtgcagtg gacgaagtcc    780

gtcgagtata tggcggcgca gggcgtggag cacctctatg aagtgggccc cggcaaggtc    840

ctcaccggcc tcaccaagcg catcgtggac accctgacgg cctcggcgct gaatgagccc    900

tcggccatgg cggctgcgct ggagctg                                         927
```

<210> SEQ ID NO 3
<211> LENGTH: 549
<212> TYPE: DNA
<213> ORGANISM: Artificial Sequence
<220> FEATURE:
<223> OTHER INFORMATION: Codon optimized E. Coli TesA sequence with periplamic targeting sequence removed.

<400> SEQUENCE: 3

```
atggctgaca ccctcctgat tcttggcgat tccctctctg ctggttaccg tatgtccgcg     60

tccgctgcct ggcctgccct cctcaacgac aagtggcaga gcaagacgag cgtcgtcaat    120

gcgtcgatct cgggcgatac ctcgcaacag ggcctggcgc gcttgccggc cctgctcaag    180

cagcatcagc cgcgctgggt gctcgtcgag ctgggcggca acgatggact gcgcggcttc    240

cagccccagc agaccgagca gacgctccgc cagatcctcc aagacgtcaa ggccgccaat    300

gcggagccgc tgctgatgca gatccgcctc ccggcgaatt atggccgccg ctataacgaa    360

gcgttctcgg ccatctatcc gaagctggcg aaagagttcg acgtgcccct gctcccgttc    420

ttcatggaag aagtctacct gaagccgcag tggatgcaag acgatggcat ccatccgaac    480

cgggacgcgc agcccttcat cgccgactgg atggccaaac agctgcagcc cctcgtgaac    540

cacgactcg                                                            549
```

<210> SEQ ID NO 4
<211> LENGTH: 1146
<212> TYPE: DNA
<213> ORGANISM: Artificial Sequence
<220> FEATURE:
<223> OTHER INFORMATION: Codon optimized Cinnamomum camphorum thioesterase sequence

<400> SEQUENCE: 4

```
atggccacaa cttcacttgc ctctgccttt tgttcgatga aagctgtcat gctcgcccgc     60

gatggacgtg gaatgaagcc gcgttcgtcg gacctccagc tccgagccgg caatgcgcag    120
```

-continued

```
acctccctga aaatgattaa cggcacgaag ttctcgtata ccgagtcgct gaagaagctc    180

ccggactgga gcatgctgtt cgcggtgatc accaccatct tctcggccgc tgagaagcaa    240

tggaccaatc tcgaatggaa gccgaagccg aatccgcccc agctgctgga cgaccacttc    300

ggcccccacg gcctcgtgtt ccgccgcacc ttcgccatcc gctcgtatga agtgggcccg    360

gaccgctcga ccagcatcgt cgccgtgatg aaccatttgc aggaagcggc gctcaatcat    420

gcgaagagtg tgggcatcct gggcgacggc ttcggtacga cgctggagat gagcaagcgc    480

gacctgatct gggtcgtcaa gcgcacgcac gtggcggtgg agcgttaccc cgcgtggggg    540

gacacggtcg aagtcgagtg ctgggtcggc gcctccggca acaatggccg ccggcacgac    600

ttcctcgtgc gcgattgcaa gaccggtgag attctcaccc gctgcacgtc gctgagcgtc    660

atgatgaata ctcgcacccg ccgcctctcg aagatccctg aggaagtgag gggcgagatc    720

ggcccggcgt tcatcgacaa cgtggccgtc aaagatgagg agatcaagaa gccccagaag    780

ctcaacgact cgaccgcgga ttacatccag ggcggactga cgccgcgttg gaacgatctg    840

gacatcaacc agcacgtcaa caacatcaag tatgtggact ggatcctcga aaccgtcccc    900

gactcgatct tcgagagcca tcatatctcg tccttcacca tcgagtaccg gcgcgagtgc    960

acgatggatt ccgtcctcca gtccctcacc acggttagcg gcggcagctc cgaggccggc   1020

ttggtctgcg agcatctgct gcagcttgag ggcggctccg aggtcctccg cgcgaaaacg   1080

gagtggcgcc ccaagctcac ggatagcttc cgcggcatct cggtgatccc ggcggagagc   1140

tcggtc                                                              1146
```

<210> SEQ ID NO 5
<211> LENGTH: 1146
<212> TYPE: DNA
<213> ORGANISM: Artificial Sequence
<220> FEATURE:
<223> OTHER INFORMATION: Codon optimized Umbellularia californica
      thioesterase sequence

<400> SEQUENCE: 5

```
atggccacta cctcccttgc ttctgccttt tgctcaatga aagctgtgat gctcgcccgt     60

gacggacgcg gtatgaagcc gcgctcgtcc gacctccagc tccgggccgg caacgcgccg    120

acctcgctca agatgattaa tggcactaag ttctcctata ccgagtcgct caagcgcctg    180

ccggattggt cgatgctgtt cgcggtcatc accacaatct tctcggccgc tgagaagcag    240

tggaccaact tggagtggaa gccgaagccg aagctgcccc agctcctgga cgaccatttc    300

ggcctccatg gcctggtgtt ccgccggacg ttcgccatcc gttcgtacga agtcggcccc    360

gaccgctcga cctccatcct ggcggtgatg aatcacatgc aagaggcgac gctcaaccat    420

gccaagtccg tcggtatcct gggcgatggc ttcggcacca ccctggagat gagcaagcgc    480

gatctcatgt gggtcgtccg ccgcacgcat gttgccgtgg agcgctatcc cacgtggggc    540

gacacggtcg aggtcgagtg ctggatcggg gcgtcgggaa ataacggcat gcgccgcgac    600

ttcctcgtcc gtgactgcaa gaccggcgag atcctcacgc gctgcacgtc gctgtcggtg    660

ctgatgaata cccgcacccg tagactgtcc accatccccg atgaagtgcg cggcgaaatc    720

ggcccggcct tcatcgacaa tgtcgccgtc aaagacgatg agatcaagaa gctgcagaag    780

ttgaacgact cgaccgcgga ctatatccag ggcggcctga cgccccgctg gaatgacctc    840

gacgtcaacc agcatgtcaa caatctcaag tacgtggcgt gggtgttcga aacggtgccg    900

gacagtatct tcgagagcca ccacatttcc agcttcacgc tcgaatatcg tcgcgagtgc    960
```

-continued acgcgcgact ccgtcctccg gtcgctgacc accgtgagcg gcggctcgtc ggaagcgggc 1020
ctggtctgcg atcacctcct gcagctggag ggcggctccg aggtcctccg cgcgaggacc 1080
gagtggcgtc cgaagctgac ggatagcttc cgcgggatca gcgtcatccc cgccgagccc 1140
cgcgtg 1146

<210> SEQ ID NO 6
<211> LENGTH: 750
<212> TYPE: DNA
<213> ORGANISM: Artificial Sequence
<220> FEATURE:
<223> OTHER INFORMATION: Codon optimized Streptococcus pyogenes acyl-ACP thioesterase sequence
<400> SEQUENCE: 6
atgggccttt cctatcaaga agaactcacc ctccccttcg agctctgcga cgtcaagtcc 60
gatatcaagc tgccgctgct gctcgactac tgcctgatgg tgagcggccg ccagtcggtc 120
cagctgggcc gttcgaacaa caatctgctg gttgactata agctcgtctg gatcgtgacc 180
gactatgaga tcaccatcca tcgcctcccg catttccagg aaacgattac catcgagaca 240
aaggccctct cgtacaacaa gttcttctgc taccgccagt tctatatcta tgaccaggag 300
ggctgcctgc tcgtcgatat cctcagctac ttcgcgctgc tgaatccgga tacgcgcaag 360
gtcgcgacca tccccgagga cctggtcgcg cccttcgaaa cggacttcgt caaaaagctc 420
caccgggtgc cgaagatgcc gctgttggag cagtcgatcg atcgcgacta ttatgtgcgc 480
tacttcgata tcgacatgaa tggtcacgtg aacaattcga agtatctcga ctggatgtac 540
gacgtcctgg gctgccagtt cctcaagacc catcagccgc tgaagatgac gctcaagtat 600
gtcaaagagg tcagccctgg cggacagatc acgtcctcgt accacctgga ccagctcacc 660
tcgtatcacc agatcatctc ggacggccag ctcaacgccc aggccatgat cgagtggcgc 720
gctattaagc agaccgagtc ggagactgat 750

<210> SEQ ID NO 7
<211> LENGTH: 1191
<212> TYPE: DNA
<213> ORGANISM: Artificial Sequence
<220> FEATURE:
<223> OTHER INFORMATION: Codon optimized Ricinus communis palmitoyl-acyl carrier protein thioesterase sequence
<400> SEQUENCE: 7
atgggaacat gctcgtatac catcaccctg ccgatccgct gcctgtctaa ttcgaacggc 60
catcacgacc cccataagca gaatctcaac aagatcaaga tcaacggcgc cagcacgagc 120
acgcgtccgc tgaagctcga tgcgccgtcg cagaccgtgg gcgtcgccac catttatctg 180
gcctccgtca gcgagaacct caccctcacc aaagaggtca tgcggcagaa catccccacg 240
aagaagcagt acatcgaccc gcaccgccag ggcctgatga tcgagggcgg cgtcggctat 300
cgccagacga tcgtcatccg ttcgtatgaa gtcggccctg ataagaccgc gacgctggag 360
agtatcctct atctcctgca ggaaacggcc ctgaatcacg tgtggctgtc gggcctgctc 420
tccaatggct tcggcgccac gcatggcatg gtgaagaata acctgatctg ggtggtgtcc 480
aagctccagg tccaggtcga ccattacccg atctggggcg aggtcgtcga gatcgatacc 540
tgggtccggg cgtccggcaa gaacggcatg aagcgtgact ggctgatccg ctcgcaggcc 600
acgggccatg ttttcgtccg cgcgacctcg acgtgggtca tgatgaacga gaaaactcgc 660
cgcctctcga agatgccgga agaagtgagg gccgagatct ccccgtggtt catcgagaag 720

| caagcgatca aggaagaggt gccggataag atcgcgaagc tcgacgataa ggctcgctac | 780 |
| gtcatctcga atttgaagcc gaagcgctcg gatctcgaca tgaaccatca cgtgaataac | 840 |
| gtgaaatatg tccgctggat gctggagatc ctcccggacc acttcctgga gtcgcatcag | 900 |
| ctctcgggca tcaccatgga gtatcgccgc gagtgcgggt cggccgacat tgtccagtcc | 960 |
| ctctgcgagc ccgacggtga cgagatcctg tccaacgaca tccccgtgct taacggattc | 1020 |
| agcctcgcgt cggagcccct gatggaaggc aacggcttcc tcgtccccct ggacaaggtc | 1080 |
| ccgctgaagt acacccacct cctgctcacg aagggtgaga gccagaatga agagatcgtc | 1140 |
| cgcggcaaga ccatttggaa gaagaaactc tgcaccatgc ccttcagcac c | 1191 |

<210> SEQ ID NO 8
<211> LENGTH: 1176
<212> TYPE: DNA
<213> ORGANISM: Artificial Sequence
<220> FEATURE:
<223> OTHER INFORMATION: Codon optimized Ricinus communis palmitoyl-acyl carrier protein thioesterase sequence

<400> SEQUENCE: 8

| atggcttcga aaggttccat ccgcctctac ttcccctgcg acttccgcaa caccctccag | 60 |
| aagaagaaca tgaagatgga catggtcatg gcccgctcgg gcttctccta ctcgctcaac | 120 |
| ccgatcgcgc cgaagatccc ccgcttctac gtggtcgcca acgcgtcgaa ccctcagcgg | 180 |
| gtcgacacga tcaatggcaa aaaggtgaac ggcattcacg tcgcggagag ctcgaattcg | 240 |
| tatgccgacc agaataagat gaacgcgacc gctggcctcg tcctggacgg caatgtcgac | 300 |
| catcagccgc tccacaagtg gctgttgggc cgtttcgtgg acgagcgcct ggtctatagt | 360 |
| caaaccttca tcatccgcag ctacgagatc ggtcccgata agaccgcgac catggagact | 420 |
| ctcatgaatc tgctccagga aaccgcgctc aatcatgtga cctcttcggg cctggcgggc | 480 |
| gatgggttcg gcgcgacgcg ggagatgtcg ctccggaagc tgatctgggt cgtcacgcgc | 540 |
| atccatatcc aggtccagcg ctattcctgc tggggcgatg tcgtcgagat cgacacgtgg | 600 |
| gtcgatggag cgggcaagaa tggcatgcgc agggattgga tcatccggga ctacaacacg | 660 |
| aaggagatca ttacccgcgc cacctcgacc tgggtcatca tgaaccgcga gacacgtaag | 720 |
| ctgtcgaaga tgccggaaca ggtgcgccag gaactggtgc cgttctatac caaccgcatc | 780 |
| gcgatcgcca aggaaaacaa cgacgtggag aagattgaca agctgaccga cgaaaccgcc | 840 |
| gagcgcatcc gtagcggcct cgcgccgcgc tggagcgata tggacgccaa ccagcatgtg | 900 |
| aacaatgtta agtatatcgg ctggatcctt gagagcgtcc cgatcaatgt cctcgaagat | 960 |
| tacaatctga cgtccatgac cctggagtat cgccgcgagt gccgccagag caacctcctg | 1020 |
| gagtcgctca cgtcgaccac ggagcattcg aataacaact cgtgcaaccg caaggcccac | 1080 |
| ctggagtata cgcacctcct gcgtatgcag gccgacaagg ccgagatcgt gcgtgcccgc | 1140 |
| accgagtggc agtccaagtc gaatcgcaag acgatc | 1176 |

<210> SEQ ID NO 9
<211> LENGTH: 1257
<212> TYPE: DNA
<213> ORGANISM: Artificial Sequence
<220> FEATURE:
<223> OTHER INFORMATION: Codon optimized Ricinus communis palmitoyl-acyl carrier protein thioesterase sequence

<400> SEQUENCE: 9

-continued atggtcgcca ccgccgccgc cgctacctcc tcgttcttcc ccgtgccgtc ccagtccgct 60
gacgccaatt tcgataaggc cccggcgagc ctgggcggca tcaagctgaa atcgacgtcg 120
tgcagccggg gcctccaggt gaaggccaat gcgcaggcgc cgccgaagat caacggctcg 180
tcggtcggct tcaccacctc ggtggagaca gtgaagaatg acggcgacat gccgctcccg 240
cctcccccca ggaccttcat taatcagctc ccggactgga gtatgctcct ggccgcgatc 300
accaccatct tcctggcggc ggagaagcag tggatgatgc tcgactggaa gccccgccgt 360
ccggatatgc tcattgaccc gttcggaatc ggccgcatcg tccaggacgg cctgatcttc 420
cgccagaact tcagcatccg ctcgtatgag atcggcgccg accgcaccgc cagcatcgaa 480
accctgatga atcatctcca ggaaaccgcg ctcaaccacg tgaaaactgc gggcctcctt 540
ggcgatggct tcggctcgac cccggagatg tcgaagcgca atctgatctg ggtggtcacg 600
cgcatgcaag tcctggtcga ccgctacccg acctggggcg acgtcgtcca ggtcgacacc 660
tgggtgtcca agtcgggcaa gaacggaatg cgccgggatt ggtgcgttcg cgacagccgc 720
acgggtgaaa ccctgacgcg tgcgagctcg gtctgggtca tgatgaacaa gctgacgcgc 780
cgcctgtcga agatccccga ggaggtgcgt ggcgagattg agccgtattt cctcaactcg 840
gacccgatcg tcgacgagga ctcgcgcaag ctccccaagc tggacgactc gaatgccgac 900
tatgtccgca agggcctcac gccgcgctgg tcggacctcg atatcaacca gcacgtcaac 960
aatgtgaagt atatcggctg gatcctggag agcgcgccac tgccgatcct cgaatcgcac 1020
gagctctcgg cgatcacgtt ggagtaccgt cgcgagtgcg gtcgtgatag cgtcctgcag 1080
tccctgacgg ccgtgtccgg caacggcatc ggcaatctcg ggaacgcggg cgacatcgag 1140
tgccagcatc tcctgcgcct ggaagatggc gcggagatcg tccggggacg cacggagtgg 1200
cgccctaagt actctagcaa cttcggcatc atgggccaga tccccgtgga gtcggcc 1257

<210> SEQ ID NO 10
<211> LENGTH: 1215
<212> TYPE: DNA
<213> ORGANISM: Artificial Sequence
<220> FEATURE:
<223> OTHER INFORMATION: Codon optimized Jatropha curcas acyl-ACP
thioesterase sequence

<400> SEQUENCE: 10
atggctgttt tcacctaccg catcgccatg ctcccgattc gctgctcctc ctccaatagt 60
accaactcgc attcgcacga cccgaaccag cagaatctcc ataagatcaa gatcaatggg 120
tcggcgtcgg ccatgatgcc cctcaaggtc gacctcccgt cgagcctcac gatcacgagc 180
gtcgcccccg tggtcgagaa tctcagcctg accaaggagc agacgcgcca gaacatcccc 240
accaagaagc agtatatcga tccgcaccgc cagggcctca tcgtcgagga gggcgtgggc 300
taccgccaga ccgtcgtgat ccgctcgtat gaggtcggcc ccgataagac cgccaccctg 360
gagatcatcc tctgcttgct gcaagagact gccctgaacc acgtctggct ctcgggcctg 420
ctcagcaacg gcttcggcgc gacgcatgga atggtgcgca ataatctcat ctgggtcgtg 480
tcgaagctcc aggtccaggt cgaccagtat cccatctggg gcgaggtcgt cgagatcgac 540
acgtgggtcg gcgcctccgg caagaacggt atgcgtcgcg actggctggt ccgctcgcag 600
gcgaccggtc aggtgttcgc gcgtgccacg tctacgtggg tgatgatgaa cgagaaaacg 660
cgccgtctgt cgaagatgcc cgaggaagtc cgggctgaga ttgcgccgtg gttcatcgag 720
aaacaggcga tcaaagaaga agtgcctgag aagatcgcga agctggacga caaggcccgc 780

```
tacgtcgtca ccaacctcaa gcccaagcgc tcggacctgg atatgaacca gcacgtgaac    840

aatgtcaagt atgtgcgctg gatgctcgaa accctgccgg atcaattctt cgagaaccat    900

cagcttagcg gcatcacgct ggagtacaag cgggagtgcg gctcctcgga tatcgtggag    960

tcgttgtgcg agccggacga ggaggagggc atcatcaata ccggcctgaa gcagaacaat   1020

gacaagtcgc tgttcaacgg cttcagcctc ccgtcggaga ttatggaagg caacggattc   1080

ctgtcgtcgc tggaaaagac cccgctgaag tatacccatc tcctcgttgc gaagggcaag   1140

acacagagcg aagagatcgt ccgcggcaag accatctgga agaagaagct gctcacgacc   1200

atgccgttct ccccg                                                    1215


<210> SEQ ID NO 11
<211> LENGTH: 1044
<212> TYPE: DNA
<213> ORGANISM: Artificial Sequence
<220> FEATURE:
<223> OTHER INFORMATION: Codon optimized Jatropha curcas acyl-ACP
      thioesterase sequence

<400> SEQUENCE: 11

atggtgtcca cggccatctc gttctccctc ctccccatca agctcatcaa agaagaaacc     60

cgcatggctt ccgcggaccg ccgcaagaat tcgatcgtca aagaattcgg ccatttcacg    120

tgccggtgcg cggcgatcga gaagcgcatc cagaagctca acaacttcct catcgatggc    180

ggcttcggct cgctggagca gaacggcctg atctatcgcc agaatatctt cattcgctcg    240

ttcgagatcg gcttcgaccg caagttgtcg ctggctgccc tcaccaattt cctccaggac    300

accgccctca accatgtccg catgatcggg ctgctggcgg ccggattcgg ctcgaccccg    360

gagatgtcga aaaaggacct catctgggtc ctctgcaccc tccagatcct cgtcgatcgc    420

catccgtcgt ggctcgatgc ggtcgaggtc gacacctgga tgtacccctc cggccagaac    480

ggccagggcc gcgattggct cgtgcgggac gccaagacgg gcaagcccct tgcccaggcg    540

agcagcgtga tggtgctgct gaacaagaaa acccgcaagc tgagtaagtt cacggaagag    600

atccgtgacg agatcgcccc tcacatgatg atggactgca acccgatcat caatagccgc    660

aagatgctgc ccttcgacgt gaacaccgcc gactatgcgc gcacgggcct gaccccgggt    720

tggaacgatc tcgacctgaa tcagcatgtc aatcacgtcc aatatatcaa ttggattctc    780

cagaatgtcc tgcgctcgct catccagcac cacaagctga gcgacatcac gctggagtat    840

cgtaaggagt gcgatatcaa tagcatcctc cagttcctgt cgaagatcgt gaagaacggc    900

agcaaccatt cgaccgacac caacaacctc attgagctgg accactcgct gctgctggag    960

aatggctcgg agatcgcgag ggccaacacg atctggaagc cgcgtgaggt caataacttc   1020

aagaacgccg tttacactcc ggcg                                          1044


<210> SEQ ID NO 12
<211> LENGTH: 1071
<212> TYPE: DNA
<213> ORGANISM: Artificial Sequence
<220> FEATURE:
<223> OTHER INFORMATION: Codon optimized Jatropha curcas acyl-ACP
      thioesterase sequence

<400> SEQUENCE: 12

atggcttcca ccgcgatctc gttcctctcc attcccatca agctgatcaa agaagaaatg     60

cgcatggcct cggcgggtcg tcggaagaat acgatcgcgg cggagttcgg ccatttcacc    120

ttcggctccg ccaccgtgga gaagaaggtc cagaagtcga acaacttcct catcgacggc    180
```

-continued ggcttcggca gcctggagca gaacggactg atctaccgcc agaatatctt cgtccgctcg 240
ttcgagatcg gcttcgaccg caagctctcg ctggccgctc tgacgaattt cctgcaggac 300
accgcgctca accactgccg catgatcggc ctgctggccg agggcttcgg ctcgacgccg 360
gagatgatca agaaagacct gatttgggtg ctctgcaccc tccagatcct ggtcgacggc 420
taccccagct ggctcgacgt tgtcgaggtc gacacctgga tgtatccgag cggccagaac 480
ggcctcggcc gcggctggct ggtgcgtgat ggcaagaccg gtcgctcgtt ggcgcagagt 540
tcgtctgtca tggtgagctt caataagaaa actcgcaagc tgagcaagct cgccaaggaa 600
atccgcgacg agatcgcccc gcacatgatg gactgcgatc cgatcatgaa caagaactcg 660
cggaagatcc tcccgttcga tgtgaacacc gccgactatg cccgcaccgg cctgaccccc 720
ggatggaacg aactggatct caatcagcat gtcaaccacg tccagtatat caactggatc 780
ctccagaatg tccgtccgag cctggtccaa catcacaagc tctcggcgat cacgctggag 840
tatcgcaaag agtgcgatat gaactcgatc ctccagtccc tctcgcgcat tgtcaagaat 900
ggcgggaacg acagcacgga caagaataac gtgatcgagc tcgaccattt cctgctcctg 960
gagaatggct cggagatcgc gcgcgccaac acgatctgga agccccgcga ggtgaataac 1020
ttcaagaatg tcgtccattc ccctgcggaa gagaatatct cgtcgatgaa c 1071

<210> SEQ ID NO 13
<211> LENGTH: 396
<212> TYPE: DNA
<213> ORGANISM: Artificial Sequence
<220> FEATURE:
<223> OTHER INFORMATION: Codon optimized E. Coli FadM sequence

<400> SEQUENCE: 13
atgcaaaccc agattaaggt ccgcggctac catctcgacg tctaccagca tgtgaataac 60
gcccgttatc tcgaattcct cgaagaagcg cgctgggacg gcctggagaa ctcggatagc 120
ttccagtgga tgaccgccca caatatcgcg ttcgtcgtgg tcaatatcaa catcaactat 180
cgccggccgg ctgtgctctc ggacctcctg accatcacct cgcagctcca gcagctgaac 240
ggcaagtcgg gaatcctgtc ccaggtgatc acgctggagc ccgagggcca ggtcgtcgcg 300
gatgccctga tcacgttcgt ttgcatcgac ctcaagacgc agaaagccct cgcgcttgag 360
ggcgagctgc gcgagaagct ggagcagatg gtcaag 396

<210> SEQ ID NO 14
<211> LENGTH: 957
<212> TYPE: DNA
<213> ORGANISM: Artificial Sequence
<220> FEATURE:
<223> OTHER INFORMATION: Codon optimized E. Coli AccA sequence

<400> SEQUENCE: 14
atgtccctga acttcttgga tttcgaacag cccatcgccg aactggaagc gaagatcgac 60
tctctgaccg ccgtgagccg ccaagatgag aagctcgaca tcaacatcga cgaagaagtc 120
caccgcctcc gcgagaaatc ggtcgagctt acccgcaaga ttttcgcgga tctgggcgcg 180
tggcagatcg cccagctcgc gcgtcatccg cagcgcccgt acacgctcga ctatgttcgt 240
ctggccttcg acgagttcga cgagctcgcc ggtgatcgcg cgtatgccga cgataaggcc 300
atcgtcggcg gcatcgccag gctggatgga cgcccggtga tgatcatcgg ccatcagaaa 360
ggccgcgaga ctaaggagaa gatccgtcgc aacttcggca tgcctgcgcc cgaggggtat 420

-continued

```
cgcaaggccc tgcgcctcat gcagatggct gagcgcttca agatgcccat catcacgttc    480

atcgacaccc cgggcgcgta tccgggcgtg ggcgccgagg aacgcggcca gagcgaggcc    540

atcgcgcgga atctccggga gatgtcgcgc ctcggagtcc cggtcgtgtg caccgtgatc    600

ggcgagggcg gctccggcgg cgcgctcgcg atcggcgtcg gcgacaaggt caacatgctg    660

cagtattcga cgtactccgt catcagcccc gagggctgcg cgtcgatcct ctggaagtcg    720

gccgacaagg cgcccctcgc cgctgaggcc atgggcatca ttgccccgcg cctgaaagag    780

ctcaagctga tcgactcgat cattccggag ccgctgggtg gcgcgcaccg caatcccgag    840

gcgatggcgg cgtcgctgaa ggcgcagctg ctcgccgatc tcgccgacct ggacgtcctc    900

tcgaccgagg acctcaagaa tcgccgctac cagcgtctga tgtcctacgg ctatgct       957
```

<210> SEQ ID NO 15
<211> LENGTH: 468
<212> TYPE: DNA
<213> ORGANISM: Artificial Sequence
<220> FEATURE:
<223> OTHER INFORMATION: Codon optimized E. Coli AccB sequence

<400> SEQUENCE: 15

```
atggacattc gtaagatcaa aaagctcatc gaactcgtcg aggaaagcgg catctccgaa     60

ctggaaatct ctgagggcga agagtcggtg cgcatcagcc gcgcggcgcc tgccgcctcg    120

ttccccgtca tgcagcaggc ctacgcggcg cccatgatgc agcagccggc tcagtcgaac    180

gccgccgcgc cggccaccgt gccctcgatg gaagcgccgg ctgcggcgga gatcagcggc    240

catatcgtgc gctcgccgat ggtcggcacc ttctatcgca cgccctcccc ggatgccaag    300

gccttcatcg aggtcggcca aaaggtcaac gttggagaca ccctgtgcat cgtcgaggcg    360

atgaagatga tgaatcagat cgaggccgac aagtcgggta cggtcaaggc catcctcgtg    420

gagtcgggcc agccggtcga gttcgacgag ccgctggtcg tgatcgag                 468
```

<210> SEQ ID NO 16
<211> LENGTH: 1347
<212> TYPE: DNA
<213> ORGANISM: Artificial Sequence
<220> FEATURE:
<223> OTHER INFORMATION: Codon optimized E. Coli AccC sequence

<400> SEQUENCE: 16

```
atgctggata agatcgttat agccaaccgt ggagaaatcg ccctgcgtat cctcagagcc     60

tgcaaagaac tcggtatcaa gaccgtcgcg gtgcatagct cggccgaccg cgacctcaag    120

cacgtgctgc tggccgacga aacggtctgc attggccccg cccccctcggt caagtcctat    180

ctcaatatcc cggcgatcat ctcggcggct gagatcaccg ggcgcggtcgc gatccacccc    240

ggctatggct tcctgtccga gaatgccaac ttcgcggagc aagtcgagcg ttcgggcttc    300

atcttcatcg gccccaaggc cgaaacgatc cgccttatgg gagacaaggt gtcggcgatc    360

gcggcgatga aaaaggctgg cgtgccgtgc gtgccgggct cggatggccc gctgggcgac    420

gacatggata agaaccgggc catcgcgaag cgtatcggct atccggtcat tatcaaggcc    480

tccggcggcg gcggcggccg cggcatgcgc gtcgtccgcg gtgacgccga gctggcgcag    540

tcgattagca tgactcgcgc cgaggcgaaa gcggcgttct cgaatgacat ggtgtatatg    600

gagaagtact tggagaaccc tcgccacgtc gagatccagg tgctcgcgga tggccagggc    660

aacgccatct atctcgcgga gcgcgattgc tcgatgcagc ggcgccacca gaaggtcgtc    720

gaggaagcgc ccgccccggg catcacgccg gagctgcgcc gctatatcgg tgagcgctgc    780
```

```
gccaaggcgt gcgtcgatat cggatatcgc ggcgccggaa ccttcgagtt cctcttcgag    840

aacggcgagt tctatttcat cgagatgaat acccgcatcc aggtcgagca tcccgttacc    900

gagatgatca ccggcgtcga tctgatcaaa gagcagctgc gcatcgccgc tggccagccg    960

ctgtcgatca agcaagaaga ggtccatgtg aggggccacg ccgtcgagtg ccgcatcaat   1020

gccgaggacc cgaacacgtt cctcccgtcc cccggcaaga ttacgcgctt ccatgcgccc   1080

ggcggcttcg gcgtccggtg ggagagccat atctacgcgg gctacaccgt gccgccgtac   1140

tacgacagca tgatcggcaa gctcatctgc tatggcgaga accgcgacgt cgcgatcgcc   1200

cgcatgaaga acgccctcca ggaactcatc atcgacggga tcaagacgaa tgtggacctc   1260

cagatccgca tcatgaacga cgagaacttc cagcatggcg gcaccaatat ccactacctg   1320

gaaaagaagc tgggcctgca ggaaaag                                       1347
```

<210> SEQ ID NO 17
<211> LENGTH: 912
<212> TYPE: DNA
<213> ORGANISM: Artificial Sequence
<220> FEATURE:
<223> OTHER INFORMATION: Codon optimized E. Coli AccD sequence

<400> SEQUENCE: 17

```
atgagctgga ttgaacgcat caagagtaat atcacccccca cccgcaaggc ctctatccct     60

gaaggcgtct ggaccaagtg cgactcgtgc ggccaggtcc tctatcgcgc cgagctggag    120

cgcaacctcg aagtctgccc caagtgcgat catcacatgc gcatgacggc gaggaatcgg    180

ctccattcgc tgctggacga gggcagcctc gtcgagctcg gctcggagct ggagccgaag    240

gacgtcctca agttccggga ttcgaagaag tacaaggacc gcctggccag cgcccagaag    300

gaaacgggcg agaaagatgc cctcgtcgtt atgaagggca ccctgtacgg catgccggtg    360

gtggccgctg cgttcgagtt cgcgttcatg ggcggcagca tgggctcggt cgtcggtgcc    420

cgcttcgtcc gtgcggtgga gcaggcgctt gaggataatt gcccgctgat ctgcttctcc    480

gcgtcgggcg gtgcgcgcat gcaagaagcg ctgatgtcgc tgatgcagat ggcgaaaacg    540

tccgccgccc tggccaagat gcaggagcgc ggactgccgt atatctcggt cctgacggac    600

ccgaccatgg ggggagtctc cgcgtccttc gcgatgctcg gcgacctgaa catcgccgag    660

ccgaaggccc tcatcggctt cgcgggcccc cgtgtcatcg agcagaccgt gcgcgagaag    720

ctcccgccgg gcttccagcg cagcgagttc ctcatcgaaa agggcgcgat cgacatgatc    780

gtgcgtcgcc cggagatgcg cctcaagctc gcgtcgatct tggccaagct catgaacctc    840

ccggcccccca accccgaggc gccccgcgag ggcgtcgtcg tgccgccggt gccggaccag    900

gagcccgagg ct                                                       912
```

<210> SEQ ID NO 18
<211> LENGTH: 2181
<212> TYPE: DNA
<213> ORGANISM: Artificial Sequence
<220> FEATURE:
<223> OTHER INFORMATION: Mutated Methylococcus capsulatus fadD sequence

<400> SEQUENCE: 18

```
gatcgtagtc gtcttcacag gtcatggctc gggtggcgga gttcatggga aggcggaggg     60

actgagtctt cgttcaaatc ggccgcactg ccggtggctg ggacgggaat gatagcgctg    120

ccatcccctc gcccgaaagg cggctagatc gtcttcttga gccggtcctc ctcccgttgg    180
```

-continued

```
ccaacggtcg ctcgagtcgc gcattcgctg ccgcctgctc cgcgtccaac gccccaggca    240
cggatcgctg acgatggcgc gcccgcccgc tgggaatcag cccggcgcca acccccgact    300
cccacgccac cgtcgccatg ggatgccacc caaagcatgc gtttgaccgg ctgttcctcg    360
aactccgccg tatatcgccg ccggctcggt ttctgtcggc cactcatcga ccaccccccc    420
caagggcttg acccgcataa atgggggct acgcaggcgt agcgagatca gcgccacgca    480
cgttcgattc cgcggacttg cagtcgatga aggccggcct gtccaccagc agcggtcgcg    540
tttccaggaa gccagccgtt tcgttcttgg tctaccccac gatgatccga ggctcggtgt    600
acctcggcat ctcctgcaga gcaatggtgg gccggacggt cagcgtagcg ggctcgtttg    660
cggccatggc cgctccaaaa gccgttgcaa gagtgtcgta tttcacgata ttcccggcgc    720
tcccaaggca gaacgaaccg gtgacgcatc accagcccgg cgctcagaga gcgtcgtaaa    780
gtttacgacc ggcccagttt gaccgcgact ggcagggttt gcggctctgg gagaaagtca    840
tcgaactgcc tcgggcgcac gcctcctcaa attccttcaa ggcagcaggc ggcgctgcaa    900
cgacgccccc gaccgcaggg acctggaccg cgacgggaat cacggaccgt tcccgcctgg    960
aaccgggggc atcggagatg cttcagagga tatcctgtca ggcatccacc ccgcgctcca   1020
cttcaccctg ccgccgcagc tgccgcttca ctattttgct tatacgtgtc gtaggtcggt   1080
ttccatccgg tataggtggc gcagcccgaa acggccacgg cggacatcag cagtatcggt   1140
acgcttttca acatggtcat gaactcctcg ctcgaaaatt ccgtccttac agcccccagc   1200
ccagatccgg ggacaggaag acgcagccac tatatcaaaa ccgggttcac gccgaacact   1260
tcgccgattc gggaatatcc ggtgcttctg ttatgatcgc atcctccgat gagcgcgatg   1320
gcccgccgcc ctcccccgaa cgaccgaatc cctgcgccga tcgacgtccc ggcacgcggt   1380
caccctcatc agacattttt cactctttga ctccccatcc tgatgcaatc gaccgaaact   1440
cccttttcct ttgccgatct ggcgatctct gcccccattc tccaggccat ccgcgaaatc   1500
ggctacgaga ctccctctcc catccaggcg gcgagcattc cccctctcct cgccggccat   1560
gatcttctgg gccaggcgca gaccggcacg ggcaaaaccg ccgctttcgc cctgccgatc   1620
ctgaacggta tcgacctcga gcgccgcgag ccgcaagcgc tggtgctggc tccgacccgc   1680
gaactcgccc tgcaagtggc cgaggccttc cagagctatg cccgccacct gcccgatttc   1740
catatcctgc cgatctatgg cggccagtcg atggatgcac agttgcgtca tctgcgccgg   1800
ggagtccacg tcatcgtcgg cacccccggc cgggtgattg accacctgcg ccgcaagagc   1860
ctcaatctgg atggcctgcg caccccttgtt ctggacgaag ccgacgagat gctgcgaatg   1920
ggcttcatcg aagacgtcga gtggatcctc gagcacactc cgcccgagcg ccagatcgca   1980
ctgttctccg ccaccatgcc ggaagcgatc cgcagggtcg ccaagcgcca cctccgccat   2040
cccaaggagg ccaagatcga ggccaagacc gccacggtcg aggcaatcac ccagcgctac   2100
tggctgggtt cgggcgcgca caaactggac gccctgaccc gcatcctcga ggtcgaggac   2160
ttcgacgcca tgatcatctt c                                            2181
```

<210> SEQ ID NO 19
<211> LENGTH: 927
<212> TYPE: DNA
<213> ORGANISM: Artificial Sequence
<220> FEATURE:
<223> OTHER INFORMATION: Codon optimized E. Coli FadD sequence

<400> SEQUENCE: 19

```
atgactcagt tcgcgttcgt ctttccaggt caaggttcac aaacagtcgg tatgctcgca     60
```

gatatggccg cctcctaccc gatcgtcgaa gaaaccttcg cggaagcctc ggcggcactg 120
ggttacgacc tgtgggccct gacgcagcaa ggcccggccg aggaactgaa caagacctgg 180
cagacgcagc ccgctctgct gaccgcctct gtggccctgt atcgcgtttg gcagcaacag 240
ggcgggaaag ctcctgcgat gatggcgggc cacagcttgg gggagtatag tgcgctggtc 300
tgtgccgggg tgatcgattt cgccgacgcg gtccggctgg tcgagatgcg cggcaagttc 360
atgcaggaag ccgtaccgga aggcaccggc gccatggccg cgataatcgg cctggacgac 420
gcctcgatcg cgaaggcgtg cgaagaagcc gccgagggcc aggttgtcag ccccgtgaac 480
ttcaactccc ccggacaggt cgtcatcgcc ggacacaaag aagccgtgga gcgggccgga 540
gcggcctgca aggctgcagg cgccaagcgc gccttgccgc tcccggtgtc ggtccccagc 600
cattgcgcgc tcatgaagcc cgctgccgat aagctggcgg tggagcttgc gaaaatcacg 660
ttcaacgccc ccaccgtgcc ggtggtaaac aacgtggacg tgaagtgcga aaccaatggc 720
gacgcgattc gggacgccct cgtgcgtcag ctgtataacc cggtgcagtg gacgaaatcg 780
gtcgagtaca tggcagccca gggcgtcgag catctctacg aagtcggccc ggggaaggtc 840
ctcaccggcc tgaccaagcg catcgtggat accctgacgg cgagcgcctt gaatgagccg 900
tccgcgatgg cagccgccct ggagctc 927

<210> SEQ ID NO 20
<211> LENGTH: 549
<212> TYPE: DNA
<213> ORGANISM: Artificial Sequence
<220> FEATURE:
<223> OTHER INFORMATION: Codon optimized E. Coli TesA sequence with periplasmic targeting sequence removed

<400> SEQUENCE: 20
atggcagata ccctccttat tcttggcgat tctctctcag ctggttaccg tatgtccgct 60
tccgccgcat ggcccgccct gctcaatgac aaatggcaaa gcaagacctc ggtcgtgaat 120
gcctcgatct cgggcgacac cagccaacag gggctggcca ggctgcctgc gttgctgaag 180
cagcatcagc cgcgctgggt gctcgtggag ctgggcggca acgatggact gcgcggcttc 240
cagccccagc agaccgagca gacgctgcgg cagatcctgc aagacgtgaa agcggccaat 300
gcggagccgc tgctcatgca gatccgcctc ccggccaact acggccggcg gtacaacgaa 360
gccttcagcg ccatctaccc aaagctggcg aaagaattcg acgttccgct gttgcccttc 420
ttcatggaag aagtctatct gaagccgcag tggatgcagg acgatggcat ccatcccaac 480
cgcgacgcgc agccgtttat cgccgactgg atggccaaac agctgcagcc gctggtcaac 540
cacgacagc 549

<210> SEQ ID NO 21
<211> LENGTH: 1146
<212> TYPE: DNA
<213> ORGANISM: Artificial Sequence
<220> FEATURE:
<223> OTHER INFORMATION: Codon optimized Cinnamomum camphorum thioesterase sequence

<400> SEQUENCE: 21
atggccacca ctagtcttgc ttcagccttt tgttctatga aagccgtaat gttagcccgc 60
gatggtagag gaatgaagcc gaggtcgtcg gacttgcagc tgcgagcggg caacgcccag 120
acctccctga agatgatcaa cggcaccaag ttcagctaca ccgagtcgtt gaaaaagctg 180

```
ccggactggt ccatgctgtt cgcggtcatc accaccatct tcagtgccgc ggagaagcag    240

tggaccaacc tggagtggaa gcccaagccg aatccgcctc agctgctgga cgaccacttc    300

ggcccacatg gcctcgtctt tcgccgcacg ttcgccatcc gcagctacga agtcggcccg    360

gatcggtcga cctccatcgt ggccgtgatg aaccatctgc aagaagcggc gctgaatcac    420

gccaagtccg tgggaatcct gggtgacggt ttcgggacga ccctggaaat gagcaagcgg    480

gatctcatct gggtggtgaa gcgcacccat gttgcggtcg aacggtaccc cgcgtggggg    540

gacaccgtcg aggtcgaatg ctgggtgggc gcctccggca ataacggacg ccgccacgat    600

ttcttggtgc gcgattgcaa aaccggcgaa attctgaccc ggtgcaccag cctgtcagtc    660

atgatgaaca cgcggacgcg ccgtctgagc aagatcccgg aagaagtcag ggcgagatc     720

ggtccggcat ttatcgataa tgtcgctgtt aaagatgaag agatcaagaa gccccagaag    780

ctcaacgact ccaccgccga ctacatccag ggcgggctga cgccccgttg gaacgaccta    840

gacatcaacc agcatgtgaa caacattaaa tatgtcgact ggatcctgga gactgtgccg    900

gatagcatat tcgaaagcca tcacatctcg tcgttcacga tcgaatatcg tcgggagtgc    960

acgatggaca gcgtcctgca gtcgttgacg accgtgagcg gcggttcctc cgaagcgggc   1020

ctcgtgtgcg aacacctcct ccagcttgag ggcgggtccg aggtcctgcg cgccaagacc   1080

gagtggcggc cgaaactgac agactcgttc cggggcatct ccgtgatccc cgcagagagc   1140

agcgtc                                                              1146
```

<210> SEQ ID NO 22
<211> LENGTH: 1146
<212> TYPE: DNA
<213> ORGANISM: Artificial Sequence
<220> FEATURE:
<223> OTHER INFORMATION: Codon optimized Umbellularia californica thioesterase sequence

<400> SEQUENCE: 22

```
atggccacca cctctctagc ttcagccttt tgttcaatga aagccgttat gctcgcacgc     60

gatggacgcg gaatgaagcc ccgcagcagc gacttgcagc tccgcgccgg caatgcaccg    120

accagcttga aaatgatcaa cggaactaag ttctcgtaca cagagtccct gaagagactg    180

ccggactggt ccatgctgtt cgcggtcatc accaccatct tctcggccgc ggaaaagcag    240

tggacgaacc tcgaatggaa gccgaagccg aaactgcccc agctgctcga cgaccacttc    300

gggctgcacg gcctcgtgtt ccggcgaacc ttcgccattc ggtcgtacga agttggcccg    360

gatcggagta cctcgattct ggccgtcatg aaccacatgc aagaagccac cctgaaccac    420

gccaaaagtg tgggtatcct cggtgacggc ttcggcacga ccctggaaat gagcaagcgg    480

gacttgatgt gggtcgtgcg taggacccat gtcgcggtcg aacgttatcc tacctggggg    540

gatacggtcg aggtcgagtg ttggataggc gcgtccggca ataacggcat gcgccgcgac    600

ttcctggtgc gcgactgcaa gacgggcgag atcttgaccc gctgcacctc gctgtcggtg    660

ctgatgaaca cccggacgcg gcgcctgagc accatccctg acgaagtccg aggcgagatc    720

ggccccgcct tcatcgacaa cgtggccgta aaagacgacg agataaagaa gctgcagaag    780

ctcaacgact ccaccgccga ctacatccag ggcggcctga ccccccggtg gaacgacctg    840

gatgtgaacc agcacgtcaa taatctgaag tacgttgcgt gggtgtttga aacggtgccc    900

gatagcatct tcgagtccca tcacatcagc tcgttcaccc tggagtatcg ccgggaatgc    960

acacgcgata gcgtgttgcg gtcgcttacc actgtcagcg gggttcgtc cgaggccgga    1020
```

-continued

```
ctggtctgcg accatctcct ccagcttgag ggcgggtcgg aagtcctgcg cgcccggacg   1080

gaatggcgtc cgaagttgac ggactccttc cgtgggatct ccgtgatccc agccgaaccg   1140

cgcgtg                                                              1146


<210> SEQ ID NO 23
<211> LENGTH: 750
<212> TYPE: DNA
<213> ORGANISM: Artificial Sequence
<220> FEATURE:
<223> OTHER INFORMATION: Codon optimized Streptococcus pyogenes acyl-ACP
      thioesterase sequence

<400> SEQUENCE: 23

atgggcctgt cctaccaaga agaactgacc ctgccattcg aactctgcga cgtgaaatcc     60

gacatcaagc tgccgcttct tctggattat tgcctcatgg tgtctggccg gcagtccgtc    120

cagctgggcc gcagcaacaa caatctgctg gtcgactaca agctcgtctg gatagtcacg    180

gactacgaga tcactatcca taggttgccg cacttccagg aaacgatcac gatcgaaacc    240

aaggccctgt cgtataacaa attcttttgt taccgccagt tctacatcta cgaccaggaa    300

ggctgcctgc tcgtcgacat cctgtcgtac ttcgcgctgc tgaaccccga tacgcgcaag    360

gtcgcgacca tccctgagga tctggtggcc cccttcgaaa ccgacttcgt gaagaaactc    420

catcgggtgc cgaagatgcc gttgctggag cagagtatcg accgtgacta ctacgttcgc    480

tacttcgaca tcgacatgaa tggacacgta aacaactcaa agtatctgga ttggatgtat    540

gatgtgctgg gctgccaatt cctcaagacc catcagccct tgaagatgac cctgaaatat    600

gtgaaagaag tcagcccggg tggtcagatt accagctcgt atcacctcga ccaattgacc    660

agctaccacc agatcatctc ggacgggcag ctcaacgccc aggccatgat tgagtggcgg    720

gcaatcaagc agaccgagtc cgagacagat                                     750


<210> SEQ ID NO 24
<211> LENGTH: 1191
<212> TYPE: DNA
<213> ORGANISM: Artificial Sequence
<220> FEATURE:
<223> OTHER INFORMATION: Codon optimized Ricinus communis palmitoyl-acyl
      carrier protein thioesterase sequence

<400> SEQUENCE: 24

atgggcacat gttcttacac catcaccctc cccatccgct gcctcagtaa ctcgaacggc     60

caccatgatc cgcacaagca gaatctgaac aagatcaaga tcaatggcgc ctcgacctcc    120

acccggcctc tgaagcttga cgccccctcc cagacggtcg gcgtcgccac catatacttg    180

gcgagcgtgt ccgagaacct caccctgacc aaagaagtca tgcgccagaa catcccgacc    240

aagaaacagt acatcgatcc ccaccgccag ggcctgatga tcgagggtgg cgtgggctat    300

aggcagacta ttgtcatccg cagctacgaa gtgggacccg acaaaaacggc cactctggag   360

agcatcctgt atctgctcca ggaaaccgcc ctcaaccatg tgtggctgtc cggtctgctg    420

tccaatgggt tcggcgcgac gcacggcatg gtcaaaaaca acctgatttg ggtggtgagc    480

aagctgcaag tccaggtcga tcattatccg atctgggggg aagtggtgga gatcgacacc    540

tgggtccgcg cctccggcaa gaatggaatg aagcgggact ggctcattcg tagccaggca    600

acggggcacg ttttcgtgcg cgcgacgtcg acctgggtga tgatgaacga aaagaccaga    660

cggctctcca aaatgccgga agaagtccga gcggagataa gcccatggtt catcgagaag    720

caagcgatca aagaagaagt acccgacaag atcgctaagt tggacgacaa ggcccggtac    780
```

-continued gtaatctcaa acctgaaacc gaagcgctcc gacctcgata tgaaccacca tgttaacaat 840
gtcaaatacg tccggtggat gctggagatc ctgcccgacc actttctgga aagccatcag 900
ctatcgggga tcaccatgga gtatcggcgt gagtgcggct cggccgatat cgtgcagagc 960
ctgtgcgaac cggacgggga cgagatcctg tcgaatgaca tcccggtgct taacggcttc 1020
agtctggcca gcgagcctct gatggaaggt aatggattct tggtcccccct ggataaggtc 1080 ccgctgaagt acacccactt gctgttgacg aagggcgagt cccagaacga agagatcgtg 1140
cgcggcaaga cgatctggaa gaaaaagctc tgcaccatgc cgttctcgac g 1191

<210> SEQ ID NO 25
<211> LENGTH: 1176
<212> TYPE: DNA
<213> ORGANISM: Artificial Sequence
<220> FEATURE:
<223> OTHER INFORMATION: Codon optimized Ricinus communis palmitoyl-acyl carrier protein thioesterase sequence

<400> SEQUENCE: 25
atggcatcta aaggctcgat caggttgtat ttcccctgtg actttcgtaa caccctgcag 60
aagaagaaca tgaagatgga tatggtcatg gcccgcagcg gattcagcta ttcgctcaac 120
ccgatcgcac caaaaatccc ccgcttctat gtcgtggcga acgccagcaa cccgcagcgg 180
gtggacacca tcaatggcaa aaaagtgaac ggtatccacg tggccgaatc ctccaactcg 240
tatgcggacc agaacaagat gaatgcgaca gccggcctcg tgctggacgg gaacgtcgac 300
catcagccgc tccacaagtg gctgctgggg cggttcgtcg atgaacgcct ggtctactcg 360
cagaccttca tcatccgctc ctatgagata ggccccgaca agaccgccac catggaaacc 420
ctgatgaatc tgctgcagga aaccgcgttg aaccacgtaa ccagtagcgg cctcgctggc 480
gacggattcg gtgcgacgcg tgagatgtcc ctgcggaaac tgatctgggt ggtgacgcgc 540
attcatatcc aagtacagcg ctacagctgc tggggggacg ttgtcgagat cgacacctgg 600
gtggatggtg ccggcaagaa tggcatgcgt cgggattgga tcatccgcga ttacaatacg 660
aaagaaatca tcactcgcgc gacctcaacc tgggtgatta tgaaccgcga aacccggaaa 720
ctgtccaaga tgccggaaca ggttcgacag gaactcgtgc ccttctacac caacaggatc 780
gcgattgcca aggaaaacaa cgacgtcgag aagatcgaca agctcacgga cgagactgcc 840
gagcgcatca gaagcggctt ggcccctcgg tggtcggata tggatgccaa tcaacacgtc 900
aacaacgtga agtacatcgg ctggatcctg gagtcggtcc cgatcaatgt ccttgaggac 960
tacaacctga cctcgatgac gctggagtac cgccgtgagt gccggcagtc caatctgttg 1020
gaatcgctga cgagcaccac cgaacattcc aacaacaata gctgcaaccg caaggcgcac 1080
ctggagtaca cgcatctcct gcggatgcag gctgacaagg ccgagatcgt ccgagcccgg 1140
accgaatggc agagtaagtc gaaccgcaag acgatc 1176

<210> SEQ ID NO 26
<211> LENGTH: 1257
<212> TYPE: DNA
<213> ORGANISM: Artificial Sequence
<220> FEATURE:
<223> OTHER INFORMATION: Codon optimized Ricinus communis palmitoyl-acyl carrier protein thioesterase sequence

<400> SEQUENCE: 26
atggtcgcca cagccgccgc cgccacctcc tcattcttcc ccgttcctag ccaatccgca 60

```
gacgccaact tcgacaaagc gccagccagc ctggggggca tcaaactgaa atccacgtcc    120

tgcagtcgcg gcctccaggt caaggccaac gcccaggcac cgcccaagat caatggtagc    180

agcgtgggct tcaccacgag cgtggaaacc gtgaagaacg acggcgacat gccccctgcca   240

ccgcctccgc ggaccttcat caatcagttg cccgattggt ccatgctgct cgctgcgatt    300

acgacgatct tcctggcggc tgagaagcag tggatgatgc tggactggaa gccgcggcgc    360

cccgacatgc tcatcgaccc cttcggcatc ggccggatcg tccaggacgg gctcatcttc    420

cggcaaaact ttagcatccg gtcgtacgag atcggggcgg atcggaccgc gtcgatcgag    480

actctgatga accatttgca ggaaactgcc ctcaaccacg tgaaaaccgc cggtctgctg    540

ggggacggct tcggcagcac cccggaaatg agcaaaagga atctgatctg ggtcgtaacc    600

cggatgcaag ttctggtgga tcgctacccg acgtggggtg acgtcgtaca ggtcgatacg    660

tgggtgtcga agtcgggtaa gaacggcatg cgccgtgatt ggtgcgtgcg cgacagtcgc    720

acgggcgaaa ccttgacccg agccagctct gtctgggtca tgatgaacaa gctgacccgt    780

agactatcga agatccccga agaagtccga ggggaaatcg agccgtattt cctgaactcc    840

gaccccatag tggacgaaga ttcccgcaag ctcccgaagc tggacgacag caatgcggac    900

tacgtccgca agggactgac gccgcgttgg tcagatcttg acatcaacca gcacgtgaat    960

aacgtcaagt acatcggctg gattctggag agcgcgccgc tcccgatcct cgaatcccac   1020

gagctttcgg ccatcaccct cgaatatcgc cgggaatgtg gccgggattc cgtcttgcag   1080

tcgttgaccg cggtgtccgg caacgggatt ggcaacctgg gcaacgccgg cgacatcgag   1140

tgccagcatc tgctgcgcct ggaagatggc gccgagatcg tgaggggacg caccgagtgg   1200

cgcccgaaat acagctcgaa tttcggaatc atgggccaga tccccgtgga gtcggcg      1257
```

```
<210> SEQ ID NO 27
<211> LENGTH: 1071
<212> TYPE: DNA
<213> ORGANISM: Artificial Sequence
<220> FEATURE:
<223> OTHER INFORMATION: Codon optimized Jatropha curcas acyl-ACP
      thioesterase sequence

<400> SEQUENCE: 27

atggctagca cggctatctc cttcctctct atcccgatca aactcatcaa agaagaaatg     60

cgcatggcgt ccgccggacg gcggaagaac accatcgcag cggagttcgg ccacttcaca    120

ttcggctcgg cgaccgttga gaagaaggtg cagaaaagca acaacttcct gatcgacggc    180

ggctttgggt cgctggagca gaacggtctt atctaccgtc aaaacatctt cgtccgcagc    240

ttcgaaatcg gtttcgatcg caagttgagc ctggcagccc tgaccaattt cttgcaggat    300

acggccctca accattgccg gatgattggc ctgttggccg aggggtttgg gtccaccccc    360

gaaatgatca agaaagacct gatctgggtc ctgtgtaccc tgcagattct cgtggacggc    420

tatccctcct ggctcgatgt ggtcgaagtc gatacgtgga tgtacccgtc gggacaaaac    480

ggcctggggc gcggctggct cgttcgcgac ggaaagactg gccggagcct ggcccagtcg    540

tccagcgtaa tggtgtcctt caacaaaaag acccgcaagc tgagtaagtt ggccaaagaa    600

attcgggacg agatagcgcc tcacatgatg gactgcgacc cgatcatgaa caagaactcc    660

cgtaagatcc tgccgttcga cgtcaatacg gcggactatg ccaggaccgg ccttaccccc    720

ggttggaatg aactggatct gaatcagcac gtcaaccatg tgcagtacat caactggatc    780

ctgcagaacg tgcgcccctc cctggtgcag caccataagc tctcagcgat caccctggag    840
```

taccgaaaag aatgcgacat gaacagcatc ctgcagtcgc tctcgcggat cgtgaagaat 900
ggcggcaacg actcgaccga caagaacaac gtgatcgaac tcgatcattt cctgctgctg 960
gagaacggca gtgagatcgc cagagccaat acgatctgga agccgcgcga ggtcaataac 1020
ttcaaaaatg tcgtccactc gccagccgaa gagaacatca gcagcatgaa c 1071

<210> SEQ ID NO 28
<211> LENGTH: 1215
<212> TYPE: DNA
<213> ORGANISM: Artificial Sequence
<220> FEATURE:
<223> OTHER INFORMATION: Codon optimized Jatropha curcas acyl-ACP thioesterase sequence

<400> SEQUENCE: 28
atggccgtgt tcacctaccg tatcgcaatg ctcccaatcc ggtgttcctc ttccaattcg 60
accaactccc atagccacga tccgaatcag cagaacttgc acaaaatcaa gatcaacggc 120
tccgcctcgg cgatgatgcc gctgaaggtt gacctcccca gcagcctgac gatcaccagc 180
gtggcccctg tggtggagaa cctgtccctg accaaagagc agacgcggca gaacattccc 240
accaagaagc agtacattga cccgcatcgt caggggctga tcgtagaaga gggcgtgggt 300
taccggcaga cagttgtcat ccgctcctac gaggtcggtc cggataagac ggccaccttg 360
gagatcattc tctgcctgtt gcaagaaacc gccctgaacc acgtctggct gagcggcctg 420
ctgagcaatg gcttcggagc cactcatggc atggtgcgca acaacttgat ctgggtcgtc 480
agcaagctcc aggtccaagt cgatcagtat cccatctggg gcgaagtagt ggagatcgat 540
acgtgggtgg gagcgagtgg caagaatggg atgcgcagag actggctggt ccggtcgcag 600
gcgaccggtc aggtctttgc acgcgcgacc tcgacgtggg tgatgatgaa cgaaaagacg 660
cgacgcctgt cgaaaatgcc ggaagaagtg agggccgaaa tcgcgccgtg gttcatcgag 720
aaacaggcca tcaaagaaga ggtcccggag aaaatcgcga agcttgacga caaggcccgc 780
tatgtggtga ccaacctgaa gccgaagcgg tccgacctcg acatgaacca acatgtcaac 840
aatgtgaaat atgtccgctg gatgctagaa accctgcccg accagttttt cgaaaatcac 900
cagctcagcg gaatcaccct ggaatacaag cgcgagtgcg gctcctcgga catcgtcgag 960
tcgctgtgcg agccggacga agaagagggc atcatcaaca ccggcctcaa gcagaacaac 1020
gataagagtc tgttcaatgg gttcagcctc ccttcggaga tcatggaagg gaacggcttc 1080
ctgtccagcc tggaaaagac cccgctgaag tacacccacc tccttgtggc taaaggcaag 1140
acccagtcag aggaaatcgt ccggggcaag actatatgga agaaaaagct gctgacaacg 1200
atgcccttct cgccg 1215

<210> SEQ ID NO 29
<211> LENGTH: 1044
<212> TYPE: DNA
<213> ORGANISM: Artificial Sequence
<220> FEATURE:
<223> OTHER INFORMATION: Codon optimized Jatropha curcas acyl-ACP thioesterase sequence

<400> SEQUENCE: 29
atggtgtcaa ccgcgatctc ctttagcctc ctgcccatca aacttatcaa agaagaaacc 60
cgcatggcct ccgccgaccg gcgcaagaac agtatcgtca aagaattcgg ccatttcacc 120
tgtcgctgcg cagccatcga aaagcgaatc cagaagctga ataacttcct gatcgacggg 180
ggcttcggat ccctggagca aaatggcctg atctataggc aaaacatctt cattcggagc 240

```
tttgagatcg gtttcgaccg caagttgtcg ctggccgcgt tgaccaactt cctgcaggat    300

acagcgctca accatgtccg tatgataggc ctgctcgctg ccggcttcgg cagcaccccg    360

gagatgtcca agaaagacct gatctgggtg ctgtgcaccc tgcagatcct tgttgatcgg    420

cacccctctt ggctggatgc ggtcgaagtg gacacgtgga tgtaccctag cggccagaac    480

gggcagggca gagattggct cgtccgcgac gccaagacgg gcaagcccct cgcccaggcg    540

tcgagcgtga tggtcctgct caacaagaaa acccgcaagc tgagcaagtt caccgaagag    600

attcgcgacg agatcgcccc acacatgatg atggactgca atccgatcat caactcgcgg    660

aagatgctcc cgttcgacgt aaataccgcc gactacgccc gcaccgggct aacgccgggt    720

tggaacgatt tggatctcaa tcagcatgtg aatcacgtgc agtacatcaa ctggatcctg    780

cagaacgtgc tccggtccct gatccagcat cacaagctgt ccgacatcac tctggagtat    840

cgtaaggaat gcgacatcaa ctccatcttg cagttcctgt cgaagatcgt caagaacggc    900

agtaaccact cgaccgatac gaacaatttg attgagctcg accactcgct gctgctggag    960

aacggaagcg agatcgcgcg ggcgaacacg atctggaaac cccgggaagt caacaacttc   1020

aaaaacgccg tctacacccc ggca                                          1044
```

<210> SEQ ID NO 30
<211> LENGTH: 396
<212> TYPE: DNA
<213> ORGANISM: Artificial Sequence
<220> FEATURE:
<223> OTHER INFORMATION: Codon optimized E. Coli FadM sequence

<400> SEQUENCE: 30

```
atgcagaccc agatcaaagt gcgcggctac cacctcgacg tctatcagca cgttaacaac     60

gctcgttacc tcgaatttct ggaagaagcc cggtgggacg gcctggagaa cagcgactcg    120

ttccagtgga tgaccgcgca taacatcgcg ttcgtggtcg tcaacatcaa tatcaactac    180

cggcgcccgg ccgtactgtc ggaccttctc accattacga gccagctgca gcagctgaat    240

ggaaagtccg ggatcctgtc ccaagtgatc accctggaac ccgagggtca agtggtggca    300

gatgcgctga tcacgttcgt ctgcatcgat ctcaagaccc agaaagccct ggccttggaa    360

ggcgagttgc gcgagaagct ggagcagatg gtcaag                              396
```

<210> SEQ ID NO 31
<211> LENGTH: 957
<212> TYPE: DNA
<213> ORGANISM: Artificial Sequence
<220> FEATURE:
<223> OTHER INFORMATION: Codon optimized E. Coli AccA sequence

<400> SEQUENCE: 31

```
atgtccctga atttcctcga cttcgaacag cccatcgccg agcttgaagc caaaatcgac     60

agcctcaccg ccgtcagccg tcaagacgag aagctggaca ttaacatcga cgaagaggtt    120

catcggctcc gggagaagtc cgtcgaactg acccgcaaga tcttcgccga tctgggggcc    180

tggcagatcg cccagctagc tcggcacccg cagcgcccct acacgctgga ctatgtacgg    240

ctcgcattcg acgagtttga tgagctcgct ggcgaccgcg cctacgcgga cgataaggcc    300

atcgtcggcg gcatcgctcg gctggacggt cgtccggtca tgatcatcgg ccaccaaaag    360

ggcagagaaa ccaaagaaaa gatccgccgt aacttcggca tgccagcgcc cgagggatac    420

cggaaggccc tgcggttgat gcagatggcc gaacgcttca agatgcccat catcacgttc    480
```

-continued

```
atcgataccc cgggagccta tccgggcgtg ggtgccgagg aaaggggcca gtccgaagcg    540

attgcccgca acttgcgaga gatgtcgcgc ctgggcgtgc cggtcgtgtg caccgtgatc    600

ggcgagggtg gcagcggcgg agcgctcgcc atcggcgtcg gggataaagt caacatgctg    660

cagtattcca cttactcggt gatcagtccc gaaggctgcg cctctatcct gtggaaaagc    720

gccgacaagg caccgctggc ggcagaggcc atggggatca ttgcgcctcg cctgaaagaa    780

ctgaagctca tagactcgat catcccggag cccttgggcg gtgcgcatcg caacccggaa    840

gcgatggcgg cgagcctcaa ggcccagctg ttggcggacc tggccgacct tgatgtgctg    900

tcaaccgagg atctgaagaa tcggcgctac cagaggctga tgtcgtacgg gtacgcg       957
```

<210> SEQ ID NO 32
<211> LENGTH: 468
<212> TYPE: DNA
<213> ORGANISM: Artificial Sequence
<220> FEATURE:
<223> OTHER INFORMATION: Codon optimized E. Coli AccB sequence

<400> SEQUENCE: 32

```
atggacatca ggaaaatcaa gaaactcatt gaattggtcg aggaaagtgg cattagcgaa     60

ctggaaatca gcgagggtga ggaatccgtt cgcatcagcc gtgcggcgcc cgccgcgtcc    120

ttcccggtca tgcaacaggc ctatgcagcc cccatgatgc agcagccagc ccagtcgaat    180

gccgcggccc ccgcgaccgt gccgagcatg gaagcaccgg ctgccgccga gatctccgga    240

cacatcgtgc ggtcccctat ggtgggcacc ttttaccgca cgccgtcgcc ggatgcgaag    300

gccttcatcg aagtcgggca gaaagtgaac gtcggcgata cgctgtgcat agtcgaggcg    360

atgaagatga tgaaccagat cgaggccgac aagtcgggca ccgtcaaggc catcctggta    420

gagtcgggcc agcccgtgga gttcgacgaa ccgctggtcg tgatcgag                 468
```

<210> SEQ ID NO 33
<211> LENGTH: 1347
<212> TYPE: DNA
<213> ORGANISM: Artificial Sequence
<220> FEATURE:
<223> OTHER INFORMATION: Codon optimized E. Coli AccC sequence

<400> SEQUENCE: 33

```
atgcttgaca aaatagtaat tgcgaataga ggggaaatag cgttgaggat cttgagggcc     60

tgcaaagaat tgggcatcaa gaccgttgcc gtccatagca gcgccgatcg ggacctcaaa    120

cacgtgttgc tggccgacga aaccgtgtgc atcgggcctg caccttccgt caagtcgtat    180

ctcaacatcc cggccattat ctccgctgcg gaaatcaccg gagccgtggc gatccacccg    240

ggctacggct tcctgagcga gaatgccaac ttcgccgaac aggtcgagcg gtcggggttt    300

atctttattg gcccaaaggc cgaaaccatc cggctgatgg gcgacaaagt gtctgcgatc    360

gccgccatga agaaagcggg agtgccctgc gtcccgggca gtgacggccc tctgggcgac    420

gacatggaca agaaccgcgc gatcgcgaag cgcatcggct acccggtaat catcaaagcg    480

agcggtgggg gtggtggacg tggtatgcgt gtggtcaggg gcgatgcgga gctcgcccag    540

agcatctcca tgacccgcgc tgaggccaag gccgccttct ccaacgatat ggtgtacatg    600

gagaagtacc tggaaaatcc ccggcacgtg gaaatccagg tcctggcaga cgggcaaggc    660

aacgcgatct acctggccga gcgggattgc tcgatgcaac gccggcatca gaaagtcgtt    720

gaagaagcgc cggcacccgg catcaccccc gagctgcgcc gctacatcgg cgagcggtgt    780

gccaaggcct gcgtcgacat cggctatcgg ggagcgggca ccttcgagtt cctgttcgag    840
```

aatggcgaat tctatttcat cgagatgaac acacgcatcc aggtcgagca tccggtgacc 900
gaaatgatca ccggggtgga cctgattaag gaacagctgc gaatcgcagc cggccagccg 960
ctctcgatca agcaagaaga agtccacgtc cggggacacg ccgtggagtg ccgtatcaac 1020
gccgaggatc cgaacacgtt cctgccctcg cccggtaaga tcacgcgctt ccatgctccg 1080
ggtggattcg gcgtccgctg ggagtcacac atctatgccg gctacacggt cccgccctac 1140
tacgactcca tgatcggcaa gctgatctgt tatggcgaga accgcgatgt ggcgatcgcc 1200
cgcatgaaga acgcgctcca ggaactgatt atcgacggca tcaagactaa cgtggacctc 1260
cagatccgga tcatgaacga cgaaaacttc cagcacggcg gcacgaatat ccattacctg 1320
gagaagaaac tgggcctcca ggaaaag 1347

<210> SEQ ID NO 34
<211> LENGTH: 912
<212> TYPE: DNA
<213> ORGANISM: Artificial Sequence
<220> FEATURE:
<223> OTHER INFORMATION: Codon optimized E. Coli AccD sequence

<400> SEQUENCE: 34
atgagctgga tcgaacgcat taagtcaaac ataaccccca ccagaaaggc gagcattccc 60
gagggcgtat ggaccaagtg cgacagctgc ggtcaagtcc tgtatcgggc tgagttggag 120
cgaaatctgg aagtgtgtcc gaagtgcgac catcacatgc ggatgactgc caggaaccgt 180
ctgcacagtc tcctggacga agggtcgctc gtcgaactgg gctccgagct ggagccgaaa 240
gacgtgctga agttccggga ctcgaagaag tataaagatc ggctggcgtc cgcccagaaa 300
gaaaccggcg agaaagatgc gttggtcgtg atgaagggga cgctgtacgg catgccggtc 360
gtggcggcag ccttcgagtt tgccttcatg ggcggctcta tgggcagcgt ggtgggagcg 420
cggttcgtcc gcgctgtgga acaggcgctc gaagataact gcccgctgat ctgcttctcg 480
gcgtcggggg gtgcgcgcat gcaagaagcc ctgatgtccc tgatgcagat ggcgaaaacg 540
tccgccgcac tcgccaagat gcaggaacgc ggcctcccct acatctcggt gctgaccgat 600
ccgacgatgg gcggtgttag cgcctccttc gccatgctcg gcgacctgaa catcgccgag 660
cccaaagccc tgatcggctt cgccggaccg cgggtcatcg aacagaccgt tcgcgagaag 720
ctccctccgg ggttccagcg ctcggagttc cttatcgaaa agggcgccat cgacatgatc 780
gtccgtcgcc ccgagatgcg gctgaagttg gccagcatcc tggccaagct gatgaatctt 840
cctgccccca accccgaggc accgcgcgag ggcgtcgtcg tgccgccagt gccggaccag 900
gaaccggaag cg 912

<210> SEQ ID NO 35
<211> LENGTH: 1668
<212> TYPE: DNA
<213> ORGANISM: Artificial Sequence
<220> FEATURE:
<223> OTHER INFORMATION: Mutated Methylomonas methanica FadD sequence

<400> SEQUENCE: 35
atgatgggat tgggtaatgt cgacatattc tgctacgata gtttgcattg agcgtcccta 60
acaatttggt ttattttcca catggcaacc tgattacatc aattattatt cgataacctg 120
aatgctcgcg gcggattccg atgctattga gcataaggat agccgaatta gttttcgtca 180
actgagcgag ttagtagcac tccaggccaa agccctacaa agcctggatt tgaaacgcca 240

```
gcaacgtgtt gcaatttacc ttcctaaaca aatcgaaacc gtcagcagct tcctggccgt    300

ttccttggcc gggcggcgtg ttcgtgacgg taaatccggt actaaaggcg ccacaggtta    360

gccacatcct caacgactga aacgtcaaaa tactgatcac ctcaaaaagc cgcctgcata    420

gtttacagac agtactgcat gaatgaaccg atctacacac catcatcctg gttgatcatg    480

acgcgggcga cgttaaactc ccgtcgtggc aaattattga ctggcaaacc tacaaccgtt    540

tagccgactc ttatccacac catccggtta ccatgatcga caccgacatg gcggcgatct    600

tgtacacctc cggcagcacg ggcaaaccga aaggcgtggt gttatctcat cgcaatatcg    660

tggccggcgc ccaaagtgtg gctgaatacc tgcaaattca ggcagacgac cgattgctcg    720

ccgtactacc ctttagtttc gactacgggc tgaatcaact aacgaccagc ctgttgaagg    780

gtgcaagttg cgtgttattg gactatttac tgcccaagga tgtgattaac gccctaggca    840

aataccaaat cacaggtctg gccgccgtcc cgcctttatg ggctcaactg gcggatttaa    900

actggccgga atccatcgat caacacttgc gctatatgac caactcgggc ggaaaaatgc    960

ccaaaaccgt actacaaaaa ctgcgctcta aagcccccaa ttcaaagttt tttctgatgt   1020

atggcctgac ggaagccttc cgttcaacct atttaccacc cgagcaaatc gacattcgtc   1080

cggactccat gggtaaagcc atcccaaacg cggaaatcat ggtagtccgt gaggacggta   1140

gcctgtgcgc tccgcacgaa ccgggcgaac tggttcaccg cggctccctg gtcagtcttg   1200

gttattggaa cgaccccgcc aaaaccgcgg aacgctttaa acccgctccc ggccaactat   1260

ccggcttacc cctgaccgaa atagccgtct ggtccggcga taccgtcacg atggatgagg   1320

atggtttttt gtattttgtc ggccgtaaag acgatatgat caaaacgtcc ggctacagag   1380

tgagtccgag tgaaattgaa gaagtcattt acgcctccgg attggttaag gaggctgcgg   1440

cgattgggat cgaacaccca aacctgggcc aggcggttgt cgttgtcgtt agcccacaac   1500

ctgatatgca attcgatcca caacaattga ttgattgctg caaaacccaa ctgccaaatt   1560

tcatggtacc cgcgcgaatt gaagagctca gcagcttacc gcgtaacccc aacggcaaaa   1620

tagatcgtaa aatgcttagc caacagtttg cccatttgtt tcagctga               1668
```

```
<210> SEQ ID NO 36
<211> LENGTH: 927
<212> TYPE: DNA
<213> ORGANISM: Artificial Sequence
<220> FEATURE:
<223> OTHER INFORMATION: Codon optimized E. Coli FabD sequence

<400> SEQUENCE: 36

atgacgcagt tcgctttcgt tttccccgga caaggatccc agaccgttgg tatgctcgct     60

gatatggccg cttcgtatcc gatcgtcgag gagactttcg cggaagcctc cgcggccctg    120

ggctacgatc tctgggccct cacccagcaa ggtccggcgg aagagttgaa taagacctgg    180

cagacgcagc ccgcgctgct caccgcgtcc gtggcgctgt atcgcgtgtg gcagcagcag    240

ggcggcaagg cccctgccat gatggcgggc cactcgctcg gcgagtattc ggccctggtc    300

tgcgccggcg tcatcgactt cgccgacgcc gtccgcctgg tcgagatgcg cggcaagttc    360

atgcaggagg ccgtccccga gggcaccggc gctatggccg ccatcatcgg cctcgacgac    420

gcgtcgatcg cgaaggcgtg cgaagaagcc gccgagggcc aggtcgtgag cccggtcaat    480

ttcaactcgc cgggtcaggt cgtcatcgcg ggccataaag aagcggtcga gcgtgccgga    540

gcggcgtgca aggccgcggg ggcgaagcgc gcgctcccgc tgccggtgtc ggtccccagc    600

cattgcgccc tcatgaagcc ggccgccgat aagctggccg tcgagctggc caagatcacg    660
```

ttcaacgccc cgaccgtccc cgtggtgaac aatgtcgacg tgaagtgcga aacgaacggc 720
gacgccatcc gggacgcgct ggtgcgccag ctctataatc cggtccagtg gaccaagagc 780
gtggagtaca tggcggcgca gggcgtcgag cacctctacg aagtgggccc cggcaaggtc 840
ctcaccggcc tgaccaagcg cattgtcgac acgctgacgg cgtcggccct gaacgagccc 900
agcgcgatgg ccgcggcgct ggagctg 927

<210> SEQ ID NO 37
<211> LENGTH: 549
<212> TYPE: DNA
<213> ORGANISM: Artificial Sequence
<220> FEATURE:
<223> OTHER INFORMATION: Codon optimized E. Coli TesA sequence with periplasmic targeting sequence removed

<400> SEQUENCE: 37
atggctgata ccctcctcat tctcggcgac tccctctctg ctggttatcg tatgtccgct 60
tccgctgcct ggcctgcgct gctcaacgac aagtggcagt cgaaaaccag cgtcgtcaac 120
gcctcgatca gcggagacac gtcgcagcag ggcctcgccc gcctgcccgc gctcctgaag 180
cagcaccagc cgcggtgggt cctggtggag ctgggcggca atgacggcct gcgtggcttc 240
cagccccagc agacggagca gaccctgcgc cagatcctgc aagacgtgaa ggccgccaac 300
gcggagccgc tcctcatgca gatccgcctg ccggcgaact acggccgccg ctataatgaa 360
gcgttctcgg cgatctaccc gaagctcgcg aaggaattcg acgtgccctt gctgccgttc 420
ttcatggagg aggtctatct caagccgcag tggatgcaag acgatggcat ccaccccaat 480
cgcgacgccc agccgttcat cgcggattgg atggccaagc agctccagcc gctggtcaac 540
catgattcg 549

<210> SEQ ID NO 38
<211> LENGTH: 1146
<212> TYPE: DNA
<213> ORGANISM: Artificial Sequence
<220> FEATURE:
<223> OTHER INFORMATION: Codon optimized Cinnamomum camphorum thioesterase sequence

<400> SEQUENCE: 38
atggccacta cctcccttgc ttctgccttt tgctctatga aagctgtgat gctcgcccgt 60
gatggacgcg gtatgaagcc gcggagctcg gatctccagc tgcgcgcggg caacgcgcag 120
acgtccctga agatgatcaa tgggaccaag ttctcctata cggagtcgct gaagaagctg 180
ccggactggt ccatgctgtt cgcggtgatc accaccatct tcagcgccgc cgagaagcag 240
tggaccaacc tcgaatggaa gcccaagccg aatcccccgc agctcctcga tgatcatttc 300
ggcccccatg gcctggtgtt ccgccgtacg ttcgcgatcc gctcgtatga ggtcggcccg 360
gaccgctcca cctcgatcgt cgccgtcatg aatcatctcc aagaagcggc cctgaaccat 420
gccaaaagcg tcggcatcct gggcgacggc ttcggcacca ccctggagat gtcgaagcgc 480
gacctgatct gggtcgtcaa acgcacccac gtcgccgtgg agcgctaccc ggcctggggc 540
gataccgtcg aggtcgagtg ctgggtgggc gcctcgggca acaacggccg tcgccacgac 600
ttcctggtcc gcgactgcaa aacgggagag atcctgaccc gctgcacaag cctgagcgtc 660
atgatgaata cccgcacgcg ccggctctcc aagatccccg aggaagtgcg cggtgagatc 720
ggacccgcgt tcatcgacaa cgtcgcggtc aaggacgaag agatcaagaa gccgcagaag 780

-continued

```
ctcaacgaca gtacggcgga ctatattcag ggcggcctga ccccccgctg gaatgacctg    840

gacatcaacc agcatgtgaa caatatcaag tacgttgact ggatcctgga gactgtgccg    900

gactcgatct tcgagtcgca tcacatttcg tcgttcacga tcgagtatcg ccgcgagtgc    960

accatggatt cggtcctcca gtccttgacc acggtcagcg gcggcagctc ggaagcgggc   1020

ctcgtctgcg agcacctcct ccagctcgaa ggcggctccg aggtcctccg ggccaagacc   1080

gagtggcgtc ctaagctcac cgactcgttc cgcggcatct cggtcatccc tgccgagtcg   1140

agcgtg                                                              1146
```

<210> SEQ ID NO 39
<211> LENGTH: 1146
<212> TYPE: DNA
<213> ORGANISM: Artificial Sequence
<220> FEATURE:
<223> OTHER INFORMATION: Codon optimized Umbellularia californica thioesterase sequence

<400> SEQUENCE: 39

```
atggccacta cctcccttgc ttctgccttt tgctcgatga aagctgtgat gctcgcccgt     60

gatggacgag gaatgaagcc gcgctcgtct gacctccagc tgcgtgcggg caatgccccg    120

acctcgctca agatgatcaa cggcacgaag ttctcgtata ccgagtccct caagcgcctc    180

ccggactggt cgatgctgtt cgccgtcatc accacgatct tcagcgccgc ggaaaagcag    240

tggaccaacc tggagtggaa gccgaagccg aagctccccc agctgttgga tgatcacttc    300

ggcctgcacg gcctcgtgtt ccgccgcacc ttcgcgatcc gcagctacga ggtcggccct    360

gatcgcagca cctcgatcct ggcggtcatg aaccacatgc aagaagccac gctgaaccac    420

gccaagtccg tcggcatcct gggcgacggc ttcggcacca ccctcgaaat gagtaagcgc    480

gacctcatgt gggtcgtccg ccgcacccat gtcgccgtcg agcgttaccc gacctggggc    540

gacaccgtcg aggtcgagtg ctggattgga gcgtcgggca acaatggcat gcgtcgcgac    600

ttcctcgtgc gcgattgcaa gaccggcgag attctgacgc gctgcacctc gctctcggtg    660

ctgatgaaca cccgcacccg ccgcctctcg accatcccgg acgaggtcag gggcgaaatc    720

ggccccgcgt tcatcgacaa cgtcgcggtg aaggacgacg agatcaaaaa gctgcagaag    780

ctcaacgact ccacggcgga ctatatccag ggcggcctga cgccccgctg gaatgacctg    840

gacgtcaacc agcatgtcaa taatctgaaa tacgtcgcct gggtgttcga gacagtgccc    900

gatagcatct tcgagagcca tcacatctcg tcgttcaccc tggagtatcg ccgggagtgc    960

acgcgggaca gcgtgctgcg gtcgctcacg accgtcagcg ggggctccag cgaagccggc   1020

ctcgtctgcg accacctcct gcagcttgag ggtggcagcg aagtcctccg tgcgcgcacg   1080

gagtggcgcc ccaagctcac ggattcgttc cgcggcatct cggtgattcc cgcggagccg   1140

cgcgtc                                                              1146
```

<210> SEQ ID NO 40
<211> LENGTH: 750
<212> TYPE: DNA
<213> ORGANISM: Artificial Sequence
<220> FEATURE:
<223> OTHER INFORMATION: Codon optimized Streptococcus pyogenes acyl-ACP thioesterase sequence

<400> SEQUENCE: 40

```
atgggactct cgtatcaaga agaactgacc ctgcctttcg agctttgcga cgtgaaatcg     60

gacatcaagc tgccgttgct gctcgattat tgcctgatgg tgtccggccg gcagtcggtc    120
```

```
cagctcggcc gcagcaacaa taatctcctc gtcgactaca agctcgtgtg gatcgtgacc    180

gattacgaga ttacgatcca tcgcctcccg cacttccagg aaaccatcac catcgagaca    240

aaggccctgt cgtataacaa gttcttctgc taccgccagt tctatatcta cgatcaggaa    300

ggctgcctgc tcgtcgacat cctgtcctat ttcgcgctcc tcaatccgga cacccgcaag    360

gtcgccacga tccccgagga cctggtcgct cccttcgaaa ccgacttcgt gaagaaactc    420

caccgtgtgc cgaagatgcc gctgctggag cagtccatcg accgcgacta ctatgtccgc    480

tatttcgaca tcgatatgaa cggtcatgtc aacaactcga agtacctcga ttggatgtat    540

gacgtcctcg gctgccagtt cctcaagacg catcagccgc tcaagatgac cctgaaatat    600

gttaaggaag tctcgcccgg cggccagatc acgtcgtcgt accatctgga tcagctgacg    660

tcgtatcacc agatcatcag cgacggccag ctgaacgcgc aggccatgat cgagtggcgc    720

gcgattaagc agaccgagag cgagactgac                                     750
```

```
<210> SEQ ID NO 41
<211> LENGTH: 1191
<212> TYPE: DNA
<213> ORGANISM: Artificial Sequence
<220> FEATURE:
<223> OTHER INFORMATION: Codon optimized Ricinus communis palmitoyl-acyl
      carrier protein thioesterase sequence

<400> SEQUENCE: 41

atgggcactt gctcctatac catcaccctc ccgatccgct gcctctcgaa ttccaacggc     60

caccatgacc cccacaagca gaacctcaat aagatcaaga ttaatggcgc gtcgaccagc    120

acgcgcccgc tcaagctcga cgccccctcg cagaccgtgg gcgtggcgac catctacctg    180

gccagcgtgt cggagaatct gaccctgacg aaagaggtca tgcgccagaa catccccacc    240

aagaagcagt atatcgatcc ccatcgccag ggcctcatga tcgagggcgg agtgggctat    300

cgccagacga tcgtcatccg ctcctacgaa gtgggccctg acaagacggc cacgcttgag    360

tcgatcctgt atctgctcca ggaaaccgcg ctcaaccacg tgtggctgtc cggcctgctc    420

tcgaacggtt tcggcgcgac gcacggaatg gtcaagaaca acctcatctg ggtcgtgtcc    480

aagctgcaag tccaggtcga ccattacccg atctggggcg aggtcgtcga gatcgacacg    540

tgggtccgcg ctagcgggaa gaacggcatg aagcgcgatt ggctgatccg cagccaggcc    600

accggccacg tgttcgtccg cgccacctcg acctgggtga tgatgaatga gaaaacacgc    660

cggctctcga agatgccgga agaagtccgt gccgagatca gcccctggtt catcgagaag    720

caggcgatca aagaagaggt ccccgacaag atcgcgaagc tggacgataa ggcgcgttat    780

gttatctcga atctgaagcc gaagcgctct gacctcgaca tgaaccacca tgtcaataat    840

gtcaagtacg tccgctggat gctggagatc ctgccggacc atttcctgga gtcgcatcag    900

ctctcgggca ttacgatgga gtatcgccgt gagtgcggca gtgcggacat cgtccagagc    960

ctgtgcgagc cggacggcga tgagatcctg tccaacgaca tcccggtgct caacggcttc   1020

tcgctggcct cggagccgct catggaaggt aatggcttcc tggtcccgct ggataaggtg   1080

ccgttgaagt acacccatct gctcctcacg aagggcgagt cccagaacga agagatcgtc   1140

cggggcaaga cgatttggaa gaaaaagctc tgcaccatgc ccttctcgac c            1191
```

```
<210> SEQ ID NO 42
<211> LENGTH: 1176
<212> TYPE: DNA
<213> ORGANISM: Artificial Sequence
```

-continued

<220> FEATURE:
<223> OTHER INFORMATION: Codon optimized Ricinus communis palmitoyl-acyl carrier protein thioesterase sequence

<400> SEQUENCE: 42

```
atggcgtcca agggctcgat ccggctgtat ttcccctgcg atttccgtaa caccctccag     60
aagaagaata tgaagatgga catggtcatg gcgcggtcgg gcttctccta ctcgctcaat    120
ccgatcgcgc ccaagattcc gcgcttctac gtggtcgcca atgccagcaa tccccagcgc    180
gtggatacga tcaacgggaa gaaagtgaac ggcatccatg tcgcggagtc gagcaatagt    240
tatgcggacc agaataagat gaacgctacg gccggactgg tcctcgacgg caatgtggat    300
caccagccgc tgcataagtg gctcctcggc cgcttcgtcg acgagcgcct cgtgtatagc    360
cagacgttca tcatccgttc gtatgagatc ggccctgaca agacggcgac catggaaacc    420
ctgatgaatc tcctgcagga aaccgcgctc aaccatgtca cctcgtcggg cctcgccggt    480
gacggcttcg gcgccacccg cgagatgtcg ctccgcaagc tgatctgggt ggttacccgc    540
atccacatcc aggtccagcg ttactcgtgc tggggcgatg tcgtcgagat cgacacgtgg    600
gtcgacggcg cgggcaagaa cggcatgcgt cgcgactgga tcatccgcga ttacaacacc    660
aaggaaatca tcacgcgcgc tacgtctacc tgggtgatca tgaaccgcga aacgcgcaag    720
ctgtccaaga tgccggagca agtccgccag gaactggtcc cgttctatac gaaccgcatc    780
gccatcgcga aagagaacaa cgacgtcgag aagattgaca agctgactga cgagacagcg    840
gagcgcatcc gctcgggcct ggcgccgcgc tggagcgaca tggacgccaa ccagcatgtg    900
aataatgtca agtatatcgg ctggatcctg gagtcggtcc ccatcaatgt ccttgaggat    960
tacaacctca cgagcatgac cctggagtat cgccgcgagt gcaggcagag caatttgctg   1020
gagtcgctca cctccaccac cgagcacagc aataacaact cgtgcaaccg caaggcccac   1080
ctggagtata cccacctcct ccgtatgcag gccgacaagg ccgagattgt gcgtgcccgg   1140
accgagtggc agtccaagtc gaaccgcaag accatc                             1176
```

<210> SEQ ID NO 43
<211> LENGTH: 1257
<212> TYPE: DNA
<213> ORGANISM: Artificial Sequence
<220> FEATURE:
<223> OTHER INFORMATION: Codon optimized Ricinus communis palmitoyl-acyl carrier protein thioesterase sequence

<400> SEQUENCE: 43

```
atggtcgcca ccgccgccgc cgctaccagc tcgttcttcc ccgtcccgtc ccagtctgcc     60
gacgccaatt ttgataaggc gccggcctcg ctggggggca tcaagctcaa gtccacgtcg    120
tgcagtcgtg gcctccaggt caaggcgaat gcgcaggcgc ctccgaagat caacggctcc    180
tcggtgggtt tcacgaccag cgtggagaca gtgaagaatg acggcgacat gccgctgccg    240
ccgcctcccc gcacgttcat caaccagctg cccgattggt ccatgctcct ggcggccatc    300
accaccatct tcctggctgc ggagaagcag tggatgatgc tggactggaa gccccggcgc    360
ccggacatgt tgatcgaccc gttcggcatc ggccggattg tccaggacgg cctcatcttc    420
cgccagaatt tctccatccg ttcctatgag atcggcgcgg atcgcacggc ctcgatcgag    480
actctcatga accatctcca ggaaacggcg ctcaaccatg tgaaaaccgc cggtctgctc    540
ggcgatggct tcggctcgac cccggagatg agcaagcgca atctcatttg ggtggtgacc    600
cgcatgcaag ttctggtcga ccgctacccg acctggggcg acgtcgtcca ggtcgacacg    660
```

-continued

```
tgggtcagca aatcgggcaa gaacggaatg cgtcgcgatt ggtgcgtgcg cgactcgcgc     720

accggcgaaa cgctgacgcg tgcgagctcg gtgtgggtca tgatgaacaa gctcacccgc     780

cgcctctcga agatccccga ggaagtccgc ggagagatcg agccgtactt cctcaatagc     840

gacccgatcg tcgacgaaga ttcgcgcaag ctgccgaagc tggacgactc gaacgccgac     900

tacgtccgca agggcctcac gccccgctgg tcggatctgg acatcaacca gcacgtcaat     960

aatgtcaagt atatcggctg gatcctggag tccgcgccgc ttcccatcct cgaatcgcat    1020

gagctgtcgg cgatcaccct ggagtatcgg cgtgagtgcg gcagggacag cgtcctgcag    1080

tcgctgaccg ccgtgtcggg caacggcatc ggcaacctcg gcaatgccgg cgacatcgag    1140

tgccagcacc tcctgcgcct cgaagatggc gcggagattg tgcgcggacg cacggagtgg    1200

cgccccaagt attcgtcgaa cttcggcatc atgggccaga tcccggtcga gagcgcg       1257
```

<210> SEQ ID NO 44
<211> LENGTH: 1215
<212> TYPE: DNA
<213> ORGANISM: Artificial Sequence
<220> FEATURE:
<223> OTHER INFORMATION: Codon optimized Jatropha curcas acyl-ACP thioesterase sequence

<400> SEQUENCE: 44

```
atggccgttt tcacctaccg catcgctatg ctccccatcc gctgcagctc gtctaactcc      60

accaattccc atagccacga cccgaaccag cagaacctcc acaagatcaa gatcaatggc     120

tcggcgagcg cgatgatgcc gctgaaggtc gatctgccct cctcgctcac gatcacgtcg     180

gtcgcccccg tcgtggagaa cctctcgctg acgaaggaac aaactcggca gaatattccc     240

accaagaagc agtatatcga cccgcatcgc cagggcctga tcgtcgagga gggcgtgggc     300

taccgccaga cggtcgtgat ccggtcgtat gaggtcggac cggacaagac ggcgaccctg     360

gagatcattt tgtgcctcct gcaggaaacg gcgctgaacc atgtctggct gtccggtctg     420

ctctcgaatg gcttcggcgc cacccacggc atggtccgca acaatctcat ttgggtggtg     480

tcgaagctcc aggtccaggt cgatcagtat cccatctggg gcgaggtcgt ggagatcgac     540

acgtgggtcg gcgcctcggg taagaacgga atgcgtcgcg actggctcgt ccgcagccag     600

gcgacgggcc aggttttcgc ccgcgcgacc agtacgtggg tcatgatgaa tgagaaaaca     660

cgccgcctca gcaagatgcc ggaagaagtc cgcgcggaga tcgccccgtg gttcatcgag     720

aaacaggcca tcaaagagga agtgccggag aagatcgcga agctcgacga taaggcccgc     780

tatgtggtga cgaacctgaa gcccaagcgc tccgacctgg acatgaacca gcatgtcaat     840

aacgtcaagt acgtgcgctg gatgctggaa accctcccgg atcagttctt cgagaatcat     900

cagttgtcgg gcatcaccct ggagtacaag cgtgagtgcg gctcgtcgga catcgtcgag     960

agcctgtgcg agcccgatga agaggagggc atcatcaaca ccggcctcaa gcagaacaac    1020

gacaagtcgc tgttcaatgg cttcagcctc ccgtcggaga tcatggaggg caacgggttc    1080

ctgtcgtcgc tggaaaagac cccgctcaag tatacccacc ttctcgtcgc gaagggcaag    1140

acccagtccg aggagatcgt gcgtggcaag accatctgga agaaaaagct cctcaccacc    1200

atgcctttct cgccg                                                     1215
```

<210> SEQ ID NO 45
<211> LENGTH: 1044
<212> TYPE: DNA
<213> ORGANISM: Artificial Sequence
<220> FEATURE:

<223> OTHER INFORMATION: Codon optimized Jatropha curcas acyl-ACP
thioesterase sequence

<400> SEQUENCE: 45

```
atggtttcca ccgccatctc tttctcgctc ctgcccatca agctcatcaa agaagaaact      60
cgcatggcct ccgcggaccg ccgcaagaac agcatcgtga aggagttcgg ccacttcacg     120
tgccgctgcg ccgcgatcga gaagcgcatc cagaagctga acaatttcct gattgacggc     180
ggcttcggct cgcttgagca gaatggcctc atctaccgcc agaatatctt catccggtcc     240
ttcgagatcg gcttcgaccg taagctgagc ctcgccgccc tcacgaattt cctccaggac     300
acggcgctga accatgtccg tatgattgga ctgctcgcgg ctggcttcgg gtccaccccg     360
gagatgtcga agaaagacct gatctgggtg ctctgcaccc tgcagatcct ggtcgaccgc     420
catccctcgt ggctcgacgc ggtcgaggtc gatacctgga tgtacccctc cggccaaaac     480
ggccagggcc gtgactggct ggtgcgggat gccaagacgg gcaagccgct ggcccaggcg     540
tcgagcgtga tggtcttgct caataagaaa acccgcaagc tcagcaagtt caccgaagag     600
atccgcgatg agatcgctcc gcacatgatg atggactgca atcccatcat taactcgcgc     660
aagatgctgc cgttcgacgt caacaccgcg gactatgcgc gcacgggcct cacgccgggt     720
tggaacgacc tcgatctcaa tcagcatgtc aaccacgtgc agtatatcaa ctggatcctc     780
cagaatgtgc tccgctcgct catccagcac cataagctgt cggacatcac cctggagtac     840
cgcaaggaat gcgatatcaa ctcgatcctg cagttcctct cgaagatcgt caagaacggc     900
tcgaaccact cgaccgacac caataacctg atcgagctgg atcattcgct gctcctggag     960
aatggcagcg agatcgcgcg cgccaacacc atctggaagc cgcgcgaggt caataacttc    1020
aagaacgccg tctatacgcc tgcg                                            1044
```

<210> SEQ ID NO 46
<211> LENGTH: 1071
<212> TYPE: DNA
<213> ORGANISM: Artificial Sequence
<220> FEATURE:
<223> OTHER INFORMATION: Codon optimized Jatropha curcas acyl-ACP
thioesterase sequence

<400> SEQUENCE: 46

```
atggcctcga ctgcgatctc cttcctctct atccccatta agcttatcaa agaagaaatg      60
cgcatggcgt ccgcgggccg ccgcaagaac accatcgcgg ccgagttcgg ccatttcacg     120
ttcggatccg cgaccgtcga gaagaaggtc cagaagtcga ataacttcct catcgacggc     180
ggcttcggct ccctggagca gaacgggctc atctaccgcc agaacatctt cgtgcgctcg     240
ttcgagattg gcttcgatcg gaagctgagc ctggcggctc tgaccaactt cctccaggac     300
acggcgctca atcattgccg catgatcggc ctgctcgccg agggcttcgg ctcgacgccg     360
gagatgatta agaaagatct catctgggtt ctgtgcacgc tgcagatcct ggtggatggc     420
tatccgtcgt ggctcgacgt ggtcgaggtc gatacgtgga tgtacccgag cggtcagaat     480
ggcctcggcc gtggctggct ggtccgcgac ggcaagacgg gtcgcagcct ggcccagtcg     540
agcagtgtga tggtgtcgtt caacaaaaag acccggaagc tctcgaagct ggccaaggaa     600
atcagggacg agatcgcccc tcacatgatg gactgcgacc cgatcatgaa caagaactcg     660
cgcaagatct tgcccttcga cgtcaacacc gcggattatg cccgcaccgg cctcaccccc     720
ggatggaatg agctggacct gaatcagcat gtcaatcacg tgcagtacat caattggatc     780
ctccagaacg tccgcccgtc cctcgtccaa caccataagc tctcggcgat cacgctggag     840
```

-continued

```
tatcgcaaag agtgcgacat gaattcgatc ctccagtcgc tcagccgcat cgtcaagaac    900

ggcggcaacg atagcaccga caagaacaac gtcatcgagc tggaccactt cctgctcctg    960

gagaacggct cggagatcgc ccgtgccaat accatctgga agccgcgtga ggtgaacaac   1020

ttcaagaatg tcgtgcatag ccccgccgaa gagaatatct cctcgatgaa t            1071
```

<210> SEQ ID NO 47
<211> LENGTH: 396
<212> TYPE: DNA
<213> ORGANISM: Artificial Sequence
<220> FEATURE:
<223> OTHER INFORMATION: Codon optimized E. Coli FadM sequence

<400> SEQUENCE: 47

```
atgcagaccc agatcaaagt gcgcggatat catctcgacg tttatcaaca tgtcaacaat     60

gctcgttacc tggagttctt ggaagaagcc cggtgggacg gcctggagaa ctcggactcg    120

ttccagtgga tgaccgcgca caacatcgcc ttcgtcgtcg tgaatatcaa catcaattac    180

cgccgcccgg cggtgctgtc ggatctgctc acgatcacgt cccagctcca gcagctcaac    240

ggcaagtcgg gcatcctcag ccaggtcatt acgctggagc ccgagggcca ggtcgtcgcg    300

gatgccctga tcaccttcgt ctgcatcgac ctcaagaccc agaaagccct cgcgctggaa    360

ggcgagctcc gcgagaagct ggagcagatg gtgaag                              396
```

<210> SEQ ID NO 48
<211> LENGTH: 957
<212> TYPE: DNA
<213> ORGANISM: Artificial Sequence
<220> FEATURE:
<223> OTHER INFORMATION: Codon optimized E. Coli AccA sequence

<400> SEQUENCE: 48

```
atgtccctca atttcctcga cttcgaacaa cccatcgccg agctggaagc caagatcgat     60

tcgctcaccg ctgttagccg ccaggacgag aagctcgaca tcaacatcga cgaggaagtg    120

catcgcctcc gcgagaagtc cgtcgagctg acgcgcaaga tcttcgccga cctgggcgcc    180

tggcagatcg cccagctcgc gcgccacccg cagcgcccgt atacgctgga ttatgtgcgc    240

cttgccttcg acgagttcga cgagctggcc ggcgaccggg cgtatgcgga cgataaggcc    300

atcgtgggcg gcatcgcgag gctggacgga cgcccggtca tgatcatcgg ccatcagaaa    360

ggccgcgaaa cgaaggaaaa gattcgccgc aacttcggca tgccggcccc cgagggctac    420

cgcaaggccc tgcgcctcat gcagatggcg gagcgtttca agatgccgat cattaccttc    480

atcgacaccc ccggcgcgta tccgggggtg ggtgccgagg aacggggcca gagcgaggcg    540

atcgctcgca acctccgcga gatgtcccgt ctgggcgtgc cggtcgtctg cacggtcatc    600

ggcgagggcg gctcgggtgg cgccctcgcg atcggcgtcg gcgacaaggt caatatgctc    660

cagtactcga cctatagcgt catctcgccc gagggctgcg cctcgatcct gtggaagtcg    720

gcggacaagg ccccgttggc ggctgaggcg atgggcatca tcgcccctcg cctcaaagaa    780

ctgaagctga tcgactcgat catcccggag ccgctgggcg gagcgcaccg taacccccgag    840

gccatggcgg ccagcctgaa ggcgcagctc ctcgcggatc tcgccgatct ggacgtcctc    900

tcgaccgagg atctgaagaa tcgccggtac cagcgcctga tgtcctacgg ctatgcg       957
```

<210> SEQ ID NO 49
<211> LENGTH: 468
<212> TYPE: DNA

<213> ORGANISM: Artificial Sequence
<220> FEATURE:
<223> OTHER INFORMATION: Codon optimized E. Coli AccB sequence

<400> SEQUENCE: 49
atggacattc ggaagatcaa gaaactcatc gaactcgtgg aagagagcgg aatctcggag 60
ctggaaatta gcgagggcga ggaatccgtc cgcatctccc gtgccgcccc cgcggcctcg 120
ttcccggtga tgcagcaagc ctacgcggct ccgatgatgc agcagccggc gcagtcgaac 180
gcggctgcgc cggcgacggt cccctcgatg gaagcccctg ccgcggcgga gatctcgggc 240
cacatcgtgc gctcccccat ggtcggcacc ttctatcgca cgccgtcgcc ggacgcgaag 300
gccttcatcg aggtcggtca gaaagtgaat gtcggcgata ccctctgcat cgtcgaggcc 360
atgaagatga tgaaccagat cgaggccgat aagagcggca ccgtcaaggc catcctggtc 420
gagtcgggcc agcccgtgga gttcgacgag ccgctggttg tcatcgag 468

<210> SEQ ID NO 50
<211> LENGTH: 1347
<212> TYPE: DNA
<213> ORGANISM: Artificial Sequence
<220> FEATURE:
<223> OTHER INFORMATION: Codon optimized E. Coli AccC sequence

<400> SEQUENCE: 50
atgcttgaca agatcgtgat cgccaatcgt ggagaaattg ctttgagaat cctgcgcgcc 60
tgcaaagaac tcggaatcaa gaccgtcgcg gtgcattcct cggccgaccg cgacctcaaa 120
cacgtcctgc tggcggatga aacggtctgc ataggccctg cgccgtcggt gaagtcgtac 180
ctcaacatcc cggccatcat ctctgccgcg gagatcaccg gcgccgtcgc catccacccc 240
ggctatggct tcctgtcgga gaatgcgaac ttcgcggaac aggttgagag gtcgggcttc 300
attttcatcg gccccaaggc cgaaaccatc cgcctgatgg gcgacaaggt gagcgcgatc 360
gcggcgatga agaaagcggg cgtgccctgc gtccccggca gcgacggccc tctcggcgac 420
gacatggata agaaccgcgc gattgcgaag cgcattggct atccggtgat catcaaggcc 480
tccggcggtg gtggcgggcg cggcatgcgg gtcgtgcgcg gcgacgcgga gctcgcccag 540
tcgatctcga tgactcgcgc cgaggccaag gctgccttct cgaacgatat ggtctatatg 600
gagaagtatc tggagaatcc gcggcacgtc gagatccagg tgctcgcgga cggccagggt 660
aatgccatct acctcgccga gcgcgattgc tccatgcagc gccgtcatca gaaggtcgtc 720
gaggaagcgc cggcccccgg catcaccccg gagctgcgtc gctatatcgg cgagcgctgc 780
gcgaaggcct gcgtggacat cggctatcgc ggcgccggca cgttcgagtt cctcttcgag 840
aacggggagt tctacttcat cgagatgaac acccgcatcc aggtcgagca tcccgtgacc 900
gagatgatca cgggcgtgga cctgatcaag gaacagctcc gcatcgcggc tggtcagccg 960
ctctcgatca agcaagagga ggtccacgtc cgtggccacg cggtcgagtg ccgcatcaac 1020
gccgaggatc cgaacacgtt cctgccgtcg ccgggaaaga tcacgcgctt ccatgccccc 1080
ggcggcttcg gcgtccgctg ggagagccat atctatgccg gatatacggt cccgccgtat 1140
tacgattcca tgatcggcaa gctgatctgc tatggcgaga atcgggacgt cgccatcgcg 1200
cgcatgaaga acgctctcca agagctcatc atcgacggca tcaagaccaa tgtcgatctg 1260
cagattcgca tcatgaacga cgagaacttc cagcacggcg gcaccaatat ccattacctg 1320
gagaagaagc tgggcctcca ggagaag 1347

<210> SEQ ID NO 51
<211> LENGTH: 912
<212> TYPE: DNA
<213> ORGANISM: Artificial Sequence
<220> FEATURE:
<223> OTHER INFORMATION: Codon optimized E. Coli AccD sequence

<400> SEQUENCE: 51
atgtcgtgga tcgagcgtat caagagcaat attaccccca cacggaaggc gagcatcccg 60
gaaggcgtct ggactaagtg cgacagctgc ggccaggtcc tctatcgtgc cgagctggag 120
cgcaatctgg aagtgtgccc gaagtgcgac catcacatgc gcatgaccgc tcgcaaccgc 180
ctgcattccc tcctggatga aggctcgctc gtcgagctgg gctcggagct ggagcccaag 240
gacgtcctga agttccgcga ttccaagaag tataaggacc gcctggcgtc ggcgcagaaa 300
gaaaccggcg agaaagacgc cctcgtcgtc atgaagggca ccctgtatgg catgccggtc 360
gttgccgcgg cgttcgagtt cgcgttcatg ggcggctcga tggggtcggt ggtcggcgcc 420
cgcttcgtcc gggcggtgga gcaggcgctt gaggacaact gcccgctgat ctgcttctcg 480
gcgagcggtg gtgcgcgcat gcaagaagcg ctcatgtccc tcatgcagat ggccaagacg 540
agtgccgctt tggccaagat gcaggaacgt ggcctcccct acatctcggt cctcacggac 600
ccgacgatgg gcggagtgtc cgcgtcgttc gcgatgctcg gcgatctcaa catcgccgag 660
ccgaaggccc tgatcggctt cgccggcccg cgcgtgatcg agcagaccgt gcgcgagaag 720
ctcccgcccg gcttccagcg ctcggagttc ctcatcgaga aaggcgcgat cgacatgatc 780
gtccgccgcc cggagatgcg cctgaagctc gcctcgatcc tggccaagct catgaatctg 840
ccggctccga accccgaggc cccgcgcgag ggagtcgtgg tgcctccggt ccccgaccaa 900
gagcccgagg cg 912

<210> SEQ ID NO 52
<211> LENGTH: 1749
<212> TYPE: DNA
<213> ORGANISM: Artificial Sequence
<220> FEATURE:
<223> OTHER INFORMATION: Mutated Methylobacterium extorquens FadD sequence

<400> SEQUENCE: 52
atggcgtagg accggagcgc ggagcgtcct tggctggccg cctatccccc cggcattccc 60
gccgatatcg acgtcgattc cgtcggcacg gtggtcgatc tgttcgaccg cagcgtgctg 120
cgcttcgcct agcgcccggc gatcacctgc ttcggcgcgc agcctgcgct accgcgaggt 180
cggcgccgcg gcgcaggcgg tggcggcgtg gctcgcccgc caacggctac ggcaaggccg 240
gcaagggaag tgagaacggc agcgagacgg gtgtggacgg catcggcgac cgcatcgcgg 300
tgatgatgcc caacgtcccg gcctgtcccg tctcgctgct cggcgtgctg gtggcgggct 360
gcaccgtcgt caacgtcaac ccgctctaca ccccgcgcga actcgccgcg cagatcaacg 420
attccggcgc ccgcgtcctc ttcgtgctgg agaacttctg ccacacggtc gcgcaggcgc 480
tgccgcagat gccgagcctg gagcggatcg tcgtggcagg ccccggcgac ctgctcgggc 540
tgaagggacg gatcgtcgat ctcgtctcgc ggcgggtgaa gcgggcggtg ccgccctaca 600
ccctgccggc cgggcggacc ctgcggttcg aggcggtggt gcgggcgggc cgcggcctca 660
agcgcccctc ggtcgcgatc gatcccggcg acgtcgcctt cctgcaatat accggcggca 720
ccaccggcat cgccaaggcg gcgatgctga cccaccgcaa catcatggcc aatgtcgagc 780
agagccgggc gtggttccgc ggcccggcgg gggaggggga cggacatgtg gcggtgacgg 840

-continued

```
cgctgccgct ctaccacatc ttcgcgctga cggcctgctt cctgttcttc ttccggctcg    900

gcggctgctg cctgctgatc ccgaacccgc gcgatctcga cggcttcgtg aagacgctca    960

gccgcacccg cttcaccaac ttcgccgggg tgaacacgct gttcaacgcg ctgaacaacc   1020

acccgaagat cggcacggtc gatttctcaa acgtggagta cgtggtcggc ggcggcatgg   1080

cggtgcagtc ggcggtggcc gcccgctgga aggcgatcac cggccagacc atcctcgaag   1140

gctacggcct gtcggagacc tcgccggtgg tgagcgtcaa cccgctcggg ctcgccaact   1200

ggaccgggac gattggttat ccgctgccct cgaccgaggt gacgatccgc gccgaggacg   1260

gcacggtgct gcccttcggc gtgcccggcg aactctgcgt gcgcgggccc caggtgatgg   1320

ccggctattg gaaccgcccg gaggagacgc gggcggcgat gaccgccgac ggcttcttcc   1380

gcaccggcga cgtggcggtg atgacgccgg acgggcagat ccgcatcgtc gaccggatga   1440

aggacatgat cctcgtctcc ggcttcaacg tctacccgaa cgaggtcgag gacgtgctcg   1500

ccacccatcc ggcggtggtc gaatgcgccg tggtcggcgc gccctgcggc gagagcggcg   1560

agatggtcgt cgcccatgtc gtcctgcgcg atccctctgt ggagccggac gcgctcaggg   1620

cgcatgcccg cgcgagcctc accggctaca aggtgccccg ccggatcgtg atccaggaca   1680

gcctgccgaa gaccaatgtc ggcaaggtgc tgcgccgggc cctgcgggac agcgggccgg   1740

cggcggtaa                                                           1749
```

<210> SEQ ID NO 53
<211> LENGTH: 927
<212> TYPE: DNA
<213> ORGANISM: Artificial Sequence
<220> FEATURE:
<223> OTHER INFORMATION: Codon optimized E. Coli FabD sequence

<400> SEQUENCE: 53

```
atgactcaat tcgccttcgt tttccccgga caaggatcgc agaccgttgg aatgctcgct     60

gatatggccg cctcctatcc catcgtcgag gaaaccttcg ccgaggcgag cgcggctctc    120

ggctatgatc tctgggccct gacccagcaa ggcccggccg aagagttgaa caagacctgg    180

cagacccagc cggccctgct gaccgcctcg gtggccctct atcgcgtgtg gcagcagcag    240

ggcggcaagg cgccggcgat gatggccggc cacagcctcg gcgagtactc ggcgcttgtc    300

tgcgcgggcg tcatcgactt cgcggacgcc gtccgcctgg tggagatgcg cggcaagttc    360

atgcaggaag ccgtcccgga aggcacgggc gcgatggcgg cgatcattgg cctcgacgac    420

gcctcgatcg cgaaggcgtg cgaagaagcg gccgagggcc aggtcgtgtc cccggtcaac    480

ttcaactcgc cgggtcaggt cgtgatcgcc ggccataaag aagcggtcga gcgcgccggc    540

gctgcctgca aagccgccgg cgcgaagcgg gccctgcccc tgccggtgag cgtgccgtcc    600

cactgcgcgc tgatgaagcc cgcggcggat aagctggccg tggagctcgc taagatcacg    660

ttcaacgcgc ctacggtccc ggtcgtcaat aatgtcgacg tgaagtgcga aacgaatggt    720

gatgcgatcc gcgacgccct cgtgcgccag ctgtacaacc ccgtccagtg gaccaagtcc    780

gtggagtaca tggccgccca gggcgtcgag catctgtatg aggtcgggcc gggcaaggtc    840

ctcaccggcc tgaccaagcg tatcgtggac acgctcacgg cgtcggcgct caatgagccg    900

tcggccatgg cggcggccct ggagctg                                        927
```

<210> SEQ ID NO 54
<211> LENGTH: 549
<212> TYPE: DNA

<213> ORGANISM: Artificial Sequence
<220> FEATURE:
<223> OTHER INFORMATION: Codon optimized E. Coli TesA sequence with periplasmic targeting sequence removed

<400> SEQUENCE: 54
atggctgata ccctcctgat ccttggcgac tccctctctg ctggttatcg tatgtccgcg 60
tccgctgcct ggcctgcgct gctcaacgat aagtggcaga gcaagacgag cgtcgtgaac 120
gcgagcatct cgggcgatac ctcgcagcag ggactggccc ggctccccgc cctcctcaag 180
cagcatcagc cccgctgggt gttggtcgag ctgggcggca acgacggcct gcgcggcttc 240
cagccgcagc agacggagca gaccctgcgc cagatcctcc aagacgtcaa ggccgccaat 300
gccgagccgc tgctgatgca gatccgcctg ccggcgaact acggccgccg ctataatgaa 360
gcgttctcgg ccatctatcc caagctcgcg aaagagttcg acgtcccct cctgccgttc 420 ttcatggaag aagtgtacct gaagccgcag tggatgcaag acgacggcat tcatcccaat 480
cgcgacgcgc agccgttcat cgccgattgg atggcgaaac agctccagcc gctcgtcaac 540
cacgactcg 549

<210> SEQ ID NO 55
<211> LENGTH: 1146
<212> TYPE: DNA
<213> ORGANISM: Artificial Sequence
<220> FEATURE:
<223> OTHER INFORMATION: Codon optimized Cinnamomum camphorum thioesterase sequence

<400> SEQUENCE: 55
atggccacaa cttcactcgc ttccgctttt tgttctatga aagccgttat gcttgcccga 60
gatggtagag gaatgaagcc gcgctccagc gatctccagc tgcgtgcggg caacgcgcag 120
acgtcgctga agatgattaa tggcacgaag ttctcgtaca ccgagtcgct caaaaagctc 180
ccggactggt cgatgctgtt cgccgtcatc accaccatct tctcggccgc ggagaagcag 240
tggaccaacc tggagtggaa gccgaagccg aatcccccgc agctcctcga cgatcacttc 300
ggcccgcatg gcctggtgtt ccgccgtact ttcgccatcc gctcgtatga agtgggcccc 360
gataggtcga cctcgatcgt cgcggtcatg aaccatctcc aagaagcggc gctgaaccac 420
gccaagtccg tgggcatact cggcgatgga ttcggaacca cgctggagat gtccaagcgc 480
gacctgatct gggtggtcaa gcggacccat gtcgccgtgg agcgctatcc cgcgtggggg 540
gacacggtcg aggtcgagtg ctgggtgggc gcgtcgggaa acaatggccg ccgccacgac 600
ttcctggttc gcgattgcaa gaccggcgag atcctgaccc gctgcacgtc gctgagtgtc 660
atgatgaata cgcgcacccg tcgcctcagc aagatccccg aagaggtccg gggcgagatc 720
ggcccggcgt tcatcgacaa tgtcgcggtc aaggacgaag agatcaaaaa gccgcagaag 780
ctcaatgaca gcaccgcgga ctatatccag ggtggcctca cgccccgttg gaacgacctg 840
gatatcaatc agcatgtcaa caacatcaag tatgtggatt ggatcctgga aaccgtcccg 900
gactcgatct tcgagagcca ccacatctcc tcgttcacca tcgagtaccg ccgcgaatgc 960
accatggaca gcgtcctcca gtccctgacc acggtgtcgg gcggcagcag cgaggccggc 1020
ttggtgtgcg agcatctcct gcagctggag ggcggctccg aggtcctccg cgccaagacg 1080
gagtggcgcc ctaagctgac cgactcgttc cgcggcatct cggtgattcc cgccgagtcg 1140
tcggtc 1146

<210> SEQ ID NO 56
<211> LENGTH: 1146
<212> TYPE: DNA
<213> ORGANISM: Artificial Sequence
<220> FEATURE:
<223> OTHER INFORMATION: Codon optimized Umbellularia californica thioesterase sequence

<400> SEQUENCE: 56

```
atggccacta ctagtctcgc ttcagccttt tgttctatga aagccgttat gctcgctcgc     60

gatggacgcg gaatgaagcc gcgttcctcc gatctgcagc tcagggccgg aaatgcgccg    120

acgtcgctca agatgatcaa cggcacgaag ttctcgtaca cggaaagcct gaagcggctc    180

cccgactggt cgatgctgtt cgccgtgatc acgaccatct tctcggccgc ggagaagcag    240

tggaccaatc tggagtggaa gccgaagccc aagctccccc agctcctcga cgaccacttc    300

ggcctgcatg gcctggtgtt ccgccgcacg ttcgcgatcc gctcctatga ggtcggcccg    360

gatcgctcga ccagcatcct ggcggtcatg aaccacatgc aggaagcgac cctgaaccat    420

gccaaaagcg ttggcatcct cggcgacggc ttcggcacca cgttggaaat gtcgaagcgc    480

gacctgatgt gggtcgtccg ccggacgcac gtcgcggtgg agcgttaccc gacctggggc    540

gacaccgtcg aggtcgagtg ctggatcggc gcgtcgggca ataacggcat gcgccgggac    600

ttcctcgtcc gggactgcaa gaccggcgag atcctcaccc gctgcacgag cctcagcgtc    660

ctgatgaata cccgcacgcg gcgcctgtcc accatcccgg acgaagtccg cggcgagatt    720

ggccccgcct tcatcgataa cgtcgctgtc aaagatgacg agatcaagaa gctccagaag    780

ctgaacgact cgaccgcgga ttatattcag ggtgggctga cccctcgctg gaacgatctc    840

gacgtcaacc agcatgtgaa caatctgaag tatgtcgcct gggtgttcga aacggtcccg    900

gattcgattt tcgagtcgca ccatatcagc tcgttcaccc tggagtatcg ccgcgagtgc    960

acgcgcgact cggtcctccg tagcctgacc accgtgagcg gcggttcgtc cgaagccggg   1020

ctggtctgcg atcacctcct ccagctggag ggcggctccg aggtgctgcg cgcgcgcacc   1080

gagtggcgcc ccaagctgac ggacagcttc cgtggcatct cggtgatccc cgccgagccg   1140

cgcgtg                                                              1146
```

<210> SEQ ID NO 57
<211> LENGTH: 750
<212> TYPE: DNA
<213> ORGANISM: Artificial Sequence
<220> FEATURE:
<223> OTHER INFORMATION: Codon optimized Streptococcus pyogenes acyl-ACP thioesterase sequence

<400> SEQUENCE: 57

```
atgggcctct cgtaccaaga agaactcacc ctgcctttcg agctctgcga cgttaaatcg     60

gacatcaagc tgccgttgct gctggactac tgcctgatgg tgtcgggccg tcagtccgtc    120

cagctcggcc ggtcgaacaa caacctcctc gtggactaca agctcgtgtg gatcgtgacc    180

gattatgaga tcaccattca ccgcctgccc catttccagg aaacgatcac catcgaaacc    240

aaggctctct cgtacaataa gttcttctgc taccgccagt tctatatcta tgaccaggag    300

ggatgcctgc tcgtcgacat cctgagctat ttcgccctgc tcaatccgga cacccgcaag    360

gtcgcgacga tccccgagga tctcgtcgcg ccgttcgaga ctgatttcgt caaaaagctg    420

catcgcgtgc ccaagatgcc gctcctggag cagtcgatcg atcgcgacta ttatgtccgt    480

tatttcgaca tcgatatgaa tggccacgtc aacaactcga agtatctcga ctggatgtat    540
```

gacgtcctgg gctgccagtt cctcaagacg caccagccgc tgaagatgac gctgaagtac 600
gtgaaggaag tcagcccggg cggccagatc acctccagct atcatctgga ccagctcacg 660
tcgtatcatc agatcatctc cgatggtcag ctcaacgcgc aggccatgat cgagtggcgc 720
gccattaagc agaccgagtc ggagacagac 750

<210> SEQ ID NO 58
<211> LENGTH: 1191
<212> TYPE: DNA
<213> ORGANISM: Artificial Sequence
<220> FEATURE:
<223> OTHER INFORMATION: Codon optimized Ricinus communis palmitoyl-acyl
carrier protein thioesterase sequence

<400> SEQUENCE: 58
atgggcactt gctcctatac catcaccctc cccatccgct gcctcagcaa cagtaacggc 60
caccacgacc cgcataagca gaacctgaat aagattaaga tcaatggggc ctcgacctcc 120
acccgccctc tcaagctgga tgccccgtcg cagaccgtcg gcgtcgcgac catctatctg 180
gcctcggttt cggagaatct gacgctcacg aaagaggtga tgcggcagaa catccccacg 240
aagaagcagt acatcgatcc gcatcgccag ggcctgatga tcgagggcgg agtgggctac 300
cgtcagacca tcgtgatccg cagctatgag gtcggaccgg acaagacggc gaccctggag 360
agcatcctgt atctcctcca ggaaacggcc ctgaaccatg tctggctttc gggcctcctc 420
tcgaacggct tcggcgcgac acatggcatg gtcaagaata atctgatctg ggtcgtgtcc 480
aagctccagg tccaggtcga ccattatccc atctggggcg aggtcgtcga gattgacacg 540
tgggtccgcg cgtcgggcaa gaacggcatg aagcgcgact ggctgattcg cagccaggcg 600
acgggccacg tgttcgtccg cgcgacctct acgtgggtca tgatgaacga aaagacccgc 660
cgcctctcga agatgcccga agaggtgcgc gctgagatct cgccgtggtt catcgagaag 720
caagccatca aggaagaggt gccggacaag atcgcgaagc tggatgataa ggcccgctat 780
gtcatcagca acctcaagcc gaagcgttcg gacctggata tgaaccacca tgtgaataac 840
gtgaaatatg tgcgctggat gctggagatc ctgccggacc acttcctgga gtcgcaccag 900
ctgtcgggca tcacgatgga gtaccgtcgg gagtgcggct cggcggacat cgtccagtcc 960
ctgtgcgagc ccgacggcga tgagatcttg tcgaatgaca tcccggtcct caatggtttc 1020
agcctcgcct cggagcccct gatggaaggc aacggcttcc tcgtcccgct cgacaaggtc 1080
cccctcaagt acacgcatct gctcctcacc aagggcgagt cccagaacga agagatcgtg 1140
cgcggtaaga ccatctggaa gaagaaactg tgcacgatgc cgttctccac c 1191

<210> SEQ ID NO 59
<211> LENGTH: 1176
<212> TYPE: DNA
<213> ORGANISM: Artificial Sequence
<220> FEATURE:
<223> OTHER INFORMATION: Codon optimized Ricinus communis palmitoyl-acyl
carrier protein thioesterase sequence

<400> SEQUENCE: 59
atggcctcca aaggtagcat ccgcctctat ttcccctgcg atttccggaa caccctccag 60
aagaagaaca tgaagatgga catggtcatg gcccgcagcg gcttctcgta ttcgctcaat 120
ccgatcgccc cgaagatccc ccgcttctat gtcgtcgcca atgcgtcgaa cccgcagcgc 180
gtcgacacga tcaacggcaa gaaagtgaac ggaatccacg tggcggagag ctccaactcg 240
tacgccgacc agaacaagat gaatgccaca gcggggctgg tcctggacgg caacgtggat 300

```
caccagcccc tccataagtg gctcctcggc cgtttcgtgg acgagcgcct cgtctattcg    360

cagacgttca tcatccgctc ctatgagatc ggaccggata agaccgccac tatggaaacg    420

ctgatgaatc tcctgcagga aaccgcgctc aatcacgtga cgagctcggg cctcgcgggc    480

gatggcttcg gcgcgacccg cgagatgagc ctccgcaagc tcatctgggt cgtgacccgc    540

atccatattc aggttcagcg ctattcgtgc tggggcgacg tggtcgagat cgacacgtgg    600

gtggacggcg ctggcaagaa cggcatgcgt cgcgattgga ttatccgcga ctacaatacc    660

aaggagatca tcacccgtgc gacgtccacg tgggtcatca tgaacaggga aacccggaag    720

ctgtccaaga tgccggagca agtccgccag gaactggtcc ccttctacac caatcgcatc    780

gcgattgcga aagagaacaa cgacgtcgag aagatcgaca agctgaccga cgaaacggcg    840

gagcgcatcc gctcgggcct ggcccctcgc tggtcggata tggacgcgaa ccagcacgtg    900

aacaatgtca agtacatcgg ctggatcctg gagtcggtcc cgatcaacgt ccttgaggat    960

tacaatctca cgtcgatgac cctggagtac cgtcgtgagt gccgccagtc taacctgttg   1020

gagtcgctga cctcgaccac cgagcatagt aataacaatt cgtgcaaccg gaaggcccat   1080

ctggagtata cccatctgct ccgcatgcag gccgacaagg ccgagatcgt ccgcgctcgc   1140

acggagtggc agtccaagag caatcgcaag accatc                             1176
```

<210> SEQ ID NO 60
<211> LENGTH: 1257
<212> TYPE: DNA
<213> ORGANISM: Artificial Sequence
<220> FEATURE:
<223> OTHER INFORMATION: Codon optimized Ricinus communis palmitoyl-acyl carrier protein thioesterase sequence

<400> SEQUENCE: 60

```
atggtcgcta ccgccgccgc tgccacctcc tccttcttcc ccgtcccgtc ccagtcagcc     60

gatgcgaatt tcgataaggc gcctgcctcg ctcggcggca tcaagctcaa gtcgacgagc    120

tgctcgcgcg gcctccaggt caaggcgaac gcgcaggccc ctccgaagat caatggcagc    180

tcggtgggct tcacgactag cgtggaaacc gtcaagaatg atggcgacat gccgctgccg    240

ccgccgcccc gcacgttcat caaccagctg ccggactggt ccatgctcct cgccgcgatc    300

acgaccatct tccttgcggc ggagaagcag tggatgatgc tggactggaa gccgcgcccgc    360

cccgacatgc tgatcgatcc cttcggcatc ggccgcatcg tgcaggacgg cctcattttc    420

cgccagaact tctcgatccg ctcctatgag attggcgcgg atcgcaccgc gtcgatcgag    480

acactcatga atcatctcca ggaaaccgcg ctcaaccatg tcaagacggc cggcctgctg    540

ggcgatggat tcggcagcac cccggagatg tcgaagcgga acctgatctg ggtcgtgacg    600

cgcatgcaag ttttggtcga ccgctacccc acctggggtg acgtcgtcca ggtcgacacc    660

tgggtgtcca agtccggcaa aaatggcatg cgccgcgact ggtgcgtccg cgactcgcgc    720

acgggagaaa cgctgacccg tgcgagctcg gtctgggtga tgatgaacaa gctcacccgg    780

cgtctgtcga agatcccgga agaggtcagg ggcgagatcg agccctactt cctcaactcg    840

gacccgatcg tggatgagga cagtcgtaag ctcccgaaac tggacgactc gaacgcggac    900

tatgtccgca agggcctcac gccgcgctgg tctgacctgg acatcaacca gcacgtgaac    960

aatgtcaagt acatcggctg gatcctggag tcggccccgc tccccatcct ggagtcgcac   1020

gagctgagcg ccattaccct ggagtatcgg cgcgagtgcg gccgcgacag cgtgctgcag   1080

tcgctgaccg ccgtcagcgg caacggcatc ggcaacctcg gcaatgcggg cgacatcgag   1140
```

-continued tgccagcatc tcctccgtct ggaagatggg gccgagatcg tccgcggtcg taccgagtgg 1200
cgcccgaagt attcgtccaa cttcggcatc atggggcaga tcccggtcga gtcggcc 1257

<210> SEQ ID NO 61
<211> LENGTH: 1215
<212> TYPE: DNA
<213> ORGANISM: Artificial Sequence
<220> FEATURE:
<223> OTHER INFORMATION: Codon optimized Jatropha curcas acyl-ACP thioesterase sequence

<400> SEQUENCE: 61
atggccgtgt tcacctatcg tatcgccatg ctccctatcc gctgctcctc ctcgaatagc 60
accaactcgc atagccacga tccgaaccag cagaatctcc acaagatcaa gattaacggc 120
tcggcgtccg ccatgatgcc gctcaaggtc gatctgccga gctcgctcac gatcacctcc 180
gtggcgcccg tggtggagaa tctcagcctc acgaaagagc agacccgcca gaacatcccg 240
acgaagaagc aatacatcga cccccatcgc cagggcctga tcgtcgagga gggcgtgggc 300
tatcggcaga ccgtcgtgat ccgctcgtat gaagtcggac cggataagac cgctaccctt 360
gagatcatcc tctgcctcct gcaggaaact gcgctcaacc atgtgtggct gtccggcctc 420
ctgtcgaatg gcttcggcgc cacccacggc atggtccgca acaacctcat ttgggtcgtc 480
agcaagctcc aggtccaggt cgatcagtat ccgatctggg gtgaggtcgt cgagatcgac 540
acgtgggtcg gcgcctcggg caagaacggc atgcgccgcg actggctggt ccgctcgcag 600
gccacgggcc aggtgttcgc gcgcgccacc tcgacctggg tcatgatgaa cgagaaaacc 660
cgtcggctga gcaagatgcc ggaagaagtc cgcgcggaga tcgcgccctg gttcatcgag 720
aagcaggcga tcaaagaaga ggtgcccgag aagatcgcca agctcgacga caaggcccgt 780
tacgtcgtca ccaatttgaa gccgaagcgc tccgacctgg acatgaacca gcacgtgaat 840
aacgtgaagt acgtccgctg gatgctggaa accctgccgg accagttctt cgagaatcac 900
cagctctcgg gaatcacgct ggagtacaag cgcgagtgcg gctcgtcgga catcgtcgag 960
tctctgtgcg agccggatga agaagagggc atcatcaata ccgggctcaa gcaaaacaac 1020
gacaagtcgc tgttcaatgg cttcagtctc ccctccgaga tcatggaagg caacggtttc 1080
ctgtcgtcgc tggagaaaac ccccgctcaag tatacgcatc tgctcgttgc gaagggcaag 1140
acgcagtcgg aagagatcgt gcgcggcaag accatttgga agaaaaagct gctcacgacg 1200
atgccgttct cgccc 1215

<210> SEQ ID NO 62
<211> LENGTH: 1044
<212> TYPE: DNA
<213> ORGANISM: Artificial Sequence
<220> FEATURE:
<223> OTHER INFORMATION: Codon optimized Jatropha curcas acyl-ACP thioesterase sequence

<400> SEQUENCE: 62
atggtcagca ccgcgatctc cttctccctc ctcccgatca agctcattaa agaagaaacc 60
cgcatggcct cggcggaccg ccgcaagaac agtatcgtga aggaattcgg ccatttcacg 120
tgccgctgcg ctgccatcga gaagcggatc cagaagctca acaacttcct gatcgacggc 180
ggcttcggct ccctggagca gaacggcctg atctaccgtc agaatatctt cattcgctcg 240
ttcgagatcg gcttcgaccg caagctcagc ctggccgcgc tgacgaactt cctccaggat 300

```
accgcgctca atcatgtccg catgatcggc ctcctcgccg ctggcttcgg atcgaccccg    360

gagatgtcca agaaagacct catctgggtg ctctgcacgc tgcagatcct cgtcgatcgc    420

cacccgtcgt ggctggacgc cgtcgaggtc gacacctgga tgtaccccag cggccaaaat    480

ggccaggggc gtgactggct cgttcgcgat gccaagactg gcaagcccct ggcgcaggcg    540

tcgtcggtca tggtcctgct gaacaagaaa acgcgcaagc tctccaagtt caccgaagag    600

atccgcgacg agatcgcgcc gcacatgatg atggactgca atccgattat caactcgcgc    660

aagatgctgc ccttcgacgt caacaccgcg gattatgccc gtaccggcct gacccccggt    720

tggaacgacc tcgatctcaa tcagcacgtg aatcacgtcc agtatatcaa ctggatcctc    780

cagaatgtgc tgcggagctt gatccagcat cacaagctct cggatatcac cctggagtat    840

cgcaaggaat gcgacatcaa ttcgatcctg cagttcctgt cgaagatcgt caagaacggc    900

agcaatcatt cgacggacac caataacctg atcgagctcg accattcgct cctgctggag    960

aacggctcgg agatcgccag ggcgaacacg atctggaagc cgcgcgaggt gaacaacttc   1020

aagaacgccg tgtatacgcc tgcg                                          1044
```

<210> SEQ ID NO 63
<211> LENGTH: 1071
<212> TYPE: DNA
<213> ORGANISM: Artificial Sequence
<220> FEATURE:
<223> OTHER INFORMATION: Codon optimized Jatropha curcas acyl-ACP thioesterase sequence

<400> SEQUENCE: 63

```
atggcctcga ccgcgatctc gttcctctcc atcccgatca agcttatcaa agaagaaatg     60

cgtatggcct ccgcgggccg ccgcaagaac accattgcgg cggagttcgg ccacttcacg    120

ttcggcagcg cgaccgtcga gaagaaagtc cagaagtcga ataacttcct catcgacggc    180

ggcttcggct cgctggagca gaacggactg atctaccggc agaacatctt cgtccgctcc    240

ttcgagatcg gcttcgatcg caagctgagc ctcgcggccc tgaccaattt cctgcaggac    300

accgcgctca accattgccg catgatcggg ctcctcgctg agggtttcgg ctccacgccg    360

gagatgatca aaaaggactt gatctgggtg ctgtgcacgc tccagatcct cgtcgacggc    420

tatccgagct ggctcgatgt ggtcgaggtc gacacctgga tgtatccctc gggccagaat    480

ggactgggcc gtggctggct cgtccgcgac ggtaagaccg gccgcagcct ggcccagtcg    540

tcatcggtca tggtgtcctt caataagaaa acccggaagc tgtcgaagct ggcgaaggaa    600

atccgcgacg agatcgcccc tcacatgatg gattgcgacc cgatcatgaa caagaactcg    660

cgcaagatcc tcccgttcga cgtgaatacg gcggactatg ctcgcacggg cctcacgccc    720

ggctggaatg aactggatct gaaccagcac gtgaaccatg tccagtacat caactggatc    780

ctccagaacg tgcgcccgtc gctcgtccag catcataagc tctcggccat tacgctggag    840

tatcgcaaag agtgcgacat gaactccatc ctgcaatcgc tctcgcgcat cgtgaagaac    900

ggcggcaacg acagcaccga taagaataac gtcatcgagc tcgaccactt cctcctgctg    960

gagaatggca gtgagattgc ccgtgccaat accatctgga agccccgcga ggtcaataac   1020

ttcaagaacg ttgtccattc gcccgccgaa gagaatatct ctagcatgaa c            1071
```

<210> SEQ ID NO 64
<211> LENGTH: 396
<212> TYPE: DNA
<213> ORGANISM: Artificial Sequence
<220> FEATURE:

<223> OTHER INFORMATION: Codon optimized E. Coli FadM sequence

<400> SEQUENCE: 64
atgcaaaccc agatcaaggt ccgcggatac catctcgatg tctatcagca tgtcaataac 60
gcccgttatc tcgaattcct cgaagaggcg cggtgggacg gcctggagaa ctcggactcg 120
ttccagtgga tgacggccca caacattgcg ttcgtggtgg tcaatatcaa catcaattac 180
cgccgcccgg cggtcctgtc cgatctgctc acgatcacct cgcagctcca gcagctgaac 240
ggcaagtcgg gcatcctcag ccaggtcatc acgctggagc ccgagggcca ggtcgtggcc 300
gacgctctga tcaccttcgt gtgcatcgac ctcaagaccc agaaagcgct ggccctcgaa 360
ggcgagctgc gcgagaagtt ggagcagatg gttaag 396

<210> SEQ ID NO 65
<211> LENGTH: 957
<212> TYPE: DNA
<213> ORGANISM: Artificial Sequence
<220> FEATURE:
<223> OTHER INFORMATION: Codon optimized E. Coli AccA sequence

<400> SEQUENCE: 65
atgtcgctca acttcctgga cttcgaacaa cccatcgccg agctcgaagc gaagatcgat 60
tccctcaccg ccgtcagccg ccaggatgag aagctcgaca tcaatatcga cgaggaggtg 120
catcgcctgc gggagaagtc cgtcgagctc acccgcaaga tcttcgccga tctgggcgcg 180
tggcagatcg ctcagctcgc gcgtcatccg cagcgcccgt acacgctgga ctatgtgcgc 240
ctggcgttcg acgagttcga cgagctggcc ggtgatcgcg cctacgccga tgacaaggcc 300
atcgtcggcg gcatcgcgcg tctggacggc cgtccggtga tgatcatcgg ccaccagaaa 360
ggccgcgaaa ccaaagagaa gatccgccgc aacttcggca tgcctgcccc cgagggctat 420
cgcaaggccc tccgcctcat gcagatggcc gagcgcttca agatgccgat tatcaccttc 480
atcgatacgc cgggcgcgta tccgggcgtc ggagccgagg aacgcggcca gagcgaggcg 540
atcgcgcgca atctccgcga gatgtcgcgc ctgggcgtcc ccgttgtctg caccgtgatc 600
ggcgagggcg gctcgggcgg tgccttggcc atcggcgtcg gcgacaaggt caacatgctc 660
cagtattcca cgtacagcgt catcagcccc gaggggtgcg cgtcgattct ctggaagtcg 720
gcggacaagg ctccgctcgc ggctgaggcg atgggcatca ttgcgccgcg cctgaaagaa 780
ctgaagctca tcgactcgat catcccggag cccctgggcg gagcccaccg taaccccgag 840
gccatggcgg cgtcgctgaa ggcccagctg ctcgcggacc tggcggacct cgatgtgctc 900
tcgaccgagg acctgaagaa taggcgctat cagcggctga tgtcgtacgg ctatgcg 957

<210> SEQ ID NO 66
<211> LENGTH: 468
<212> TYPE: DNA
<213> ORGANISM: Artificial Sequence
<220> FEATURE:
<223> OTHER INFORMATION: Codon optimized E. Coli AccB sequence

<400> SEQUENCE: 66
atggacattc gcaaaatcaa gaaactcatc gaactggtcg aggaaagcgg catttcggaa 60
ctggagatct cggaaggtga agagtcggtg cgtatctcgc gcgcggcccc tgcggcgtcg 120
ttccccgtca tgcagcaagc gtatgccgct ccgatgatgc agcagccggc gcagtccaat 180
gcggcggccc cggccaccgt cccgagcatg gaagcgccgg cggccgctga gatctcgggc 240
catatcgtgc gcagccccat ggtcggaacg ttctaccgca ccccgtcccc cgacgcgaag 300
gccttcatcg aagttggcca aaaggtcaac gtgggcgata cgctctgcat cgtcgaggcc 360
atgaagatga tgaaccagat cgaggccgat aagtccggca ccgtgaaggc catcctggtc 420
gagtcgggcc agcccgtcga gttcgacgag ccgctcgtcg tgatcgag 468

<210> SEQ ID NO 67
<211> LENGTH: 1347
<212> TYPE: DNA
<213> ORGANISM: Artificial Sequence
<220> FEATURE:
<223> OTHER INFORMATION: Codon optimized E. Coli AccC sequence

<400> SEQUENCE: 67
atgttggata agatcgtcat cgccaatcgc ggagaaatag ccctcaggat tctcagagct 60
tgcaaagaac tcggaatcaa gactgtcgcg gtccactcca gcgcggaccg cgatctcaag 120
catgtcctgc tggcggacga aacggtctgc atcggccccg ccccctcggt caagtcctat 180
ctgaacatcc ccgccatcat ctctgccgcg gagatcaccg ggcggtggc tatccacccc 240 ggctacggct tcctctcgga gaatgccaac ttcgcggaac aggtcgagcg ctcgggcttc 300
atcttcatcg gcccgaaggc cgagacaatt cgcctgatgg gcgacaaggt gtcggccatc 360
gcggccatga agaaagcggg cgtcccgtgc gtgccgggct cggacggccc tctcggcgac 420
gacatggata agaaccgcgc gatcgcgaag cgcatcggct acccggtcat catcaaggcc 480
agcggtggcg gcggcggccg tggcatgcgc gtcgtgcgcg gtgacgcgga gctcgcgcag 540
tcgatctcca tgacccgggc tgaggccaag gccgccttct cgaacgacat ggtgtatatg 600
gagaagtacc tcgaaaatcc gcggcacgtt gagattcagg tcctcgccga cgggcagggc 660
aatgcgatct atctggcgga gcgcgattgc tccatgcagc gtcgccatca gaaggtcgtc 720
gaggaagcgc cggctccggg tattaccccc gagcttcgcc gctatatcgg cgagcgctgc 780
gcgaaggcct gcgtggacat tggctatcgc ggcgcgggca cgttcgagtt cctgttcgag 840
aacggcgagt tctacttcat cgagatgaac acgcgcatcc aggtcgagca cccggtgacc 900
gagatgatca cgggcgtgga cctgatcaag gaacagctcc gcatcgccgc gggccagccc 960
ctgagcatca agcaagaaga ggtgcacgtc cggggccatg cggtggagtg ccgcatcaac 1020
gccgaggacc cgaatacctt cctcccgtcg ccgggcaaga tcacccgctt ccatgcccct 1080
ggcggcttcg gagtccgctg ggagtcccat atctacgccg gctataccgt cccgccctat 1140
tatgattcga tgatcggaaa gctcatctgc tacggcgaga accgtgacgt ggcgatcgcg 1200
cgtatgaaga acgccctgca ggaactgatc atcgacggca tcaagaccaa tgtcgacctc 1260
cagatccgca tcatgaacga cgagaatttc cagcatggcg gcaccaacat ccattacctg 1320
gagaagaaac tgggcctgca agagaag 1347

<210> SEQ ID NO 68
<211> LENGTH: 912
<212> TYPE: DNA
<213> ORGANISM: Artificial Sequence
<220> FEATURE:
<223> OTHER INFORMATION: Codon optimized E. Coli AccD sequence

<400> SEQUENCE: 68
atgagctgga tcgaacgcat caaaagcaac attaccccta cccgcaaggc ttccatcccc 60
gagggcgtct ggacgaagtg cgactcgtgc ggccaggtcc tctaccgcgc ggagctggag 120
cgcaacctcg aagtctgccc caagtgcgac catcacatgc gcatgacggc gcgcaatcgc 180

-continued ctgcacagcc tgctggacga gggttccctc gtggagctgg gatcggagtt ggagccgaag 240
gatgtcctca agttccgcga ctcgaagaag tataaggatc ggctggcgtc ggcccagaaa 300
gaaacgggcg agaaagacgc cctcgtggtc atgaagggca ccctctatgg catgccggtc 360
gtcgcggcgg cgttcgagtt cgccttcatg ggcggctcga tgggctcggt cgtcggcgct 420
cgcttcgtcc gggcggtgga gcaggccctg gaagataatt gcccgctgat ctgcttctcg 480
gcgagcggtg gcgctcgtat gcaagaagcc ctgatgtcgc tcatgcagat ggccaagacc 540
tccgccgccc tggcgaagat gcaggaacgc gggctcccgt acatctccgt gctcaccgac 600
ccgaccatgg gcggcgtgtc ggcgtcgttc gccatgctcg gcgacctgaa catcgccgag 660
ccgaaggccc tcatcggctt cgccggaccg cgcgtcatcg agcagacggt gcgcgagaag 720
ctgcccccgg gcttccagag gtcggagttc ctgatcgaga agggcgcgat cgacatgatc 780
gtgcgccgtc cggagatgcg cctcaagctg gcgtcgatcc tcgccaagct gatgaacctc 840
ccggccccga accccgaggc gccccgtgag ggcgtggtcg ttccgcccgt cccggaccag 900
gaacccgagg cg 912

<210> SEQ ID NO 69
<211> LENGTH: 744
<212> TYPE: DNA
<213> ORGANISM: Artificial Sequence
<220> FEATURE:
<223> OTHER INFORMATION: Codon optimized E. Coli FabD sequence

<400> SEQUENCE: 69
atgacacagt tcgcattcgt attcccagga caaggatcac agacagttgg aatgttagca 60
gatatggcag catcataccc aatagtagag gaaacatttg cagaggcatc agcagcatta 120
ggatacgact tatgggcact aacacaacag ggaccagcag aagagttaaa caagacatgg 180
cagacacagc cagcactatt aacagcatca gtagcattat acagggtatg gcagcaacag 240
ggtggaaagg caccagcaat gatggcagga cactcattag gagagtattc agcattagta 300
tgcgcaggag taatagactt cgcagacgca gtaaggttag tagagatgag ggaaagttt 360 atgcaggaag cagtaccaga gggaacagga gcaatggcag ctataatagg attagatgac 420
gcatcaatag caaaggcatg cgaggaggca gcagagggac aggtagtatc accagtaaac 480
ttcaactcac caggacaagt agtaatagca ggacacaaag aggcagtaga gagagctgga 540
gcagcatgta aggcagctgg agcaaaaagg gcattaccat taccagtatc agtaccatca 600
cattgcgcat taatgaagcc agcagcagac aagttagcag tagagttagc aaagataaca 660
ttcaacgcac caacagtacc agtagtaaac aatgtagatg taaagtgcga aacaaacggt 720
gacgcaataa gggacgcatt agta 744

<210> SEQ ID NO 70
<211> LENGTH: 549
<212> TYPE: DNA
<213> ORGANISM: Artificial Sequence
<220> FEATURE:
<223> OTHER INFORMATION: Codon optimized E. Coli TesA sequence with
periplasmic targeting sequence removed

<400> SEQUENCE: 70
atggcagaca cattattaat attaggagac tcattatcag ctggatacag aatgtcagca 60
tcagcagcat ggccagcatt attaaatgac aagtggcaga gtaagacatc agtagtaaac 120
gcatcaatat ctggagatac atcacagcaa ggattagcaa ggctaccagc attactaaag 180

-continued

```
cagcaccagc ctagatgggt attagtagag cttggaggaa atgatggatt aaggggattc    240

cagccacagc agacagagca gacattaagg cagatattac aagacgtaaa ggcagcaaac    300

gcagagccat tactaatgca gataaggtta ccagcaaact acggaagaag gtataacgaa    360

gcattctcag caatataccc aaagttagca aaagagtttg acgtaccact attaccattc    420

tttatggaag aagtatactt aaagccacag tggatgcaag atgacggaat acatccaaac    480

agggacgcac agccattcat agcagattgg atggcaaaac agttacagcc attagtaaac    540

cacgactca                                                            549
```

<210> SEQ ID NO 71
<211> LENGTH: 1146
<212> TYPE: DNA
<213> ORGANISM: Artificial Sequence
<220> FEATURE:
<223> OTHER INFORMATION: Codon optimized Cinnamomum camphorum thioesterase sequence

<400> SEQUENCE: 71

```
atggcaacaa catcattagc atcagcattt tgcagtatga aagcagtaat gttagcaagg     60

gacggaaggg gaatgaagcc taggtcatca gatttacagt taagggcagg aaacgcacag    120

acatcattaa agatgataaa tggaacaaag ttctcataca cagagtcatt aaagaaatta    180

ccagactggt caatgttatt cgcagtaata acaacaatat tctcagcagc agagaagcag    240

tggacaaact tagagtggaa gccaaagcca aacccaccac agttattaga cgatcacttc    300

ggaccacacg gattagtatt taggagaaca ttcgcaataa gatcatacga ggtaggacca    360

gacaggtcta catcaatagt agctgtaatg aaccatttac aagaagcagc attaaaccac    420

gcaaagtcag ttggaatact aggtgacgga ttcggaacaa cattagagat gtcaaaaagg    480

gacctaatat gggtagtaaa gagaacacat gtagcagtag aaaggtaccc agcatgggga    540

gacacagtag aggtagagtg ctgggtagga gcatcaggaa ataacggaag gagacacgac    600

ttcttagtaa gggattgcaa gacaggtgag atactaacaa gatgcacatc attatcagta    660

atgatgaaca ctaggacaag gagactttca aagataccag aagaagtaag gggagagata    720

ggaccagcat tcatagacaa cgtagcagta aaagatgaag agataaagaa gccacaaaag    780

ttaaacgatt caacagcaga ctatatacag ggaggattaa caccaaggtg gaatgactta    840

gacataaacc agcacgtaaa caatataaaa tatgtagact ggatactaga gacagtacca    900

gattcaatat tcgagtcaca ccatatatca tcatttacaa ttgagtacag aagagagtgc    960

acaatggact cagtattaca gtcattaaca acagtatctg gaggatcatc agaggctgga   1020

ctagtatgtg agcacttatt acagttagag ggaggatcag aggtattaag ggcaaagaca   1080

gagtggaggc caaagttaac agatagtttt aggggaatat cagtaatacc agcagagtca   1140

tcagta                                                              1146
```

<210> SEQ ID NO 72
<211> LENGTH: 1146
<212> TYPE: DNA
<213> ORGANISM: Artificial Sequence
<220> FEATURE:
<223> OTHER INFORMATION: Codon optimized Umbellularia californica thioesterase sequence

<400> SEQUENCE: 72

```
atggcaacaa caagtttagc atcagcattt tgcagtatga aggcagtaat gttagcaagg     60

gacggaaggg gaatgaagcc aaggtcatca gatttacagt taagggcagg aaacgcacca    120
```

acatcattaa agatgataaa cggaacaaag ttctcataca cagagtcact aaaaagatta 180
ccagactggt caatgctttt tgcagtaata acaacaatat tctcagcagc agagaagcaa 240
tggacaaact tagaatggaa gccaaagcca aagttaccac agttattaga cgatcacttt 300
ggattacacg gattagtatt cagaagaaca ttcgctataa ggtcttatga ggtaggacca 360
gacaggtcaa catcaatact agcagtaatg aaccacatgc aagaagcaac attaaaccac 420
gcaaagtcag ttggaatact aggagatgga ttcggaacaa cattagagat gtcaaaaagg 480
gacttaatgt gggtagtaag aagaacacac gtagcagtag aaaggtaccc aacatgggga 540
gacacagtag aggtagagtg ctggatagga gcatcaggta ataacggaat gagaagggac 600
ttcttagtaa gggactgcaa gacaggagag atactaacaa ggtgcacttc attatcagta 660
ctaatgaata caaggacaag aaggctatca acaataccag atgaagtaag gggagaaata 720
ggaccagcat tcatagacaa tgtagcagta aaagacgatg agataaagaa attacagaag 780
ttaaacgact caacagcaga ttacatacag ggaggattaa cacctaggtg gaacgactta 840
gacgtaaatc agcacgtaaa caacttaaag tacgtagcat gggtatttga gacagtacca 900
gactcaatat tcgagtcaca ccatatatca tcattcacat tagagtatag aagagagtgt 960
acaagggatt cagtattaag gtcattaaca acagtatctg gaggatcatc agaggctgga 1020
ttagtatgcg accatctatt acagttagag ggaggatcag aggtattaag ggcaaggaca 1080
gagtggaggc caaagttaac agactcattc aggggaatat cagtaatacc agcagagcca 1140
agggta 1146

<210> SEQ ID NO 73
<211> LENGTH: 750
<212> TYPE: DNA
<213> ORGANISM: Artificial Sequence
<220> FEATURE:
<223> OTHER INFORMATION: Codon optimized Streptococcus pyogenes acyl-ACP thioesterase sequence

<400> SEQUENCE: 73
atgggattat catatcaaga agagttaaca ttaccatttg agttatgcga cgtaaagtca 60
gacataaagt taccattact attagattat tgcttaatgg tatctggaag gcaatcagta 120
cagttaggaa gatcaaacaa caacttatta gtagactata agttagtatg gatagtaaca 180
gactacgaga taacaataca caggttacca cacttccaag agacaataac aatagagaca 240
aaggcattat catacaacaa gtttttctgt tacaggcagt tctacatata cgaccaagag 300
ggatgcttac tagtagacat actatcatac ttcgcattac taaacccaga tacaagaaag 360
gtagcaacaa taccagagga tttagtagca ccattcgaaa cagactttgt aaagaaatta 420
cacagggtac caaagatgcc attactagag cagtcaatag atagggacta ctatgtaagg 480
tacttcgaca tagacatgaa tggacatgta aacaactcaa agtacttaga ctggatgtac 540
gacgtattag gttgccagtt cttaaagaca caccagccat taaagatgac attaaaatac 600
gtaaaagaag tatcacctgg aggacagata acttcatcat atcatttaga tcagttaaca 660
tcataccacc agataatatc agatggacag ttaaatgcac aggcaatgat agagtggaga 720
gcaataaagc agacagagag tgagacagac 750

<210> SEQ ID NO 74
<211> LENGTH: 1191
<212> TYPE: DNA
<213> ORGANISM: Artificial Sequence
<220> FEATURE:
<223> OTHER INFORMATION: Codon optimized Ricinus communis palmitoyl-acyl carrier protein thioesterase sequence

<400> SEQUENCE: 74
atgggaacat gctcatacac aataacatta ccaataagat gcttatcaaa ctcaaacgga 60
caccacgacc cacataagca gaacttaaac aagataaaga taaatggagc atctacatca 120
acaaggccat taaagttaga cgcaccatca cagacagttg gagtagcaac aatatactta 180
gcatcagtat cagagaactt aactttaaca aaagaagtaa tgagacagaa tataccaaca 240
aagaagcagt acatagatcc acacaggcag ggattaatga tagagggtgg agtaggatat 300
aggcagacaa tagtaataag atcttacgag gtaggaccag acaagacagc aacattagag 360
tcaatactat acttattaca agagacagca ttaaaccacg tatggttatc aggactatta 420
tcaaacggat tcggagcaac acatggaatg gtaaagaata acctaatatg ggtagtatca 480
aagttacagg tacaggtaga ccactaccca atatggggag aggtagtaga gatagacaca 540
tgggtaaggg caagtggaaa gaacggaatg aaaagggact ggttaataag atcacaagca 600
acaggacatg tatttgtaag ggcaacatca acatgggtaa tgatgaatga gaaaactaga 660
aggctatcaa agatgccaga ggaagtaagg gcagagatat caccatggtt catagagaag 720
caagcaataa aagaagaagt acctgataag attgctaagt tagacgacaa ggcaaggtat 780
gtaatatcaa acttaaagcc aaaaagatca gacttagaca tgaaccatca cgtaaacaat 840
gtaaaatatg taaggtggat gttagagata ttaccagatc acttcttaga gtcacaccag 900
ttaagtggaa taacaatgga gtacaggaga gagtgtggat cagcagacat agtacagtca 960
ttatgcgagc cagacggaga tgagatacta tcaaacgata taccagtact aaatggattt 1020
tcattagcat cagagccatt aatggaagga aacggattct tagtaccatt agataaggta 1080
ccattaaagt acacacactt actattaaca aagggagagt cacagaacga agagatagta 1140
aggggaaaga caatatggaa gaaaaagtta tgcacaatgc cattctcaac a 1191

<210> SEQ ID NO 75
<211> LENGTH: 1176
<212> TYPE: DNA
<213> ORGANISM: Artificial Sequence
<220> FEATURE:
<223> OTHER INFORMATION: Codon optimized Ricinus communis palmitoyl-acyl carrier protein thioesterase sequence

<400> SEQUENCE: 75
atggcatcaa agggatcaat aaggctatac tttccatgcg acttcaggaa cacactacag 60
aagaagaata tgaagatgga catggtaatg gcaaggtcag gattttcata ctcattaaac 120
ccaatagcac caaagatacc aaggttctat gtagtagcaa atgcatcaaa tccacagagg 180
gtagatacaa taaacggaaa gaaagtaaac ggaatacacg tagcagagtc atcaaactca 240
tacgcagacc agaataagat gaacgcaaca gcaggattag tattagacgg aaacgtagat 300
catcagccat tacacaagtg gttattaggt aggttcgtag acgagaggtt agtatattca 360
cagacattca taataagatc atacgagata ggaccagaca agacagcaac aatggagaca 420
ttaatgaact tattacaaga gacagcatta aaccacgtaa catcaagtgg attagcagga 480
gatggattcg gagcaacaag agagatgtca ttaagaaagc taatatgggt agtaacaagg 540
atacacatac aggtacaaag gtactcatgc tggggagatg tagtagagat agatacatgg 600
gtagacggag ctggaaagaa cggaatgaga agggactgga taataaggga ttacaacaca 660

```
aaagaaataa taacaagggc aacatcaaca tgggtaataa tgaataggga aactagaaag    720

ttatcaaaga tgccagaaca ggtaaggcag gaattagtac cattctacac aaataggata    780

gcaatagcaa aagagaataa cgacgttgag aagatagata agttaacaga cgagacagca    840

gaaaggataa ggtctggatt agcaccaaga tggagtgaca tggacgcaaa ccagcacgta    900

aacaacgtaa agtacatagg atggatacta gagtcagtac caataaacgt attagaggac    960

tataacttaa cttcaatgac attagagtac agaagagagt gcaggcagtc aaacttatta   1020

gagtcattaa catcaacaac agagcattca aacaacaatt cttgtaacag gaaagcacac   1080

ttagagtata cacacttact aagaatgcaa gcagacaagg cagagatagt aagggcaagg   1140

acagagtggc agtcaaagtc aaacagaaag acaata                             1176
```

<210> SEQ ID NO 76
<211> LENGTH: 1257
<212> TYPE: DNA
<213> ORGANISM: Artificial Sequence
<220> FEATURE:
<223> OTHER INFORMATION: Codon optimized Ricinus communis palmitoyl-acyl carrier protein thioesterase sequence

<400> SEQUENCE: 76

```
atggtagcaa cagcagcagc agcaacatca tcattctttc cagtaccatc acagtcagca     60

gatgcaaact tcgataaggc accagcatca ttaggaggaa taaagttaaa gtcaacttca    120

tgctcaaggg gactacaggt taaggcaaac gcacaggcac caccaaagat aaacggatca    180

tctgtaggat ttacaacatc agtagagaca gtaaagaacg acggagacat gccattacca    240

ccaccaccaa gaacattcat aaaccagtta ccagattggt caatgttatt agcagcaata    300

acaacaatat tcttagcagc agagaagcaa tggatgatgt tagattggaa gccaagaagg    360

ccagacatgt taatagaccc atttggaata ggaaggatag tacaagacgg attaatattc    420

aggcagaatt tctcaataag atcatacgag ataggagcag acaggacagc atcaatagag    480

acattaatga atcacttaca ggaaacagca ttaaaccatg taaagacagc aggactatta    540

ggtgacggat tcggatcaac accagagatg tcaaaaagaa acctaatatg ggtagtaaca    600

agaatgcaag tattagtaga taggtatcca acatggggag atgtagtaca ggtagacaca    660

tgggtatcaa agagtggaaa gaacggaatg agaagggact ggtgcgtaag ggactcaagg    720

acaggagaga cactaacaag ggcatcatca gtatgggtaa tgatgaataa gttaacaaga    780

aggctatcaa agataccaga agaagtaagg ggagagatag agccatactt cttaaactca    840

gacccaatag tagacgaaga ttctaggaaa ttaccaaagt tagacgattc aaacgcagac    900

tacgtaagga aaggattaac acctaggtgg agtgatttag acataaatca gcacgtaaac    960

aatgtaaagt acataggatg gattttagag tcagcaccat taccaatact agagtcacac   1020

gagttatcag caataacatt agagtataga agagagtgcg gaagggactc agtattacag   1080

tcattaacag cagtatcagg aaacggaata ggaaacttag gaaacgctgg agacatagaa   1140

tgtcagcact tactaaggtt agaggacgga gcagagatag taaggggaag gacagagtgg   1200

aggccaaagt actcatcaaa ctttggaata atgggacaga taccagtaga gtctgca      1257
```

<210> SEQ ID NO 77
<211> LENGTH: 1215
<212> TYPE: DNA
<213> ORGANISM: Artificial Sequence
<220> FEATURE:
<223> OTHER INFORMATION: Codon optimized Jatropha curcas acyl-ACP thioesterase sequence -continued

<400> SEQUENCE: 77
atggcagtat ttacatacag aatagcaatg ttaccaataa gatgttcatc atcaaactca 60
acaaattcac actcacacga cccaaaccaa cagaatttac acaagataaa gataaacgga 120
tcagcttcag caatgatgcc attaaaggta gacttaccat catcattaac aataacatca 180
gtagcaccag tagtagagaa cttatcttta acaaaagagc agacaaggca gaacatacca 240
acaaagaagc agtatataga cccacatagg cagggactaa tagtagagga gggtgtagga 300
tacaggcaga cagtagtaat aagatcatac gaggtaggac cagacaagac agcaacatta 360
gagataatac tatgcttatt acaagagaca gcattaaacc acgtatggtt atcaggatta 420
ctatcaaacg gatttggagc aacacacgga atggtaagaa ataacctaat atgggtagta 480
tcaaagttac aggtacaggt agaccagtac ccaatatggg gagaggtagt agagatagac 540
acatgggtag gagcatctgg aaagaacgga atgagaaggg attggttagt aaggtcacag 600
gcaactggac aggttttcgc aagggcaaca agtacatggg taatgatgaa tgagaaaaca 660
agaaggctat caaagatgcc agaggaagta agggcagaga tagcaccatg gttcatagag 720
aagcaagcaa taaaagaaga agtaccagag aagatagcaa agttagacga taaggcaagg 780
tatgtagtaa caaacttaaa gcctaagagg tcagatttag acatgaatca acatgtaaac 840
aacgtaaaat acgtaaggtg gatgttagag acattaccag accagttctt cgagaaccac 900
cagttaagtg gaataacttt agagtataag agagagtgcg gatcatcaga tatagtagag 960
tcattatgcg agccagatga agaagaggga ataataaaca caggattaaa gcagaacaac 1020
gacaagtcat tattcaatgg attctcatta ccatcagaga taatggaagg aaacggattc 1080
ttatcatcat tagaaaagac accattaaag tacacacact tattagtagc aaagggaaag 1140
acacagtcag aggaaatagt aaggggaaag acaatatgga agaaaaagtt actaacaaca 1200
atgccatttt cacca 1215

<210> SEQ ID NO 78
<211> LENGTH: 1044
<212> TYPE: DNA
<213> ORGANISM: Artificial Sequence
<220> FEATURE:
<223> OTHER INFORMATION: Codon optimized Jatropha curcas acyl-ACP thioesterase sequence

<400> SEQUENCE: 78
atggtatcaa cagcaatatc attttcacta ttaccaataa agttaataaa agaagagaca 60
agaatggcat cagcagatag gagaaagaac tcaatagtaa aagaattcgg acacttcaca 120
tgcagatgtg cagcaataga gaagagaata caaaagttaa acaacttctt aatagacgga 180
ggattcggat cattagagca aaatggatta atatataggc agaacatatt cataaggtca 240
ttcgagatag gattcgacag aaagttatca ttagcagcat taactaattt cttacaggat 300
acagcattaa accacgtaag aatgatagga ttactagctg caggatttgg atcaacacca 360
gagatgtcaa agaaagactt aatatgggta ttatgcacat tacagatatt agtagacagg 420
cacccatctt ggttagacgc agtagaggta gacacatgga tgtacccatc aggacagaac 480
ggacagggaa gggactggtt agtaagggac gcaaagacag gaaagccatt agcacaggca 540
tcaagtgtaa tggtattatt aaacaaaaag acaaggaagc tatcaaagtt cacagaagag 600
ataagggacg agatagcacc acacatgatg atggactgca acccaataat aaattctagg 660
aagatgttac cattcgatgt aaatacagca gattacgcaa ggacaggatt aacaccaggt 720

-continued

```
tggaacgatt tagacttaaa tcagcatgta aaccatgtac agtacataaa ctggatatta    780

cagaacgtat taaggtcact aatacagcat cacaagttat cagatataac attagagtac    840

agaaaggaat gcgacataaa ctcaatacta cagtttctat caaagatagt taagaatgga    900

tcaaaccact caacagacac aaataactta atagagttag accactcatt actattagag    960

aacggatcag agatagcaag ggcaaacaca atatggaagc caagagaagt aaacaacttt   1020

aagaacgcag tatatacacc agca                                           1044
```

<210> SEQ ID NO 79
<211> LENGTH: 1071
<212> TYPE: DNA
<213> ORGANISM: Artificial Sequence
<220> FEATURE:
<223> OTHER INFORMATION: Codon optimized Jatropha curcas acyl-ACP thioesterase sequence

<400> SEQUENCE: 79

```
atggcatcaa ctgcaatatc attcttaagt ataccaataa agttaataaa agaagagatg     60

agaatggcat ctgcaggaag gagaaagaac acaatagcag cagagttcgg acattttaca    120

ttcggatcag caacagtaga gaaaaaagta cagaagtcaa ataacttcct aatagacgga    180

ggatttggat cattagagca gaacggatta atatacaggc agaacatatt tgtaaggtca    240

tttgagatag gattcgatag aaagttatca ttagcagcat taacaaactt cttacaggac    300

acagcattaa accactgcag aatgatagga ttactagcag agggattcgg atcaacacca    360

gagatgataa agaaagattt aatatgggta ttatgtacat tacagatatt agtagacgga    420

tatccaagtt ggctagacgt agtagaggta gatacatgga tgtacccatc aggacaaaac    480

ggattaggta ggggatggtt agtaagggac ggaaagacag gaaggtcatt agcacagtca    540

tcatcagtaa tggtatcatt caataagaaa acaaggaaac tatcaaagtt agcaaaggag    600

ataagggacg agatagcacc acacatgatg gactgcgacc caataatgaa caagaactca    660

agaaagatat taccattcga cgtaaataca gctgattatg caaggacagg tttaacacca    720

ggatggaacg aattagactt aaaccaacac gtaaatcacg tacagtacat aaactggata    780

ttacagaatg taaggccatc attagttcag catcacaagt tatcagcaat tacattagag    840

tacagaaaag agtgcgacat gaattctata ctacagtcat tatcaaggat agtaaagaac    900

ggaggaaacg attcaacaga caagaacaac gtaatagagt tagaccactt cttactatta    960

gagaacggat cagagatagc aagggcaaac acaatatgga agccaagaga agtaaacaac   1020

tttaagaatg tagtacactc accagcagaa gagaacatat catcaatgaa t            1071
```

<210> SEQ ID NO 80
<211> LENGTH: 396
<212> TYPE: DNA
<213> ORGANISM: Artificial Sequence
<220> FEATURE:
<223> OTHER INFORMATION: Codon optimized E. Coli FadM sequence

<400> SEQUENCE: 80

```
atgcagacac agataaaggt aaggggatat cacttagacg tataccaaca cgtaaacaac     60

gcaaggtact tagagttctt agaagaagca agatgggatg gattagagaa ctcagattca    120

ttccagtgga tgacagcaca taacatagca tttgttgtag taaacataaa tataaactac    180

agaaggccag cagtattatc agacctatta acaataacat cacagttaca gcagttaaat    240

ggaaagtcag gaatactatc acaggtaata acattagagc cagagggaca ggtagtagca    300
```

gacgcactaa taacattcgt atgcatagac ttaaagacac aaaaggcatt agcattagag 360
ggagagttaa gggagaaatt agagcagatg gtaaag 396

<210> SEQ ID NO 81
<211> LENGTH: 957
<212> TYPE: DNA
<213> ORGANISM: Artificial Sequence
<220> FEATURE:
<223> OTHER INFORMATION: Codon optimized E. Coli AccA sequence

<400> SEQUENCE: 81
atgtcattaa acttcttaga tttcgagcag ccaatagcag agttagaggc aaagatagac 60
tcattaacag cagtatcaag gcaagatgag aagttagaca taaacataga cgaagaagta 120
cataggttaa gggagaagtc agtagagtta acaagaaaga tattcgcaga cttaggagca 180
tggcagatag cacagctagc aaggcaccca cagaggccat acacattaga ctatgtaagg 240
ttagcattcg acgagttcga tgagcttgca ggagacaggg catacgcaga cgataaggca 300
atagtaggag gaatagcaag gttagacgga aggccagtaa tgataatagg acaccaaaag 360
ggaagggaga caaaagagaa gataagaaga aactttggaa tgcctgctcc agagggatac 420
agaaaggcat taaggttaat gcagatggca gaaaggttta agatgccaat aataacattc 480
atagacacac caggagcata cccaggagta ggagcagagg aaaggggaca gagtgaggca 540
atagcaagaa acttaaggga aatgtcaagg ttaggtgtac cagtagtatg cacagtaata 600
ggagagggag gatctggagg agcattagca ataggagtag gtgacaaggt aaacatgtta 660
cagtactcaa catattcagt aatatcacca gagggatgcg catcaatact atggaaatca 720
gcagataagg caccattagc tgcagaggca atgggaataa tagcaccaag gctaaaagaa 780
ctaaagttaa tagactcaat aataccagag ccattaggag gagcacacag aaatccagag 840
gcaatggcag catcattaaa ggcacagcta ttagcagatt tagcagactt agatgtatta 900
tcaacagagg acttaaagaa tagaagatac cagaggttaa tgtcatacgg atatgca 957

<210> SEQ ID NO 82
<211> LENGTH: 468
<212> TYPE: DNA
<213> ORGANISM: Artificial Sequence
<220> FEATURE:
<223> OTHER INFORMATION: Codon optimized E. Coli AccB sequence

<400> SEQUENCE: 82
atggacataa gaaagataaa gaaattaata gagttagtag aagagtcagg aatatcagag 60
ttagaaatat cagagggaga ggaatcagta agaatatcaa gggcagctcc agcagcatca 120
ttcccagtaa tgcaacaggc atacgcagca ccaatgatgc agcagcctgc acagagtaac 180
gcagcagcac cagcaacagt accatcaatg gaagcaccag cagcagcaga gatatctgga 240
cacatagtaa ggtcaccaat ggtaggaaca ttctatagga caccatcacc agacgcaaag 300
gcattcatag aggtaggaca aaaggtaaac gttggagata cattatgcat agtagaggca 360
atgaagatga tgaatcagat agaggcagat aagtcaggaa cagtaaaggc aatactagta 420
gagtcaggac agccagtaga gtttgacgag ccattagtag taatagag 468

<210> SEQ ID NO 83
<211> LENGTH: 1347
<212> TYPE: DNA
<213> ORGANISM: Artificial Sequence
<220> FEATURE:

<223> OTHER INFORMATION: Codon optimized E. Coli AccC sequence

<400> SEQUENCE: 83
atgttagaca agatagtaat agcaaatagg ggagagatag cattaagaat actaagggca 60
tgcaaagagt taggaataaa gacagtagct gtacactcat cagcagacag ggacttaaaa 120
catgtattac tagcagatga gacagtttgt ataggaccag caccatcagt aaagtcatac 180
ttaaacatac cagcaataat atcagcagca gagataacag gagcagtagc aatacaccca 240
ggatacggat tcttatcaga aaacgcaaat ttcgcagagc aagtagagag atcaggattc 300
atattcatag gaccaaaggc agagacaata aggctaatgg gagacaaggt atcagcaata 360
gcagcaatga agaaagctgg agtaccatgc gtaccaggat cagacggacc attaggtgat 420
gacatggata agaatagggc aatagcaaaa aggataggat acccagtaat aataaaggca 480
agtggaggag gtggaggaag gggaatgaga gtagtaaggg gagatgcaga gttagcacag 540
tcaatatcaa tgacaagggc agaggcaaag gcagcattct caaatgacat ggtatacatg 600
gagaagtact tagagaaccc aaggcacgta gagatacagg tattagcaga cggacaggga 660
aacgcaatat acttagcaga gagggactgc tcaatgcaga gaaggcacca gaaagtagta 720
gaagaagcac cagctccagg aataacacca gagttaagaa gatacatagg agagaggtgc 780
gcaaaggcat gcgtagacat aggatatagg ggagcaggaa catttgagtt cttattcgag 840
aacggagagt tttacttcat agagatgaac acaaggatac aggtagagca cccagtaaca 900
gagatgataa caggagtaga cttaataaag gaacagttaa ggattgcagc aggacagcca 960
ttatctataa agcaagaaga agtacacgta aggggacatg cagtagagtg caggataaac 1020
gcagaggatc ctaacacatt tctaccatca ccaggaaaga taacaagatt ccatgcacca 1080
ggaggattcg gagtaaggtg ggagtcacac atatatgcag gatacacagt accaccatat 1140
tacgattcaa tgataggtaa gctaatatgc tacggagaga acagggacgt agcaatagca 1200
agaatgaaga acgcattaca ggaattaata atagacggaa taaagacaaa tgtagattta 1260
cagataagga taatgaacga cgagaacttt cagcacggag gaacaaacat acactattta 1320
gagaaaaagt taggattaca agagaag 1347

<210> SEQ ID NO 84
<211> LENGTH: 912
<212> TYPE: DNA
<213> ORGANISM: Artificial Sequence
<220> FEATURE:
<223> OTHER INFORMATION: Codon optimized E. Coli AccD sequence

<400> SEQUENCE: 84
atgtcatgga tagagaggat aaagtcaaac ataacaccaa caagaaaggc atcaatacct 60
gagggagtat ggacaaagtg cgactcatgc ggacaggtac tatatagggc agaattagag 120
agaaacttag aggtatgccc aaagtgcgat catcacatga gaatgacagc aaggaatagg 180
ttacactcat tattagatga aggatcatta gtagagttag gatcagagtt agagccaaag 240
gacgtactaa agtttaggga cagtaagaag tacaaggaca ggttagcatc agcacagaaa 300
gagacaggag agaaagacgc attagtagta atgaagggaa cattatacgg aatgccagta 360
gtagcagcag catttgagtt cgcattcatg ggaggatcaa tgggatcagt agtaggagca 420
aggttcgtaa gggcagtaga gcaagcttta gaggacaact gcccattaat atgtttctca 480
gcatctggag gtgcaagaat gcaagaagca ttaatgtcat taatgcagat ggcaaagaca 540
tcagcagcat tagcaaaaat gcaggaaagg ggactaccat acatatcagt attaacagat 600

```
ccaacaatgg gaggagtatc agcatcattc gcaatgttag gagacttaaa catagctgag    660

ccaaaggcac taataggatt cgcaggacca agggtaatag agcagacagt aagggagaag    720

ttaccaccag gatttcagag gtcagagttc ttaatagaaa agggagcaat agacatgata    780

gttagaaggc cagagatgag attaaagtta gcatcaatac tagcaaagtt aatgaattta    840

ccagcaccaa acccagaggc accaagagag ggagtagtag taccaccagt accagatcag    900

gaaccagagg ca                                                        912
```

<210> SEQ ID NO 85
<211> LENGTH: 1716
<212> TYPE: DNA
<213> ORGANISM: Artificial Sequence
<220> FEATURE:
<223> OTHER INFORMATION: Mutated Clostridium ljungdahlii FadD sequence

<400> SEQUENCE: 85

```
atggatgaaa ttaaaataaa tgatagccaa aaaagatagt atgaaaaaat gggctattgg     60

ggtaaaaaaa cactctaaga ttactggcat acgtcggtaa aaaagtatag agataaggaa    120

tttgtagtag atgatagagg atatcgttac acctagggac aattggatga aaaagcaggt    180

attgttgctt cctattttct tagtattgga gtaaagcctc tagatgttat ttcttttcaa    240

ataccaatat ggagtgaatt tgtaattgtt agtattgcat gcatgaaggt ggggagctgt    300

tgttaaccca attggcatgt gctatagtgg tccgggaagt ttcatatctt ttgaatttat    360

gtaaaagtaa agtttttctc tgccctacat ggtacaataa gacaaattat gaaaaattga    420

ttctatcagt caaaaaggat gtaaaaagtt taaaacacat tgtattactt gacaatctta    480

aagaaaaaga aagtaacagt attactttaa aacatatatt atcatcatac ttttccttga    540

acataaaaga tgaggtaatg gttgacagta atgatgtagc agctatcctt tgcacatccg    600

gtactactgg atgtgcaaag ggagccatgc tgactcataa taacataata tttagtgaaa    660

aatactttaa taaggaactt ggcattacaa aagatgatat tatgtttatg ccggcacctt    720

taaatcatgc aactggcttt catcatggaa ttattgcacc tatgcttatt ggatcaaaag    780

tggttttaca gcagaagttt aaaagtaaaa aggcaataga acttatgaat agagaaaaat    840

gcacctggtc aatgggagct acaccattta tatatgatat tttgaaaaac attagagagg    900

atgaagttta ccttagttcg ttaaaatttt atctttgtgg tggagctgta gtaccagaag    960

aaatggtaag gcaagcctat gaatatggaa taaaattatg tgaagtttat ggatctacag   1020

aaagtgttcc acatgtattt gtaagaccag atgaaaatat tgagttaaca tttggcactg   1080

caggaagggc tatggaaggc gtagaagtta aaattgtaga tgaaaataga aaagagatac   1140

tacctggaaa tctaggggaa gaagtatcga gaggtccaaa tgtatttgta ggatatatag   1200

gtgataaatc agctacaaat aaggtactgg atgatgaagg atggttttat agtggcgatt   1260

tatgtgtaag tgatataagt ggcaatatta atatcattgg gagaaaaaaa gacataattg   1320

ttagaggcgg tgaaaatctc aactcgaatc atataagtca gtatatttca aaatttccac   1380

taattaaaga tgaggcagtt attggaatgc ctgataagcg tcttggtgaa cgaatttgtg   1440

cttatgtcgt attgaaaaaa gaagttaatt ctctgaaatt agaagaactt ttagagtaca   1500

tggaaaagga aaaaatccct aaaaggtatt ggccggaaca cctggagatt atagataaaa   1560

ttcccagaac tgacagtgga aaggtgaaaa aaaatttatt ggcaaaggat ttaaaagttc   1620

gaatgagtag acaggaggag tcaagttgga agggcgagaa ttcggtccaa gaagatcaag   1680
```

agaaacaaca aaaccaaggg ttgtgtgccc caataa 1716

<210> SEQ ID NO 86
<211> LENGTH: 927
<212> TYPE: DNA
<213> ORGANISM: Artificial Sequence
<220> FEATURE:
<223> OTHER INFORMATION: Codon optimized E. Coli FabD sequence

<400> SEQUENCE: 86
atgactcaat tcgcgttcgt ttttccaggg caaggttctc agaccgtagg tatgttagca 60
gatatggcag catcatatcc aattgtagag gaaacctttg cagaagcatc agcggcgtta 120
ggctatgact tatgggcgct tacccaacag ggcccagcag aggaacttaa taagacttgg 180
cagacccagc cagcgttact aaccgcatca gttgcgcttt atagagtttg gcagcaacag 240
ggcggcaagg cgccagcgat gatggcaggg cattcattag gtgagtattc agcgcttgtg 300
tgtgcgggcg tcattgactt cgcggacgcg gtgagactag ttgaaatgag aggtaagttc 360
atgcaagaag cagtaccaga gggtaccgga gcaatggcag ccattattgg gcttgacgat 420
gcgagtatag cgaaagcgtg tgaagaagcg gccgagggtc aggttgtgtc accagtcaat 480
ttcaattcac caggacaagt tgttattgcc ggtcataaag aagcggttga gagagctggc 540
gcagcatgta aagcagcggg agcaaagaga gcacttccat taccagtttc agttccttca 600
cattgtgcct taatgaagcc tgcggcggac aagttagcgg ttgagttagc gaagattacc 660
ttcaatgcgc caactgtacc agttgtcaat aatgttgacg ttaaatgtga aaccaatggc 720
gacgcgatta gagatgcact tgtgagacaa ctttataatc cagttcaatg gaccaaatca 780
gttgagtata tggcggcaca gggtgttgaa catctttatg aagtcggccc aggtaaagta 840
cttaccggcc ttaccaagag aattgtagac acccttactg cgtcagcgtt aaatgagcct 900
tcagcgatgg cggcagcgct tgagtta 927

<210> SEQ ID NO 87
<211> LENGTH: 549
<212> TYPE: DNA
<213> ORGANISM: Artificial Sequence
<220> FEATURE:
<223> OTHER INFORMATION: Codon optimized E. Coli TesA sequence with
periplasmic targeting sequence removed

<400> SEQUENCE: 87
atggcagata ccttacttat tcttggcgac agtttatcag cgggttatag aatgtcagca 60
tcagcagcgt ggcctgcgtt actaaatgac aaatggcaat caaagacctc agttgttaat 120
gcatcaatat ctggtgacac ttcacaacag ggattagcga gacttccagc gttacttaag 180
cagcatcagc caagatgggt attagttgag cttggtggga atgacggcct tagaggtttc 240
caaccacagc aaaccgagca aaccttaaga cagattcttc aagatgtgaa agcggcgaat 300
gcggagcctc ttcttatgca gattagactt cctgcgaatt atggcagaag atataatgaa 360
gcgttttcag ccatttatcc aaagttagca aaagaattcg acgttccatt acttccattt 420
ttcatggaag aagtctatct aaagccacag tggatgcaag atgacggcat tcatccaaat 480
agagatgcac aaccattcat tgcggactgg atggcaaaac agcttcagcc attagtaaat 540
catgactca 549

<210> SEQ ID NO 88
<211> LENGTH: 1146
<212> TYPE: DNA

<213> ORGANISM: Artificial Sequence
<220> FEATURE:
<223> OTHER INFORMATION: Codon optimized Cinnamomum camphorum
      thioesterase sequence

<400> SEQUENCE: 88

```
atggcaacca ccagtttagc gagtgcgttt tgttcaatga aagccgttat gttagcaaga     60

gatgggagag gaatgaaacc aagatcatca gaccttcaac ttagagcggg caatgcgcag    120

acctcattaa agatgattaa tggtaccaaa ttctcatata ccgaatcatt aaagaaactt    180

ccagactggt caatgctttt cgcagttatt accactattt tctcagccgc ggaaaagcaa    240

tggaccaatt tagagtggaa acctaagcca aatcctccac agttattaga tgaccatttc    300

ggtccacatg gtttagtatt cagaagaact tttgcgatta gatcttatga agttggccca    360

gacagatcaa cctcaatagt tgcggtcatg aatcatttac aagaagcagc gcttaatcat    420

gcgaaatcag ttggcattct aggcgacggt ttcggcacta cccttgaaat gtcaaagaga    480

gatcttattt gggttgtgaa gagaacccat gtagcagttg agagatatcc agcgtgggga    540

gataccgttg aagttgaatg ttgggttgga gcatcaggga ataatggtag acgacatgac    600

ttcttagtaa gagactgtaa aactggcgag attcttacca gatgtacttc actttcagta    660

atgatgaata ccagaaccag aagattatca aagattccag aagaagtgag aggtgagatt    720

ggtccagcgt ttattgataa tgttgcggtg aaagatgaag agattaagaa gccacaaaag    780

cttaatgatt caaccgcaga ctatattcag ggtggcctta cccctagatg gaatgactta    840

gacattaatc agcatgtcaa taatattaaa tatgtcgact ggattcttga aactgttcca    900

gactcaattt tcgagtcaca tcatatttca tcatttacca ttgaatatag aagagagtgt    960

accatggact cagtcctaca atcattaacc accgtttctg gcgggtcatc agaggcaggc   1020

cttgtgtgtg agcatcttct acagcttgag ggcggatcag aagttttaag agcgaaaacc   1080

gagtggaggc caaagcttac tgactcattc agaggtattt cagtaatacc agcggagtca   1140

tcagtt                                                              1146
```

<210> SEQ ID NO 89
<211> LENGTH: 1146
<212> TYPE: DNA
<213> ORGANISM: Artificial Sequence
<220> FEATURE:
<223> OTHER INFORMATION: Codon optimized Umbellularia californica
      thioesterase sequence

<400> SEQUENCE: 89

```
atggcaacta cttcattagc gtcagcattt tgttcaatga aagccgtaat gttagcaaga     60

gatgggagag gaatgaagcc aagatcaagt gacttacagt taagagcggg taatgcgcca    120

acttcactta agatgataaa tggtaccaaa ttctcatata ccgaatcatt aaagagactt    180

ccagactggt caatgttatt cgcggtgatt accaccattt tctcagcggc cgagaaacaa    240

tggaccaatc tagagtggaa acctaagcca aaacttccac aactacttga cgaccatttt    300

ggcttacatg gtcttgtttt cagaagaacc tttgcgatta gatcttatga agttggccct    360

gacagatcaa cttctattct tgcggttatg aatcacatgc aagaagcaac tcttaatcat    420

gcaaagtcag ttggtattct tggtgacggt ttcgggacca ctcttgaaat gtcaaagaga    480

gacttaatgt gggtagtaag aagaactcat gtcgcggttg aaagatatcc aacctgggga    540

gacaccgttg aggttgaatg ttggattggt gcgtcaggca ataatggcat gagaagagac    600

tttcttgtga gagattgtaa gaccggagag attcttacca gatgtacctc actttcagtt    660
```

-continued cttatgaata cccgtaccag aagattatca accatacctg acgaagtgag aggcgaaatt 720
gggccagcgt tcattgacaa tgttgcggtt aaagatgatg agattaaaaa gcttcaaaag 780
cttaatgact caaccgcaga ctatattcag ggcggcttaa ccccaagatg gaatgacctt 840
gacgttaatc agcatgtcaa taatctaaaa tatgtagcgt gggttttcga aaccgttcca 900
gactcaattt tcgaatcaca tcatatttca tcattcacct tagagtatag aagagaatgt 960
accagagatt cagttttaag gtcattaacc accgtaagtg gtggttcatc agaggcaggc 1020
cttgtctgtg atcatctttt acagttagag ggcggatcag aggtgcttag agcgagaacc 1080
gagtggcgac caaagttaac tgattcattc agaggcattt cagttattcc agcggagcca 1140
agagtt 1146

<210> SEQ ID NO 90
<211> LENGTH: 750
<212> TYPE: DNA
<213> ORGANISM: Artificial Sequence
<220> FEATURE:
<223> OTHER INFORMATION: Codon optimized Streptococcus pyogenes acyl-ACP thioesterase sequence

<400> SEQUENCE: 90
atgggcttat catatcaaga agagttaacc ttaccatttg aattatgtga tgttaagtca 60
gacattaaac ttccattact tttagactat tgtcttatgg tttcaggcag acagtcagtg 120
cagcttggta gatcaaataa taatctttta gtcgactata aacttgtatg gatagttact 180
gactatgaga ttaccattca tagattacca catttccaag aaaccattac cattgaaacc 240
aaagcgctaa gttataataa gttcttttgt tatagacaat tctatattta tgaccaagag 300
ggctgtcttt tagttgacat tctatcatat ttcgcgcttc ttaatccaga taccagaaag 360
gttgcaacta ttccagagga cttagtcgcc ccattcgaga ctgactttgt taagaaatta 420
catagagttc caaaaatgcc tttacttgag cagtcaattg acagagacta ttatgtaaga 480
tatttcgata ttgacatgaa tggacatgtt aataattcaa agtatcttga ctggatgtat 540
gatgttttag gctgtcaatt ccttaagacc catcagccac ttaagatgac ccttaaatat 600
gtgaaagaag tatcacctgg tggtcaaatt acctcatcat atcatcttga ccagttgacc 660
tcatatcatc agattatatc agatgggcag cttaatgcac aggcgatgat tgaatggaga 720
gcgattaagc aaaccgagtc tgaaaccgat 750

<210> SEQ ID NO 91
<211> LENGTH: 1191
<212> TYPE: DNA
<213> ORGANISM: Artificial Sequence
<220> FEATURE:
<223> OTHER INFORMATION: Codon optimized Ricinus communis palmitoyl-acyl carrier protein thioesterase sequence

<400> SEQUENCE: 91
atggggacct gttcatatac cattaccctt ccaattcgat gtttatcaaa ttcaaatggc 60
catcatgatc cacataagca gaatcttaat aagataaaga taaatggcgc gtcaactagt 120
accagaccac ttaagttaga cgcaccttca caaaccgttg gtgttgcgac catttatcta 180
gcatcagttt cagaaaatct taccccttacc aaagaagtca tgagacagaa tattccaacc 240
aagaaacagt atattgaccc acatagacaa gggttaatga ttgagggtgg agttggttat 300
agacaaacta ttgtcattag aagttatgaa gttggcccag acaaaaccgc gactttagag 360

```
tcaattcttt atcttttaca ggaaaccgcc ttaaatcatg tatggctttc aggtctactt    420

tcaaatggct tcggggcgac ccatggcatg gtaaagaata atttgatttg ggtagtgtct    480

aagcttcagg ttcaagtgga tcattatcca atttggggag aggttgtaga gattgacacc    540

tgggttagag catcaggtaa gaatggtatg aaaagagact ggcttattag atcacaagca    600

accggccatg tatttgttag agcgacctca acttgggtta tgatgaatga gaaaaccaga    660

agattatcaa agatgccaga agaagtcaga gcggagattt caccatggtt cattgaaaag    720

caagcgatta aagaagaagt gccagacaaa attgcaaagt tagacgacaa ggcgagatat    780

gttatttcaa atctaaaacc taaaagatca gaccttgata tgaatcatca tgtgaataat    840

gtcaaatatg ttagatggat gcttgagatt ttaccagatc atttcttaga gtctcatcag    900

ttatcaggca taactatgga gtatagaaga gaatgtggat cagcagatat tgttcaatca    960

ttatgtgagc ctgacggtga cgagattctt tcaaatgaca ttcctgttct taatggtttc   1020

tcacttgcgt cagaaccatt aatggaaggc aatggtttcc ttgtaccatt agataaggtt   1080

ccattaaagt atacccatct tttacttacc aaaggcgagt cacagaatga agagattgtt   1140

agaggaaaaa ccatttggaa gaagaaactt tgtactatgc cattttcaac c            1191
```

<210> SEQ ID NO 92
<211> LENGTH: 1176
<212> TYPE: DNA
<213> ORGANISM: Artificial Sequence
<220> FEATURE:
<223> OTHER INFORMATION: Codon optimized Ricinus communis palmitoyl-acyl carrier protein thioesterase sequence

<400> SEQUENCE: 92

```
atggcatcaa agggctcaat tagattatat tttccatgtg acttcagaaa tactttacag     60

aaaaagaata tgaaaatgga catggtaatg gcgagatcag gattctcata ttcacttaat    120

ccaattgcgc caaagattcc aagattctat gttgtcgcta atgcgtcaaa tccacagaga    180

gttgatacca ttaatggcaa aaaagttaat ggtatacatg ttgcagagtc atcaaattct    240

tatgcggatc agaataagat gaatgcaacc gcgggtttag tcttagacgg caatgtagat    300

catcagccac ttcataagtg gcttttaggt agattcgttg acgaaagact tgtttattca    360

caaaccttca ttattagaag ttatgagatt ggtccagata agaccgcgac tatggaaacc    420

ttaatgaatt tacttcaaga aaccgcactt aatcatgtta cctcatcagg ccttgcggga    480

gatggttttg gtgcgactag agagatgtca ctaagaaaac taatttgggt ggtaactaga    540

attcatattc aagtccagag gtattcatgt tggggggatg tggttgaaat agacacctgg    600

gttgacggcg caggcaagaa tggaatgaga agagactgga ttattagaga ctataatacc    660

aaagaaataa ttactagagc aacctcaacc tgggtcatta tgaatagaga aactagaaag    720

ctttcaaaga tgccagagca agttagacaa gagttagttc cattctatac caatagaatt    780

gcaattgcga aagagaataa tgacgttgag aaaattgaca agttaaccga cgaaaccgcg    840

gagagaattc gatcagggct tgcgcctaga tggtcagaca tggacgccaa tcaacatgtg    900

aataatgtta agtatattgg ctggattctt gaatcagtac ctattaatgt acttgaggac    960

tataatctta cctcaatgac ccttgagtat agaagagaat gtagacagtc aaatctttta   1020

gagtcattaa ccagtaccac cgaacattca aataataatt cttgtaatag aaaggcccat   1080

ttagaatata cccatttact tagaatgcaa gcggataaag cggaaattgt tagagcaaga   1140

actgagtggc agtcaaagtc aaatagaaaa accatt                             1176
```

<210> SEQ ID NO 93
<211> LENGTH: 1257
<212> TYPE: DNA
<213> ORGANISM: Artificial Sequence
<220> FEATURE:
<223> OTHER INFORMATION: Codon optimized Ricinus communis palmitoyl-acyl carrier protein thioesterase sequence

<400> SEQUENCE: 93

```
atggtggcga ccgcagcagc agcaacctca tcatttttcc cagtcccatc acaatcagcc     60
gacgcgaatt tcgacaaagc accagcgtca cttggcggca ttaaactaaa atcaacttca    120
tgttctagag gattacaggt taaagcaaat gcacaagcgc ctccaaagat aaatggatca    180
tcagttggtt tcaccacttc agtagaaacc gttaagaatg acggtgatat gcctttacct    240
ccaccaccaa gaaccttcat taatcagtta ccagactggt ctatgttact tgcggccatt    300
accaccattt tcttagcggc tgaaaagcag tggatgatgc ttgattggaa gccacgtaga    360
ccagacatgc ttattgatcc atttggcatt ggaagaattg tccaagacgg gttaatattt    420
agacagaatt tctcaattag aagttatgag attggtgcag acagaaccgc gtcaattgag    480
actttaatga atcatcttca agaaaccgcg ttaaatcatg ttaaaaccgc gggtctttta    540
ggtgacggtt tcggttcaac tccagaaatg agtaaaagaa atctaatttg ggttgtcacc    600
agaatgcaag ttttagtaga cagatatcca acctggggtg atgttgttca ggttgatact    660
tgggtttcaa aatctggtaa gaatggcatg agaagagact ggtgtgtgag agactcaaga    720
accggcgaaa cccttacccg agcgtcatca gtatgggtaa tgatgaataa gcttaccaga    780
agattatcaa agattccaga agaagtgaga ggcgaaattg agccatattt ccttaattca    840
gacccaattg tagacgaaga ttcaagaaag cttcctaaac ttgacgactc aaatgcggac    900
tatgttagaa aaggtttaac ccctagatgg tcagatcttg acataaatca acatgtgaat    960
aatgttaagt atattggttg gattcttgag tcagcgccat taccaattct agagtcacat   1020
gaactttcag cgattaccct tgagtataga agagaatgtg ggagagactc agttcttcag   1080
tcacttaccg cggtttcagg caatggcatt ggcaatcttg gcaatgcggg ggatattgag   1140
tgtcagcatt tacttagatt agaagatgga gcagagattg ttagaggtag aactgagtgg   1200
aggccaaagt attcatcaaa tttcggcatt atgggccaaa ttccagtcga gtcagcg      1257
```

<210> SEQ ID NO 94
<211> LENGTH: 1215
<212> TYPE: DNA
<213> ORGANISM: Artificial Sequence
<220> FEATURE:
<223> OTHER INFORMATION: Codon optimized Jatropha curcas acyl-ACP thioesterase sequence

<400> SEQUENCE: 94

```
atggcagtat tcacctatag aattgcgatg ttaccaatta gatgttcatc atcaaattca     60
accaattcac attcacatga cccaaatcaa cagaatttac ataagattaa gattaatggc    120
tcagcgtcag cgatgatgcc tcttaaggtt gatttaccaa gttcattgac gattacctca    180
gttgcaccag ttgtagagaa tctttcatta actaaagaac aaaccagaca gaatattcca    240
accaagaagc agtatattga cccacataga caaggtctta ttgtcgaaga gggcgttggt    300
tatagacaga ccgtcgttat tagatcttat gaagttggcc ctgacaaaac cgcaaccctt    360
gagattatac tttgtctact tcaagagact gcgttaaatc atgtttggtt atcaggctta    420
ctttcaaatg gttttggggc gacccatgga atggtgagaa ataatcttat ttgggttgtt    480
```

```
tcaaaacttc aggtacaagt tgatcaatat ccaatttggg gcgaagttgt cgagattgac    540

acttgggttg gcgcgagtgg caagaatggt atgcgaagag actggcttgt tagatcacag    600

gcgaccggcc aggtatttgc aagggccacc tcaacctggg ttatgatgaa tgagaaaact    660

agaagattat caaaaatgcc agaagaagtg agagcggaaa ttgcgccatg gttcattgag    720

aagcaagcga ttaaagaaga agtgccagag aagattgcaa aactagacga taaggcgaga    780

tatgtagtta ccaatcttaa gcctaaaaga tcagaccttg acatgaatca gcatgtgaat    840

aatgtcaaat atgttagatg gatgcttgaa accttaccag atcaattctt cgagaatcat    900

cagttatcag gtattacttt agagtataag agagaatgtg gatcatcaga tatagtagag    960

tcattatgtg agccagacga agaggaaggg attataaata ccggacttaa gcagaataat   1020

gacaaatcac tattcaatgg tttctcactt ccatcagaga ttatggaagg taatggtttc   1080

ctttcatcat tagaaaagac ccctcttaag tatactcatc ttttagttgc aaaagggaaa   1140

acccaatctg aggaaattgt tagaggcaag accatttgga aaaagaaatt acttaccacc   1200

atgccatttt cacca                                                    1215
```

```
<210> SEQ ID NO 95
<211> LENGTH: 1044
<212> TYPE: DNA
<213> ORGANISM: Artificial Sequence
<220> FEATURE:
<223> OTHER INFORMATION: Codon optimized Jatropha curcas acyl-ACP
      thioesterase sequence

<400> SEQUENCE: 95

atggtttcaa ccgcgatttc attttcactt ttaccaatta agttaattaa agaagaaact     60

agaatggcct cagcggacag aagaaagaat tcaattgtaa aagaattcgg tcatttcacc    120

tgtagatgtg cagcgattga aaagagaatt caaaaactta ataatttctt aatagacggc    180

ggcttcggct cattagagca aaatggtctt atatatagac agaatatttt cattagatca    240

ttcgagattg gattcgacag aaagctttca ttagcagcgt tgaccaattt ccttcaggac    300

accgcgctta atcatgttag aatgattggc ttacttgcag cgggtttcgg cagtactcca    360

gaaatgtcaa agaaagacct tatttgggtt ttatgtacct tacagattct tgttgacaga    420

catccttcat ggttagatgc agttgaggtc gacacctgga tgtatccatc aggccagaat    480

gggcaaggta gagactggct tgttagagat gcgaaaaccg gaaagccact tgcgcaggca    540

tcttcagtta tggttctatt aaataaaaag accagaaaac tttctaagtt taccgaagag    600

attagagatg aaattgcgcc acatatgatg atggactgta atccaattat taattcaaga    660

aaaatgctac catttgacgt gaatactgcg gattatgcaa gaaccggtct taccccaggt    720

tggaatgacc ttgaccttaa tcagcatgta aatcatgtcc aatatattaa ttggatttta    780

caaaatgttt taagatcact tattcaacat cataagttat cagatattac cttagagtat    840

agaaaagagt gtgacataaa ttcaattctt cagttccttt caaagattgt gaaaaatggg    900

tcaaatcatt caaccgatac caataatcta attgagttag accattcact tcttttagaa    960

aatggctcag agattgcgcg agcgaatact atttggaagc caagagaagt aaataatttt   1020

aagaatgcag tttatacccc tgcc                                          1044
```

```
<210> SEQ ID NO 96
<211> LENGTH: 1071
<212> TYPE: DNA
<213> ORGANISM: Artificial Sequence
```

-continued

<220> FEATURE:
<223> OTHER INFORMATION: Codon optimized Jatropha curcas acyl-ACP thioesterase sequence

<400> SEQUENCE: 96

```
atggcatcaa ccgcgattag tttcctttca attccaatta agcttattaa agaagagatg     60
agaatggcgt cagcgggaag aagaaagaat actattgcag cagaattcgg ccatttcacc    120
ttcggctcag cgactgttga gaaaaaagtc caaaagtcaa ataatttctt aattgatggc    180
gggtttggct cattagaaca gaatgggtta atatatagac agaatatttt cgtgaggtca    240
ttcgagattg gttttgaccg aaagttatca ttagcagcgc ttaccaattt tctacaggac    300
actgcgctta atcattgtag aatgattggc ttattagccg agggtttcgg atcaacccca    360
gaaatgatta agaaagacct tatttgggtt ctttgtaccc ttcaaattct tgttgacgga    420
tatccatcat ggcttgacgt tgttgaggtc gacacctgga tgtatccttc aggtcaaaat    480
ggtcttggca gaggttggtt agtaagagat ggcaagactg gcagatcatt agcgcagtca    540
tcatcagtta tggtgtcatt caataagaaa accagaaaac tttctaagtt agcgaaagaa    600
attagagatg agattgcacc acacatgatg gattgtgacc caattatgaa taagaattca    660
agaaagatac ttccattcga tgtaaatacc gcagactatg cgagaaccgg ccttacccca    720
ggttggaatg aattagactt aaatcagcat gttaatcatg tccagtatat taattggatt    780
ttacaaaatg ttagaccttc acttgttcaa catcataagc tttcagcgat taccttagaa    840
tatagaaaag agtgtgacat gaattcaatt ctacaatcac tttcaagaat tgttaagaat    900
ggtgggaatg atagtaccga caagaataat gttattgagt tagaccattt tcttcttcta    960
gagaatggtt cagaaattgc gagagcgaat accatttgga aaccaagaga agtaaataat   1020
ttcaaaaatg tagtgcattc accagcagaa gagaatatat cttcaatgaa t            1071
```

<210> SEQ ID NO 97
<211> LENGTH: 396
<212> TYPE: DNA
<213> ORGANISM: Artificial Sequence
<220> FEATURE:
<223> OTHER INFORMATION: Codon optimized E. Coli FadM sequence

<400> SEQUENCE: 97

```
atgcaaactc agattaaggt tagaggctat catctagacg tttatcaaca tgtgaataat     60
gcgagatatc ttgagttcct tgaagaagcc agatgggacg gtttagagaa ttcagattca    120
tttcagtgga tgaccgcaca taatattgca ttcgtagtgg tcaatattaa tataaattat    180
agacgaccag cggtcttatc agacctttta accattacct cacaacttca acagttaaat    240
ggaaagtcag ggattctttc acaggttatt acccttgaac cagagggtca ggttgtagca    300
gatgcgctta ttaccttcgt ttgtattgac cttaaaactc aaaaagcgtt agcgcttgaa    360
ggcgagttaa gagaaaagtt agagcagatg gttaaa                              396
```

<210> SEQ ID NO 98
<211> LENGTH: 957
<212> TYPE: DNA
<213> ORGANISM: Artificial Sequence
<220> FEATURE:
<223> OTHER INFORMATION: Codon optimized E. Coli AccA sequence

<400> SEQUENCE: 98

```
atgtcattaa atttcttaga ctttgaacaa ccaatagcag aacttgaagc gaaaattgat     60
tcattaaccg cagtttcaag acaagatgaa aagttagaca ttaatataga cgaagaagtc    120
```

```
catagactta gagaaaaatc agttgagtta actagaaaga ttttcgcaga ccttggtgca    180

tggcagattg cgcaacttgc aagacatcca caaagaccat ataccttaga ctatgtaaga    240

ttagcatttg acgagttcga cgagcttgcg ggtgaccgag cgtatgcgga cgataaagca    300

attgttggtg gcattgccag attagacgga aggccagtta tgattattgg acatcagaaa    360

gggagagaga ctaaggaaaa gattagaaga aatttcggca tgccagcacc agagggctat    420

agaaaggcac ttagacttat gcagatggcg gaaagattca agatgccaat tataaccttc    480

attgataccc ctggagcgta tccaggcgtt ggcgccgaag agagaggcca atcagaggcg    540

attgcgagaa atcttagaga gatgtcaaga ctaggtgtgc ctgtagtatg taccgttatt    600

ggcgagggtg gaagtggcgg tgcccttgcg attggggttg gtgacaaagt gaatatgtta    660

cagtattcaa cctattcagt catttcacct gagggctgtg cgtcaattct ttggaaatca    720

gcggacaaag cgccattagc ggcagaggcg atggggatta ttgcaccaag acttaaagaa    780

ctaaagctta ttgattcaat tattccagag ccacttggtg gtgcgcatag aaatccagaa    840

gcgatggcag cgtcattaaa ggcgcagtta ttagcggatc tagcggactt agacgttctt    900

tcaaccgaag atcttaagaa tagaagatat cagagactta tgtcttatgg ttatgca       957
```

```
<210> SEQ ID NO 99
<211> LENGTH: 468
<212> TYPE: DNA
<213> ORGANISM: Artificial Sequence
<220> FEATURE:
<223> OTHER INFORMATION: Codon optimized E. Coli AccB sequence

<400> SEQUENCE: 99

atggatatta gaaagataaa gaaactaatt gagttagtcg aagagagtgg tatatcagag     60

ttagaaattt cagagggtga agaatcagtt agaatttcaa gagcggcacc agcggcctct    120

ttcccagtca tgcagcaagc gtatgcggca ccaatgatgc agcaaccagc ccagtcaaat    180

gcggcagcgc cagcgaccgt accatcaatg gaagcgccag cagcagcgga gatttcaggc    240

catattgtta gatcacctat ggttggtacc ttctatagaa ccccttcacc agacgcgaaa    300

gcgtttattg aagtgggaca aaaggttaat gtaggcgata ccctttgtat tgttgaggca    360

atgaaaatga tgaatcagat tgaagcggac aaatcaggca ctgttaaggc aattcttgta    420

gagtcagggc aaccagttga gttcgacgaa ccacttgtgg ttattgaa                 468
```

```
<210> SEQ ID NO 100
<211> LENGTH: 1347
<212> TYPE: DNA
<213> ORGANISM: Artificial Sequence
<220> FEATURE:
<223> OTHER INFORMATION: Codon optimized E. Coli AccC sequence

<400> SEQUENCE: 100

atgttagaca agattgttat tgcaaataga ggggaaattg cgcttagaat tcttagagcg     60

tgtaaagaat taggcattaa gactgttgca gttcattcat cagcagacag agatcttaaa    120

catgttttac ttgcggacga aaccgtttgt attggtccag caccatcagt aaagtcatat    180

cttaatattc cagccattat ttcagccgcg gagattaccg gagcggtagc gattcatcca    240

ggttatggct tcttatcaga gaatgcgaat ttcgcagaac aagttgagag atcaggattc    300

attttcattg gtccaaaggc agaaaccatt agattaatgg gcgacaaggt ttcagcgatt    360

gcggcgatga aaaaggcagg cgtcccatgt gttccaggct cagatggccc attaggtgac    420
```

gatatggaca agaatagagc catagcgaaa agaatagggt atccagtaat tataaaggcg 480
tctgggggtg gcggtggtag aggtatgaga gtagtcagag gcgacgcaga gctagcacaa 540
tcaatttcaa tgaccagagc ggaagcaaaa gcggcattct caaatgacat ggtgtatatg 600
gagaagtatt tagagaatcc aagacatgtg gagattcaag ttcttgcgga cggccagggt 660
aatgcgattt atcttgcgga aagagactgt agtatgcaga gaaggcatca gaaagttgtt 720
gaagaagcac cagcgccagg tattacccct gaacttagaa gatatatagg cgagagatgt 780
gcaaaggcgt gtgttgacat tggttataga ggggcaggga cctttgagtt tctttttgag 840
aatggagagt tctatttcat tgaaatgaat accagaattc aagttgaaca tcctgttacc 900
gagatgatta ccggcgtgga cttaattaaa gagcaattaa gaattgcagc gggccagcca 960
ctttcaatta agcaagaaga agtccatgtt agaggacatg cggtcgagtg tagaattaat 1020
gcggaagatc ctaatacttt cttaccatca ccaggcaaga ttaccagatt ccatgcacct 1080
ggtggtttcg gtgtaagatg ggaatcacat atttatgcgg gctatactgt tccaccatat 1140
tatgactcaa tgattggtaa acttatttgt tatggagaga atagagatgt agcgattgcg 1200
agaatgaaaa atgctttaca agaactaatt attgacggta ttaagaccaa tgtggatctt 1260
cagattcgaa ttatgaatga tgagaatttt cagcatggcg gcaccaatat acattatctt 1320
gagaagaaac ttggattaca ggaaaaa 1347

<210> SEQ ID NO 101
<211> LENGTH: 912
<212> TYPE: DNA
<213> ORGANISM: Artificial Sequence
<220> FEATURE:
<223> OTHER INFORMATION: Codon optimized E. Coli AccD sequence

<400> SEQUENCE: 101
atgtcatgga tagaaagaat taagtcaaat attaccccaa ccagaaaggc gtcaattcca 60
gagggcgtat ggaccaagtg tgactcatgt ggtcaggttc tttatagagc cgaattagaa 120
agaaatcttg aggtttgtcc aaaatgtgac catcacatga gaatgaccgc aagaaataga 180
ttacattcac ttttagacga aggctcactt gtggaattag gctcagagct tgaaccaaaa 240
gacgttctta agttcagaga cagtaagaag tataaagata gattagcatc agcacagaaa 300
gagactgggg agaaagatgc gttagtggtc atgaaaggta ccttatatgg aatgcctgtc 360
gttgcagctg cgttcgaatt cgcgtttatg ggcggttcaa tgggttcagt tgtaggcgcg 420
agattcgtta gagcagttga acaggcgtta gaagataatt gtccactaat ttgtttttca 480
gcgtctggtg gtgcaagaat gcaagaagca ctaatgtcac ttatgcaaat ggcgaaaact 540
tcagcggcgc ttgcaaagat gcaagagaga gggttaccat atatttcagt tcttaccgac 600
ccaaccatgg ggggtgtctc agcgtcattc gcgatgttag gcgacttaaa tattgccgag 660
ccaaaagcac ttattggctt cgcgggacca agagtgattg aacagaccgt tagggaaaag 720
cttccacctg gatttcagag atcagagttc cttattgaaa aaggcgcgat tgatatgata 780
gttagacgac cagagatgag attaaagctt gcgtcaattc ttgcaaagtt aatgaatctt 840
ccagcgccta atccagaagc accaagagag ggtgttgtag tacctccagt tccagaccaa 900
gagccagagg cg 912

<210> SEQ ID NO 102
<211> LENGTH: 568
<212> TYPE: DNA
<213> ORGANISM: Artificial Sequence
<220> FEATURE:
<223> OTHER INFORMATION: Codon optimized E. Coli TesA with periplasmic targeting sequence removed

<400> SEQUENCE: 102
ggtctctaat ggcagacaca cttttgatct tgggcgactc actttccgcg ggctatcgta 60
tgagtgcgtc cgcggcgtgg cccgcgctgc tgaacgacaa gtggcagagc aagacctccg 120
tcgtcaacgc gtccatctcg ggcgacacga gccagcaggg actggcccgc ctcccggcgc 180
tgctcaagca gcatcagcca cgctgggtgc tcgtcgagct gggtggcaac gacgggctcc 240
gcggcttcca accgcagcag accgaacaga ccctccggca aattctccaa gacgtcaaag 300
cggccaacgc ggagcccctg ctgatgcaga tccgcctgcc ggcgaactac ggtcggcgtt 360
ataatgaggc gttcagcgcc atctatccga agctggccaa ggaattcgac gtgcccctcc 420
tcccgttttt catggaagaa gtgtacctca agccccagtg gatgcaagac gacggcatcc 480
acccgaatcg cgacgcgcag ccgttcatcg cggactggat ggcgaagcag ctgcagccgc 540
tcgtaaacca cgactcgtaa aagagacc 568

<210> SEQ ID NO 103
<211> LENGTH: 568
<212> TYPE: DNA
<213> ORGANISM: Artificial Sequence
<220> FEATURE:
<223> OTHER INFORMATION: Codon optimized E. Coli TesA with periplasmic targeting sequence removed

<400> SEQUENCE: 103
ggtctctaat ggctgatacc ctcttgattc ttggtgattc ccttagcgcc ggctaccgca 60
tgtccgcgag cgccgcatgg ccggcgctgc tgaatgacaa gtggcagtcc aagacctcgg 120
tcgtcaatgc gagcatcagc ggcgacacct cgcagcaggg cctcgcgcgg ctgccggccc 180
tcctgaagca acatcagccg cgctgggtac tcgtggagct cggcggcaat gatgggctgc 240
gtggcttcca gccccaacag accgagcaga cgttgaggca gatcctccaa gacgtgaagg 300
cagcgaatgc ggagcctctc ctcatgcaga tccggctgcc cgcgaattat ggccgccgtt 360
acaacgaggc cttctcggcg atctatccga agctcgcgaa agagttcgac gtcccgctgc 420
tgcccttctt tatggaggag gtgtacctga agccgcaatg gatgcaggat gacggcatcc 480
acccgaaccg ggacgcgcag cccttcatcg ccgattggat ggcgaagcag ctgcagccgc 540
tggttaatca tgacagttaa aagagacc 568

<210> SEQ ID NO 104
<211> LENGTH: 568
<212> TYPE: DNA
<213> ORGANISM: Artificial Sequence
<220> FEATURE:
<223> OTHER INFORMATION: Codon optimized E. Coli TesA with periplasmic targeting sequence removed

<400> SEQUENCE: 104
ggtctctaat ggccgatacc ctgctgatcc tcggcgattc acttagcgct ggataccgca 60
tgagcgcctc ggctgcgtgg cctgcactcc tcaacgacaa gtggcagagc aagacctcgg 120
tggtcaacgc gtccatttcg ggcgacacca gtcagcaggg cctcgccagg ctgcctgccc 180
tgctgaagca acatcagccg cgctgggtcc tggtcgagct tggcggcaac gacggcctcc 240
gggggttcca gccgcaacag acggagcaga cgttgcggca gattctccag gatgtaaagg 300
cggcgaatgc cgagccgctc ctgatgcaga tcaggctccc ggccaactat ggtcgccgct 360

-continued

```
ataacgaggc gttctccgca atctacccca agctggcaaa agaattcgac gtgccgctgc    420

tgccattttt catggaagaa gtgtacctca agccgcagtg gatgcaagat gatggtatcc    480

accccaaccg ggacgcccaa cccttcatcg ccgactggat ggcgaagcag ctgcagcccc    540

ttgtcaatca cgactcctaa aagagacc                                       568
```

BIOREFINERY SYSTEM, METHODS AND COMPOSITIONS THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200206_404_SEQUENCE_LISTING.txt. The text file is 146 KB, was created on Jul. 12, 2013, and is being submitted electronically via EFS-Web.

BACKGROUND

1. Technical Field

The present disclosure relates to bioengineering approaches for producing biofuel and, in particular, to the use of a $C_1$ metabolizing microorganism reactor system for converting $C_1$ substrates, such as methane or methanol, into biomass and subsequently into biofuels, bioplastics, or the like.

2. Description of the Related Art

With the ever increasing depletion of fossil fuel deposits, the increasing production of greenhouse gases and recent concerns about climate change, substituting biofuels (e.g., ethanol, biodiesel) for fossil fuels has become an industrial focus. But, biofuels generated to date have their own difficulties and concerns. First generation biofuels are derived from plants (e.g., starch; cane sugar; and corn, rapeseed, soybean, palm, and other vegetable oils), but these fuel crops compete with crops grown for human and animal consumption. The amount of farm land available is not sufficient to satisfy both global food and fuel needs. Therefore, second generation biofuels are being produced from, for example, cellulose or algae. But, technical difficulties in production, along with the high cost of production, have not made second generation biofuels any more cost-effective or accessible.

Third or next generation biofuels made from alternative feedstocks (i.e., not sugar, corn, algae) are needed. In this regard, methane is one of the most abundant domestic carbon feedstocks and is sourced primarily from natural gas. The recent rise in domestic production of methane (from 48 $bft^3$/day in 2006 to 65 $bft^3$/day in 2012) has driven the cost of natural gas to record lows (from about $14.00/MMBTU in 2006 to about $2.50/MMBTU in 2012). Domestic natural gas is primarily produced by hydraulic fracturing ("fracking"), but methane can also be obtained from other sources, such as landfills and sewage. In addition, capturing methane sources will have a significant environmental benefit since methane has a 23× greater greenhouse gas contribution relative to $CO_2$.

But, methane's volatility makes transportation and direct usage as a fuel problematic. For this reason, there is a strong incentive to convert the gas to a liquid form to allow for easy transport to the point of use. Two main approaches are currently being pursued: liquefaction leading to liquefied natural gas (LNG) and chemical conversion to convert gas-to-liquid (GTL) (Patel, 7th World Congress of Chemical Engineering, Glasgow, Scotland, UK, 2005). The Fischer-Tropsch (F-T) process is currently the most prevalent GTL approach for converting methane from natural gas to higher-order hydrocarbons (Patel, 2005). Note that the F-T process takes syngas as an input which is produced from natural gas by steam reforming (syngas can also be sourced from coal gasification, by high-temperature reaction with water and oxygen). The F-T process yields petroleum products consistent with today's fuel supply, but suffers from a number of drawbacks, including low yields, poor selectivity (making downstream utilization complex), and requires significant capital expenditure and scale to achieve economical production (Spath and Dayton, December 2003 NREL/TP-510-34929). The massive scale required for an F-T plant (more than $2B capital cost for a typical plant [Patel, 2005]) also represents a significant limitation due to the large amount of methane feedstock required to supply continuous operation of such a plant. As methane transportation is prohibitively expensive in most cases, such a plant must be co-located with either a large gas source or a pipeline. An additional cost and scaling factor is the economics of gas-scrubbing technologies (Spath and Dayton, 2003), as F-T catalysts are highly sensitive to common contaminants in natural gas that survive the syngas conversion process.

F-T plants have been in operation semi-continuously since 1938. Several companies are currently investigating introduction of new plants given the current availability and price of methane discussed above. However, despite significant research and development over the last 70+ years, the limitations of F-T technology prevent broad adoption of commercial GTL processes. The requirements for ready access to large volumes of clean gas, combined with massive capital investment, currently limit natural gas based F-T plants to successful operation in only a few locations world-wide (Spath and Dayton, 2003). The high minimum processing requirement for a GTL or LNG plant, combined with the high cost of transport, result in smaller methane sources being referred to as 'stranded' gas (for example, natural gas produced at off-shore oil wells, or methane off-gas from landfills). In the current absence of efficient small-scale conversion technologies, such stranded gas sources are typically vented to atmosphere or flared, as methane accumulation presents a significant safety risk.

In view of the limitations associated with the production of first, second and next generation biofuels, there is clearly a need in the art for new methods of efficiently and cost-effectively producing alternative fuels without taxing the environment or competing with food production. The present invention solves this problem by providing efficient and cost-effective methods for producing biofuels and other products using bioengineering.

BRIEF SUMMARY

In one aspect, the present disclosure provides a method for making fuel by refining an oil composition derived from a $C_1$ metabolizing non-photosynthetic microorganism (e.g., in a refining unit) to produce fuel. Additionally, this disclosure provides a method for making fuel by converting biomass from a culture primarily comprising a $C_1$ metabolizing non-photosynthetic microorganism into an oil composition and refining the oil composition into a fuel. In yet another aspect, this disclosure provides a biorefinery that includes a processing unit in which an oil composition is derived from a $C_1$ metabolizing non-photosynthetic microorganism; and a refining unit for refining the oil composition to produce a fuel. In still another aspect, the instant disclosure provides an oil composition or biofuel composition having molecules comprising hydrogen and carbon atoms, wherein the hydrogen and carbon atoms are at least about 50% to about 99% of the weight of the composition and wherein the $\delta^{13}C$ of the composition ranges from about −35‰ to about −50‰, −45‰ to about −35‰, or about −50‰ to about −40‰, or about −45‰ to about −65‰, or about −60‰ to about −70‰, or about −30‰ to about −70‰.

In certain embodiments, the present disclosure provides $C_1$ metabolizing microorganisms that are prokaryotes or bacteria, such as *Methylomonas, Methylobacter, Methylococcus, Methylosinus, Methylocystis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas*, or *Pseudomonas*. In further embodiments, $C_1$ metabolizing bacteria are a methanotroph or a methylotroph. Exemplary methanotrophs include *Methylomonas, Methylobacter, Methylococcus, Methylosinus, Methylocystis, Methylomicrobium, Methanomonas*, or a combination thereof.

Exemplary methanotroph species include *Methylomonas* sp. 16a (ATCC PTA 2402), *Methylosinus trichosporium* OB3b (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylococcus capsulatus* Bath (NCIMB 11132), *Methylobacter capsulatus* Y (NRRL B-11,201), *Methylobacterium organophilum* (ATCC 27,886), *Methylomonas* sp. AJ-3670 (FERM P-2400), *Methylomicrobium alcaliphilum, Methylocella silvestris, Methylacidiphilum infernorum, Methylibium petroleiphilum, Methylococcus capsulatus* Bath, or high growth variants thereof.

Exemplary methylotroph species include *Methylobacterium extorquens, Methylobacterium radiotolerans, Methylobacterium populi, Methylobacterium chloromethanicum, Methylobacterium nodulans*, or a combination thereof.

In still further embodiments, the present disclosure provides $C_1$ metabolizing microorganisms that are syngas metabolizing bacteria, such as *Clostridium, Moorella, Pyrococcus, Eubacterium, Desulfobacterium, Carboxydothermus, Acetogenium, Acetobacterium, Acetoanaerobium, Butyribaceterium, Peptostreptococcus*, or any combination thereof. Exemplary syngas metabolizing bacteria include *Clostridium autoethanogenum, Clostridium ljungdahli, Clostridium ragsdalei, Clostridium carboxydivorans, Butyribacterium methylotrophicum, Clostridium woodii, Clostridium neopropanologen*, or any combination thereof.

In certain other embodiments, $C_1$ metabolizing microorganisms are eukaryotes such as yeast, including *Candida, Yarrowia, Hansenula, Pichia, Torulopsis*, or *Rhodotorula*.

In further embodiments, the $C_1$ metabolizing non-photosynthetic microorganism is a recombinant microorganism comprising a heterologous polynucleotide encoding a fatty acid producing enzyme, a formaldehyde assimilation enzyme, or a combination thereof. In certain embodiments, the heterologous polynucleotide encodes a thioesterase, a malonyl CoA-acyl carrier protein transacylase, an acetyl-CoA carboxylase, or any combination thereof. For example, the thioesterase may be a codon optimized *E. coli* tesA lacking a periplasmic targeting sequence; the malonyl CoA-acyl carrier protein transacylase may be a codon optimized *E. coli* fabD; and the acetyl-CoA carboxylase may be a codon optimized *E. coli* accA, accB, accC, accD, or any combination thereof. In certain further embodiments, the $C_1$ metabolizing microorganism further comprises a mutation that minimizes or eliminates fatty acid-CoA ligase activity.

DETAILED DESCRIPTION

Figure 1:
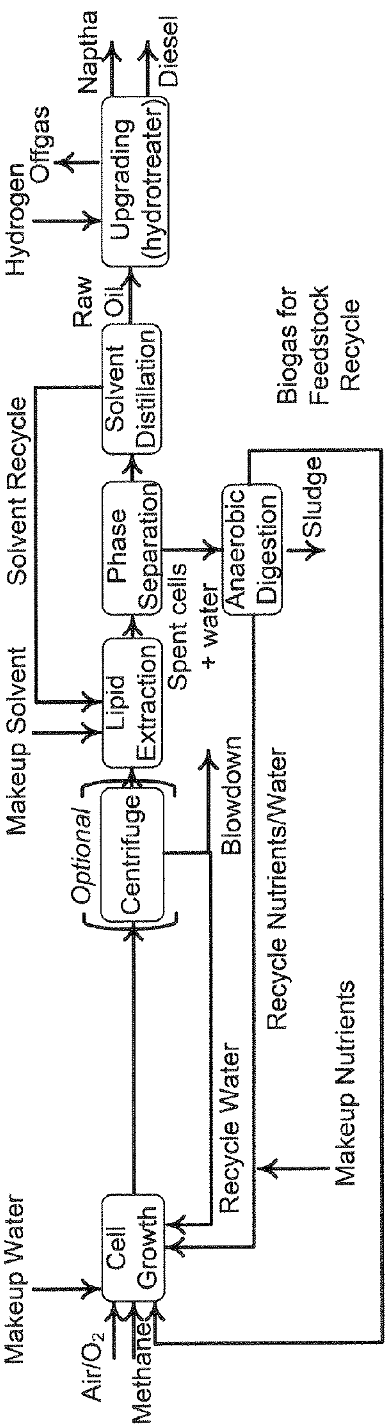
FIG. 1 shows an exemplary conceptual model of a $C_1$ metabolizing microorganism reactor system for methane capture and conversion into an alkane fuel in accordance with certain embodiments of this disclosure.

The instant disclosure provides compositions, methods and systems for generating biofuels and bioplastics, in which $C_1$ metabolizing microorganisms are cultured to generate biomass maximized for bio-oil accumulation. For example, a methane-to-biofuel fermentation process is provided, which is a scalable commercial process. This new approach can use, for example, methylotroph or methanotroph bacteria as a new host system to generate biomass for biofuel in the form of, for example, esterified biodiesel or alkane fuels for hydrotreatment, or for bioplastics in form of polyhydroalkanoates (PHAs). Furthermore, an oil composition of interest can be obtained from methylotroph or methanotroph bacteria because these organisms can accumulate significant quantities of membrane lipids under conditions described herein and, moreover, these microorganisms produce high membrane content.

By way of background, methane from a variety of sources, including natural gas, represents an abundant domestic resource. Chemical approaches developing gas-to-liquids (GTL) technology to improve the use of methane as a fuel have met with only limited success to date despite significant investment. In contrast, little effort has been expended to deploy modern bioengineering approaches toward GTL process development. Several limitations, most notably the cost of sugar feedstocks, have prevented the economical production of biofuels using microbial systems. Exploiting inexpensive, domestically abundant carbon feedstocks, such as methane, represents an economically sustainable biofuel production alternative. New production microorganisms have been developed with new bioengineering tools and techniques to provide an industrial-scale GTL bioprocess as described herein. Furthermore, fuel properties following refining and upgrading of extracted lipids demonstrate the drop-in potential for applications such as diesel, gasoline, jet fuel, or olefins.

In one aspect, the present disclosure provides a method for making fuel by refining an oil composition derived from a $C_1$ metabolizing non-photosynthetic microorganism in a refining unit to produce fuel. Additionally, this disclosure provides a method for making fuel by converting biomass from a culture primarily comprising a $C_1$ metabolizing non-photosynthetic microorganism into an oil composition and refining the oil composition into a fuel. In another aspect, this disclosure provides a biorefinery that includes a processing unit in which an oil composition is derived from a $C_1$ metabolizing non-photosynthetic microorganism; and a refining unit for refining the oil composition to produce a fuel.

In still another aspect, the instant disclosure provides an oil composition or biofuel composition derived therefrom having molecules comprising hydrogen and carbon atoms, wherein the hydrogen and carbon atoms are at least about 50% to about 99% of the weight of the composition and wherein the $\delta^{13}C$ of the composition is less than −30‰ or ranges from about −70‰ to about −35‰, or, when blended with a fuel component to produce a fuel product, ranges from about −37‰ to about −10‰. In a related aspect, the instant disclosure provides a biomass having a $\delta^{13}C$ of less than −30‰ or ranging from about −35‰ to about −50‰, −45‰ to about −35‰, or about −50‰ to about −40‰, or about −45‰ to about −65‰, or about −60‰ to about −70‰, or about −30‰ to about −70‰.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. The term "consisting essentially of" limits the scope of a claim to the specified materials or steps, or to those that do not materially affect the basic and novel characteristics of the claimed invention. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

As used herein, "$C_1$ substrate" or "$C_1$ compound" refers to any carbon containing molecule or composition that lacks a carbon-carbon bond. Exemplary $C_1$ substrates include natural gas, unconventional natural gas, syngas, methane, methanol, formaldehyde, formic acid or a salt thereof, carbon monoxide, carbon dioxide, methylated amines (e.g., methylamine, dimethylamine, trimethylamine, etc.), methylated thiols, methyl halogens (e.g., bromomethane, chloromethane, iodomethane, dichloromethane, etc.), cyanide, or any combination thereof.

As used herein, "$C_1$ metabolizing microorganism" or "$C_1$ metabolizing non-photosynthetic microorganism" refers to any microorganism having the ability to use a $C_1$ substrate as a source of energy or as its primary source of energy and biomass, and may or may not use other carbon substrates (such as sugars and complex carbohydrates) for energy and biomass. For example, a $C_1$ metabolizing microorganism may oxidize a $C_1$ substrate, such as methane or methanol. $C_1$ metabolizing microorganisms include bacteria (such as methanotrophs and methylotrophs) and yeast. In certain embodiments, a $C_1$ metabolizing microorganism does not include a photosynthetic microorganism, such as algae. In certain embodiments, the $C_1$ metabolizing microorganism will be an "obligate $C_1$ metabolizing microorganism," meaning its sole source of energy are $C_1$ substrates. In further embodiments, a $C_1$ metabolizing microorganism (e.g., methanotroph) will be cultured in the presence of a $C_1$ substrate feedstock (i.e., using the $C_1$ substrate as a source of energy).

As used herein, the term "methylotrophic bacteria" refers to any bacteria capable of oxidizing any compound in any form (e.g., solid, liquid, gas) that contains at least one carbon and that do not contain carbon-carbon bonds. In certain embodiments, a methylotrophic bacterium may be a methanotroph. For example, "methanotrophic bacteria" refers to any methylotrophic bacteria that have the ability to oxidize methane as a source of carbon and energy, which may be the primary source of carbon and energy. Exemplary methanotrophic bacteria include *Methylomonas, Methylobacter, Methylococcus, Methylosinus, Methylocystis, Methylomicrobium*, or *Methanomonas*. In certain embodiments, the methylotrophic bacterium is an "obligate methylotrophic bacterium," which refers to bacteria that are limited to the use of $C_1$ substrates for the generation of energy. In certain embodiments, methylotrophic bacteria are "facultative methanotrophic bacteria" that are naturally able to use multi-carbon substrates, such as acetate, pyruvate, succinate, malate, or ethanol, in addition to $C_1$ substrates as their carbon and energy source. Facultative methanotrophs include some species of *Methylocella, Methylocystis, Methylocapsa* (e.g., *Methylocella silvestris, Methylocella palustris, Methylocella tundrae, Methylocystis daltona* SB2, *Methylocystis bryophila*, and *Methylocapsa aurea* KYG), and *Methylobacterium organophilum* (ATCC 27,886).

As used herein, the term "CO utilizing bacterium" refers to a bacterium that naturally possesses the ability to oxidize carbon monoxide (CO) as a source of carbon and energy. Carbon monoxide may be utilized from "synthesis gas" or "syngas", a mixture of carbon monoxide and hydrogen produced by gasification of any organic feedstock, such as coal, coal oil, natural gas, biomass, or waste organic matter. CO utilizing bacteria does not include bacteria that must be genetically modified for growth on CO as its carbon source.

As used herein, "syngas" refers to a mixture comprising carbon monoxide (CO) and hydrogen ($H_2$). Syngas may also include $CO_2$, methane, and other gases in smaller quantities relative to CO and $H_2$.

"Growth" is defined as an increase in cell mass. This may occur through cell division (replication) and the formation of new cells during "balanced growth," or during "unbalanced growth" when cellular mass increases due to the accumulation of a specific compound or polymer, such as certain lipids. In the latter case, growth may be manifest as an increase in cell size due to the accumulation of a biopolymer within the cell.

During "balanced cell growth," all of the feedstocks (electron donors and electron acceptors) and all of the nutrients are present in the ratios required to make all of the macromolecular components of a cell. That is, no feedstock or nutrient limits the synthesis of proteins, complex carbohydrate polymers, fats, or nucleic acids. In contrast, during "unbalanced cell growth," a feedstock or nutrient needed to make one or more of a cell's macromolecules is not present in an amount or ratio required for balanced growth. Accordingly, this feedstock or nutrient becomes limiting and is referred to as a "limiting nutrient."

Some cells may still achieve net growth under unbalanced conditions, but the growth is unbalanced and polymers that can be synthesized in the absence of the limiting feedstock or nutrient will accumulate. These polymers include lipids or intracellular storage products, such as the polydroxyalkanoates (PHAs), including polyhydroxybutyrate (PHB), polyhdroxyvalerate (PHV), and polyhydroxyhexanoate (PHHx)-glycogen, or secreted materials, such as extracellular polysaccharide. Such oil compositions are useful in the production of bioplastics.

Exemplary balanced and unbalanced growth conditions may differ in the nitrogen content in the media. For example, nitrogen constitutes about 12% of dry cell weight, which means that 12 mg/L nitrogen must be supplied (e.g., in a nitrate or ammonium salt form, along with a feedstock and other nutrients in the required stoichiometric ratios) to grow 100 mg/L dry cell weight. Without wishing to be bound by theory, this assumes that fixation of atmospheric nitrogen into ammonia (i.e., via nitrogen fixation) does not represent a significant source of nitrogen for biosynthetic intermediates or cellular constituents. If other feedstock and nutrients are available in the quantities needed to produce 100 mg/L of dry cell weight, but less than 12 mg/L nitrogen is provided, then unbalanced cell growth may occur, with accumulation of polymers that do not contain nitrogen. If nitrogen is subsequently provided, the stored polymer may serve as feedstock for the cell, allowing balanced growth, with replication and production of new cells.

As used herein, the term "growth cycle" as applied to a cell or microorganism refers to the metabolic cycle through which a cell or microorganism moves in culture conditions. For example, the cycle may include various stages, such as a lag phase, an exponential phase, the end of exponential phase, and a stationary phase.

The term "exponential growth", "exponential phase growth", "log phase" or "log phase growth" refer to the rate at which microorganisms are growing and dividing. For example, during log phase, microorganisms are growing at their maximal rate given their genetic potential, the nature of the medium, and the conditions under which they are grown. Microorganism rate of growth is constant during exponential phase and the microorganism divides and doubles in number at regular intervals. Cells that are "actively growing" are those that are growing in log phase. In contrast, "stationary phase" refers to the point in the growth cycle during which cell growth of a culture slows or even ceases. The term "growth-altering environment" refers to energy, chemicals, or living things that have the capacity to either inhibit cell growth or kill cells. Inhibitory agents may include mutagens, drugs, antibiotics, UV light, extreme temperature, pH, metabolic byproducts, organic chemicals, inorganic chemicals, bacteria, viruses, or the like.

As used herein, "high growth variant" refers to an organism, microorganism, bacterium, yeast, or cell capable of growth with a $C_1$ substrate, such as methane or methanol, as the sole or primary carbon and energy source and which possesses an exponential phase growth rate that is faster than the parent, reference or wild-type organism, microorganism, bacterium, yeast, or cell—that is, the high growth variant has a faster doubling time and consequently a high rate of growth and yield of cell mass per gram of $C_1$ substrate metabolized as compared to a parent cell (see, e.g., U.S. Pat. No. 6,689,601).

As used herein, "biofuel" refers to a fuel at least partially derived from "biomass."

As used herein, "biomass" or "biological material" refers to organic material having a biological origin, which may include one or more of whole cells, lysed cells, extracellular material, or the like. For example, the material harvested from a cultured microorganism (e.g., bacterial or yeast culture) is considered the biomass, which can include cells, cell membranes, cell cytoplasm, inclusion bodies, products secreted or excreted into the culture medium, or any combination thereof. In certain embodiments, biomass comprises the $C_1$ metabolizing microorganisms of this disclosure together with the media of the culture in which the $C_1$ metabolizing microorganisms of this disclosure were grown. In other embodiments, biomass comprises a $C_1$ metabolizing microorganisms (whole or lysed or both) of this disclosure recovered from a culture grown on a $C_1$ substrate (e.g., natural gas, methane). In still other embodiments, biomass comprises the spent media supernatant from a culture of $C_1$ metabolizing microorganism cultured on a $C_1$ substrate. Such a culture may be considered a renewable resource.

As used herein, "oil composition" refers to the lipid content of a biomass (e.g., bacterial culture), including fatty acids, fatty acid esters, triglycerides, phospholipids, polyhydroxyalkanoates, isoprenes, terpenes, or the like. An oil composition of a biomass may be extracted from the rest of the biomass material by methods described herein, such as by hexane or chloroform extraction. In addition, an "oil composition" may be found in any one or more areas of a culture, including the cell membrane, cell cytoplasm, inclusion bodies, secreted or excreted into the culture medium, or any combination thereof. An oil composition is neither natural gas nor crude petroleum.

As used herein, the term "host" refers to a cell or microorganism (e.g., methanotroph) that may be genetically modified with an exogenous nucleic acid molecule to produce a polypeptide of interest (e.g., thioesterase [tesA], acetyl-CoA carboxylase [accABCD], malonyl-CoA-ACP transacylase [fabD]). In certain embodiments, a host cell may optionally already possess or be modified to include other genetic modifications that confer desired properties related or unrelated to the lipid biosynthesis (e.g., deleted, altered or truncated long-chain fatty acid-CoA ligase [fadD]). For example, a host cell may possess genetic modifications that minimize or reduce the degradation of fatty acids, minimize or reduce production of host cell growth inhibitors, provide high growth, tolerance of contaminants or particular culture conditions (e.g., acid tolerance, biocide resistance), ability to metabolize additional carbon substrates, or ability to synthesize further desirable products or intermediates.

As used herein, "recombinant" or "non-natural" refers to an organism, microorganism, cell, nucleic acid molecule, or vector that has at least one genetic alteration or has been modified by the introduction of a heterologous nucleic acid molecule, or refers to a cell that has been altered such that the expression of an endogenous nucleic acid molecule or gene can be controlled. Recombinant also refers to a cell that is derived from a cell or is progeny of a cell having one or more such modifications. Genetic alterations include, for example, modifications introducing expressible nucleic acid molecules encoding proteins or enzymes, or other nucleic acid molecule additions, deletions, substitutions or other functional alteration of a cell's genetic material. For example, recombinant cells may express genes or other nucleic acid molecules that are not found in identical form within the native cell (i.e., unmodified or wild type cell), or may provide an altered expression pattern of endogenous genes, such genes that may otherwise be over-expressed, under-expressed, minimally expressed, or not expressed at all.

Recombinant methods for expression of exogenous or heterologous nucleic acids in microbial organisms are well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exemplary exogenous proteins or enzymes to be expressed include thioesterase, one or more acetyl-CoA carboxylases, malonyl-CoA-ACP transacylase, or any combination thereof. Genetic modifications to nucleic acid molecules encoding enzymes, or functional fragments thereof, can confer a biochemical or metabolic capability to a recombinant cell that is altered from its naturally occurring state.

As used herein, the term "endogenous" or "native" refers to a gene, protein, compound or activity that is normally present in a host cell. The term "homologous" or "homolog" refers to a molecule or activity from an exogenous (non-native) source that is the same or similar molecule or activity as that found in or derived from a host cell, species or strain.

As used herein, "heterologous" nucleic acid molecule, construct or sequence refers to a nucleic acid molecule or portion of a nucleic acid molecule sequence that is not native to a cell in which it is expressed, a nucleic acid molecule or portion of a nucleic acid molecule native to a host cell that has been altered or mutated, or a nucleic acid molecule with an altered expression as compared to the native expression levels under similar conditions. For example, a heterologous control sequence (e.g., promoter, enhancer) may be used to regulate expression of a gene or a nucleic acid molecule in a way that is different than the gene or a nucleic acid molecule that is normally expressed in nature or culture. In certain embodiments, a heterologous nucleic acid molecule may be homologous to a native host cell gene, but may have an altered expression level or have a different sequence or both. In other embodiments, heterologous or exogenous nucleic acid molecules may not be endogenous to a host cell or host genome, but instead may have been added to a host cell by conjugation, transformation, transfection, electroporation, or the like, wherein the added molecule may integrate into the host genome or can exist as extra-chromosomal genetic material (e.g., plasmid or other self-replicating vector).

In certain embodiments, more than one heterologous or exogenous nucleic acid molecule can be introduced into a host cell as separate nucleic acid molecules, as a polycistronic nucleic acid molecule, as a single nucleic acid molecule encoding a fusion protein, or any combination thereof, and still be considered as more than one heterologous or exogenous nucleic acid. For example, a $C_1$ metabolizing microorganism can be modified to express two or more heterologous or exogenous nucleic acid molecules, which may be the same or different, that encode one or more thioesterases as disclosed herein. In certain embodiments, multiple copies of a thioesterase (TE) encoding polynucleotide molecule are introduced into a host cell, which may be two, three, four, five, six, seven, eight, nine, ten or more copies of the same TE or different TE encoding polynucleotides.

When two or more exogenous nucleic acid molecules are introduced into a host $C_1$ metabolizing microorganism, it is understood that the two more exogenous nucleic acid molecules can be introduced as a single nucleic acid molecule (e.g., on a single vector), on separate vectors, integrated into the host chromosome at a single site or multiple sites, and each of these embodiments is still to be considered two or more exogenous nucleic acid molecules. Thus, the number of referenced heterologous nucleic acid molecules or protein activities refers to the number of encoding nucleic acid molecules or the number of protein activities, not the number of separate nucleic acid molecules introduced into a host cell.

The "percent identity" between two or more nucleic acid sequences is a function of the number of identical positions shared by the sequences (i.e., % identity=number of identical positions/total number of positions×100), taking into account the number of gaps, and the length of each gap that needs to be introduced to optimize alignment of two or more sequences. The comparison of sequences and determination of percent identity between two or more sequences can be accomplished using a mathematical algorithm, such as BLAST and Gapped BLAST programs at their default parameters (e.g., Altschul et al., *J. Mol. Biol.* 215:403, 1990; see also BLASTN at www.ncbi.nlm.nih.gov/BLAST).

A "conservative substitution" is recognized in the art as a substitution of one amino acid for another amino acid that has similar properties. Exemplary conservative substitutions are well known in the art (see, e.g., WO 97/09433, p. 10; Lehninger, Biochemistry, $2^{nd}$ Edition; Worth Publishers, Inc. NY:N.Y. (1975), pp. 71-77; Lewin, Genes IV, Oxford University Press, NY and Cell Press, Cambridge, Mass. (1990), p. 8).

As used herein, "overexpressed" when referring to a gene or a protein means an increase in expression or activity of the gene or protein. Increased expression or activity includes expression or activity of a gene or protein being increased above the level of a wild-type (non-genetically engineered) control or reference microorganism. A gene or protein is overexpressed if the expression or activity is in a microorganism where it is not normally expressed or active. A gene or protein is overexpressed if the expression or activity is extended or present longer in the recombinant microorganism than in a wild-type control or reference microorganism.

"Inhibit" or "inhibited," as used herein, refers to an alteration, reduction, down regulation, abrogation or deletion, directly or indirectly, in the expression of a target gene or in the activity of a target molecule (e.g., long-chain fatty acid-CoA ligase) relative to a control, endogenous or reference molecule, wherein the alteration, reduction, down regulation or abrogation is statistically, biologically, industrially, or clinically significant.

As used herein, "biorefinery" refers to a facility that integrates biomass conversion processes and equipment to produce fuels from biomass.

As used herein, "refinery" refers to an oil refinery, or aspects thereof, at which oil compositions (e.g., biomass, biofuel, or fossil fuels such as crude oil, coal or natural gas) may be processed. Exemplary processes carried out at such refineries include cracking, transesterification, reforming, distilling, hydroprocessing, isomerization, or any combination thereof.

Biofuel Production Systems

The systems for generating biofuels of the instant disclosure may include separate units (e.g., close or adjacent to each other, or not), integrated units, or the system itself may be interconnected and partially or fully integrated. The systems of this disclosure may use biomass from a microorganism grown in an integrated biorefinery to generate fuel compositions and fuel products, particularly biofuels. In certain embodiments, a biorefinery uses a single biomass or a mixed biomass to generate fuel (e.g., diesel fuel, jet fuel, gasoline), such as a $C_1$ metabolizing microorganism (e.g., a methanotroph such as *Methylosinus trichosporium* OB3b, *Methylococcus capsulatus* Bath, *Methylomonas* sp. 16a, *Methylomonas methanica, Methylomicrobium alcaliphilum*, or a high growth variants thereof) as the biomass.

An exemplary biorefinery system is illustrated in FIG. 1. Such a system can perform one or more of the following steps: culturing a microorganism strain of interest (e.g., a methanotroph, methylotroph or yeast) which may have one or more improved properties (e.g., recombinant, higher growth rate, ability to grow in high pH, improved utilization of nutrients, temperature stability, increased biomass yield), recovering a product such as an oil composition (e.g., fatty acids, triglycerides, phospholipids, isoprenes, terpenes, PHA, or any combination thereof) from the microorganism, and refining the oil composition to produce plastic precursors or one or more fuels, such as jet fuel, diesel fuel, gasoline, or a combination thereof. Different biofuel compositions and products can be produced by the system simultaneously or in series. For example, the system can include a hydrotreating plant or unit that can convert the oil composition to jet fuel and diesel. The system can also include a petroleum refinery that can convert the crude oil and products from the hydrotreating plant to gasoline. For example, the production of jet fuel and diesel fuel can result in additional products, such as naphtha and light hydrocarbons, including propane, that are then used for generating gasoline. Exemplary light hydrocarbons include methane, ethane, propane, butane, pentane, butanol, and isobutanol. In another example, production of gasoline can result in additional products, such as diesel, which can be used for producing jet fuel.

Figure 2:
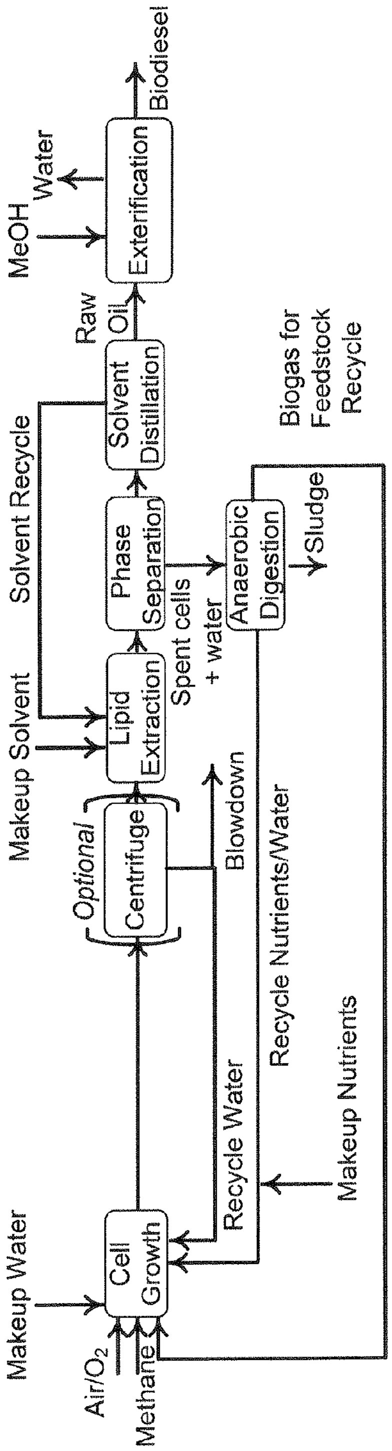
FIG. 2 shows an exemplary conceptual model of a $C_1$ metabolizing microorganism reactor system for methane capture and conversion into biodiesel in accordance with certain embodiments of this disclosure.

An alternative exemplary biorefinery system is illustrated in FIG. 2. Such a system can perform one or more of the following steps: culturing a microorganism strain of interest (e.g., a methanotroph, methylotroph or yeast) which may have one or more improved properties (e.g., recombinant, higher growth rate, ability to grow in high pH, improved utilization of nutrients, temperature stability, increased biomass yield), recovering a product such as an oil composition (e.g., fatty acids, fatty acid esters, triglycerides, phospholipids, isoprenes, terpenes, PHA, or any combination thereof) from the microorganism, and modifying the oil composition to produce a biodiesel composition. For example, the system can include an esterification plant or unit that can convert the oil composition to biodiesel by reaction with an alcohol. Exemplary alcohols include methanol, ethanol, propanol, butanol, or longer chain fatty alcohols.

In some embodiments, the systems disclosed herein use bacteria, such as methylotrophs or methanotrophs, or yeast as the microorganism. The bacteria or yeast can be harvested and separated from the culture media (if not grown as, for example, a biofilm), resulting in a bacterial or yeast paste. The bacterial or yeast biomass may optionally be dried prior to obtaining an oil composition from the biomass. In certain embodiments, the bacterial or yeast biomass remains wet to some extent and need not be fully dried before the oil composition is derived, separated, or extracted. Bacterial or yeast oil compositions may be extracted from the biomass and be separated from the bacterial or yeast solids or sludge.

Extraction of an oil composition may be accomplished using various different methods or solvents (e.g., a polar solvent, a non-polar solvent, a neutral solvent, an acidic solvent, a basic solvent, hexane, or a combination thereof), such as hexane or acidic methanol or chloroform/methanol mix, in processes such as those described in more detail herein or other extraction methods known in the art.

In certain embodiments, a $C_1$ metabolizing microorganism (e.g., methanotroph) oil composition contained within a harvested biomass is separated from the biomass using high-shear contact with an organic solvent (e.g., hexane) and a conditioning agent. By way of background, the oil dissolves into hexane, or other similar solvents, forming a solution of miscella, whereas water and cellular solids do not dissolve and can be separated from the miscella. The immiscibility of water and hexane is used to produce the desired separation. In certain embodiments, following high-shear mixing, the oil composition/hexane/water mixture is sent to a decanter where it separates into two distinct liquids: a lighter hexane and oil composition phase (miscella), and a heavier water and spent solids phase. In still further embodiments, the miscella from the decanter is fed into a distillation process where the oil composition is separated from the solvent, which allows recovery and reuse of the solvent, and purifies the oil to a point where it is ready for downstream processing. Distillation, for example, takes advantage of the difference in boiling points of the solvent and oil to separate the two components.

In certain embodiments, an oil composition of the present disclosure is refined. Refining may include cracking, transesterification, reforming, distilling, hydroprocessing, isomerization, or a combination thereof. Optionally, refining can involve removal of contaminants. For example heteroatoms and metals can be removed by hydrotreating (e.g., hydrodenitrogenation (HDN), hydrodeoxygenation (HDO), hydrodesulfurization (HDS), hydrodemetallization (HDM)). Hydrotreatment may also be saturation of olefins, distillate hydrotreating, vacuum gas oil hydrotreating, fixed-bed residue hydrotreating, or a combination thereof. Hydrotreatment of an oil composition can produce jet fuel or diesel. The oil composition can also be refined by cracking, such as catalytic cracking to produce gasoline. Representative cracking processes may include catalytic cracking, fluid catalytic cracking, steam cracking, hydrocracking, thermal cracking, thermal catalytic cracking, or a combination thereof. The refining by hydrotreating and cracking can occur concurrently (both processes occurring) or alternatively (one or the other is occurring). The refining processes can also be subsequent to each other, for example, products produced by hydrotreatment, can then be processed by cracking. Products from one refining process (e.g., $H_2$) can also be further used by another refining process. The refining processes can be separate units of the system, or in the same unit. Moreover, the bacterial or yeast solids or sludge can be used to produce fuels, animal feed, or energy, such as methane released from digestion of the solids or sludge.

In certain embodiments, the instant disclosure provides a biorefinery comprising (a) a processing unit in which an oil composition is derived from a $C_1$ metabolizing non-photosynthetic microorganism; and (b) a refining unit for refining the oil composition to produce a fuel. In further embodiments, the biorefinery may further comprise a controlled culturing unit for culturing a $C_1$ metabolizing non-photosynthetic microorganism in the presence of a feedstock comprising a $C_1$ substrate, wherein the cultured bacteria produce the oil composition.

Exemplary controlled culturing units include a fermentor, a bioreactor, a hollow fiber cell, packed bed bioreactor, or the like. In further embodiments, the culture may be grown in the form of liquid-phase fermentation or solid phase fermentation. For example, bacteria, such as methylotrophs or methanotrophs, may be cultured in a bioreactor containing balanced media, or unbalanced media that has limiting quantities of phosphorus, nitrogen, trace elements, oxygen, or any combination thereof, so that certain lipids or other polymers of interest (e.g., PHAs) accumulate in the cells.

In certain embodiments, cultures include a bacterial community, including a variety of methylotrophs or methanotrophs that produce the highest levels of an oil composition of interest (i.e., high w/w ratios of lipids to biomass). A range of bioreactor configurations may be used, including sequencing membrane bioreactors and a continuous multistage dispersed growth configuration. In certain embodiments, a bioreactor is operated to select for bacteria that efficiently produce an oil composition of interest from methane, e.g., bioreactor conditions may select against bacteria that either do not produce an oil composition of interest from methane or produce such a composition inefficiently.

In further embodiments, the present disclosure provides a controlled culturing unit in which a $C_1$ substrate (e.g., methane or syngas) is delivered in a gas phase to microbial biofilms in solid phase fermentation. In other embodiments, balanced or unbalanced growth conditions are established in solid phase fermentation. In still other embodiments, methylotrophs or methanotrophs are grown under balanced growth conditions, harvested and separated from liquid phase, and transferred to a solid phase fermentation chamber where $C_1$ substrate is delivered under unbalanced conditions (e.g., nitrogen is not included) and the bacteria consume the substrate to generate an oil composition of interest.

In certain embodiments, the instant disclosure provides a biorefinery comprising (a) a controlled culturing unit for culturing a $C_1$ metabolizing non-photosynthetic microorganism in the presence of a feedstock comprising a $C_1$ substrate, wherein the cultured bacteria produce the oil composition; (b) a processing unit in which an oil composition is derived or extracted from a $C_1$ metabolizing non-photosynthetic microorganism; and (c) a refining unit for refining the oil composition to produce a fuel. In further embodiments, the feedstock $C_1$ substrate used in the biorefinery is methane, methanol, formaldehyde, formic acid or a salt thereof, carbon monoxide, carbon dioxide, syngas, a methylamine, a methylthiol, or a methylhalogen.

In further biorefinery embodiments, the $C_1$ metabolizing non-photosynthetic microorganism is a methanotroph or methylotroph, the feedstock $C_1$ substrate is natural gas or methane, and the bacteria are cultured under aerobic conditions. In further embodiments, the methanotroph is *Methylosinus trichosporium* OB3b, *Methylococcus capsulatus* Bath, *Methylomonas* sp. 16a, *Methylomonas methanica, Methylomicrobium alcaliphilum*, any combination thereof, or a high growth variant thereof, and the methylotroph is *Methylobacterium extorquens, Methylobacterium radiotolerans, Methylobacterium populi, Methylobacterium chloromethanicum, Methylobacterium nodulans*, any combination thereof, or a high growth variant thereof. In certain other embodiments, the $C_1$ metabolizing non-photosynthetic microorganism is an obligate $C_1$ metabolizing non-photosynthetic microorganism, such as an obligate methanotroph or methylotroph.

In further embodiments, the $C_1$ metabolizing non-photosynthetic microorganism is a recombinant microorganism comprising a heterologous polynucleotide encoding a fatty acid producing enzyme, a formaldehyde assimilation enzyme, or a combination thereof. For example, biosynthesis of free fatty acids (FFAs), which can be used as precursors for the production of fuels or other high value chemicals, can be enhanced by introducing a thioesterase (TE) gene into a $C_1$ metabolizing non-photosynthetic microorganism of this disclosure (e.g., *Methylosinus trichosporium* OB3b, *Methylococcus capsulatus* Bath, *Methylomonas* sp. 16a, *Methylomonas methanica*). Biosynthesis of FFAs can also be enhanced by optionally introducing more than one TE gene, malonyl CoA-acyl carrier protein transacylase (FabD, also referred to as MCT) gene, one or more genes from the acetyl-CoA carboxylase operon (AccABCD), or any combination thereof. In certain embodiments, the production of FFAs can be improved by over-expressing a malonyl CoA-acyl carrier protein transacylase (FabD, also referred to as MCT) since the first committed step of fatty acid biosynthesis is the conversion of acetyl-CoA to malonyl-CoA by an adenosine triphosphate (ATP)-dependent acetyl-CoA carboxylase followed by the conversion of malonyl-CoA to malonyl-ACP through the FabD enzyme.

In further embodiments, a $C_1$ metabolizing non-photosynthetic microorganism is a recombinant microorganism comprising a genetic modification that minimizes or reduces the degradation of fatty acids. For example, a $C_1$ metabolizing non-photosynthetic microorganism is a recombinant microorganism comprising one or more mutations that truncate or knock-out long-chain fatty acid-CoA ligase activity encoded by one or more endogenous fadD genes.

The nucleic acid sequences encoding wild-type FadD proteins are the reference standard starting point for designing mutant fadD genes. For example, the wild-type FadD protein sequence encoded by *M. trichosporium* OB3b, *M. capsulatus* Bath, *M. methanica, M. extorquens*, and *C. ljungdahlii* are provided in GenBank Accession Nos. EFH00931.1, YP_114021.1, YP_004512148.1, YP_002964871.1, and YP_003782065.1, respectively. In certain embodiments, a nucleic acid molecule of afadD gene encoding any one of above-noted proteins is individually modified to mutate fadD. In Example 2 herein, the fadD gene from various $C_1$ metabolizing microorganism were synthesized to incorporate several stop mutations and frame shifts in the 5'-region of the gene from *M. trichosporium* OB3b (SEQ ID NO.:1), *M. methanica* (SEQ ID NO.:35), *M. extorquens* (SEQ ID NO.:52), and *C. ljungdahlii* (SEQ ID NO.:85). For the *M. capsulatus* fadD gene, a nucleic acid molecule comprising an internal deletion was synthesized so that the remaining 5' and 3' ends of the gene could be joined to maintain the original reading frame (SEQ ID NO.:18).

For certain $C_1$ metabolizing microorganisms wherein the fadD gene sequence is not known (e.g., *Clostridium autoethanogenum*), the genome can be sequenced and the fadD homolog to *E. coli* is identified via a tblastn search (a search of the translated nucleotide gene sequences with the protein sequence of the *E. coli* FadD). For example, a nucleic acid molecule of the *C. autoethanogenum* fadD gene is synthesized to incorporate several stop mutations and frame shifts in the 5'-region of the gene.

In certain embodiments, a mutant fadD nucleic acid molecule is cloned into a plasmid expression vector (and optionally lacking a $C_1$ metabolizing microorganism origin of replication and encoding antibiotic resistance) for conjugation, electroporation, or transformation into a $C_1$ metabolizing microorganism using methods described herein. In certain embodiments, a fadD mutant incorporates into a host cell genome by homologous recombination and results in recombinant cells that lack or have minimal long-chain fatty acid-CoA ligase activity.

In certain embodiments, any one or all of the TE, MCT, and Acc genes introduced into $C_1$ metabolizing microorganisms of this disclosure can be over-expressed and the $C_1$ metabolizing microorganisms may optionally have a mutation that minimizes or eliminates fatty acid-CoA ligase activity (e.g., a fadD knock-out).

In certain embodiments, the biorefinery processing unit is capable of deriving the oil composition by a wet extraction, a supercritical fluid extraction, dry extraction, thermal extraction (e.g., steam stripping, hydrothermal liquefaction, pressure cooking), enzymatic hydrolysis (e.g., of the cell wall), pulsed electric field extraction, microbubbles, hollow fiber extraction, or the like. In further embodiments, the wet extraction comprises use of a polar solvent, a non-polar solvent, a neutral solvent, an acidic solvent, a basic solvent, hexane, or a combination thereof. In certain embodiments, an oil composition is derived or extracted from a cell membrane of the $C_1$ metabolizing non-photosynthetic microorganism or may be recovered from a culture supernatant if secreted or excreted, or a combination thereof. In further embodiments, the biorefinery further comprises a second processing unit, wherein the second processing unit is a waste processing unit for processing residual matter from the refined oil composition, which includes an anaerobic digester, an aerobic digester, or both. In still further embodiments, the biorefinery further comprises a conduit for delivering at least one product from the waste processing unit for use in culturing or maintaining the $C_1$ metabolizing non-photosynthetic microorganism.

In still further embodiments, the biorefinery processing unit further comprises a controlled culturing unit, wherein the controlled culturing unit is a solid phase fermentation unit in which the culturing and processing (e.g., extraction) can occur in the same unit or even the same chamber. In certain embodiments, the biorefinery combined culturing/processing unit includes supercritical fluid extraction, such as by supercritical fluid comprising $CO_2$, methanol, or $H_2O$.

In certain aspects, any of the aforementioned biorefineries are integrated.

$C_1$ Metabolizing Microorganisms

The $C_1$ metabolizing microorganisms of the instant disclosure may be natural, strain adapted (e.g., performing fermentation to select for strains with improved growth rates and increased total biomass yield compared to the parent strain), or recombinantly modified to produce lipids of interest (e.g., genetically altered to express a fatty acid producing enzyme, a formaldehyde assimilation enzyme, or a combination thereof) or to have increased growth rates or both. In certain embodiments, the $C_1$ metabolizing microorganisms are not $C_1$ metabolizing non-photosynthetic microorganisms, such as algae or plants.

In certain embodiments, the present disclosure provides $C_1$ metabolizing microorganisms that are prokaryotes or bacteria, such as *Methylomonas, Methylobacter, Methylococcus, Methylosinus, Methylocystis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas*, or *Pseudomonas*.

In further embodiments, the $C_1$ metabolizing bacteria are a methanotroph or a methylotroph. Exemplary methanotrophs include *Methylomonas, Methylobacter, Methylococcus, Methylosinus, Methylocystis, Methylomicrobium, Methanomonas, Methylocella*, or a combination thereof. Exemplary methylotrophs include *Methylobacterium extorquens, Methylobacterium radiotolerans, Methylobacterium populi, Methylobacterium chloromethanicum, Methylobacterium nodulans*, or a combination thereof.

In certain embodiments, methanotrophic bacteria are genetically engineered with the capability to convert a $C_1$ substrate feedstock into an oil composition. Methanotrophic bacteria have the ability to oxidize methane as a carbon and energy source. Methanotrophic bacteria are classified into three groups based on their carbon assimilation pathways and internal membrane structure: type I (gamma proteobacteria), type II (alpha proteobacteria, and type X (gamma proteobacteria). Type I methanotrophs use the ribulose monophosphate (RuMP) pathway for carbon assimilation whereas type II methanotrophs use the serine pathway. Type X methanotrophs use the RuMP pathway but also express low levels of enzymes of the serine pathway. Methanotrophic bacteria include obligate methanotrophs, which can only utilize $C_1$ substrates for carbon and energy sources, and facultative methanotrophs, which naturally have the ability to utilize some multi-carbon substrates as a carbon and energy source.

Exemplary facultative methanotrophs include some species of *Methylocella, Methylocystis*, and *Methylocapsa* (e.g., *Methylocella silvestris, Methylocella palustris, Methylocella tundrae, Methylocystis daltona* strain SB2, *Methylocystis bryophila*, and *Methylocapsa aurea* KYG), *Methylobacterium organophilum* (ATCC 27,886), *Methylibium petroleiphilum*, or high growth variants thereof. Exemplary obligate methanotrophic bacteria include *Methylococcus capsulatus* Bath (NCIMB 11132), *Methylomonas* sp. 16a (ATCC PTA 2402), *Methylosinus trichosporium* OB3b (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* Y (NRRL B-11,201), *Methylomonas flagellata* sp. AJ-3670 (FERM P-2400), *Methylacidiphilum infernorum* and *Methylomicrobium alcaliphilum*, or high growth variants thereof.

In still further embodiments, the present disclosure provides $C_1$ metabolizing microorganisms that are syngas metabolizing bacteria, such as *Clostridium, Moorella, Pyrococcus, Eubacterium, Desulfobacterium, Carboxydothermus, Acetogenium, Acetobacterium, Acetoanaerobium, Butyribaceterium, Peptostreptococcus*, or any combination thereof. Exemplary syngas metabolizing bacteria include *Clostridium autoethanogenum, Clostridium ljungdahli, Clostridium ragsdalei, Clostridium carboxydivorans, Butyribacterium methylotrophicum, Clostridium woodii, Clostridium neopropanologen*, or any combination thereof.

In certain other embodiments, $C_1$ metabolizing microorganisms are eukaryotes such as yeast, including *Candida, Yarrowia, Hansenula, Pichia, Torulopsis*, or *Rhodotorula*.

In certain other embodiments, the $C_1$ metabolizing non-photosynthetic microorganism is an obligate $C_1$ metabolizing non-photosynthetic microorganism, such as an obligate methanotroph or methylotroph. In further embodiments, the $C_1$ metabolizing non-photosynthetic microorganism is a recombinant microorganism comprising a heterologous polynucleotide encoding a fatty acid producing enzyme, a formaldehyde assimilation enzyme, or a combination thereof. In certain embodiments, any one or all of the TE, MCT, and Acc genes introduced into a $C_1$ metabolizing microorganism of this disclosure can be over-expressed and the $C_1$ metabolizing microorganisms may optionally have a mutation that minimizes or eliminates fatty acid-CoA ligase activity (e.g., a fadD knock-out).

Each of the microorganisms of this disclosure may be grown as an isolated culture, with a heterologous organism that may aid with growth, or one or more of these bacteria may be combined to generate a mixed culture. In still further embodiments, $C_1$ metabolizing non-photosynthetic microorganisms of this disclosure are obligate $C_1$ metabolizing non-photosynthetic microorganisms.

Any one of the aforementioned $C_1$ metabolizing microorganisms can be used as a parent or reference host cell to make a recombinant $C_1$ metabolizing microorganisms of this disclosure.

Codon Optimization

Expression of recombinant proteins may be difficult outside their original host. For example, variation in codon usage bias has been observed across different species of bacteria (Sharp et al., *Nucl. Acids. Res.* 33:1141, 2005). Over-expression of recombinant proteins even within their native host may also be difficult. In certain embodiments, nucleic acid molecules (e.g., nucleic acids encoding thioesterase, fabD, accABCD) to be introduced into a host as described herein may be subjected to codon optimization prior to introduction into the host to ensure protein expression is effective or enhanced. Codon optimization refers to alteration of codons in genes or coding regions of nucleic acids before transformation to reflect the typical codon usage of the host without altering the polypeptide encoded by the non-natural DNA molecule. Codon optimization methods for optimum gene expression in heterologous hosts have been previously described (see, e.g., Welch et al., *PLoS One* 4:e7002, 2009; Gustafsson et al., *Trends Biotechnol.* 22:346, 2004; Wu et al., *Nucl. Acids Res.* 35:D76, 2007; Villalobos et al., *BMC Bioinformatics* 7:285, 2006; U.S. Patent Publication Nos. 2011/0111413 and 2008/0292918; disclosure of which methods are incorporated herein by reference, in their entirety).

Similarly, exogenous nucleic acid molecules of this disclosure encoding polypeptide variants may be designed using the phylogenetic-based methods described in the references noted above (U.S. Pat. No. 8,005,620; Gustafsson et al.; Welch et al.; Villalobos et al.; Minshull et al.). Each variant polypeptide generated by these methods will retain at least 50% activity (preferably 100% or more activity) and have a polypeptide sequence that is at least 90%, at least 91%, at least 92%, at least 93%, at least 94%, at least 95%, at least 96%, at least 97%, at least 98%, at least 99% identical, or 100% identical to a reference or parental wild-type polypeptide sequence. In certain embodiments, variant polypeptides will include at least one amino acid substitution (e.g., 1, 2, 3, 5, 6, 7, 8, 9 or 10 or more or up to 20, 25, or 30 substitutions) at a pre-determined position relative to a reference or parental wild-type enzyme, provided that a variant retains an activity of interest (e.g., thioesterase activity or fatty acid production).

In certain embodiments, an *E. coli, Cinnamomum camphorum, Umbellularia californica, Streptoccus pyogenes, Ricinius communis*, or *Jatropha curcus* thioesterase is codon optimized for expression in a $C_1$ metabolizing microorganism of this disclosure (e.g., methanotroph, methylotroph, *Clostridium*). In further embodiments, any one or more of the codon optimized thioesterase sequences are introduced (e.g., transformed, conjugated, electroporated) into a $C_1$ metabolizing microorganism of this disclosure. Exemplary codon optimized thioesterase sequences are set forth in (1) SEQ ID NOS.:3-13 for *M. trichosporium* OB3b; (2) SEQ ID NOS.: 20-30 for *M. capsulatus* Bath; (3) SEQ ID NOS.:37-47 for *M. methanica*; (4) SEQ ID NOS.:54-64 for *M. extorquens*; (5) SEQ ID NOS.:70-80 for *C. autoethanogenum*; and (6) SEQ ID NOS.:87-97 for *C. ljungdahlii.*

In certain embodiments, an *E. coli* malonyl CoA-acyl carrier protein transacylase (fabD) sequence is codon optimized for expression in a $C_1$ metabolizing microorganism of this disclosure (e.g., methanotroph, methylotroph, *Clostridium*). In further embodiments, any one or more of the codon optimized fabD sequences are introduced (e.g., transformed, conjugated, electroporated) into a $C_1$ metabolizing microorganism of this disclosure. Exemplary codon optimized fabD sequences are set forth in (1) SEQ ID NO.:2 for *M. trichosporium* OB3b; (2) SEQ ID NO.:19 for *M. capsulatus* Bath; (3) SEQ ID NO.:36 for *M. methanica*; (4) SEQ ID NO.:53 for *M. extorquens*; (5) SEQ ID NO.:69 for *C. autoethanogenum*; and (6) SEQ ID NO.:86 for *C. ljungdahlii.*

In certain embodiments, one or more acetyl-CoA carboxylase sequence (e.g., accA, accB, accC, and accD from *E. coli*) is codon optimized for expression in a $C_1$ metabolizing microorganism of this disclosure (e.g., methanotroph, methylotroph, *Clostridium*). In further embodiments, any one or more of the codon optimized Acc sequences are introduced (e.g., transformed, conjugated, electroporated) into a $C_1$ metabolizing microorganism of this disclosure. In other embodiments, a codon optimized accA is introduced or a codon optimized accABCD is introduced. Exemplary codon optimized accA, accB, accC, and accD sequences are set forth, respectively, in (1) SEQ ID NOS.:14-17 for *M. trichosporium* OB3b; (2) SEQ ID NOS.:31-34 for *M. capsulatus* Bath; (3) SEQ ID NOS.:48-51 for *M. methanica*; (4) SEQ ID NOS.:65-68 for *M. extorquens*; (5) SEQ ID NOS.:81-84 for *C. autoethanogenum*; and (6) SEQ ID NOS.:98-101 for *C. ljungdahlii.*

Transformation Methods

Any of the recombinant $C_1$ metabolizing microorganisms or methanotrophic bacteria described herein may be transformed to comprise at least one exogenous nucleic acid to provide the host with a new or enhanced activity (e.g., enzymatic activity) or may be genetically modified to remove or substantially reduce an endogenous gene function using any of a variety of methods known in the art.

Transformation refers to the introduction of a nucleic acid molecule (e.g., exogenous or heterologous nucleic acid molecule) into a host cell. The transformed host cell may carry the exogenous or heterologous nucleic acid molecule extra-chromosomally or integrated in the chromosome. Integration into a host cell genome and self-replicating vectors generally result in genetically stable inheritance of the transformed nucleic acid molecule. Host cells containing the transformed nucleic acid molecules are referred to as "non-naturally occurring" or "genetically engineered" or "recombinant" or "transformed" or "transgenic" cells (e.g., bacteria).

Expression systems and expression vectors useful for the expression of heterologous nucleic acids in $C_1$ metabolizing microorganisms (e.g., methanotrophic bacteria) are known.

Electroporation of $C_1$ metabolizing bacteria is described herein and has been previously described in, for example, Toyama et al., *FEMS Microbiol. Lett.* 166:1, 1998; Kim and Wood, *Appl. Microbiol. Biotechnol.* 48:105, 1997; Yoshida et al., *Biotechnol. Lett.* 23:787, 2001, and U.S. Patent Appl. Pub. No. 2008/0026005.

Bacterial conjugation, which refers to a particular type of transformation involving direct contact of donor and recipient cells, is more frequently used for the transfer of nucleic acid molecules into $C_1$ metabolizing bacteria. Bacterial conjugation involves mixing "donor" and "recipient" cells together in close contact with each other. Conjugation occurs by formation of cytoplasmic connections between donor and recipient bacteria, with unidirectional transfer of newly synthesized donor nucleic acid molecules into the recipient cells. A recipient in a conjugation reaction is any cell that can accept nucleic acids through horizontal transfer from a donor bacterium. A donor in a conjugation reaction is a bacterium that contains a conjugative plasmid, conjugative transposon, or mobilized plasmid. The physical transfer of the donor plasmid can occur through a self-transmissible plasmid or with the assistance of a "helper" plasmid. Conjugations involving $C_1$ metabolizing bacteria is described herein and have been previously described in Stolyar et al., *Mikrobiologiya* 64:686, 1995; Motoyama et al., *Appl. Micro. Biotech.* 42:67, 1994; Lloyd et al., *Arch. Microbiol.* 171:364, 1999; PCT Publication No. WO 02/18617; and Ali et al., *Microbiol.* 152:2931, 2006.

Expression of heterologous nucleic acids in $C_1$ metabolizing bacteria is known in the art (see, e.g., U.S. Pat. No. 6,818,424, U.S. Patent Appl. Pub. No. 2003/0003528). Mu transposon based transformation of methylotrophic bacteria has been described (Akhverdyan et al., *Appl. Microbiol. Biotechnol.* 91:857, 2011). A mini-Tn7 transposon system for single and multicopy expression of heterologous genes without insertional inactivation of host genes in *Methylobacterium* has been described (U.S. Patent Appl. Pub. No. 2008/0026005).

Various methods for inactivating, knocking-out, or deleting endogenous gene function in $C_1$ metabolizing bacteria may be used. Allelic exchange using suicide vectors to construct deletion/insertion mutants in slow growing $C_1$ metabolizing bacteria have also been described herein and in, for example, Toyama and Lidstrom, *Microbiol.* 144:183, 1998; Stolyar et al., *Microbiol.* 145:1235, 1999; Ali et al., *Microbiol.* 152:2931, 2006; Van Dien et al., *Microbiol.* 149:601, 2003.

Suitable homologous or heterologous promoters for high expression of exogenous nucleic acid molecules may be utilized. For example, U.S. Pat. No. 7,098,005 describes the use of promoters that are highly expressed in the presence of methane or methanol for heterologous gene expression in $C_1$ metabolizing bacteria. Additional promoters that may be used include deoxy-xylulose phosphate synthase methanol dehydrogenase operon promoter (Springer et al., *FEMS Microbiol. Lett.* 160:119, 1998); the promoter for PHA synthesis (Foellner et al., *Appl. Microbiol. Biotechnol.* 40:284, 1993); the pyruvate decarboxylase promoter (Tokuhiro et al., *Appl. Biochem. Biotechnol.* 131:795, 2006); or promoters identified from native plasmid in methylotrophs (EP 296484). Non-native promoters include the lac operon Plac promoter (Toyama et al., *Microbiol.* 143:595, 1997) or a hybrid promoter such as Ptrc (Brosius et al., *Gene* 27:161, 1984).

In certain embodiments, promoters or codon optimization are used for high constitutive expression of exogenous polynucleotides encoding one or more lactate production enzymes in host methanotrophic bacteria. Regulated expression of an exogenous nucleic acid in a host methanotrophic bacterium may also be utilized. In certain embodiments, regulated expression of exogenous nucleic acids encoding one or more thioesterase, acetyl-CoA carboxylase, or malonyl-CoA-ACP transacylase enzymes may be desirable to optimize lipid production by the non-naturally occurring methanotrophic bacteria. For example, an inducible/regulatable system of recombinant protein expression in methylotrophic and methanotrophic bacteria as described in, for example, U.S. Patent Appl. No. US 2010/0221813 may be used.

Recombinant $C_1$ Metabolizing Microorganisms

As noted herein, any of the recombinant $C_1$ metabolizing microorganisms (e.g., methanotrophic bacteria) described herein may be used as a parent or reference host cell to make recombinant $C_1$ metabolizing microorganisms. In certain embodiments, the instant disclosure provides a recombinant $C_1$ metabolizing non-photosynthetic microorganism, wherein the microorganism comprises a heterologous nucleic acid sequence related to fatty acid biosynthesis and wherein expression heterologous nucleic acid sequence leads to accumulation of an increased level of fatty acids or an overexpression of fatty acids in the recombinant $C_1$ metabolizing microorganism as compared to a parent or reference $C_1$ metabolizing non-photosynthetic microorganism.

In certain embodiments, a recombinant $C_1$ metabolizing non-photosynthetic microorganism comprises a heterologous polynucleotide encoding a fatty acid producing enzyme, a formaldehyde assimilation enzyme, or any combination thereof. In further embodiments, the heterologous polynucleotide encodes a thioesterase, a malonyl CoA-acyl carrier protein transacylase, an acetyl-CoA carboxylase, or any combination thereof. For example, a thioesterase may be an *E. coli, Cinnamomum camphorum, Umbellularia californica, Streptoccus pyogenes, Ricinius communis*, or *Jatropha curcus* thioesterase. Exemplary fabD, accA, accB, accC, and accD genes may be from *E. coli* or any other organism of choice.

In further embodiments, the recombinant $C_1$ metabolizing non-photosynthetic microorganism comprises a heterologous nucleic acid sequence codon optimized for efficient expression in the $C_1$ metabolizing non-photosynthetic microorganism. In certain embodiments, any one or more of thioesterase, fabD, accA, accB, accC, and accD are codon optimized for a $C_1$ metabolizing non-photosynthetic microorganism. In one embodiment, a codon optimized thioesterase is an *E. coli* tesA lacking a periplasmic targeting sequence.

In yet other embodiments, any of the aforementioned recombinant $C_1$ metabolizing non-photosynthetic microorganisms further comprises a mutation that minimizes or eliminates fatty acid-CoA ligase activity.

Exemplary organisms for use in making recombinant $C_1$ metabolizing non-photosynthetic microorganisms of this disclosure include bacteria or yeast. In certain embodiments, the parent or reference $C_1$ metabolizing bacteria used to make a recombinant $C_1$ metabolizing bacteria of this disclosure is a methanotroph or methylotroph, such as a *Methylomonas* sp. 16a (ATCC PTA 2402), *Methylosinus trichosporium* OB3b (NRRL B-11,196), *Methylosinus sporium* (NRRL B-11, 197), *Methylocystis parvus* (NRRL B-11,198), *Methylomonas methanica* (NRRL B-11,199), *Methylomonas albus* (NRRL B-11,200), *Methylobacter capsulatus* Y (NRRL B-11,201), *Methylococcus capsulatus* Bath (NCIMB 11132), *Methylobacterium organophilum* (ATCC 27,886), *Methylomonas* sp. AJ-3670 (FERM P-2400), *Methylomicrobium alcaliphilum, Methylocella silvestris, Methylacidiphilum infernorum, Methylibium petroleiphilum, Methylobacterium extorquens, Methylobacterium radiotolerans, Methylobacterium populi, Methylobacterium chloromethanicum, Methylobacterium nodulans*, or any combination thereof.

In further embodiments, a parent or reference $C_1$ metabolizing bacteria used to make a recombinant $C_1$ metabolizing bacteria of this disclosure is a syngas metabolizing bacteria, such as *Clostridium autoethanogenum, Clostridium ljungdahli, Clostridium ragsdalei, Clostridium carboxydivorans, Butyribacterium methylotrophicum, Clostridium woodii, Clostridium neopropanologen*, or a combination thereof.

Culture Methods and Methods of Making Oil Compositions

A variety of culture methodologies may be used for the microorganisms, bacteria and yeast described herein. For example, $C_1$ metabolizing microorganisms (such as methanotroph or methylotroph bacteria) may be grown by batch culture or continuous culture methodologies. In certain embodiments, the cultures are grown in a controlled culture unit, such as a fermentor, bioreactor, hollow fiber cell, or the like. Generally cells in log phase are often responsible for the bulk production of a product or intermediate of interest in some systems, whereas stationary or post-exponential phase production can be obtained in other systems.

A classical batch culturing method is a closed system in which the media composition is set when the culture is started and is not altered during the culture process. That is, media is inoculated at the beginning of the culturing process with one or more microorganisms of choice and then are allowed to grow without adding anything to the system. As used herein, a "batch" culture is in reference to not changing the amount of a particular carbon source initially added, whereas control of factors such as pH and oxygen concentration can be monitored and altered during the culture. In batch systems, metabolite and biomass compositions of the system change constantly up to the time the culture is terminated. Within batch cultures, cells (e.g., bacteria such as methylotrophs) will generally move from a static lag phase to a high growth logarithmic phase to a stationary phase where growth rate is reduced or stopped (and will eventually lead to cell death if conditions do change).

A fed-batch system is a variation on the standard batch system in which a carbon substrate of interest is added in increments as the culture progresses. Fed-batch systems are useful when cell metabolism is likely to be inhibited by catabolite repression and when it is desirable to have limited amounts of substrate in the media. Since it is difficult to measure actual substrate concentration in fed-batch systems, an estimate is made based on changes of measurable factors such as pH, dissolved oxygen, and the partial pressure of waste gases. Batch and fed-batch culturing methods are common and known in the art (see, e.g., Thomas D. Brock, Biotechnology: A Textbook of Industrial Microbiology, $2^{nd}$ Ed. (1989) Sinauer Associates, Inc., Sunderland, Mass.; Deshpande, *Appl. Biochem. Biotechnol.* 36:227, 1992).

Continuous cultures are "open" systems in the sense that defined culture media is continuously added to a bioreactor while an equal amount of used ("conditioned") media is removed simultaneously for processing. Continuous cultures generally maintain the cells at a constant high, liquid phase density where cells are primarily in logarithmic growth phase. Alternatively, continuous culture may be practiced with immobilized cells (e.g., biofilm) where carbon and nutrients are continuously added and valuable products, byproducts, and waste products are continuously removed from the cell mass. Cell immobilization may be achieved with a wide range of solid supports composed of natural materials, synthetic materials, or a combination thereof.

Continuous or semi-continuous culture allows for the modulation of one or more factors that affect cell growth or end product concentration. For example, one method may maintain a limited nutrient at a fixed rate (e.g., carbon source, nitrogen) and allow all other parameters to change over time. In other embodiments, several factors affecting growth may be continuously altered while cell concentration, as measured by media turbidity, is kept constant. The goal of a continuous culture system is to maintain steady state growth conditions while balancing cell loss due to media being drawn off against the cell growth rate. Methods of modulating nutrients and growth factors for continuous culture processes and techniques for maximizing the rate of product formation are well known in the art (see Brock, 1992).

In certain embodiments, culture media includes a carbon substrate as a source of energy for a $C_1$ metabolizing microorganism. Suitable substrates include $C_1$ substrates, such as methane, methanol, formaldehyde, formic acid (formate), carbon monoxide, carbon dioxide, methylated amines (methylamine, dimethylamine, trimethylamine, etc.), methylated thiols, or methyl halogens (bromomethane, chloromethane, iodomethane, dichloromethane, etc.). In certain embodiments, culture media may comprise a single $C_1$ substrate as the sole carbon source for a $C_1$ metabolizing microorganism, or may comprise a mixture of two or more $C_1$ substrates (mixed $C_1$ substrate composition) as multiple carbon sources for a $C_1$ metabolizing microorganism.

Additionally, some $C_1$ metabolizing organisms are known to utilize non-$C_1$ substrates, such as sugar, glucosamine or a variety of amino acids for metabolic activity. For example, some *Candida* species can metabolize alanine or oleic acid (Sulter et al., *Arch. Microbiol.* 153:485, 1990). *Methylobacterium extorquens* AM1 is capable of growth on a limited number of $C_2$, $C_3$, and $C_4$ substrates (Van Dien et al., *Microbiol.* 149:601, 2003). Alternatively, a $C_1$ metabolizing microorganism may be a recombinant variant having the ability to utilize alternative carbon substrates. Hence, it is contemplated that a carbon source in culture media may comprise a mixture of carbon substrates, with single and multi-carbon compounds, depending on the $C_1$ metabolizing microorganism selected.

In certain embodiments, the instant disclosure provides a method for making fuel, comprising converting biomass from a culture primarily comprising a $C_1$ metabolizing non-photosynthetic microorganism into an oil composition and refining the oil composition into a fuel. In certain embodiments, the $C_1$ metabolizing non-photosynthetic microorganism is an obligate $C_1$ metabolizing non-photosynthetic microorganism, such as an obligate methanotroph or methylotroph. In further embodiments, the $C_1$ metabolizing non-photosynthetic microorganism is a recombinant microorganism comprising a heterologous polynucleotide encoding a fatty acid producing enzyme, a formaldehyde assimilation enzyme, or a combination thereof. In certain embodiments, any one or all of the TE, MCT, and Acc genes introduced into $C_1$ metabolizing microorganisms of this disclosure can be over-expressed and the $C_1$ metabolizing microorganisms may optionally have a mutation that minimizes or eliminates fatty acid-CoA ligase activity (e.g., a fadD knock-out). In further embodiments, the oil composition is derived or extracted from a cell membrane of the $C_1$ metabolizing non-photosynthetic microorganism (e.g., methylotroph, methanotroph, yeast) or may be recovered from a culture supernatant if secreted or excreted, or a combination thereof.

In further embodiments, the step of converting biomass into an oil composition comprises extracting the oil composition, such as by wet extraction, supercritical fluid extraction, dry extraction, thermal extraction (e.g., steam stripping, hydrothermal liquefaction, pressure cooking), enzymatic hydrolysis (e.g., of the cell wall), pulsed electric field extraction, microbubbles, hollow fiber extraction, or the like. Exemplary extraction methods are known in the art, such as the Folch chloroform:methanol (2:1 v/v) (CM solution) method (see Folch et al., *J. Biol. Chem.* 226:497, 1957), or a modified method thereof (see Example 3); the Hara and Radin hexane: isopropanol (HIP) extraction method (see Hara and Radin, *Anal. Biochem.* 90:420, 1978); the Bligh and Dyer chloroform:methanol:water method (see Bligh and Dyer, *Canadian J. Biochem. Physiol.* 37:911, 1959); or the like. Other exemplary extraction methods include solid phase extraction columns (Pinkart et al., *J. Microbiol. Meth.* 34:9, 1998), single step reactive extraction (Nelson, *All Graduate Theses and Dissertations*. Paper 642, digitalcommons.usu.edu/etd/642), an α-hydroxysulfonic acid extraction (U.S. Patent Pub. No. 2013/0144078), high temperature and pressure extraction (U.S. Patent Pub. No. 2012/0110898), or accelerated solvent extraction (ASE), soxhlet, ultrasonic extraction and oscillator extraction methods (see Liu et al., *J. Earth Sci.* 21:300, 2010). Each of these extraction methods are incorporated herein by reference in their entireties, and can be used in any of the aforementioned methods or biorefinery systems described herein.

In certain embodiments, the instant disclosure provides a method for making fuel by refining an oil composition (e.g., in a refining unit) to produce fuel, wherein the oil composition is derived from a $C_1$ metabolizing non-photosynthetic microorganism, such as a methylotroph or methanotroph. In further embodiments, the method further comprises extracting the oil composition or use of a processing unit for extracting the oil composition from the $C_1$ metabolizing non-photosynthetic microorganism. In still further embodiments, the method comprises (a) culturing $C_1$ metabolizing bacteria in the presence of a feedstock comprising a $C_1$ substrate in a controlled culturing unit, wherein the cultured bacteria produce an oil composition; (b) extracting the oil composition from the cultured bacteria or extracting the oil composition in a processing unit; and (c) refining the extracted oil composition or refining the oil composition in a refining unit to produce fuel. In certain embodiments, the feedstock $C_1$ substrate is methane, methanol, formaldehyde, formic acid, carbon monoxide, carbon dioxide, a methylamine, a methylthiol, or a methylhalogen.

In any of the aforementioned methods of making fuel or biofuel, the $C_1$ metabolizing non-photosynthetic microorganism is a methanotroph, methylotroph or *Clostridium*, the feedstock $C_1$ substrate is natural gas, syngas or methane, and the bacteria are cultured under aerobic or anaerobic conditions. In further embodiments, the methanotroph is *Methylosinus trichosporium* OB3b, *Methylococcus capsulatus* Bath, *Methylomonas* sp. 16a, *Methylomonas methanica, Methylomicrobium alcaliphilum*, any combination thereof, or a high growth variant thereof; the methylotroph is *Methylobacterium extorquens, Methylobacterium radiotolerans, Methylobacterium populi, Methylobacterium chloromethanicum, Methylobacterium nodulans*, any combination thereof, or a high growth variant thereof; and the *Clostridium* is *Clostridium autoethanogenum, Clostridium ljungdahli, Clostridium ragsdalei, Clostridium carboxydivorans, Clostridium woodii, Clostridium neopropanologen*, or any combination thereof, or a high growth variant thereof. In certain other embodiments, the $C_1$ metabolizing non-photosynthetic microorganism is an obligate $C_1$ metabolizing non-photosynthetic microorganism, such as an obligate methanotroph, methylotroph or *Clostridium*.

In any of the aforementioned methods of making fuel or biofuel, the $C_1$ metabolizing non-photosynthetic microorganism is a methanotroph, the feedstock $C_1$ substrate is natural gas or methane, and the bacteria are cultured under aerobic conditions. In further embodiments, the $C_1$ metabolizing non-photosynthetic microorganism is a methanotroph, the $C_1$ substrate is natural gas or methane, and the bacteria are cultured with limiting quantities of phosphorus, nitrogen, trace elements, oxygen, or any combination thereof.

Fuel Compositions and Fuel Products

Figure 7:
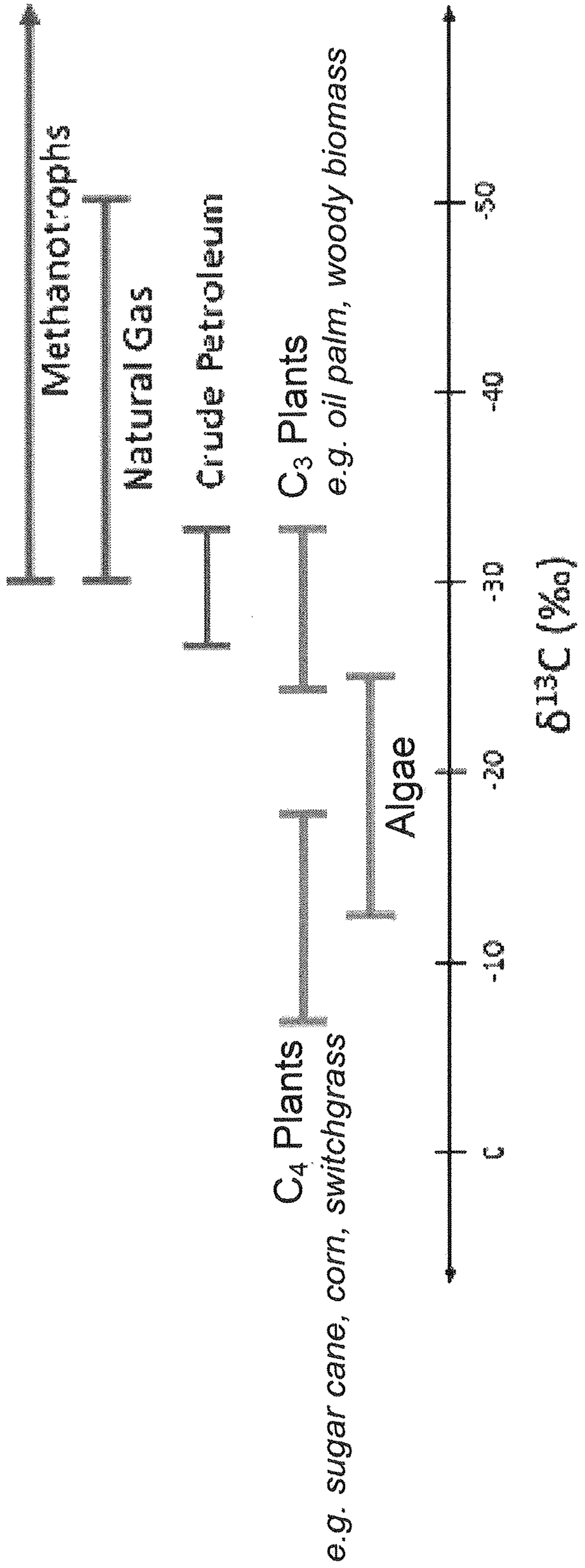
FIG. 7 shows a schematic of the $\delta^{13}C$ distribution of various carbon sources.

By way of background, stable isotopic measurements and mass balance approaches are widely used to evaluate global sources and sinks of methane (see Whiticar and Faber, *Org. Geochem.* 10:759, 1986; Whiticar, *Org. Geochem.* 16: 531, 1990). To use $\delta^{13}C$ values of residual methane to determine the amount oxidized, it is necessary to know the degree of isotopic fractionation caused by microbial oxidation of methane. For example, aerobic methanotrophs can metabolize methane through a specific enzyme, methane monoxygenase (MMO). Methanotrophs convert methane to methanol and subsequently formaldehyde. Formaldehyde can be further oxidized to $CO_2$ to provide energy to the cell in the form of reducing equivalents (NADH), or incorporated into biomass through either the RuMP or Serine cycles (Hanson and Hanson, *Microbiol. Rev.* 60:439, 1996), which are directly analogous to carbon assimilation pathways in photosynthetic organisms. More specifically, a Type I methanotroph uses the RuMP pathway for biomass synthesis and generates biomass entirely from $CH_4$, whereas a Type II methanotroph uses the serine pathway that assimilates 50-70% of the cell carbon from $CH_4$ and 30-50% from $CO_2$ (Hanson and Hanson, 1996). Methods for measuring carbon isotope compositions are provided in, for example, Templeton et al. (*Geochim. Cosmochim. Acta* 70:1739, 2006), which methods are hereby incorporated by reference in their entirety. The $^{13}C/^{12}C$ stable carbon ratio of an oil composition from a biomass (provided as a "delta" value ‰, $\delta^{13}C$) can vary depending on the source and purity of the $C_1$ substrate used (see, e.g., FIG. 7).

Oil compositions produced using the $C_1$ metabolizing non-photosynthetic microorganisms and methods described herein, as well as biofuel compositions derived therefrom, may be distinguished from oil and fuels produced from petrochemicals or from photosynthetic microorganisms or plants by carbon fingerprinting. In certain embodiments, a biomass, an oil composition, or a biofuel derived from the biomass or oil composition has a $\delta^{13}C$ of less than −30‰, less than −31‰, less than −32‰, less than −33‰, less than −34‰, less than −35‰, less than −36‰, less than −37‰, less than −38‰, less than −39‰, less than −40‰, less than −41‰, less than −42‰, less than −43‰, less than −44‰, less than −45‰, less than −46‰, less than −47‰, less than −48‰, less than −49‰, less than −50‰, less than −51‰, less than −52‰, less than −53‰, less than −54‰, less than −55‰, less than −56‰, less than −57‰, less than −58‰, less than −59‰, less than −60‰, less than −61‰, less than −62‰, less than −63‰, less than −64‰, less than −65‰, less than −66‰, less than −67‰, less than −68‰, less than −69‰, or less than −70‰.

In certain embodiments, a $C_1$ metabolizing microorganism biomass comprises an oil composition, wherein the biomass has a $\delta^{13}C$ of about −35‰ to about −50‰, −45‰ to about −35‰, or about −50‰ to about −40‰, or about −45‰ to about −65‰, or about −60‰ to about −70‰, or about −30‰ to about −70‰. In further embodiments, the biomass oil composition comprises at least 50% fatty acids or comprises at least 50% free fatty acids. In still further embodiments, the biomass oil composition comprises a mixture of diacylglycerides and triacylglycerides. In yet further embodiments, the biomass oil composition comprises a majority (more than 50% w/w) of fatty acids having carbon chain lengths ranging from C14 to C18 or from C16 to C18, or a majority of fatty acids having carbon chain lengths of less than C16. In further embodiments, the biomass oil composition comprises more than 50% w/w terpenoid or isoprenoid compounds, wherein the terpenoid may be farnesene or limonene.

In further embodiments, a $C_1$ metabolizing non-photosynthetic microorganism biomass has a $\delta^{13}C$ of less than about −30‰, or ranges from about −40‰ to about −60‰. In certain embodiments, the biomass comprises a recombinant $C_1$ metabolizing non-photosynthetic microorganism together with the spent media, or the biomass comprises a spent media supernatant composition from a culture of a recombinant $C_1$ metabolizing non-photosynthetic microorganism, wherein the $\delta^{13}C$ of the biomass is less than about −30‰. In certain other embodiments, the an oil composition is extracted or concentrated from a biomass, which can comprise recombinant $C_1$ metabolizing non-photosynthetic microorganisms together with the spent media from a culture, or a spent media supernatant composition from a culture of a recombinant $C_1$ metabolizing non-photosynthetic microorganism.

In certain embodiments, biomass is of a recombinant $C_1$ metabolizing non-photosynthetic microorganism comprises a heterologous polynucleotide encoding a fatty acid producing enzyme, a formaldehyde assimilation enzyme, or any combination thereof. In further embodiments, the heterologous polynucleotide encodes a thioesterase, a malonyl CoA-acyl carrier protein transacylase, an acetyl-CoA carboxylase, or any combination thereof. For example, a thioesterase may be an *E. coli, Cinnamomum camphorum, Umbellularia californica, Streptoccus pyogenes, Ricinius communis*, or *Jatropha curcus* thioesterase. Exemplary fabD, accA, accB, accC, and accD genes may be from *E. coli* or any other organism of choice.

In further embodiments, biomass is of a recombinant $C_1$ metabolizing non-photosynthetic microorganism comprising a heterologous nucleic acid sequence codon optimized for efficient expression in the $C_1$ metabolizing non-photosynthetic microorganism. In certain embodiments, any one or more of thioesterase, fabD, accA, accB, accC, and accD are codon optimized for a $C_1$ metabolizing non-photosynthetic microorganism. In one embodiment, a codon optimized thioesterase is an *E. coli* tesA lacking a periplasmic targeting sequence.

In yet other embodiments, any of the aforementioned biomass is of a recombinant $C_1$ metabolizing non-photosynthetic microorganism further comprises a mutation that minimizes or eliminates fatty acid-CoA ligase activity.

Exemplary organisms for use in generating biomass is of a recombinant $C_1$ metabolizing non-photosynthetic microorganisms of this disclosure include bacteria or yeast. In certain embodiments, biomass is of a $C_1$ metabolizing bacteria from a methanotroph or methylotroph, such as a *Methylomonas* sp. 16a (ATCC PTA 2402), *Methylosinus trichosporium* OB3b (NRRL B-11,196), *Methylosinus sporium* (NRRL B-11, 197), *Methylocystis parvus* (NRRL B-11,198), *Methylomonas methanica* (NRRL B-11,199), *Methylomonas albus* (NRRL B-11,200), *Methylobacter capsulatus* Y (NRRL B-11,201), *Methylococcus capsulatus* Bath (NCIMB 11132), *Methylobacterium organophilum* (ATCC 27,886), *Methylomonas* sp. AJ-3670 (FERM P-2400), *Methylomicrobium alcaliphilum, Methylocella silvestris, Methylacidiphilum infernorum, Methylibium petroleiphilum, Methylobacterium extorquens, Methylobacterium radiotolerans, Methylobacterium populi, Methylobacterium chloromethanicum, Methylobacterium nodulans*, or any combination thereof.

In further embodiments, biomass is of a $C_1$ metabolizing bacteria from a recombinant $C_1$ metabolizing bacteria of this disclosure is a syngas metabolizing bacteria, such as *Clostridium autoethanogenum, Clostridium ljungdahli, Clostridium ragsdalei, Clostridium carboxydivorans, Butyribacterium methylotrophicum, Clostridium woodii, Clostridium neopropanologen*, or a combination thereof.

In certain embodiments, an oil composition has a $\delta^{13}C$ of about −35‰ to about −50‰, −45‰ to about −35‰, or about −50‰ to about −40‰, or about −45‰ to about −65‰, or about −60‰ to about −70‰, or about −30‰ to about −70‰. In further embodiments, an oil composition comprises at least 50% w/w fatty acids or comprises at least 50% w/w free fatty acids. In still further embodiments, an oil composition comprises a mixture of diacylglycerides and triacylglycerides. In yet further embodiments, an oil composition comprises a majority of fatty acids having carbon chain lengths ranging from C14 to C18 or from C16 to C18, or a majority of fatty acids having carbon chain lengths of less than C16. In further embodiments, an oil composition comprises more than 50% w/w terpenoid or isoprenoid compounds, wherein the terpenoid compounds may be farnesene, limonene, or both.

In certain embodiments, a biofuel derived from a biomass or an oil composition has a $\delta^{13}C$ of about −35‰ to about −50‰, −45‰ to about −35‰, or about −50‰ to about −40‰, or about −45‰ to about −65‰, or about −60‰ to about −70‰, or about −30‰ to about −70‰. In certain other embodiments, a biofuel derived from an oil composition has a $\delta^{13}C$ of about −35‰ to about −50‰, −45‰ to about −35‰, or about −50‰ to about −40‰, or about −45‰ to about −65‰, or about −60‰ to about −70‰, or about −30‰ to about −70‰.

In further embodiments, a biofuel comprises at least 50% w/w fatty acid methyl esters (FAMEs). In related embodiments, a biofuel comprises at least 50% FAMEs, wherein the majority of FAMEs have carbon chain lengths of C14-C18, C16-C18, or less than C16. In still further embodiments, a biofuel comprises at least 50% w/w fatty acid ethyl esters (FAEEs). In related embodiments, a biofuel comprises at least 50% FAEEs, wherein the majority of FAEEs have carbon chain lengths of C14-C18, C16-C18, or less than C16. In yet further embodiments, a biofuel comprises at least 50% w/w hydrogenated terpenoids, such as farnesane or limonane. In certain embodiments, the majority of hydrogenated terpenoids are comprised of farnesane, limonane, or both. In certain embodiments, a biofuel comprises a hydrogenated biomass. In certain embodiments, the majority of the hydrogenated biomass comprises a mixture of linear and branched alkanes. In certain embodiments, a biofuel comprises a majority of fatty acids having carbon chain lengths ranging from C14 to C18 or from C16 to C18, or a majority of fatty acids having carbon chain lengths of less than C16. In further embodiments, a biofuel comprises more than 50% w/w terpenoid or isoprenoid compounds, wherein the terpenoid may be farnesene or limonene.

In certain embodiments, an oil composition of a $C_1$ metabolizing microorganism (which may optionally be an extract or isolate from the $C_1$ metabolizing microorganism biomass) comprises hydrogen and carbon atoms of at least about 50% to about 80% of the weight of the composition, and wherein the $\delta^{13}C$ of the composition is less than about −35‰ or less than about −36‰ or less than about −37‰ or less than about −38‰ or less than about −39‰ or less than about −40‰. In certain embodiments, an oil or biofuel composition derived therefrom comprises molecules having hydrogen and carbon atoms, wherein the hydrogen and carbon atoms are at least 50%, at least 55%, at least 60%, at least 65%, at least 70%, at least 75%, or at least 80%, or at least 90%, or at least 95% of the weight of the composition and wherein the $\delta^{13}C$ of the composition ranges from about −30‰ to about −70‰, or wherein the $\delta^{13}C$ in the biomass decreases as cell density increases by about −5‰ to about −20‰, or wherein the $\delta^{13}C$ of the biomass was higher than $CO_2$ produced at the same time by an average of 5‰ to 15‰ when cultured in the presence or absence of copper.

In further embodiments, an oil composition of a $C_1$ metabolizing microorganism of this disclosure (which may optionally be extracted or isolated from the $C_1$ metabolizing microorganism biomass) comprises hydrogen and carbon atoms at about at least 85%, 90%, 91%, 92%, 93%, 94%, 95%, 96%, 97%, 98%, 99%, or 100% of the weight of the composition. In certain embodiments, an oil composition or a biofuel composition derived therefrom comprises molecules having hydrogen and carbon atoms, wherein the hydrogen and carbon atoms are at least about 90% of the weight of the composition and wherein the $\delta^{13}C$ of the composition ranges from about −40‰ to about −55‰.

A fuel component, as described herein and known in the art, can be a fossil fuel or a mixing blend for generating a fuel product. For example, a mixture for fuel or biofuel blending may be a hydrocarbon mixture that is suitable for blending with another hydrocarbon mixture to generate a fuel or biofuel product. For example, a mixture of light alkanes may not have a certain octane number to be suitable for a type of fuel; however, it can be blended with a high octane mixture to generate a fuel product. In certain embodiments, a biomass, an oil composition or biofuel derived therefrom of this disclosure is a fuel or biofuel component after being refined.

In certain embodiments, a biofuel composition comprises molecules having hydrogen and carbon atoms, wherein the hydrogen and carbon atoms are at least 80% of the weight of the composition and wherein the $\delta^{13}C$ distribution of the composition ranges from about −37% to about −10%, or wherein the $\delta^{13}C$ distribution in the biomass increases as cell density increases from −22% to −9%, or wherein the $\delta^{13}C$ composition of the biomass was higher than $CO_2$ produced at the same time by an average of 5% to 15% when cultured in the presence or absence of copper.

A biofuel product as described herein is a product generated by blending an oil composition or a biofuel composition derived therefrom of the instant disclosure with a fuel or biofuel component. In some instances, a biofuel product has a $\delta^{13}C$ distribution of greater than −60‰ or greater than −50‰ or greater than −40‰ or greater than −30‰, provided the oil composition or biofuel composition derived therefrom portion of the blend is not derived from a photosynthetic microorganism or a plant. In certain embodiments, the fuel component used for blending is a petroleum-based composition or a fuel additive (e.g., oxygenates like methanol, ethanol, isopropanol; ethers such as methyl tert-butyl ether, tertiary amyl methyl ether; antioxidants such as butylated hydroxytoluene, ethylene diamine; anti-knock agents such as tetraethyllead, ferrocene toluene; lead scavengers such as tricresyl phosphate; dyes; or the like). For example, an oil composition of a $C_1$ metabolizing microorganism can be blended with a fuel component prior to refining (e.g., transesterification; cracking) in order to generate a fuel product as described herein. In still other embodiments, an oil composition is a liquid or a solid, and is refined into a fuel additive for use in producing a biofuel product. In certain embodiments, an oil composition comprises a terpene, terpenoid, isoprene, or an isoprenoid. In still other embodiments, a biofuel product has an octane number of 85-120 or an octane number greater than 90.

EXAMPLES

Example 1

Culture and Bioreactor Conditions for Lipid Production by $C_1$ Metabolizing Microorganisms Exemplary $C_1$ metabolizing microorganisms of the instant disclosure (methanotrophs, methylotrophs, clostridia) were cultured in tubes, in vials, in bottles, on plates, or in a bioreactor (fermentation). Growth conditions, media, and carbon source for various microorganisms are described in this example.

*Methylosinus trichosporium* Strain OB3b (NCIMB 11131); *Methylomonas* sp. Strain 16a (ATCC PTA-2402); or *Methylomonas methanica*

For serum bottles, the bacteria were cultured at 30° C. in Higgins minimal nitrate salts medium (NSM; Cornish et al., *J. Gen. Microbiol.* 130:2565, 1984; Park et al., *Biotechnol. Bioeng.* 38:423, 1991) or MM-W1 medium. The headspace composition was adjusted to a 1:1 volume of methane:air. The bottles were shaken at a rate of 200-250 rpm. Alternatively, the culture was maintained on NSM-media plates containing 1.5% w/v agar grown in a gas-tight chamber containing a 1:1 (v/v) methane:air gas mixture, or in the presence of methanol vapor (via 0.5 mL methanol in the lid of parafilm-sealed plates) or on NSM-media plates supplemented with 0.5% methanol. Plates were incubated inverted in a humidified chamber at 30° C.

The composition of the NSM medium used was as follows: 1.0 g $MgSO_4*7H_2O$, 0.20 g $CaCl_2*6H_2O$, 2.0 ml chelated iron solution (0.1 g ferric (III) ammonium citrate or 0.5 g ferric (III) chloride; 0.2 g EDTA, sodium salt; 0.3 ml HCl, concentrated; 100.0 ml distilled deionized $H_2O$), 1.0 g $KNO_3$, 0.5 ml trace element solution (500.0 mg EDTA, 200.0 mg $FeSO_4.7H_2O$, 10.0 mg $ZnSO_4*7H_2O$, 3.0 mg $MnCl_2*4H_2O$, 30.0 mg $H_3BO_3$, 20.0 mg $CoCl_2*6H_2O$, 1.0 mg $CaCl_2*2H_2O$, 2.0 mg $NiCl_2*6H_2O$, 3.0 mg $Na_2MoO_4*2H_2O$, 1.0 L distilled water), 0.272 g $KH_2PO_4$, 0.717 g $Na_2HPO_4*12H_2O$, optionally 12.5 g purified agar (e.g., Oxoid L28 or Bacto™ agar; used when making plates), 1.0 L distilled deionized water, pH adjusted to 6.8 and autoclaved at 121° C. for 15 minutes.

For fermentation, a 2-liter bioreactor containing 1 L of sterilized defined media MM-W1 was inoculated with cells from serum bottle batch cultures (10-20% v/v) grown in MM-W1 supplied with a 1:1 (v/v) mixture of methane and air. The composition of medium MM-W1 used was as follows: 0.8 mM $MgSO_4*7H_2O$, 10 mM $NaNO_3$, 0.14 mM $CaCl_2$, 1.2 mM $NaHCO_3$, 2.35 mM $KH_2PO_4$, 3.4 mM $K_2HPO_4$, 20.7 μM $Na_2MoO_4*2H_2O$, 1 μM $CuSO_4*5H_2O$, 10 μM $Fe^{III}$—Na-EDTA, and 1 mL per liter of trace metals solution (containing, per liter 500 mg $FeSO_4*7H_2O$, 400 mg $ZnSO_4*7H_2O$, 20 mg $MnCl_2*7H_2O$, 50 mg $CoCl_2*6H_2O$, 10 mg $NiCl_2*6H_2O$, 15 mg $H_3BO_3$, 250 mg EDTA). Phosphate, bicarbonate, and $Fe^{III}$—Na-EDTA were added after the media was autoclaved and cooled. Bicarbonate was added up to 0.1% (w/v) in certain fermentations. The reactor contents were stirred with an overhead impeller at a constant 750 rpm. The culture was fed with a constant methane sparging at about 60 mL/min to about 120 mL/min, while concentrated oxygen (at least 85%) was supplied at a variable rate of about 10-100 mL/min to maintain a dissolved oxygen level of about 40% to about 80% (relative to air saturation of the media).

Temperature in the bioreactor was maintained at 30° C. and pH was maintained at 7.1±0.1 using automated addition of 0.5M NaOH and 0.5M HCl, along with other additions, to the culture about every 4 hours to about 24 hours (corresponding to an $OD_{600}$ increase of approximately 5 OD units). The other additions alternated between a metal addition (10 μM $CuSO_4$, 5 μM $FeSO_4$, 5 μM $Fe^{III}$—Na-EDTA final concentrations) and a nutrient addition (5.75 mM KxHyPO4, 10 mM NaNO3). Under these conditions, essentially linear growth was observed, with an effective biomass generation rate of about 2.7 to about 3.3 grams dry cell weight per liter per day to an $OD_{600}$ of greater than 20. Culture biomass was harvested by centrifugation, washed once in MM-W1 media, and recovered biomass was either frozen at −80° C. or used immediately for fractionation of cellular components (e.g., lipid extraction).

A semi-continuous fermentation approach can also be applied to maintain biomass productivity and reduce time associated with fermentation shut-down and start-up (i.e., turn-around time or lead time).

Harvesting of the bacterial biomass was performed at approximately 12-24 hour intervals, as the culture density approached (but before entering) stationary phase. Approximately half of the bioreactor volume was removed by transferring to a separate container via centrifugal pump. An equal volume of sterilized or recycled media was then returned to the bioreactor such that the optical density of the reactor was approximately half of its initial value. The bioreactor fermentation was continued according to the above protocol so that multiple cycles of growth and biomass recovery could be carried out during a single fermentation run.

*Methylococcus capsulatus* Bath (NCIMB 11132)

The bacteria were cultured at 42° C. in serum bottles containing Higgins minimal nitrate salts medium (NSM) or MM-W1 medium. The headspace composition was adjusted to a 1:1 volume of methane:air. The bottles were shaken at a rate of 200-250 rpm. Alternatively, the culture was maintained on NSM-media plates solidified with 1.5% w/v agar grown in a gas-tight chamber containing a 1:1 (v/v) methane:air gas mixture. Plates were incubated inverted in the chamber at 42° C.

For fermentation, a 3-liter bioreactor containing 1.25 L sterilized media MMF1.1 was inoculated with cells from serum bottle batch cultures (10-20% v/v) grown in the same media supplied with a 1:1 (v/v) mixture of methane and air. The composition of medium MMF1.1 was as follows: 0.8 mM $MgSO_4$*$7H_2O$, 40 mM $NaNO_3$, 0.14 mM $CaCl_2$, 6 mM $NaHCO_3$, 4.7 mM $KH_2PO_4$, 6.8 mM $K_2HPO_4$, 20.7 μM $Na_2MoO_4$*$2H_2O$, 6 μM $CuSO_4$*$5H_2O$, 10 μM $Fe^{III}$—Na-EDTA, and 1 mL per liter of trace metals solution (containing, per liter 500 mg $FeSO_4$*$7H_2O$, 400 mg $ZnSO_4$*$7H_2O$, 20 mg $MnCl_2$*$7H_2O$, 50 mg $CoCl_2$*$6H_2O$, 10 mg $NiCl_2$*$6H_2O$, 15 mg $H_3BO_3$, 250 mg EDTA). Phosphate, bicarbonate, and $Fe^{III}$—Na-EDTA were added after media was autoclaved and cooled. The reactor contents were stirred with an overhead impeller at a constant 750 rpm. The culture was fed with a constant methane sparging at about 60 to about 200 mL/min, while concentrated oxygen (>85%) was supplied at a variable rate of 15-90 mL/min and the dissolved oxygen level was maintained below 10% (relative to air saturation of the media).

Temperature in the bioreactor was maintained at 44° C. and pH was maintained at 7.0±0.1 using automated addition of 0.5M NaOH and 0.5M HCl, along with additions of copper and iron (5 μM $CuSO_4$, 5 μM $FeSO_4$, 10 μM $Fe^{III}$—Na-EDTA final concentration) to the culture every 3-6 hours (corresponding to an $OD_{600}$ increase of approximately 3-5 OD units after reaching OD 5). Under these conditions, essentially linear growth was observed, with effective biomass generation rate of more than 5 grams dry cell weight per liter per day to an $OD_{600}$ of greater than 10. Culture biomass was harvested by centrifugation, the cells washed once in MM-W1 media and cell pellets were either frozen at −80° C. or used immediately for fractionation of cellular components.

Nutrient depletion was recognized as an issue that could limit the growth yield during fermentation. To avoid limitation of nutrients, mainly nitrogen and phosphate, nutrient feeds composed of 2-fold concentrated MMF1.1 were initiated after culture $OD_{600}$ exceeded 5. The nutrient feed was initiated at dilution rates corresponding to approximately half of the cultures' growth rate to avoid wash-out and to maintain an increase in OD while expanding the culture volume. The bioreactor fermentation was continued according to the above protocol so that multiple cycles of growth and biomass recovery could be carried out during a single fermentation run.

*Methylobacterium extorquens* or *Methylosinus trichosporium* Strain OB3b (NCIMB 11131)

The bacteria is cultured at 30° C. in tubes containing Higgins minimal nitrate salts medium (NSM) supplemented with 0.5% methanol. The tubes are shaken at a rate of 200-250 rpm. Alternatively, the cultures are maintained on NSM-media plates containing 1.5% w/v agar grown in the presence of methanol vapor (via 0.5 mL methanol in the lid of parafilm-sealed plates) or supplemented with 0.5% methanol. Plates are incubated inverted in a humidified chamber under normal atmosphere at 30° C.

For fermentation, a 2-liter bioreactor containing 1 L defined media MM-W1 is inoculated with cells from culture tube batch culture (10-20% v/v). The composition of medium MM-W1 was as described above. The reactor contents are stirred with an overhead impeller at a constant 800 rpm. The culture is fed with an initial bolus of methanol to a final concentration of 0.5% and variable methanol feed, while pure oxygen was supplied at a variable rate of 30-100 mL/min to maintain a dissolved oxygen level of 60-90% (relative to air saturation of the media).

Temperature in the bioreactor was maintained at 30° C. and pH was maintained at 7.1±0.1 using automated addition of 0.5M NaOH and 1M HCl, along with the metal and nutrient additions as described above. Under these conditions, essentially linear growth is observed, with effective biomass generation rate 2.7 to 3.3 grams dry cell weight per liter per day to an $OD_{600}$ of greater than 20. Culture biomass was harvested by centrifugation, the cells washed once in MM-W1 media and cell pellets were either frozen at −80° C. or used immediately for fractionation of cellular components.

A semi-continuous fermentation approach can also be applied to maintain biomass productivity and reduce time associated with fermentation shut-down and start-up (i.e., turn-around time or lead time).

Harvesting of the accumulated bacterial biomass was performed at approximately 12-24 hour intervals, as the culture density approached (but before entering) stationary phase. Approximately half of the bioreactor volume was removed by transferring to a separate container via centrifugal pump. An equal volume of fresh or recycled media was then returned to the bioreactor such that the optical density of the reactor was approximately half of its initial value. The bioreactor fermentation was continued according to the above protocol so that multiple cycles of growth and biomass recovery was carried out during a single fermentation run.

*Clostridium autoethanogenum* and *Clostridium ljungdahlii*

The *Clostridium* bacteria are cultivated anaerobically in 100 mL modified PETC medium (ATCC medium 1754) at 37° C. in plastic-coated 500 ml-Schott Duran® GL45 bottles with butyl rubber stoppers and 200 kPa steel mill waste gas. Growth is monitored by measuring the optical density at 600 nm ($OD_{600}$).

The modified PETC medium contains (per liter) 1 g $NH_4Cl$, 0.4 g KCl, 0.2 g $MgSO_4$*7 $H_2O$, 0.8 g NaCl, 0.1 g $KH_2PO_4$, 20 mg $CaCl_2$*2 $H_2O$, 10 ml trace elements solution (see below), 10 ml Wolfe's vitamin solution (see below), 2 g $NaHCO_3$, and 1 mg resazurin. After the pH is adjusted to 5.6, the medium is boiled, dispensed anaerobically, and autoclaved at 121° C. for 15 min. Steel mill waste gas (composition: 44% CO, 32% $N_2$, 22% $CO_2$, 2% $H_2$) or equivalent synthetic mixtures are used as a carbon source. The media has a final pH of 5.9 and is reduced with cysteine-HCl and $Na_2S$ at a concentration of 0.008% (w/v).

The trace elements solution contains 2 g nitrilotriacetic acid (adjusted to pH 6 with KOH before addition of the remaining ingredients), 1 g $MnSO_4$, 0.8 g $Fe(SO_4)_2(NH_4)_2$*$6H_2O$, 0.2 g $CoCl_2$*6 $H_2O$, 0.2 mg $ZnSO_4$*7 $H_2O$, 20 mg $CuCl_2$*2 $H_2O$, 20 mg $NiCl_2$*$6H_2O$, 20 mg $Na_2MoO_4$*2 $H_2O$, 20 mg $Na_2SeO_4$, and 20 mg $Na_2WO_4$ per liter.

Wolfe's vitamin solution (Wolin et al., *J. Biol. Chem.* 238: 2882, 1963) contains (per liter) 2 mg biotin, 2 mg folic acid, 10 mg pyridoxine hydrochloride, 5 mg thiamine-HCl, 5 mg riboflavin, 5 mg nicotinic acid, 5 mg calcium D-(+)-pantothenate, 0.1 mg vitamin B12, 5 mg p-aminobenzoic acid, and 5 mg thioctic acid.

a. *Clostridium autoethanogenum* Fermentation

Fermentation of *Clostridium autoethanogenum* is conducted using methods similar to those described in, for example, U.S. Patent Appl. No. 2011/0300593. Briefly, a 2-liter bioreactor containing 1.3 L Solution A (3.083 g $NH_4Ac$; 0.61 g $MgCl_2$*$6H_2O$; 0.294 g $CaCl_2$*$2H_2O$; 0.15 g KCl; 0.12 g NaCl (optional); up to 1 L with distilled water) is sparged with $N_2$ gas. An 85% solution of $H_3PO_4$ (2.025 mL, 30 mM) is added and the pH adjusted to 5.3 using concentrated, aqueous $NH_4OH$. Then 13.5 mL Solution B (20.0 mg Biotin; 20.0 mg Folic acid; 10.0 mg pyridoxine HCl; 50.0 mg thiamine*HCl; 50.0 mg Riboflavin; 50.0 mg nicotinic acid; 50.0 mg calcium D-(*)-pantothenate; 50.0 mg vitamin B12; 50.0 mg p-aminobenzoic acid; 50.0 mg thioctic acid; up to 1 L with distilled water) is added and the solution sparged with $N_2$ gas. Chromium (II) chloride is added until the oxidation-reduction potential (ORP) of the solution decreases to approximately −200 mV, wherein resazurin (1.35 mL of a 2 g/L solution) is added. Sodium polysulfide (5.4 mL of a 3M solution, see below) is added and the solution sparged with $N_2$ and then CO containing gas (1% $H_2$; 13% $N_2$; 71% CO; 15% $CO_2$). A metal sulfide solution (150 mL, see below) is added and the solution sparged a further 30 minutes, before inoculation with an actively growing *C. autoethanogenum* culture at a level of approximately 5% (v/v).

The sodium polysulfide solution is prepared in a 500 ml flask that is charged with $Na_2S$ (93.7 g, 0.39 mol) and 200 ml $H_2O$. The solution is stirred until the salt dissolves and sulfur (25 g, 0.1 mol) is added under constant $N_2$ flow. After stirring at room temperature for 2 hours, the sodium polysulfide solution (about 4 M with respect to Na and about 5 M with respect to sulfur), now a clear reddish brown liquid, is transferred into $N_2$ purged serum bottles, and wrapped in aluminum foil.

The chromium (II) solution is prepared in a 1 L three necked flask that is fitted with a gas tight inlet and outlet to allow working under inert gas and subsequent transfer of the desired product into a suitable storage flask. The flask is charged with $CrCl_3$*6 $H_2O$ (40 g, 0.15 mol), zinc granules [20 mesh] (18.3 g, 0.28 mol), mercury (13.55 g, 1 mL, 0.0676 mol) and 500 mL distilled water. Following flushing with $N_2$ for one hour, the mixture is warmed to about 80° C. to initiate the reaction. Following two hours of stirring under a constant $N_2$ flow, the mixture is cooled to room temperature and continuously stirred for another 48 hours by which time the reaction mixture turns into a deep blue solution. The solution is transferred into $N_2$ purged serum bottles and stored at 4° C. for future use.

The metal sulfide solution is prepared by adding about 950 mL Solution A into a 1 L fermenter and sparging with $N_2$ gas. An 85% solution of $H_3PO_4$ (1.5 mL, 30 mM) is added and the pH adjusted to 5.3 using concentrated aqueous $NH_4OH$. Solution B (10 mL) is added and the solution sparged with $N_2$. Chromium (II) chloride is added until the oxidation-reduction potential (ORP) of the solution decreases to approximately −200 mV, wherein resazurin (1 mL of a 2 g/L solution) is added. Solution C (1/10; 10 ml $FeCl_3$; 5 ml $CoCl_2$; 5 ml $NiCl_2$; 1 ml $H_3BO_3$; 1 ml $Na_2MoO_4$; 1 ml $MnCl_2$; 1 ml $Na_2WO_4$; 1 ml $ZnCl_2$; 1 ml $Na_2SeO_3$; into 1 L media) is added, then sodium polysulfide (2 mL of a 3M solution) is added, and then the solution is sparged with $N_2$ gas.

Fermentation of a substrate comprising CO by *C. autoethanogenum* under batch conditions in the presence of polysulfide results in a substantially increased rate of accumulation and a final biomass accumulation of approximately 4 g/L over a 2-3 day period. For example, following a short lag phase of approximately 1 day, the biomass can increase from about 0.5 g/L up to at least 3.5 g/L over approximately 36 hours of fermentation. Furthermore, acetate is not produced during the growth phase in the presence of polysulfide (as is typically found in batch fermentations) and in certain circumstances some of the acetate is consumed, such that there is a net decrease in the amount of acetate in the fermenter. Culture biomass was harvested by centrifugation, the cells washed once in media and cell pellets were either frozen at −80° C. or used immediately for fractionation of cellular components.

A semi-continuous fermentation approach can also be applied to maintain biomass productivity and reduce time associated with fermentation shut-down and start-up (i.e., turn-around time or lead time).

Harvesting of the accumulated bacterial biomass was performed at approximately 12-24 hour intervals, as the culture density approached (but before entering) stationary phase. Approximately half of the bioreactor volume was removed by transferring to a separate container via centrifugal pump. An equal volume of fresh or recycled media was then returned to the bioreactor such that the optical density of the reactor was approximately half of its initial value. The bioreactor fermentation was continued according to the above protocol so that multiple cycles of growth and biomass recovery was carried out during a single fermentation run.

b. *Clostridium ljungdahlii* Fermentation

Fermentation of *Clostridium ljungdahlii* is performed using similar methods to those described in, for example, U.S. Pat. Nos. 5,173,429 and 5,593,886. Briefly, batch fermentations are conducted using a biologically pure culture of *C. ljungdahlii*. Preparation of the medium ((1) 80.0 mL of a salt comprising $KH_2PO_4$ 3.00 g/L, $K_2HPO_4$ 3.00 g/L, $(NH_4)_2SO_4$ 6.00 g/L, NaCl 6.00 g/L, $MgSO_4$*$2H_2O$ 1.25 g/L; (2) 1.0 g of yeast extract; (3) 1.0 g of trypticase; (4) 3.0 ml of PFN (Pfenning) trace metal solution comprising $FeCl_2$*$4H_2O$ 1500 mg, $ZnSO_4$*$7H_2O$ 100 mg, $MnCl_2$*$4H_2O$ 30 mg, $H_3BO_3$ 300 mg, $CoCl_2$*$6H_2O$ 200 mg, $CuCl_2$*$H_2O$ 10 mg, $NiCl_2$*$6H_2O$ 20 mg, $NaMoO_4$*$2H_2O$ 30 mg, $Na_2SeO_3$ 10 mg, and distilled water up to 1 L; (5) 10.0 ml of B vitamins comprising Pyridoxal HCl 10 mg, Riboflavin 50 mg, Thiamine HCl 50 mg, Nicotinic acid 50 mg, Ca-D-Pantothenate 50 mg, Lipoic acid 60 mg, p-aminobenzoic acid 50 mg, Folic acid 20 mg, Biotin 20 mg, cyanocobalamin 50 mg, and distilled water up to 1 L; (6) 0.5 g of cysteine HCl; (7) 0.06 g $CaCl_2$*$2H_2O$; (8) 2.0 g $NaHCO_3$; (9) 1.0 mL resazurin (0.01%); and (10) 920.0 mL distilled water) is carried out anaerobically in an atmosphere of 80% nitrogen and 20% $CO_2$. The pH of the medium is controlled during fermentation and maintained at 5.0 with HCl. If required, adjustments to the pH are made with sterile 10% NaOH or 1.0% acetic acid solution. The medium is transferred to 157.5 mL serum bottles and sealed with butyl rubber stoppers and aluminum seals. The bottles are then autoclaved at 121° C. for 20 minutes.

Approximately 48 hours before commencing the experiment, a seed culture is prepared from a stock culture of the *C. ljungdahlii* in a bottle similar to those as described above. The seed culture is grown in a shaker incubator at 37° C. and shaken at 100 rpm. Reducing solutions (2.0 ml $Na_2S$, 2.5% solution and 2.0 ml cysteine-HCl, 3.5% solution) are added to the culture, which is placed in the shaker incubator for approximately 15 minutes to allow for complete oxygen removal and temperature acclimation. Unlike the procedure used for isolating a biologically pure culture of the organism, addition of methane inhibitors is not required in batch fermentations.

Fermentation with *C. ljungdahlii* is performed in a New Brunswick Scientific Bioflow IIc 2.5-liter fermenter containing nutrient media at 37° C., and a constant fluid level of 1.5 liters is maintained while the fluid is agitated at variable rates of up to 1,000 revolutions per minute with gas introduced at a rate of approximately 500 cubic centimeters per minute. Optimal gas retention times are in the range of three minutes. The gas feed is varied with its uptake by the bacteria, which is in turn a function of the cell density.

Harvesting of the accumulated bacterial biomass was performed at approximately 12-24 hour intervals, as the culture density approached (but before entering) stationary phase.

Approximately half of the bioreactor volume was removed by transferring to a separate container via centrifugal pump. An equal volume of fresh or recycled media was then returned to the bioreactor such that the optical density of the reactor was approximately half of its initial value. The bioreactor fermentation was continued according to the above protocol so that multiple cycles of growth and biomass recovery was carried out during a single fermentation run.

Example 2

$C_1$ Metabolizing Microorganisms Engineered for Enhanced Lipid Production

Host cells were engineered to possess genetic modifications to minimize or reduce the degradation of fatty acids—by knocking-out long-chain fatty acid-CoA ligase activity encoded by the endogenous fadD gene. Furthermore, biosynthesis of free fatty acids (FFAs) was enhanced by introducing a thioesterase (TE) gene into a methanotroph of this disclosure (*Methylococcus capsulatus*). Such recombinant alterations are further described in this example.

Recombinant Nucleic Acid Molecules

The nucleic acid sequences encoding wild-type FadD proteins were the reference standard starting point for designing mutant fadD genes. For example, the wild-type FadD protein sequence encoded by *M. trichosporium* OB3b, *M. capsulatus* Bath, *M. methanica, M. extorquens*, and *C. ljungdahlii* are provided in GenBank Accession Nos. EFH00931.1, YP_114021.1, YP_004512148.1, YP_002964871.1, and YP_003782065.1, respectively. Hence, a nucleic acid molecule of the fadD genes encoding the above-noted proteins were individually synthesized to incorporate several stop mutations and frame shifts in the 5'-region of the gene from *M. trichosporium* OB3b (SEQ ID NO.:1), *M. methanica* (SEQ ID NO.:35), *M. extorquens* (SEQ ID NO.:52), and *C. ljungdahlii* (SEQ ID NO.:85). For the *M. capsulatus* fadD gene, a nucleic acid molecule comprising an internal deletion was synthesized so that the remaining 5' and 3' ends of the gene could be joined to maintain the original reading frame (SEQ ID NO.:18).

For *C. autoethanogenum*, the genome is sequenced and the fadD homolog to *E. coli* is identified via a tblastn search (a search of the translated nucleotide gene sequences with the protein sequence of the *E. coli* FadD). A nucleic acid molecule of the *C. autoethanogenum* fadD gene is synthesized to incorporate several stop mutations and frame shifts in the 5'-region of the gene.

The mutant fadD nucleic acid molecules are individually cloned into a plasmid vector (lacking a methanotroph or clostridia origin of replication and encoding kanamycin resistance) for conjugation, electroporation, or transformation into a $C_1$ metabolizing microorganism using methods described herein. Such a vector (that does not replicate in a $C_1$ metabolizing microorganism) ensures that any kanamycin resistant $C_1$ metabolizing microorganism will have the resistance gene incorporated into the host cell genome due to homologous recombination and replacement of the endogenous fadD gene with the above-noted fadD mutants (such that the recombinant cells would lack or have minimal long-chain fatty acid-CoA ligase activity).

In addition, one or more selected thioesterase sequences, a malonyl CoA-acyl carrier protein transacylase (fabD) sequence, and an acetyl-CoA carboxylase sequence (e.g., accA, accB, accC, and accD from *E. coli*) were codon optimized and synthesized with appropriate promoters. One or more thioesterase genes and an acetyl-CoA carboxylase gene (e.g., accA or accABCD) are then cloned into an appropriate expression vector and conjugated, electroporated or transformed into wild-type or fadD-knockout $C_1$ metabolizing microorganisms as described herein.

Codon optimized thioesterase sequences are set forth in (1) SEQ ID NOS.:3-13 for *M. trichosporium* OB3b; (2) SEQ ID NOS.:20-30 for *M. capsulatus* Bath; (3) SEQ ID NOS.:37-47 for *M. methanica*; (4) SEQ ID NOS.:54-64 for *M. extorquens*; (5) SEQ ID NOS.:70-80 for *C. autoethanogenum*; and (6) SEQ ID NOS.:87-97 for *C. ljungdahlii*. Codon optimized fabD sequences are set forth in (1) SEQ ID NO.:2 for *M. trichosporium* OB3b; (2) SEQ ID NO.:19 for *M. capsulatus* Bath; (3) SEQ ID NO.:36 for *M. methanica*; (4) SEQ ID NO.:53 for *M. extorquens*; (5) SEQ ID NO.:69 for *C. autoethanogenum*; and (6) SEQ ID NO.:86 for *C. ljungdahlii*. Codon optimized accA, accB, accC, and accD sequences are set forth, respectively, in (1) SEQ ID NOS.:14-17 for *M. trichosporium* OB3b; (2) SEQ ID NOS.:31-34 for *M. capsulatus* Bath; (3) SEQ ID NOS.:48-51 for *M. methanica*; (4) SEQ ID NOS.:65-68 for *M. extorquens*; (5) SEQ ID NOS.: 81-84 for *C. autoethanogenum*; and (6) SEQ ID NOS.:98-101 for *C. ljungdahlii*.

Conjugation

The procedure for conjugating plasmids from *Escherichia coli* into *M. trichosporium* OB3b or *M. methanica* was based on the method developed by Martin and Murrell (*FEMS Microbiol. Lett.* 127:243, 1995), while the procedure for conjugating plasmids from *E. coli* into *M. capsulatus* was based on the method reported by Ali and Murrell (*Microbiology* 155:761, 2009).

Briefly, a mobilizable plasmid containing one or more genes of interest (e.g., mutant fadD, MCT, one or more TE, one or more Acc) and encoding kanamycin resistance was first transformed into *E. coli* S 17-1 using standard electroporation methods. Transformation was confirmed by selection of kanamycin-resistant colonies on LB-agar containing 30 μg/mL kanamycin. Transformed colonies were inoculated into LB media containing 30 μg/mL kanamycin and shaken overnight at 37° C. A 10 mL aliquot of the overnight culture was then collected on a sterile 47 mm nitrocellulose filter (0.2 mm pore size). The *E. coli* donor cells were washed on the filter with 50 mL sterile NSM media to remove residual media and antibiotic.

In parallel, a sample of the *M. trichosporium* OB3b, *M. methanica*, or *M. capsulatus* Bath recipient strains were separately inoculated into 100 mL serum bottles containing 20-50 mL NSM media. The headspace of the bottles was then flushed with a 1:1 mixture of oxygen and methane, and the bottles were sealed with butyl rubber septa and crimped. The bottles were shaken continuously in a 30° C. (*M. trichosporium* OB3b, *M. methanica*) or a 45° C. (*M. capsulatus* Bath) incubator until reaching an $OD_{600}$ of approximately 0.3. The cells were then collected on the same filter as the *E. coli* donor strain. The filter was again washed with 50 mL of sterile NSM media. The filter was placed (cells up) on an NSM agar plate containing 0.2% yeast extract and incubated for 24 h at 30° C. (*M. trichosporium* OB3b, *M. methanica*) or 37° C. (*M. capsulatus* Bath) in the presence of a 1:1 mixture of methane and air. After 24 h, cells were re-suspended in 10 mL sterile (NSM) medium before being concentrated by centrifugation. The harvested cells were re-suspended in 1 mL sterile NSM media and aliquots (100 μL) were spread onto NSM agar plates containing 10 μg/mL kanamycin.

The plates were incubated in sealed chambers containing a 1:1 mixture of methane and air and maintained at 30° C. (*M. trichosporium* OB3b, *M. methanica*) or 45° C. (*M. capsulatus*

Bath). The gas mixture was replenished every 2 days until colonies formed, typically after 7-14 days. Colonies were streaked onto NSM plates containing kanamycin to confirm kanamycin resistance as well as to further isolate transformed methanotroph cells from residual *E. coli* donor cells.

Electroporation—*Methanobacterium*

The procedure for introducing plasmids into *M. extorquens* is based on the procedure described by Ueda et al., *Appl. Environ. Microbiol.* 57:924, 1991. Briefly, wild-type (wt) *M. extorquens* is cultured at 30° C. in NSM media supplemented with 0.5% methanol. Cells of *M. extorquens* NR-2 grown to the mid-log phase ($1.4\times10^9$/ml) are harvested by centrifugation at 6,000×g for 10 min and washed with electroporation buffer (10 mM Tris-HCl, 2 mM $MgCl_2.6H_2O$, 10% [wt/vol] sucrose [pH 7.5]). Cells are re-suspended in the same buffer at a cell concentration of $7.0\times10^{10}$/ml. The cell suspension and vector (70 μg/mL) are mixed at a ratio of 9:1 (vol/vol) in a tube, and then 10 μL is transferred into a space between the electrodes of a chamber where it is equilibrated for 3 minutes. After being subjected to 10 pulses of a 10 kV/cm electric field for 300 μsec/pulse, a 5 μL aliquot of the mixture is transferred to a clean tube and 0.2 mL NSM medium is added. The cell suspension is then incubated for 2 h at 30° C. to allow expression of the antibiotic resistance genes prior to plating on NSM plates containing 0.5 methanol and 20 μg/mL kanamycin.

The plates were incubated at 30° C. until colonies formed. Colonies were streaked onto duplicate plates to confirm kanamycin resistance as well as to further isolate transformed methylotroph cells from residual *E. coli* donor cells.

Electroporation—*Clostridium*

Transformation methods for *C. autoethanogenum* or *C. ljungdahlii* are performed as described in U.S. Patent Pub. No. 2011/0236941, or using a modified protocol for *C. tyrobutyricum* (Zhu et al., *Biotechnol. Bioeng.* 90:154, 2005). Briefly, to make competent cells, a 50 mL culture of *C. autoethanogenum* is subcultured to fresh media for 3 consecutive days according to the culturing conditions described herein. These cells are used to inoculate 50 mL PETC media containing 40 mM DL-threonine at an $OD_{600}$ of 0.05. When the culture reaches an $OD_{600}$ of 0.4, the cells are transferred into an anaerobic chamber and harvested at 4,700×g and 4° C. The culture is washed twice with ice-cold electroporation buffer (270 mM sucrose, 1 mM $MgCl_2$, 7 mM sodium phosphate, pH 7.4) and finally suspended in a volume of 600 μl fresh electroporation buffer. This mixture is transferred into a pre-cooled electroporation cuvette with a 0.4 cm electrode gap containing 1 μg of vector (lacking a *Clostridium* origin of replication and containing a nucleic acid molecule of interest and encoding clarithromycin resistance) and immediately pulsed using the Gene pulser Xcell electroporation system (Bio-Rad) with the following settings: 2.5 kV, 600 μl, and 25 μF. Time constants of 3.7-4.0 ms are achieved. The culture is transferred into 5 ml fresh media. Regeneration of the cells is monitored at a wavelength of 600 nm using a Spectronic Helios Epsilon Spectrophotometer (Thermo) equipped with a tube holder. After an initial drop in biomass, the cells start growing again. Once the biomass has doubled from that point, the cells are harvested, suspended in 200 μl fresh media and plated on selective PETC plates (containing 1.2% Bacto™ Agar (BD)) with clarithromycin. After 4-5 days of incubation with 30 psi steel mill gas at 37° C., colonies are clearly visible.

Alternatively, after the electroporation pulse, the cells are transferred into 5 mL prewarmed medium in a Hungate tube and incubated at 37° C. until growth is visible (measured in Hungate tubes in a photometer). Aliquots of the transformants are inoculated into 5 mL liquid medium and spread onto clarithromycin-containing plates to develop mutant colonies.

The selected recombinant colonies are used to inoculate 2 ml PETC media containing 4 μg/μl clarithromycin. When growth occurs, the culture is scaled up into 5 ml and later 50 ml PETC media containing 4 μg/μl clarithromycin and 30 psi steel mill gas as the carbon source.

Recombinant $C_1$ Metabolizing Bacteria

Transformation is confirmed by resistance of the cells to antibiotic selection, and gene expression is confirmed by PCR, northern blot, western blot, or ELISA methods. For example, to verify transfer, plasmid DNA can be isolated and subjected to PCR using the illustra PuReTaq Ready-To-Go™ PCR Beads (GE Healthcare) using standard conditions (95° C. for 5 min; 32 cycles of 95° C. for 30 s, 50° C. for 30 s, and 72° C. for 1 min; 72° C. for 10 min). As a further control, 1 μl each of the isolated plasmids are re-transformed into *E. coli* XL1-Blue MRF' Kan (Stratagene, La Jolla, Calif.), from where the plasmids can be isolated cleanly and verified by restriction digests.

Methods for identifying homologous recombination events are well-established in the art, such as PCR and sequencing using unique primers in the genome and the vector to confirm proper insertion. Recombinant bacteria identified as having a proper insertion are then grown in the absence of selective pressure (e.g., without kanamycin or clarithromycin) for several generations, and kanamycin-sensitive clones are identified by replica plating (or equivalent technique). Approximately 50% of the kanamycin-sensitive revertants should possess the mutated form of the target gene in place of wild-type, which is confirmed by PCR and sequencing. Loss of fadD expression or function can be verified by one or more of (1) PCR and sequencing, (2) northern blot analysis, and (3) assaying for acyl-CoA synthetase activity.

For acyl-CoA synthetase activity, the method of, for example, Kameda et al. (*J. Biol. Chem.* 256:5702, 1981) can be used by growing cells to mid-log phase in NSM with antibiotics as required, harvesting cells by centrifugation, washing twice with NSM, suspending the cells to a density of $1.2\times10^9$ cells/mL in 10 mM Tris-HCl, pH 7.5, and then lysing by three cycles of sonication on ice. Reaction mixtures are prepared, in a total volume of 0.5 ml, to include 200 mM Tris-HCl, pH 7.5, 2.5 mM ATP, 8 mM MgCl, 2 mM EDTA, 20 mM NaF, 0.1% Triton® X-100, 10 pM [$^3$H]oleate, 0.5 mM coenzyme A, and cell extract. The enzyme reactions are initiated with the addition of coenzyme A, incubated at 35° C. for 10 minutes, and terminated by the addition of 2.5 ml isopropyl alcohol:n-heptane:1M $H_2SO_4$ (40:10:1). The radioactive oleic acid is removed by organic extraction using n-heptane, while oleoyl-CoA formed during the reaction remains in the aqueous fraction to be quantified by scintillation counting. Protein concentrations in the enzyme extracts are determined using the Bradford assay with bovine serum albumin as a standard.

Production of Fatty Acids from $C_1$ Substrates ($CH_4$ and CO)

For methanotrophs, wild-type or fadD-knockout *M. trichosporium* OB3b, *M. methanica, M. extorquens*, or *M. capsulatus* Bath transformed with a vector containing genes encoding one or more thioesterase genes or overexpressing acetyl-CoA carboxylase genes are used to inoculate 100 mL serum bottles or culture tubes containing 20-50 mL NSM media and 10 μg/mL kanamycin. For *M. extorquens*, the media is supplemented with 0.5% methanol as a carbon source, whereas the bottle headspace is flushed with a 1:1 mixture of oxygen and methane as the carbon source for *M. trichosporium* OB3b, *M. methanica*, and *M. capsulatus* Bath. The bottles are sealed with butyl rubber septa and crimped. The bottles or tubes are then shaken continuously at a rate of 200-250 rpm during incubation at 30° C. (*M. trichosporium* OB3b, *M. methanica*, *M. extorquens*) or 42-45° C. (*M. capsulatus* Bath).

For Clostridia, wild-type or fadD-knockout *C. autoethanogenum* or *C. ljungdahlii* transformed with a vector containing genes encoding one or more thioesterase enzymes and with or without acetyl-CoA carboxylase genes are used to inoculate 2 ml PETC media containing 4 μg/μl clarithromycin. When growth occurs, the culture is scaled up into 5 ml and later 50 ml PETC media containing 4 μg/μl clarithromycin and 30 psi steel mill gas as the carbon source. The bottles are then shaken continuously at a rate of 200-250 rpm during incubation at 37° C.

Quantification of fatty acids produced by the recombinant $C_1$ metabolizing bacteria is performed using a gas chromatograph/mass spectrometer (GC/MS). Fatty acids in the cell culture are extracted by vortexing vigorously with butyl acetate containing undecanoic acid as an internal standard for GC/MS analysis of the extract. After brief centrifugation of the mixture, a small portion of the organic layer was transferred to a separate vial, followed by addition of an equal volume of N,O-Bis(trimethylsilyl) trifluoroacetamide. The sample was analyzed by GC with a mass spectrometer detector (HP 5792) using an Agilent HP-5MS GC/MS column (30.0 m×250 μM×0.25 μM film thickness). A split ratio of 20:1 at 250° C. was used for the injector and helium was the carrier gas at a flow of 1.2 mL/min. The oven temperature was held at 60° C. for the 1 minute, followed by a temperature gradient increase of 19° C./min until reaching a temperature of 250° C. The concentration of fatty acids in the cell culture was calculated using selective ion mode based on the calibration curves of fatty acid standards. Since methane was the only carbon source provided to the cells, all fatty acids produced must have been derived from methane.

Results

The fatty acid profile of *M. capsulatus* Bath was altered by knocking out fadD and by introducing and expressing an *E. coli* thioesterase gene. First, the *E. coli* thioesterase gene with the periplasmic targeting sequence removed (TesA') was synthesized using three different codon compositions (TesA'-3, SEQ ID NO:102; TesA'-37, SEQ ID NO:103; and TesA'-20, SEQ ID NO:104) designed to generate variants with differing expression levels. The TesA' variants were cloned into an IncP-based plasmid (comprising an Inc-P oriV and oriT) and operatively connected to a promoter that functions in methanotrophs. The recombinant expression vector containing TesA' was transformed into *M. capsulatus* as described herein. *M. capsulatus* cultures in a 5 mL volume in 150 mL sealed serum bottles were grown with 40 mL methane and 80 mL oxygen for 5 days. After the growth stage, 1 mL of each culture was assayed for fatty acid concentration and composition using GC/MS as described herein. Measured free fatty acid values were normalized to $OD_{600}$ by culture. Note that the C16:1 fraction is comprised of at least three different isomers with the most abundant being Δ9-cis palmitoleic acid (data not shown).

In parallel, a homolog of the *E. coli* acyl coenzyme A (CoA) synthetase (fadD) was recombinantly knocked-out with SEQ ID NO:18 in the *M. capsulatus* genome as described herein and confirmed by PCR analysis. FadD knockout has been shown in several other microbial strains to increase free fatty acid levels (see, e.g., Lennen et al., *Trends Biotechnol.* 12:659, 2012). The *M. capsulatus* fadD knockout mutant did not show a significant increase in free fatty acid levels, which indicates that one or more additional FadD homologs may be present in the *M. capsulatus* genome, but lipid profile was shifted since there was an increase C18:0 lipids.

Figure 3:
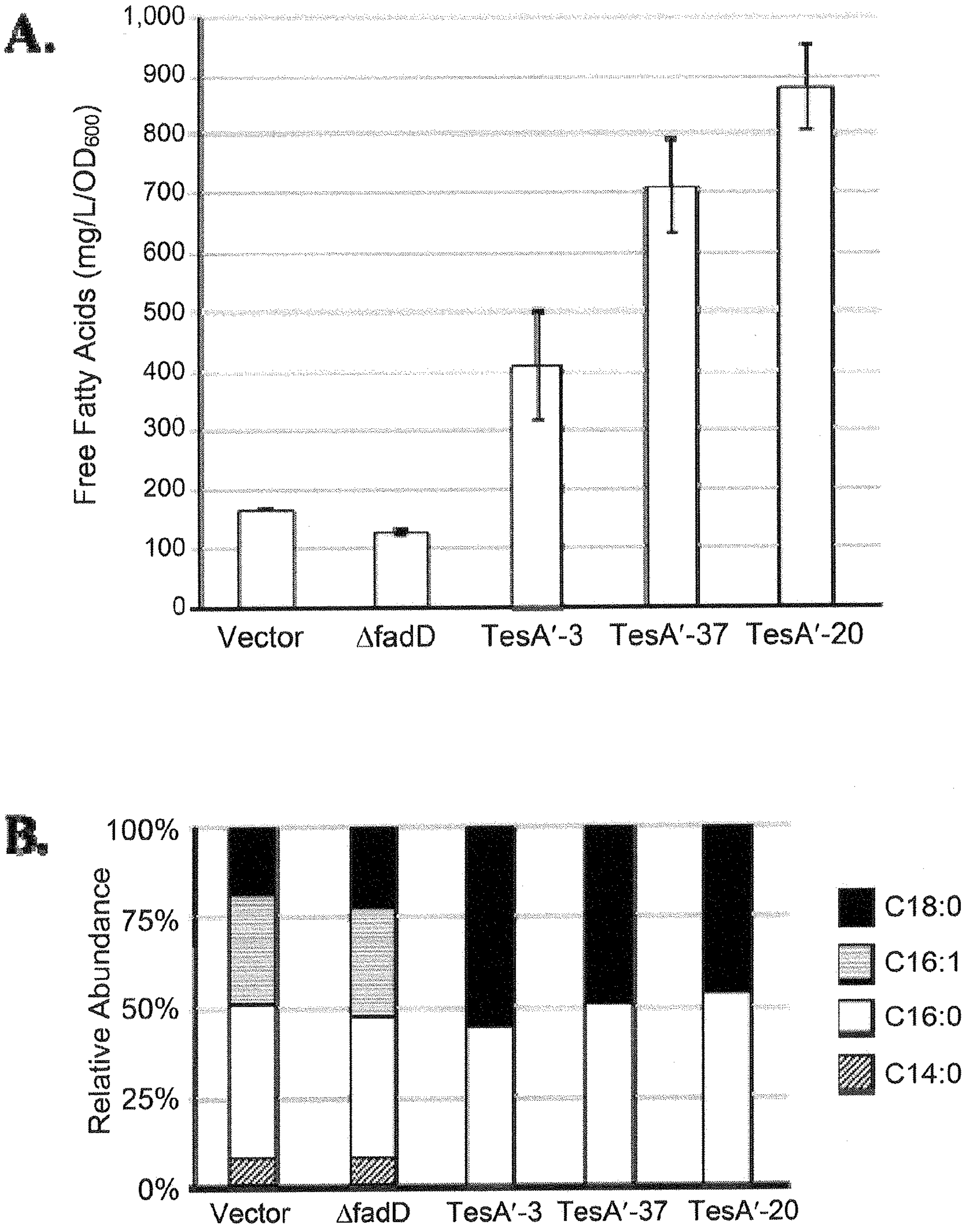
FIGS. 3A and 3B show that recombinant *Methylobacter capsulatus* expressing TesA' (TesA gene from *E. coli* with the periplasmic targeting sequence removed) causes (A) an increase in free fatty acid production, and (B) the increase was primarily due to increased levels of C16:0 and C18:0 lipids.

The free fatty acid pools in the transformed cells increased dramatically (see FIG. 3A), with the increase primarily attributed to increased levels of C16:0 and C18:0 lipids (see FIG. 3B).

Example 3

Lipid Extraction from $C_1$ Metabolizing Microorganisms

The oil composition contained within a harvested bacterial biomass was extracted using a modified version of Folch's extraction protocol (Folch et al., *J. Biol. Chem.* 226:497, 1957), performed at 20° C. (i.e., room temperature) and in an extraction solution made up of one volume methanol in two volumes chloroform (CM solution). About 5 g wet cell weight (WCW) of either fresh bacterial biomass (or bacterial biomass stored at −80° C. and subsequently thawed) was used for extractions. A 100 mL CM solution was added to the cell material and the mixture was extracted vigorously in a separatory funnel. After at least 10 minutes, three phases were resolved. The organic phase containing extracted lipids settled at the bottom of the separatory funnel, which was drained into a clean glass bottle. The middle layer contained primarily lysed cellular materials and could be separated from the light water phase containing salts and other soluble cellular components.

Optionally, solids in the water phase can be concentrated using a centrifuge or other mechanical concentration equipment. The water removed from the solids may be recycled, while the solids, with some residual water, can be fed to a solids processing unit.

To enhance the lipid extraction efficiency, a second extraction step was carried out by adding an additional 100 mL fresh CM solution directly into the separatory funnel containing the remaining lysed cell mass and residual water. The mixture was again mixed thoroughly, the phases allowed to separate, and the bottom organic phases from the two extractions were pooled. The pooled organic phases were then washed with 100 mL deionized water in a separatory funnel to remove any residual water-soluble material. The separated organic fraction was again isolated from the bottom of the separatory funnel and solvent was removed by rotary evaporation with heat, preferably in the absence of oxygen, or by evaporation at 55° C. under a stream of nitrogen.

TABLE 1

Extracted Lipid Content from Three Different Methanotrophs

| Batch No. | Reference Strain | Lipid Fraction (g/g DCW)* |
|---|---|---|
| 68C | *Methylosinus trichosporium* OB3b | 40.1 |
| 62A | *Methylococcus capsulatus* Bath | 10.3 |
| 66A | *Methylomonas* sp. 16a | 9.3 |

*Grams of extracted material per gram of dry cell weight (DCW)

The solidified oil compositions extracted from the harvested cultures of *M. trichosporium* OB3b, *Methylococcus capsulatus* Bath, and *Methylomonas* sp. 16a were each weighed and are shown as the weight fraction of the original dry cell weight (DCW) in Table 1. These data show that a significant fraction of the DCW from these $C_1$ metabolizing microorganisms is made up of lipids.

The oil composition from *Methylomonas* sp. 16a biomass was also extracted using hexane:isopropanol (HIP) extraction method of Hara and Radin (*Anal. Biochem.* 90:420, 1978). Analysis of the oil composition extracted using the HIP method showed that the oil composition was essentially identical to the oil composition extracted using the modified Folch method (data not shown).

Example 4

Fatty Acid Methyl Ester Conversion of Lipids from $C_1$ Metabolizing Microorganisms The lipid fractions extracted from *M. capsulatus* Bath, *M. trichosporium* OB3b, and *Methylomonas* sp. 16a culture biomass in the form of dry solids were individually hydrolyzed with potassium hydroxide (KOH) and converted into fatty acid methyl esters (FAMEs) via reaction with methanol in a single step. About 5 g of extracted solid lipids in a 10 mL glass bottle were dissolved with 5 mL of 0.2 M KOH solution of toluene:methanol (1:1 v/v). The bottle was agitated vigorously and then mixed at 250 rpm at 42° C. for 60 minutes, after which the solution was allowed to cool to ambient temperature and transferred to a separatory funnel. Approximately 5 mL distilled water and 5 mL CM solution were added to the separatory funnel, mixed, and then the phases were allowed to separate by gravity or by centrifugation (3,000 rpm, 25° C.) for 5 minutes. The top aqueous layer was removed, which contains dissolved glycerol phosphate esters, while the heavy oil phase (bottom) was collected and concentrated to dryness by rotary evaporation or by a constant nitrogen stream.

Analysis of FFAs and FAMEs found in lipids from each methanotroph culture was performed using a gas chromatograph/mass spectrometer (GC/MS). The solids collected before and after the hydrolysis/transesterification step were dissolved in 300 μL butyl acetate containing undecanoic acid as an internal standard for GC/MS analysis. The resulting solution was centrifuged for 5 minutes at 14,000 rpm to remove insoluble residues. The same volume equivalent of N,O-Bis(trimethylsilyl)trifluoroacetamide was added to the supernatant from the centrifugation step and vortexed briefly. Samples were loaded on an GC equipped with mass spectrometer detector (HP 5792), and an Agilent HP-5MS GC/MS column (30.0 m×250 μm×0.25 μm film thickness) was used to separate the FFAs and FAMEs. Identity of FFAs and FAMEs was confirmed with retention time and electron ionization of mass spectra of their standards. The GC/MS method utilized helium as the carrier gas at a flow of 1.2 mL/min. The injection port was held at 250° C. with a split ratio of 20:1. The oven temperature was held at 60° C. for 1 minute followed by a temperature gradient comprising an 8° C. increase/min until 300° C. The % area of each FFA and FAME was calculated based on total ions from the mass detector response.

The solid residue collected before and after hydrolysis/transesterification were analyzed for FFAs and FAMEs by GC/MS (see Table 2). Also, chromatograms from the GC/MS analysis are provided in FIGS. 4-6.

TABLE 2

Relative composition of FFA and FAME in Extracted Lipids Before and After KOH Hydrolysis/Esterification

| | *M. capsulatus* Bath | | *M. trichosporium* OB3b | | *Methylomonas* sp. 16a | |
|---|---|---|---|---|---|---|
| Fatty Acid Type | With hydrolysis % Area | Without hydrolysis | With hydrolysis % Area | Without hydrolysis | With hydrolysis % Area | Without hydrolysis |
| C14:0 FFA | — | — | — | — | — | 12.9 |
| C16:0 FFA | 0.5 | 84.1 | — | 43.7 | — | 8.1 |
| C16:1 FFA | — | 13.4 | — | — | — | 76.1 |
| C18:0 FFA | 0.4 | 2.5 | — | 31.2 | — | 1.3 |
| C18:1 FFA | — | — | — | 25.1 | — | 1.5 |
| C14:0 FAME | 3.4 | — | — | — | 7.2 | — |
| C16:0 FAME | 54.4 | — | 1.4 | — | 14.7 | — |
| C16:1 FAME | 41.3 | — | 6.8 | — | 61.3 | — |
| C18:0 FAME | — | — | 1.0 | — | N.D. | — |
| C18:1 FAME | — | — | 90.8 | — | 16.8 | — |

* — = Not detectable; % Area: MS detector response − Total ions

Figure 4:
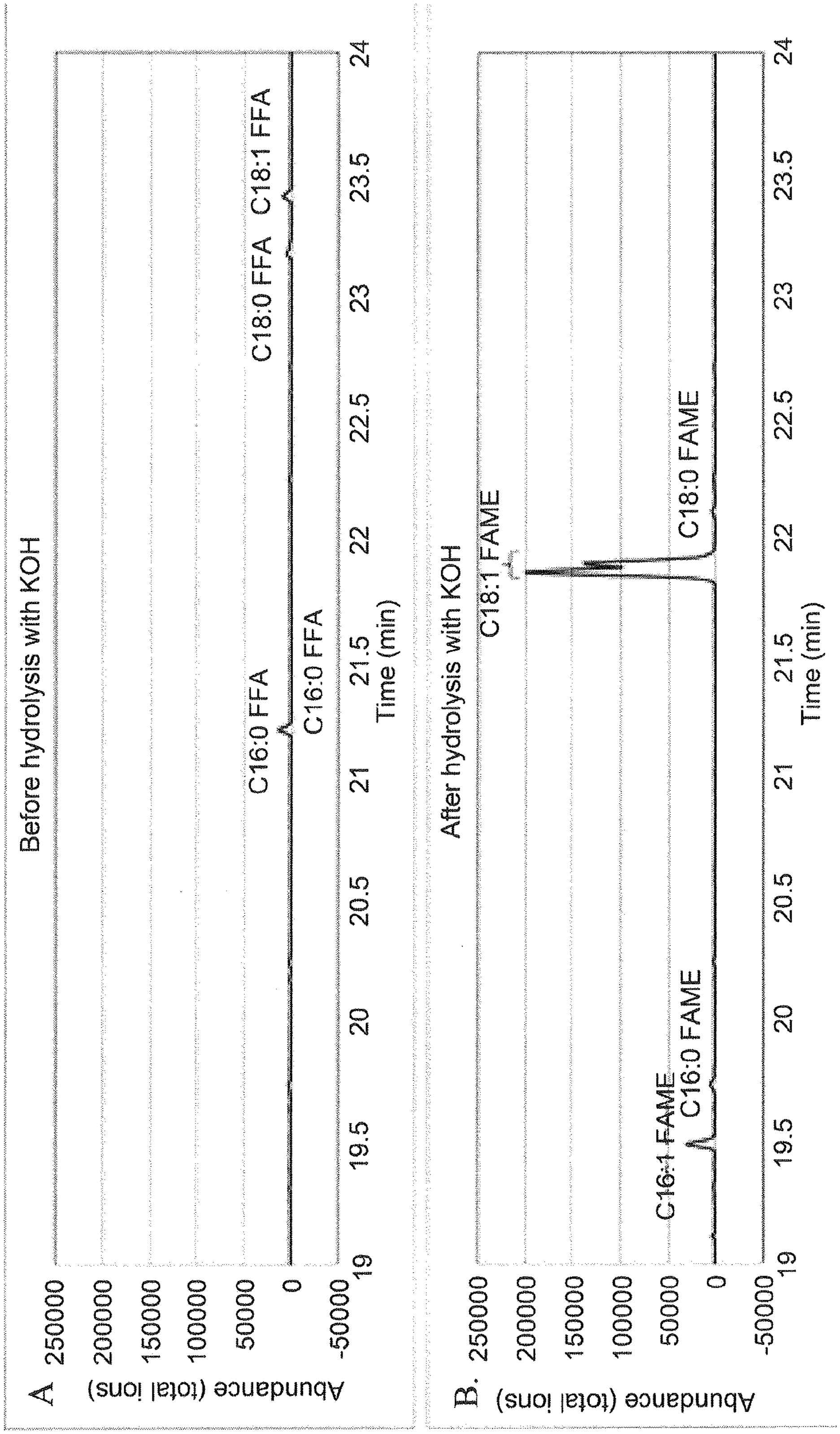
FIGS. 4A and 4B show GC/MS chromatograms of an oil composition extracted from *M. trichosporium* before (A) and after (B) hydrolysis and transesterification with KOH in toluene:methanol.
Figure 5:
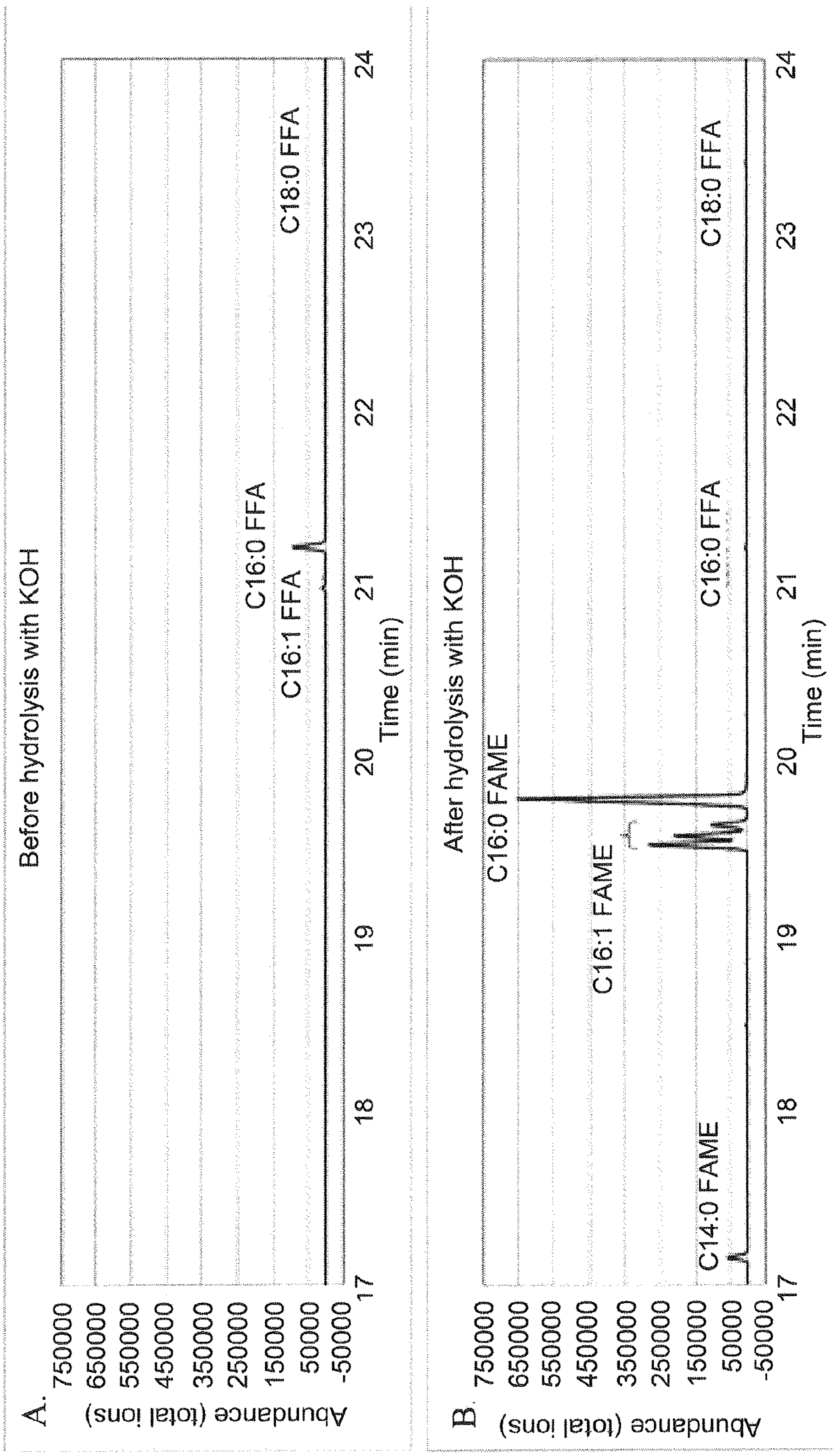
FIGS. 5A and 5B show GC/MS chromatograms of an oil composition extracted from *M. capsulatus* before (A) and after (B) hydrolysis and transesterification with KOH in toluene:methanol.
Figure 6:
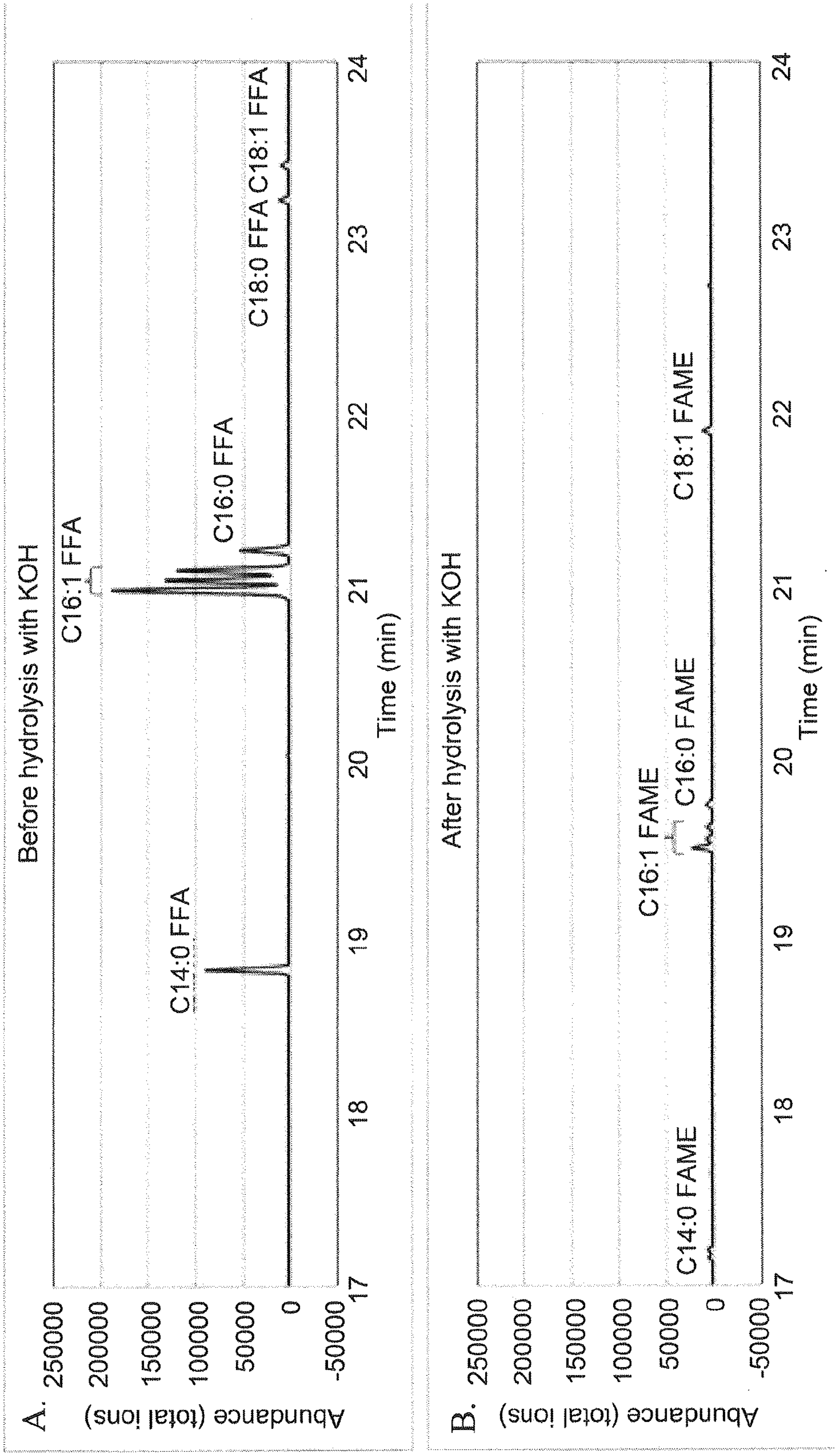
FIGS. 6A and 6B show GC/MS chromatograms of an oil composition extracted from *Methylomonas* sp. 16a before (A) and after (B) hydrolysis and transesterification with KOH in toluene:methanol.

As is evident from Table 2, and FIGS. 4-6, extracted oil compositions before hydrolysis/transesterification have abundant free fatty acids and additional fatty acids present as (most likely) di- and tri-acyl glycerides (which are not detected on the GC/MS trace), but the FFAs are converted into fatty acid methyl esters of various lengths after hydrolysis/transesterification. These data indicate that oil compositions from the $C_1$ metabolizing microorganisms of this disclosure can be refined and used to make high-value molecules.

Example 5

Biofuel Production Using Oil Compositions from $C_1$ Metabolizing Microorganisms The extracted oil compositions from $C_1$ metabolizing microorganisms can be processed at a co-located refinery or transported to a distant refinery. A refinery is used to convert triglycerides from bio-renewable feeds (such as fats, greases, and methanotroph oils) into a mixture of liquid hydrocarbon fuels, primarily biodiesel and biojet fuel, a high quality synthetic paraffinic kerosene (SPK). The process requires hydrogen, which can be produced on-site using methane reforming or is provided by co-locating the fermentation facility at an existing refinery.

The refinery can be run in a Mixed Mode, wherein the output is a mixture of biodiesel and biojet fuel, or a Diesel Mode, wherein the output is primarily biodiesel.

During refining, fatty acids and glycerides are converted to SPK in three steps. First, raw feedstocks are treated to remove catalyst contaminants and water as needed. In the second step, fatty acid chains are transformed into n-paraffins in a hydrotreater. An example is oleic acid conversion to n-octadecane via the hydrogenation and deoxygenation reactions in the hydrotreater. For most bio-oils, fats, and greases, the hydrotreater liquid product is mainly a $C_{15}$-$C_{18}$ n-paraffin composition. In the third step of the process, these long straight-chain paraffins are hydrocracked into shorter branched paraffins. The hydrocracked products fall mainly in the kerosene boiling range.

The produced SPK preferably meets or exceeds all jet fuel fit-for-purpose specifications except density. The high H-to-C ratio of SPK, which gives its excellent thermal stability and low particulate emission attribute, means a lower density hydrocarbon composition: 760-770 kg/$m^3$ compared to the minimum ASTM specification value of 775 $kg/m^3$. But, this is not an issue with petroleum jet fuel:SPK blends (e.g., 50/50).

Example 6

Stable Carbon Isotope Distribution in Lipids from $C_1$ Metabolizing Microorganisms Dry samples of *M. trichosporium* biomass and lipid fractions were analyzed for carbon and nitrogen content (% dry weight), and carbon ($^{13}C$) and nitrogen ($^{15}N$) stable isotope ratios via elemental analyzer/continuous flow isotope ratio mass spectrometry using a CHNOS Elemental Analyzer (vario ISOTOPE cube, Elementar, Hanau, Germany) coupled with an IsoPrime100 IRMS (Isoprime, Cheadle, UK). Samples of methanotrophic biomass cultured in fermenters or serum bottles were centrifuged, resuspended in deionized water and volumes corresponding to 0.2-2 mg carbon (about 0.5-5 mg dry cell weight) were transferred to 5×9 mm tin capsules (Costech Analytical Technologies, Inc., Valencia, Calif.) and dried at 80° C. for 24 hours. Similarly, previously extracted lipid fractions were suspended in chloroform and volumes containing 0.1-1.5 mg carbon were transferred to tin capsules and evaporated to dryness at 80° C. for 24 hours. Standards containing 0.1 mg carbon provided reliable $\delta^{13}C$ values.

The isotope ratio is expressed in "delta" notation (‰), wherein the isotopic composition of a material relative to that of a standard on a per million deviation basis is given by $\delta^{13}C$ (or $\delta^{15}N$)=$(R_{Sample}/R_{Standard}-1)\times 1{,}000$, wherein R is the molecular ratio of heavy to light isotope forms. The standard for carbon is the Vienna Pee Dee Belemnite (V-PDB) and for nitrogen is air. The NIST (National Institute of Standards and Technology) proposed SRM (Standard Reference Material) No. 1547, peach leaves, was used as a calibration standard. All isotope analyses were conducted at the Center for Stable Isotope Biogeochemistry at the University of California, Berkeley. Long-term external precision for C and N isotope analyses is 0.10‰ and 0.15‰, respectively.

*M. trichosporium* strain OB3b was grown on methane in three different fermentation batches, *M. capsulatus* Bath was grown on methane in two different fermentation batches, and *Methylomonas* sp. 16a was grown on methane in a single fermentation batch. The biomass from each of these cultures was analyzed for stable carbon isotope distribution ($\delta^{13}C$ values; see Table 3).

TABLE 3

Stable Carbon Isotope Distribution in Different Methanotrophs

| Methanotroph | Batch No. | EFT (h)† | $OD_{600}$ | DCW* | $\delta^{13}C$ Cells |
|---|---|---|---|---|---|
| Mt OB3b | 68A | 48 | 1.80 | 1.00 | −57.9 |
| | | 64 | 1.97 | 1.10 | −57.8 |
| | | 71 | 2.10 | 1.17 | −58.0 |
| | | 88 | 3.10 | 1.73 | −58.1 |
| | | 97 | 4.30 | 2.40 | −57.8 |
| | | 113 | 6.00 | 3.35 | −57.0 |
| | | 127 | 8.40 | 4.69 | −56.3 |
| Mt OB3b | 68B | 32 | 2.90 | 1.62 | −58.3 |
| | | 41 | 4.60 | 2.57 | −58.4 |
| | | 47 | 5.89 | 3.29 | −58.0 |
| | | 56 | 7.90 | 4.41 | −57.5 |
| Mt OB3b | 68C | 72 | 5.32 | 2.97 | −57.9 |
| | | 79.5 | 5.90 | 3.29 | −58.0 |
| | | 88 | 5.60 | 3.12 | −57.8 |
| | | 94 | 5.62 | 3.14 | −57.7 |
| Mc Bath | 62B | 10 | 2.47 | 0.88 | −59.9 |
| | | 17.5 | 5.80 | 2.06 | −61.0 |

TABLE 3-continued

Stable Carbon Isotope Distribution in Different Methanotrophs

| Methanotroph | Batch No. | EFT (h)† | $OD_{600}$ | DCW* | $\delta^{13}C$ Cells |
|---|---|---|---|---|---|
| | | 20 | 7.32 | 2.60 | −61.1 |
| | | 23 | 9.34 | 3.32 | −60.8 |
| | | 26 | 10.30 | 3.66 | −60.1 |
| Mc Bath | 62A | 10 | 2.95 | 1.05 | −55.9 |
| | | 13.5 | 3.59 | 1.27 | −56.8 |
| | | 17.5 | 5.40 | 1.92 | −55.2 |
| | | 23 | 6.08 | 2.16 | −57.2 |
| | | 26 | 6.26 | 2.22 | −57.6 |
| Mms 16a | 66B | 16 | 2.13 | 0.89 | −65.5 |
| | | 18 | 2.59 | 1.09 | −65.1 |
| | | 20.3 | 3.62 | 1.52 | −65.5 |
| | | 27 | 5.50 | 2.31 | −66.2 |
| | | 40.5 | 9.80 | 4.12 | −66.3 |

*DCW, Dry Cell Weight is reported in g/L calculated from the measured optical densities ($OD_{600}$) using specific correlation factors relating OD of 1.0 to 0.558 g/L for Mt OB3b, OD of 1.0 to 0.355 g/L for Mc Bath, and OD of 1.0 to 0.42 g/L for Mms 16a. For Mt OB3b, the initial concentration of bicarbonate used per fermentation was 1.2 mM or 0.01% (Batch No. 68C) and 0.1% or 12 mM (Batch Nos. 68A and 68B).

†EFT = effective fermentation time in hours

In addition, stable carbon isotope analysis was performed for biomass and corresponding lipid fractions (see Table 4) from strains *Methylosinus trichosporium* OB3b (Mt OB3b), *Methylococcus capsulatus* Bath (Mc Bath), and *Methylomonas* sp. 16a (Mms 16a) grown on methane in bioreactors as described in Example 1.

TABLE 4

Stable Carbon Isotope Distribution in Cells and Lipids

| Batch No. | Strain | $\delta^{13}C$ Cells | $\delta^{13}C$ Lipids |
|---|---|---|---|
| 68C | Mt OB3b | −57.7 | −48.6 |
| 62A | Mc Bath | −57.6 | −52.8 |
| 66A | Mms 16a | −64.4 | −42.2 |

Biomass from strains Mt OB3b, Mc Bath and Mms 16a were harvested at 94 h (3.14 g DCW/L), 26 h (2.2 g DCW/L) and 39 h (1.14 g DCW/L), respectively. The $\delta^{13}C$ values for lipids in Table 4 represent an average of duplicate determinations.

Example 7

Effect of Methane Source and Purity on Stable Carbon Isotope Distribution in Lipids To examine methanotroph growth on methane containing natural gas components, a series of 0.5-liter serum bottles containing 100 mL defined media MMS1.0 were inoculated with *Methylosinus trichosporium* OB3b or *Methylococcus capsulatus* Bath from a serum bottle batch culture (5% v/v) grown in the same media supplied with a 1:1 (v/v) mixture of methane and air. The composition of medium MMS1.0 was as follows: 0.8 mM $MgSO_4{*}7H_2O$, 30 mM $NaNO_3$, 0.14 mM $CaCl_2$, 1.2 mM $NaHCO_3$, 2.35 mM $KH_2PO_4$, 3.4 mM $K_2HPO_4$, 20.7 μM $Na_2MoO_4{*}2H_2O$, 6 μM $CuSO_4{*}5H_2O$, 10 μM $Fe^{III}$—Na-EDTA, and 1 mL per liter of a trace metals solution (containing, per L: 500 mg FeSO4*7$H_2O$, 400 mg $ZnSO_4{*}7H_2O$, 20 mg $MnCl_2$*7H2O, 50 mg $CoCl_2{*}6H_2O$, 10 mg $NiCl_2{*}6H_2O$, 15 mg $H_3BO_3$, 250 mg EDTA). Phosphate, bicarbonate, and $Fe^{III}$—Na-EDTA were added after media was autoclaved and cooled. The final pH of the media was 7.0±0.1.

The inoculated bottles were sealed with rubber sleeve stoppers and injected with 60 mL methane gas added via syringe through sterile 0.45 μm filter and sterile 27G needles. Duplicate cultures were each injected with 60 mL volumes of (A) methane of 99% purity (grade 2.0, Praxair through Alliance Gas, San Carlos, Calif.), (B) methane of 70% purity representing a natural gas standard (Sigma-Aldrich; also containing 9% ethane, 6% propane, 3% methylpropane, 3% butane, and other minor hydrocarbon components), (C) methane of 85% purity delivered as a 1:1 mixture of methane sources A and B; and (D) >93% methane (grade 1.3, Specialty Chemical Products, South Houston, Tex.; in-house analysis showed composition >99% methane). The cultures were incubated at 30° C. (*M. trichosporium* strain OB3b) or 42° C. (*M. capsulatus* Bath) with rotary shaking at 250 rpm and growth was measured at approximately 12 hour intervals by withdrawing 1 mL samples to determine $OD_{600}$. At these times, the bottles were vented and headspace replaced with 60 mL of the respective methane source (A, B, C, or D) and 60 mL of concentrated oxygen (at least 85% purity). At about 24 hour intervals, 5 mL samples were removed, cells recovered by centrifugation (8,000 rpm, 10 minutes), and then stored at −80° C. before analysis.

Analysis of carbon and nitrogen content (% dry weight), and carbon ($^{13}C$) and nitrogen ($^{15}N$) stable isotope ratios, for methanotrophic biomass derived from *M. trichosporium* strain OB3b and *M. capsulatus* Bath were carried out as described in Example 6. Table 5 shows the results of stable carbon isotope analysis for biomass samples from *M. capsulatus* Bath grown on methane having different levels of purity and in various batches of bottle cultures.

TABLE 5

Stable Carbon Isotope Distribution of *M. capsulatus* Bath Grown on Different Methane Sources having Different Purity

| Methane* | Batch No. | Time (h)† | $OD_{600}$ | DCW (g/L) | $\delta^{13}C$ Cells |
|---|---|---|---|---|---|
| A | 62C | 22 | 1.02 | 0.36 | −40.3 |
| | | 56 | 2.01 | 0.71 | −41.7 |
| | | 73 | 2.31 | 0.82 | −42.5 |
| | 62D | 22 | 1.14 | 0.40 | −39.3 |
| | | 56 | 2.07 | 0.73 | −41.6 |
| | | 73 | 2.39 | 0.85 | −42.0 |
| B | 62E | 22 | 0.47 | 0.17 | −44.7 |
| | | 56 | 0.49 | 0.17 | −45.4 |
| | | 73 | 0.29 | 0.10 | −45.4 |
| | 62F | 22 | 0.62 | 0.22 | −42.3 |
| | | 56 | 0.63 | 0.22 | −43.6 |
| | | 73 | 0.30 | 0.11 | −43.7 |
| C | 62G | 22 | 0.70 | 0.25 | −40.7 |
| | | 56 | 1.14 | 0.40 | −44.8 |
| | | 73 | 1.36 | 0.48 | −45.8 |
| | 62H | 22 | 0.62 | 0.22 | −40.9 |
| | | 56 | 1.03 | 0.37 | −44.7 |
| | | 73 | 1.23 | 0.44 | −45.9 |

*Methane purity: A: 99% methane, grade 2.0 (min. 99%); B: 70% methane, natural gas standard (contains 9% ethane, 6% propane, 3% methylpropane, 3% butane); C: 85% methane (1:1 mix of A and B methane)
†Time = bottle culture time in hours The average $\delta^{13}C$ for *M. capsulatus* Bath grown on one source of methane (A, 99%) was −41.2±1.2, while the average $\delta^{13}C$ for *M. capsulatus* Bath grown on a different source of methane (B, 70%) was −44.2±1.2. When methane sources A and B were mixed, an intermediate average $\delta^{13}C$ of −43.8±2.4 was observed. These data show that the $\delta^{13}C$ of cell material grown on methane sources A and B are significantly different from each other due to the differences in the $\delta^{13}C$ of the input methane. But, cells grown on a mixture of the two gasses preferentially utilize $^{12}C$ and, therefore, show a trend to more negative $\delta^{13}C$ values.

A similar experiment was performed to examine whether two different methanotrophs, *Methylococcus capsulatus* Bath and *Methylosinus trichosporium* OB3b, grown on different methane sources and in various batches of bottle cultures showed a difference in $\delta^{13}C$ distribution (see Table 6).

TABLE 6

Stable Carbon Isotope Distribution of Different Methanotrophs Grown on Different Methane Sources of Different Purity

| Strain | Methane* | Batch No. | Time (h)† | $OD_{600}$ | DCW (g/L) | $\delta^{13}C$ Cells |
|---|---|---|---|---|---|---|
| Mc Bath | A | 62I | 18 | 0.494 | 0.18 | −54.3 |
| | | | 40 | 2.33 | 0.83 | −42.1 |
| | | | 48 | 3.08 | 1.09 | −37.1 |
| Mc Bath | D | 62J | 18 | 0.592 | 0.21 | −38.3 |
| | | | 40 | 1.93 | 0.69 | −37.8 |
| | | | 48 | 2.5 | 0.89 | −37.8 |
| Mc Bath | D | 62K | 18 | 0.564 | 0.20 | −38.6 |
| | | | 40 | 1.53 | 0.54 | −37.5 |
| | | | 48 | 2.19 | 0.78 | −37.6 |
| Mt OB3b | A | 68D | 118 | 0.422 | 0.24 | −50.2 |
| | | | 137 | 0.99 | 0.55 | −47.7 |
| | | | 162 | 1.43 | 0.80 | −45.9 |
| Mt OB3b | A | 68E | 118 | 0.474 | 0.26 | −49.9 |
| | | | 137 | 1.065 | 0.59 | −47.6 |
| | | | 162 | 1.51 | 0.84 | −45.2 |
| Mt OB3b | D | 68F | 118 | 0.534 | 0.30 | −45.6 |
| | | | 137 | 1.119 | 0.62 | −38.7 |
| | | | 162 | 1.63 | 0.91 | −36.4 |
| Mt OB3b | D | 68G | 118 | 0.544 | 0.30 | −44.8 |
| | | | 137 | 1.131 | 0.63 | −39.1 |
| | | | 162 | 1.6 | 0.89 | −34.2 |

*Methane sources and purity: A: 99% methane (grade 2.0); D: >93% methane (grade 1.3)
†Time = bottle culture time in hours The average $\delta^{13}C$ for *M. capsulatus* grown on a first methane source (A) was −44.5±8.8, while the average $\delta^{13}C$ for *M. trichosporium* was −47.8±2.0 grown on the same methane source. The average $\delta^{13}C$ for *M. capsulatus* grown on the second methane source (B) was −37.9±0.4, while the average $\delta^{13}C$ for *M. trichosporium* was −39.8±4.5. These data show that the $\delta^{13}C$ of cell material grown on a methane source is highly similar to the $\delta^{13}C$ of cell material from a different strain grown on the same source of methane. Thus, the observed $\delta^{13}C$ of cell material appears to be primarily dependent on the composition of the input gas rather than a property of a particular bacterial strain being studied.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to U.S. Patent Application No. 61/671,542, are incorporated herein by reference in their entirety. Aspects of the embodiments can be modified, if necessary, to employ concepts of the various patents, applications and publications to provide further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A methanotroph bacteria, wherein said methanotroph bacteria comprises a heterologous polynucleotide encoding a thioesterase, a malonyl-CoA-acyl carrier protein transacylase, an acetyl-CoA carboxylase or any combination thereof, and wherein said methanotroph bacteria accumulates an increased level of fatty acids when grown on a $C_1$ substrate as a carbon source when compared to a wild-type methanotroph bacteria without said heterologous polynucleotide and grown under same conditions.

2. The methanotroph bacteria of claim 1, wherein said methanotroph bacteria is selected from the group consisting of *Methylomonas* sp. 16a (ATCC PTA 2402), *Methylosinus trichosporium* OB3b (NRRL B-11,196), *Methylosinus sporium* (NRRL B-11,197), *Methylocystis parvus* (NRRL B-11, 198), Methylomona *methanica* (NRRL B-11,199), *Methylomonas albus* (NRRL B-11,200), *Methylobacter capsulatus* Y (NRRL B-11,201), *Methylococcus capsulatus* Bath (NCIMB 11132), *Methylobacterium organophilum* (ATCC 27,886), *Methylomonas* sp. AJ-3670 (FERM P-2400), *Methylomicrobium alcaliphilum, Methylocella silvestris, Methylacidiphilum infernorum, Methylibium petroleiphilum, Methylobacterium populi*, and any combination thereof.

3. The methanotroph bacteria of claim 1, wherein said heterologous polynucleotide encoding said thioesterase is codon optimized for expression in said methanotroph bacteria.

4. The methanotroph bacteria of claim 1, wherein said heterologous polynucleotide encoding said malonyl CoA-acyl carrier protein transacylase is an *E. coli* fabD and wherein said heterologous polynucleotide is codon optimized for expression in said methanotroph bacteria.

5. The methanotroph bacteria of claim 1, wherein said heterologous polynucleotide encoding said acetyl-CoA carboxylase is an *E. coli* accA, accB, accC, accD, or any combination thereof and wherein said heterologous polynucleotide is codon optimized for expression in said methanotroph bacteria.

6. The methanotroph bacteria of claim 1, wherein said methanotroph bacteria further comprises a mutation that minimizes or eliminates fatty acid-CoA ligase activity, wherein said mutation is in an endogenous fatty acid-CoA ligase gene.

7. A method for making an oil composition, comprising converting a biomass into said oil composition, wherein said biomass comprises (a) a culture of the methanotroph bacteria of claim 1 together with a culture media in which said methanotroph bacteria were grown; (b) the methanotroph bacteria of claim 1 recovered from said culture media; or (c) a spent media composition recovered from said culture media comprising the methanotroph bacteria of claim 1.

8. The method of claim 7, wherein said $C_1$ substrate is selected from the group consisting of natural gas, unconventional natural gas, methane, a methylamine, a methylthiol, a methylhalogen, and any combination thereof.

9. The method of claim 7, wherein said biomass comprises said methanotroph bacteria recovered from said culture media.

10. The method of claim 7, wherein said biomass comprises said recovered spent media composition and said recovered spent media composition is converted into said oil composition by extraction or concentration of said recovered spent media composition.

11. The method of claim 7, wherein said oil composition is extracted from said biomass and contains cell membranes of said methanotroph bacteria, is extracted from a culture supernatant, or a combination thereof.

12. The method of claim 7, wherein said methanotroph bacteria are cultured in a controlled culture unit selected from the group consisting of a fermentor, a bioreactor, a hollow fiber cell, a packed bed bioreactor, and combinations thereof.

13. The method of claim 12, wherein said methanotroph bacteria are cultured in a bioreactor comprising balanced media or cultured in a bioreactor comprising unbalanced media having limited quantities of phosphorus, nitrogen, trace elements, oxygen relative to a balanced media, or any combination thereof.

14. The method of claim 7, wherein said biomass is converted into said oil composition by extraction.

15. The method of claim 14, wherein said extraction is by high-shear contact with an organic solvent and a conditioning agent.

16. The method of claim 14, wherein said extraction is selected from the group consisting of wet extraction, supercritical fluid extraction, dry extraction, thermal extraction, enzymatic hydrolysis extraction, pulsed electric field extraction, microbubble extraction, and hollow fiber extraction.

17. The method of claim 7, wherein said oil composition comprises molecules comprising hydrogen and carbon atoms, wherein said hydrogen and carbon atoms are at least 50% of the weight of said oil composition and wherein a $\delta^{13}C$ of said oil composition ranges from 70‰ to 30‰.

18. The method of claim 17, wherein said hydrogen and carbon atoms are at least 80%, 85%, 90%, 95%, 99%, or 100% of the weight of said oil composition.

19. The method of claim 7, wherein said oil composition comprises at least 50% w/w fatty acids.

20. The method of claim 19, wherein said fatty acids are free fatty acids.

21. The method of claim 19, wherein said fatty acids comprise a mixture of diacylglycerides and triacylglycerides.

22. The method of claim 19, wherein a majority of said fatty acids comprise carbon chain lengths of C14 to C18.

23. The method of claim 19, wherein a majority of said fatty acids comprise carbon chain lengths of C16 to C18.

24. The method of claim 19, wherein a majority of said fatty acids comprise carbon chain lengths of less than C16.

25. The method of claim 7, wherein said oil composition comprises at least 50% w/w terpenoid compounds, isoprenoid compounds, or a combination thereof.

26. The method of claim 25, wherein said terpenoid is farnesene.

27. The method of claim 25, wherein said terpenoid is limonene.

28. The method of claim 7, further comprising hydrotreatment to produce light hydrocarbons, wherein said light hydrocarbons are selected from the group consisting of methane, methanol, ethane, ethanol, propane, propanol, butane, pentane, butanol, and isobutanol.

29. The method of claim 28, wherein said light hydrocarbon is methane, ethane, propane, butane, or pentane.

30. The method of claim 28, wherein said light hydrocarbon is butanol or isobutanol.

* * * * *